US007897372B2

(12) United States Patent
Duchateau et al.

(10) Patent No.: US 7,897,372 B2
(45) Date of Patent: Mar. 1, 2011

(54) I-CREI MEGANUCLEASE VARIANTS WITH MODIFIED SPECIFICITY, METHOD OF PREPARATION AND USES THEREOF

(75) Inventors: Philippe Duchateau, Gandelu (FR); Frederic Paques, Bourg-la-Reine (FR)

(73) Assignee: Cellectis, Romainville (FR)

( * ) Notice: Subject to any disclaimer, the term of this patent is extended or adjusted under 35 U.S.C. 154(b) by 756 days.

(21) Appl. No.: 11/908,798

(22) PCT Filed: Mar. 15, 2006

(86) PCT No.: PCT/IB2006/001203

§ 371 (c)(1),
(2), (4) Date: Sep. 17, 2007

(87) PCT Pub. No.: WO2006/097853

PCT Pub. Date: Sep. 21, 2006

(65) Prior Publication Data

US 2010/0021448 A1    Jan. 28, 2010

(30) Foreign Application Priority Data

Mar. 15, 2005  (WO) ............... PCT/IB2005/000981
Sep. 19, 2005  (WO) ............... PCT/IB2005/003083

(51) Int. Cl.
*C12N 9/00*     (2006.01)
*C12N 9/22*     (2006.01)
*C12N 1/12*     (2006.01)
*C12N 15/00*    (2006.01)
*C07H 21/04*    (2006.01)

(52) U.S. Cl. .................... 435/199; 435/183; 435/252.3; 435/320.1; 536/23.2

(58) Field of Classification Search ....................... None
See application file for complete search history.

(56) References Cited

U.S. PATENT DOCUMENTS

| 6,610,545 | B2 | 8/2003 | Dujon et al. |
| 7,309,605 | B1 | 12/2007 | Dujon et al. |
| 2004/0002092 | A1 | 1/2004 | Arnould et al. |
| 2006/0078552 | A1 | 4/2006 | Arnould et al. |
| 2006/0206949 | A1 | 9/2006 | Arnould et al. |
| 2010/0021448 | A1 | 1/2010 | Duchateau et al. |
| 2010/0144012 | A1 | 6/2010 | Arnould et al. |

FOREIGN PATENT DOCUMENTS

| WO | WO 96/14408 | 5/1996 |
| WO | 2004 067736 | 8/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Sussman, D. et al.,"Isolation and Characterization of New Homing Endonuclease Specificities at Individual Target Site Positions", J. Mol. Biol., vol. 342, No. 1, pp. 31-41, 2004.
Seligman, D. et al.,"Mutations Altering the Cleavage Specificity of a Homing Endonuclease", Nucleic Acids Research, vol. 30, No. 17, pp. 3870-3879, 2002.
Arnould, S. et al.,"Engineering of Large Numbers of Highly Specific Homing Endonucleases that Induce Recombination on Novel DNA Targets", J. Mol. Biol., vol. 355, No. 3, pp. 443-458, 2006.
U.S. Appl. No. 12/091,216, filed Apr. 23, 2008, Paques.
Cabaniols et al., "Robust Cell Lin Development Using Meganucleases," Methods in Molecular Biology, vol. 435: 31-45, 2008.
Chames et al., "In Vivo Selection of Engineered Homing Endonucleases using Double-Strand Break Induced Homologous Recombination," Nucleic Acids Res., 33: e178 (2005).
Chevalier et al., "Design, Activity, and Structure of a Highly Specific Artificial Endonuclease," Molecular Cell, 10: 895-905 (2002).
Choulika et al., "The Yeast I-Sce I Meganuclease Induces Site-Directed Chromosomal Recombination in Mammalian Cells," C R Acad Sci III,1994 317:1013-9 (1994).
Colleaux et al., "Universal Code Equivalent of a Yeast Mitochondrial Intron Reading Frame Is Expressed into *E. coli* as a Specific Double Strand Endonuclease," Cell, 44:521-533 (1986).
Delahodde et al., "Site-Specific DNA Endonuclease and RNA Mautrase Activities of Two Homologous Intron-Encoded Proteins from Yeast Mitochondria," Cell, 56: 431-441 (1989).
Dujon et al., "Group I Introns as Mobile Genetic Elements: Facts and Mechanistic Speculations—a Review," Gene, 82: 91-126 (1989).
Dujon et al., "Cellectis. Celletis' 5th Scientific Advisory Board Meeting. Report of the Meeting," p. 1-4, Dec. 16-17, 2004.
Dujon et al., "Homing Endonucleases and the Yeast Mitochondrial Locus—a Historical Perspective," Nucleic Acids and Molecular Biology, 16: 11-31 (2005).
Durrenberger et al., "Chloroplast Ribosomal Intron of Chlamydomonas Reinhardtil: In Vitro Self-Splicing, DNA Endonuclease Activity and in Vivo Mobility," the EMBO J, 10:3495-3501 (1991).
Epinat et al., "A Novel Engineered Meganuclease Induces Homologous Recombination in Yeast and Mammalian Cells", Nucleic Acids Research, 31: 2952-2962 (2003).
Galetto et al., "Target Approaches for Gene Therapy and the Emergence of Engineered Meganucleases," Expert Opin. Biol. Ther, 9:1289-1303 (2009).
Lacroix et al., "Automated Discovery and Design of Novel Meganucleases," Cellectis S.A., 1-21. (2009).

(Continued)

*Primary Examiner* — Christian L Fronda
(74) *Attorney, Agent, or Firm* — Oblon, Spivak, McClelland, Maier & Neustadt, L.L.P.

(57) ABSTRACT

Method of preparing 1-CreI meganuclease variants having a modified cleavage specificity, variants obtainable by said method and their applications either for cleaving new DNA target or for genetic engineering and genome engineering for non-therapeutic purposes. Nucleic acids encoding said variants, expression cassettes comprising said nucleic acids, vectors comprising said expression cassettes, cells or organisms, plants or animals except humans, transformed by said vectors.

54 Claims, 59 Drawing Sheets

OTHER PUBLICATIONS

Figure 1:
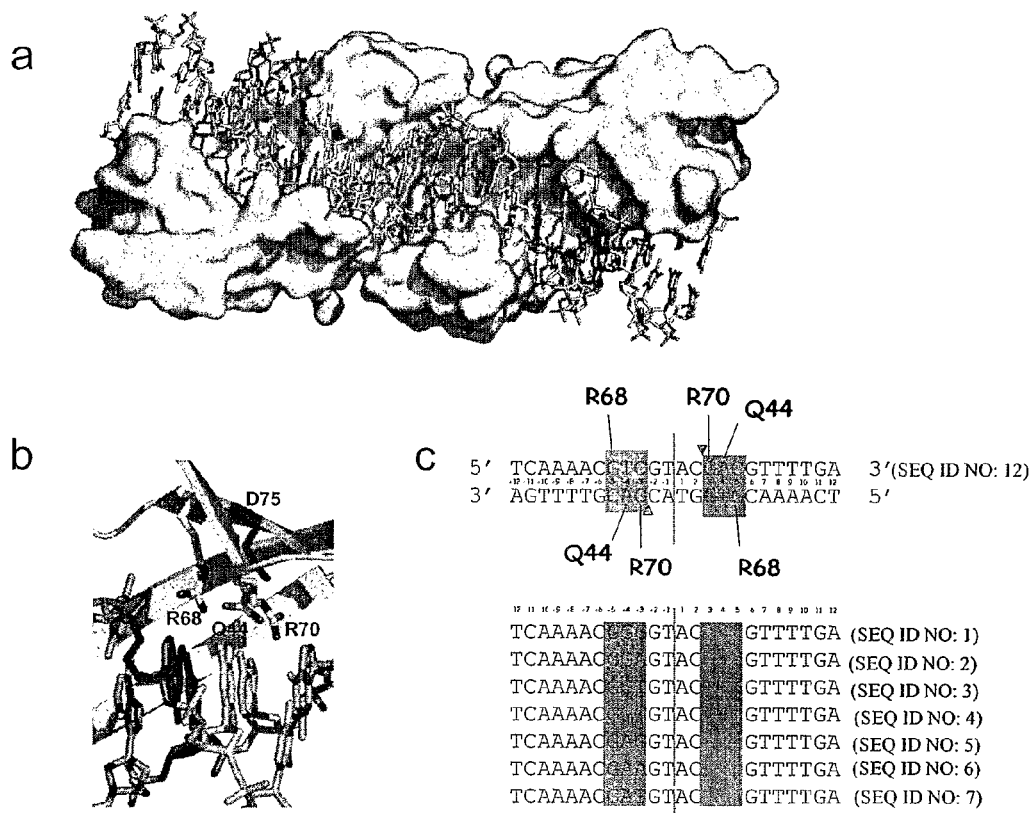

Maggos, "Technology, Industrializing DNA Modification," BioCentury, Cellectis091508, PREC197169 (Jan. 22, 2007).

Marcaida et al., "Crystal Structure of I-Dmol in Complex with its Target DNA Provides New Insights into Meganuclease Engineering," PNAS, 105: 16888-16893 (2008).

Meganuclease I-Sce I (Omega-Nuclease). Cat No 11 362 399 001, Version Nov. 2004, Roche.

Paques et al., "Meganucleases and DNA Double-Strand Break-Induced Recombination: Perspectives for Gene Therapy," Current Gene Therapy, 7: 49-66 (2007).

Prieto et al., "Generation and Analysis of Mesophilic Variants of the Thermostable Archael I-DMOI Homing Endonuclease," J. Biol. Chem., 283: 4364-4374 (2008).

Schiestl et al., "Integration of DNA Fragments by Illegitimate Recombination in *Saccharonmyces cerevisiae*," Proc. Natl. Acad. Sci., 88: 7585-7589 (1991).

Thierry et al., "Cleavage of Yeast and Bacteriophage T7 Genomes at a Single Site Using the Rare Cutter Endonuclease I-Sce I," Nucleic Acids Research, 19:189-190 (1991).

Plaintiff Cellectis's Brief in Support of its Proposed Claim Construction, Nov. 2, 2009.

Stoddard, Expert Report of Bary L. Stoddard, Ph.D. on the Meaning of the Asserted Claims in Cellectis's Patents, Jan. 16, 2009.

Office Action from related U.S. Appl. No. 10/543,556, mailed May 14, 2009.

Office Action from related U.S. Appl. No. 11/908,934, mailed Oct. 14, 2010.

Office Action from related U.S. Appl. No. 10/388,230, mailed May 24, 2010.

Office Action from related U.S. Appl. No. 10/507,736, mailed Jun. 25, 2010.

Office Action from related U.S. Appl. No. 12/710,969 mailed Jul. 14, 2010.

Notice of Opposition to a European Patent No. 1 485 475, dated Jun. 5, 2008.

Response to Opposition to European Patent No. 1 485475, filed Jan. 13, 2009.

Summons to Attend Oral Proceedings issued for European Patent No. 1 485475, dated Jun. 30, 2009 (w/English Translation).

Response to Oral Proceedings to European Patent No. 1 485475, received Jun. 30, 2009, filed Sep. 18, 2009.

Response to Summons to Attend Oral Proceedings for European Patent No. 1 485475, filed Sep. 18, 2009.

Interlocutory Decision in Opposition Proceedings issued for EP 03744485.8-2405, Feb. 8, 2010.

Appeal filed for European Patent No. 1 485475, filed Jun. 8, 2010. (French).

Appeal filed for European Patent No. 1 485475, filed Jun. 17, 2010.

Minutes of Oral Proceedings before the Opposition Division, Nov. 18, 2009.

Emmanuel Fajardo-Sanchez. "Computer design of obligate heterodimer meganucleases allows efficient cutting of custom DNA sequences", Nucleic Acids Research, 2008, vol. 36, No. 7, pp. 2163-2173.

Jesús Prieto, et al., "The C-terminal loop of the homing endonuclease I-CreI is essential for site recognition, DNA binding and cleavage", Nucleic Acids Research, 2007, vol. 35, No. 10, pp. 3262-3271.

Brett S. Chevalier, et al., "The homing endonuclease I-CreI uses three metals, one of which is shared between the two active sites", Nature Structural Biology, vol. 8, No. 4, Apr. 2001, pp. 312-316.

Redondo et al., "Molecular Basis of Xeroderma Pigmentosum Group C DNA Recognition by Engineered Meganucleases," Nature, 456: 107-111, (2008).

Quirk et al., "Intron Mobility in the T-Even Phages: Hight Frequency Inheritance of Group I Introns Promoted by Intron Open Reading Frames," Cell, 56: 455-465 (1989).

Office Action from related U.S. Appl. No. 10/543,556, mailed Aug. 19, 2008.

Office Action from related U.S. Appl. No. 11/908,934, mailed Jan. 25, 2010.

Office Action from related U.S. Appl. No. 10/388,230, mailed Nov. 25, 2008.

Office Action from related U.S. Appl. No. 10/388,230, mailed Jun. 14, 2007.

Office Action from related U.S. Appl. No. 10/388,230, mailed Feb. 9, 2006.

Office Action from related U.S. Appl. No. 10/507,736, mailed Aug. 5, 2009.

Office Action from related U.S. Appl. No. 10/507,736, mailed Aug. 1, 2008.

* cited by examiner

```
       -12-11-10 -9 -8 -7 -6 -5 -4 -3 -2 -1 | 1  2  3  4  5  6  7  8  9 10 11 12
C1234   T  C  A  A  A  A  C  G  T  C  G  T | G  A  G  A  C  A  G           C
(SEQ ID NO: 65)

C4334   C  C  A  A  A  C  T  G  T  C  T  C | G  A  G  A  C  A           G  G
(SEQ ID NO: 66)

C1221   T  G  A  A  A  A  C  G  T  C  G  T | A  C  G  A  C  G  T           G  A
(SEQ ID NO: 12)
```

*Fig. 2A*

|     | -12 | -11 | -10 | -9 | -8 | -7 | -6 | -5 | -4 | -3 | -2 | -1 | 1 | 2 | 3 | 4 | 5 | 6 | 7 | 8 | 9 | 10 | 11 | 12 |
|---|---|---|---|---|---|---|---|---|---|---|---|---|---|---|---|---|---|---|---|---|---|---|---|---|
| | T | C | A | A | A | A | C | | | | | | G | T | A | C | | | G | T | T | T | T | G | A |
| | T | C | A | A | A | A | C | | | | | | G | T | A | C | T | C | G | G | T | T | T | T | G | A |
| | T | C | A | A | A | A | C | | G | | | | G | T | A | C | A | C | C | G | T | T | T | T | G | A |
| | T | C | A | A | A | A | C | | | | | | G | T | A | C | | | | G | T | T | T | T | G | A |
| | T | C | A | A | A | A | C | | A | | | | G | T | A | C | C | T | | G | T | T | T | T | G | A |
| | T | C | A | A | A | A | C | | | | | | G | T | A | C | T | T | C | G | T | T | T | T | G | A |
| | T | C | A | A | A | A | C | | | | | | G | T | A | A | A | T | C | G | T | T | T | T | G | A |
| | T | C | A | A | A | A | C | | A | | | | G | T | A | C | C | T | | G | T | T | T | T | G | A |
| | T | C | A | A | A | A | C | | | G | | | G | T | A | C | C | A | C | G | T | T | T | T | G | A |
| | T | C | A | A | A | A | C | | | | | | G | T | A | C | T | A | C | G | T | T | T | T | G | A |
| | T | C | A | A | A | A | C | | | | | | G | T | A | C | A | A | | G | T | T | T | T | G | A |
| | T | C | A | A | A | A | C | G | | C | | | G | T | A | C | G | A | C | G | T | T | T | T | G | A |
| | T | C | A | A | A | A | C | G | | | | | G | T | A | C | C | G | G | G | T | T | T | T | G | A |
| | T | C | A | A | A | A | C | G | | | | | G | T | A | C | T | G | C | G | T | T | T | T | G | A |
| | T | C | A | A | A | A | C | | | | | | G | T | A | C | A | G | C | G | T | T | T | T | G | A |
| | T | C | A | A | A | A | C | G | | | | | G | T | A | C | G | G | C | G | T | T | T | T | G | A |
| | T | C | A | A | A | A | C | | | | | | G | T | A | C | C | C | T | G | T | T | T | T | G | A |
| | T | C | A | A | A | A | C | | | | | | G | T | A | C | T | G | T | G | T | T | T | T | G | A |
| | T | C | A | A | A | A | C | | | | | | G | T | A | C | G | T | T | G | T | T | T | T | G | A |
| | T | C | A | A | A | A | C | | | | | | G | T | A | C | A | T | T | G | T | T | T | T | G | A |
| | T | C | A | A | A | A | C | | | | | | G | T | A | C | C | T | T | G | T | T | T | T | G | A |
| | T | C | A | A | A | A | C | | | | | | G | T | A | C | T | T | T | G | T | T | T | T | G | A |
| | T | C | A | A | A | A | C | | | | | | G | T | A | C | A | T | T | G | T | T | T | T | G | A |
| | T | C | A | A | A | A | C | | | | | | G | T | A | C | G | T | T | G | T | T | T | T | G | A |
| | T | C | A | A | A | A | C | | | G | | | G | T | A | C | C | A | T | G | T | T | T | T | G | A |
| | T | C | A | A | A | A | C | | T | | | | G | T | A | C | T | A | T | G | T | T | T | T | G | A |
| | T | C | A | A | A | A | C | | | | | | G | T | A | C | A | A | T | G | T | T | T | T | G | A |
| | T | C | A | A | A | A | C | | | | | | G | T | A | C | C | A | T | G | T | T | T | T | G | A |
| | T | C | A | A | A | A | C | | | | | | G | T | A | C | C | G | T | G | T | T | T | T | G | A |
| | T | C | A | A | A | A | C | | | | | | G | T | A | C | T | G | T | G | T | T | T | T | G | A |
| | T | C | A | A | A | A | C | | | | | | G | T | A | C | A | G | T | G | T | T | T | T | G | A |
| | T | C | A | A | A | A | C | | | | | | G | T | A | C | C | G | T | G | T | T | T | T | G | A |

SEQ ID NO: 69
1    ATGGCCAATA CCAAATATAA CAAAGAGTTC CTGCTGTACC TGGCCGGCTT
51   TGTGGACGGT GACGGTAGCA TCATCGCTCA GATTAAACCA AACCAGTCTT
101  ATAAGTTTAA ACATCAGCTA AGCTTGACCT TTCAGGTGAC TCAAAAGACC
151  CAGCGCCGTT GGTTTCTGGA CAAACTAGTG GATGAAATTG GCGTTGGTTA
201  CGTACGTGAT CGCGGATCCG TTTCCAACTA CATCTTAAGC GAAATCAAGC
251  CGCTGCACAA CTTCCTGACT CAACTGCAGC CGTTTCTGAA ACTGAAACAG
301  AAACAGGCAA ACCTGGTTCT GAAAATTATC GAACAGCTGC CGTCTGCAAA
351  AGAATCCCCG GACAAATTCC TGGAAGTTTG TACCTGGGTG GATCAGATTG
401  CAGCTCTGAA CGATTCTAAG ACGCGTAAAA CCACTTCTGA AACCGTTCGT
451  GCTGTGCTGG ACAGCCTGAG CGAGAAGAAG AAATCCTCCC CGGCGGCCGA
501  C

Figure 4A

UlibIIfor (SEQ ID NO: 67)
GTTTAAACAT CAGCTAAGCT TGACCTTTVV KGTGACTCAA AAGACCCAG

UlibIIrev (SEQ ID NO: 68)
GATGTAGTTG GAAACGGATC CMBBATCMBB TACGTAACCA ACGCC

V = A or G or C

M = A or C

B = G or C or T

K = G or T

Figure 4B

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| A | A | A | 0 | 0 | 0 | 0 | 1 | 0 | 1 | 0 | 0 | 0 | 0 | 0 | 0 | 0 | 0 | 0 |
| A | A | G | 0 | 0 | 0 | 0 | 0 | 0 | 1 | 0 | 0 | 0 | 0 | 0 | 0 | 0 | 0 | 0 |
| A | A | H | 0 | 0 | 0 | 0 | 1 | 0 | 1 | 1 | 0 | 0 | 0 | 0 | 0 | 0 | 0 | 0 |
| A | A | K | 0 | 0 | 0 | 0 | 1 | 0 | 1 | 1 | 0 | 0 | 1 | 1 | 0 | 0 | 0 | 0 |
| A | A | N | 0 | 0 | 0 | 0 | 1 | 0 | 1 | 0 | 0 | 0 | 0 | 0 | 0 | 0 | 0 | 0 |
| A | A | Q | 0 | 0 | 0 | 0 | 1 | 0 | 1 | 0 | 0 | 0 | 0 | 0 | 0 | 0 | 0 | 0 |
| A | A | R | 0 | 0 | 0 | 0 | 1 | 0 | 1 | 1 | 0 | 0 | 0 | 0 | 0 | 0 | 0 | 0 |
| A | A | S | 0 | 0 | 0 | 0 | 1 | 0 | 1 | 0 | 0 | 0 | 0 | 0 | 0 | 0 | 0 | 0 |
| A | A | T | 0 | 0 | 0 | 0 | 0 | 0 | 1 | 0 | 0 | 0 | 0 | 0 | 0 | 0 | 0 | 0 |
| A | D | H | 0 | 0 | 0 | 0 | 0 | 0 | 1 | 0 | 0 | 0 | 0 | 0 | 0 | 0 | 0 | 0 |
| A | D | K | 0 | 0 | 0 | 0 | 0 | 0 | 1 | 0 | 0 | 0 | 0 | 0 | 0 | 0 | 0 | 0 |
| A | D | R | 0 | 0 | 0 | 0 | 1 | 0 | 1 | 1 | 0 | 0 | 0 | 0 | 0 | 0 | 0 | 0 |
| A | G | H | 0 | 0 | 0 | 0 | 0 | 0 | 0 | 0 | 0 | 0 | 0 | 0 | 0 | 0 | 0 | 0 |
| A | G | K | 0 | 0 | 0 | 0 | 0 | 0 | 1 | 0 | 0 | 0 | 0 | 0 | 0 | 0 | 0 | 0 |
| A | G | N | 0 | 0 | 0 | 0 | 1 | 0 | 1 | 0 | 0 | 0 | 0 | 0 | 0 | 0 | 0 | 0 |
| A | G | P | 0 | 0 | 0 | 0 | 0 | 0 | 1 | 1 | 0 | 0 | 1 | 0 | 0 | 0 | 0 | 1 |
| A | G | R | 0 | 0 | 0 | 0 | 0 | 0 | 0 | 1 | 0 | 0 | 0 | 0 | 0 | 0 | 0 | 0 |
| A | H | A | 0 | 0 | 0 | 0 | 1 | 0 | 1 | 1 | 0 | 0 | 0 | 0 | 0 | 0 | 0 | 0 |
| A | H | G | 0 | 0 | 0 | 0 | 0 | 0 | 1 | 1 | 0 | 0 | 0 | 0 | 0 | 0 | 0 | 0 |
| A | H | H | 0 | 0 | 0 | 0 | 1 | 0 | 1 | 0 | 0 | 0 | 0 | 0 | 0 | 0 | 0 | 0 |
| A | H | K | 0 | 0 | 0 | 0 | 0 | 0 | 1 | 0 | 0 | 0 | 0 | 0 | 0 | 0 | 0 | 0 |
| A | H | N | 0 | 0 | 0 | 0 | 1 | 0 | 1 | 1 | 0 | 0 | 0 | 0 | 0 | 0 | 0 | 0 |
| A | H | Q | 0 | 0 | 0 | 0 | 1 | 0 | 1 | 1 | 0 | 0 | 0 | 0 | 0 | 0 | 0 | 0 |
| A | H | R | 0 | 0 | 0 | 0 | 1 | 0 | 1 | 1 | 0 | 0 | 0 | 0 | 0 | 0 | 0 | 0 |
| A | H | S | 0 | 0 | 0 | 0 | 1 | 0 | 1 | 0 | 0 | 0 | 0 | 0 | 0 | 0 | 0 | 0 |
| A | H | T | 0 | 0 | 0 | 0 | 0 | 0 | 1 | 0 | 0 | 0 | 0 | 0 | 0 | 0 | 0 | 0 |
| A | K | A | 0 | 0 | 0 | 0 | 0 | 0 | 1 | 0 | 0 | 0 | 0 | 0 | 0 | 0 | 0 | 0 |
| A | K | G | 0 | 0 | 0 | 0 | 0 | 0 | 1 | 0 | 0 | 0 | 0 | 0 | 0 | 0 | 0 | 0 |
| A | K | H | 0 | 0 | 0 | 0 | 1 | 0 | 1 | 1 | 0 | 0 | 0 | 0 | 0 | 0 | 0 | 0 |
| A | K | K | 0 | 0 | 0 | 0 | 1 | 0 | 1 | 1 | 0 | 0 | 0 | 0 | 0 | 0 | 0 | 0 |
| A | K | N | 0 | 0 | 0 | 0 | 1 | 0 | 1 | 1 | 0 | 0 | 0 | 0 | 0 | 0 | 0 | 0 |
| A | K | Q | 0 | 0 | 0 | 0 | 1 | 0 | 1 | 0 | 0 | 0 | 0 | 0 | 0 | 0 | 0 | 0 |
| A | K | R | 0 | 0 | 0 | 0 | 1 | 0 | 1 | 1 | 0 | 0 | 0 | 0 | 0 | 0 | 0 | 0 |
| A | K | S | 0 | 0 | 0 | 0 | 0 | 0 | 1 | 0 | 0 | 0 | 0 | 0 | 0 | 0 | 0 | 0 |
| A | K | T | 0 | 0 | 0 | 0 | 0 | 0 | 1 | 0 | 0 | 0 | 0 | 0 | 0 | 0 | 0 | 0 |

*Fig. 7.1a*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| A | N | A | 0 | 0 | 0 | 0 | 1 | 0 | 1 | 0 | 0 | 0 | 0 | 0 | 0 | 0 | 0 | 0 |
| A | N | E | 0 | 0 | 0 | 0 | 1 | 0 | 1 | 0 | 0 | 0 | 0 | 0 | 0 | 0 | 0 | 0 |
| A | N | G | 0 | 0 | 0 | 0 | 1 | 0 | 1 | 0 | 0 | 0 | 0 | 0 | 0 | 0 | 0 | 0 |
| A | N | H | 0 | 0 | 0 | 0 | 1 | 0 | 1 | 0 | 0 | 0 | 0 | 0 | 0 | 0 | 0 | 0 |
| A | N | K | 0 | 0 | 0 | 0 | 1 | 0 | 1 | 1 | 0 | 0 | 1 | 1 | 0 | 0 | 0 | 0 |
| A | N | N | 0 | 0 | 0 | 0 | 1 | 0 | 1 | 1 | 0 | 0 | 0 | 0 | 0 | 0 | 0 | 0 |
| A | N | Q | 0 | 0 | 0 | 0 | 1 | 0 | 1 | 0 | 0 | 0 | 0 | 0 | 0 | 0 | 0 | 0 |
| A | N | R | 0 | 0 | 0 | 0 | 1 | 0 | 1 | 1 | 0 | 0 | 0 | 0 | 0 | 0 | 0 | 0 |
| A | N | S | 0 | 0 | 0 | 0 | 1 | 0 | 1 | 0 | 0 | 0 | 0 | 0 | 0 | 0 | 0 | 0 |
| A | N | T | 0 | 0 | 0 | 0 | 0 | 0 | 1 | 0 | 0 | 0 | 0 | 0 | 0 | 0 | 0 | 0 |
| A | Q | A | 0 | 0 | 0 | 0 | 0 | 0 | 1 | 0 | 0 | 0 | 0 | 0 | 0 | 0 | 0 | 0 |
| A | Q | D | 0 | 0 | 0 | 0 | 0 | 0 | 0 | 0 | 0 | 0 | 0 | 0 | 0 | 0 | 0 | 0 |
| A | Q | G | 0 | 0 | 0 | 0 | 1 | 0 | 1 | 0 | 0 | 0 | 0 | 0 | 0 | 0 | 0 | 0 |
| A | Q | H | 0 | 0 | 0 | 0 | 0 | 0 | 1 | 1 | 0 | 0 | 0 | 0 | 0 | 0 | 0 | 0 |
| A | Q | N | 0 | 0 | 0 | 0 | 1 | 0 | 1 | 0 | 0 | 0 | 0 | 0 | 0 | 0 | 0 | 0 |
| A | Q | R | 0 | 0 | 0 | 0 | 0 | 0 | 1 | 1 | 0 | 0 | 0 | 0 | 0 | 0 | 0 | 0 |
| A | Q | S | 0 | 0 | 0 | 0 | 1 | 0 | 1 | 0 | 0 | 0 | 0 | 0 | 0 | 0 | 0 | 0 |
| A | R | A | 0 | 0 | 0 | 0 | 1 | 0 | 1 | 1 | 0 | 1 | 1 | 0 | 0 | 0 | 0 | 0 |
| A | R | D | 0 | 0 | 0 | 0 | 1 | 0 | 1 | 1 | 0 | 0 | 0 | 0 | 0 | 0 | 0 | 0 |
| A | R | E | 0 | 0 | 0 | 0 | 1 | 0 | 1 | 1 | 0 | 0 | 0 | 0 | 0 | 0 | 0 | 0 |
| A | R | G | 0 | 0 | 0 | 0 | 1 | 0 | 1 | 1 | 0 | 0 | 1 | 0 | 0 | 0 | 1 | 0 |
| A | R | H | 0 | 0 | 0 | 0 | 1 | 0 | 1 | 1 | 0 | 0 | 0 | 0 | 0 | 0 | 0 | 0 |
| A | R | K | 0 | 0 | 0 | 1 | 1 | 0 | 1 | 1 | 0 | 0 | 0 | 1 | 0 | 0 | 0 | 0 |
| A | R | L | 0 | 0 | 0 | 0 | 1 | 0 | 1 | 1 | 0 | 0 | 0 | 1 | 0 | 0 | 0 | 0 |
| A | R | N | 0 | 0 | 0 | 0 | 1 | 0 | 1 | 1 | 0 | 0 | 1 | 1 | 0 | 0 | 0 | 0 |
| A | R | R | 1 | 0 | 0 | 0 | 1 | 0 | 1 | 1 | 0 | 0 | 0 | 1 | 0 | 0 | 0 | 0 |
| A | R | S | 0 | 0 | 0 | 0 | 1 | 0 | 1 | 1 | 1 | 0 | 1 | 1 | 0 | 0 | 1 | 0 |
| A | R | T | 0 | 0 | 0 | 0 | 1 | 0 | 1 | 1 | 0 | 0 | 1 | 1 | 0 | 0 | 1 | 1 |
| A | S | A | 0 | 0 | 0 | 0 | 1 | 0 | 1 | 1 | 0 | 0 | 0 | 0 | 0 | 0 | 0 | 0 |
| A | S | G | 0 | 0 | 0 | 0 | 1 | 0 | 1 | 0 | 0 | 0 | 0 | 0 | 0 | 0 | 0 | 0 |
| A | S | K | 0 | 0 | 0 | 0 | 1 | 0 | 1 | 1 | 0 | 0 | 1 | 1 | 0 | 0 | 0 | 0 |
| A | S | N | 0 | 0 | 0 | 0 | 1 | 0 | 1 | 0 | 0 | 0 | 0 | 0 | 0 | 0 | 0 | 0 |
| A | S | Q | 0 | 0 | 0 | 0 | 1 | 0 | 1 | 0 | 0 | 0 | 0 | 0 | 0 | 0 | 0 | 0 |
| A | S | R | 0 | 0 | 0 | 0 | 1 | 0 | 1 | 1 | 0 | 0 | 0 | 0 | 0 | 0 | 0 | 0 |

*Fig.7.1b*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| A | A | A | 0 | 0 | 0 | 0 | 0 | 0 | 1 | 0 | 0 | 0 | 0 | 0 | 0 | 0 | 0 | 0 |
| A | A | G | 0 | 0 | 0 | 0 | 0 | 0 | 1 | 0 | 0 | 0 | 0 | 0 | 0 | 0 | 0 | 0 |
| A | A | H | 0 | 0 | 0 | 0 | 1 | 0 | 1 | 1 | 0 | 0 | 0 | 0 | 0 | 0 | 0 | 0 |
| A | A | K | 0 | 0 | 0 | 0 | 0 | 0 | 0 | 0 | 0 | 0 | 0 | 0 | 0 | 0 | 0 | 0 |
| A | A | N | 0 | 0 | 0 | 0 | 1 | 0 | 1 | 0 | 0 | 0 | 0 | 0 | 0 | 0 | 0 | 0 |
| A | A | Q | 0 | 0 | 0 | 0 | 0 | 0 | 1 | 0 | 0 | 0 | 0 | 0 | 0 | 0 | 0 | 0 |
| A | A | R | 0 | 0 | 0 | 0 | 0 | 0 | 0 | 1 | 0 | 0 | 0 | 0 | 0 | 0 | 0 | 0 |
| A | A | S | 0 | 0 | 0 | 0 | 0 | 0 | 1 | 0 | 0 | 0 | 0 | 0 | 0 | 0 | 0 | 0 |
| A | A | T | 0 | 0 | 0 | 0 | 0 | 0 | 1 | 0 | 0 | 0 | 0 | 0 | 0 | 0 | 0 | 0 |
| A | D | H | 0 | 0 | 0 | 0 | 0 | 0 | 0 | 0 | 0 | 0 | 0 | 0 | 0 | 0 | 0 | 0 |
| A | D | K | 0 | 0 | 0 | 0 | 0 | 0 | 0 | 0 | 0 | 0 | 0 | 0 | 0 | 0 | 0 | 0 |
| A | D | R | 0 | 0 | 0 | 0 | 0 | 0 | 0 | 0 | 0 | 0 | 0 | 0 | 0 | 0 | 0 | 0 |
| A | G | H | 0 | 0 | 0 | 0 | 0 | 0 | 1 | 0 | 0 | 0 | 0 | 0 | 0 | 0 | 0 | 0 |
| A | G | K | 0 | 0 | 0 | 0 | 0 | 0 | 0 | 0 | 0 | 0 | 0 | 0 | 0 | 0 | 0 | 0 |
| A | G | N | 0 | 0 | 0 | 0 | 1 | 0 | 1 | 0 | 0 | 0 | 0 | 0 | 0 | 0 | 0 | 0 |
| A | G | P | 0 | 0 | 0 | 0 | 0 | 0 | 1 | 0 | 0 | 0 | 0 | 0 | 0 | 0 | 0 | 0 |
| A | G | R | 0 | 0 | 0 | 0 | 0 | 0 | 0 | 1 | 0 | 0 | 0 | 0 | 0 | 0 | 0 | 0 |
| A | H | A | 0 | 0 | 0 | 0 | 1 | 0 | 1 | 1 | 0 | 0 | 0 | 0 | 0 | 0 | 0 | 0 |
| A | H | G | 0 | 0 | 0 | 0 | 0 | 0 | 1 | 0 | 0 | 0 | 0 | 0 | 0 | 0 | 0 | 0 |
| A | H | H | 0 | 0 | 0 | 0 | 1 | 0 | 1 | 0 | 0 | 0 | 0 | 0 | 0 | 0 | 0 | 0 |
| A | H | K | 0 | 0 | 0 | 0 | 0 | 0 | 0 | 0 | 0 | 0 | 0 | 0 | 0 | 0 | 0 | 0 |
| A | H | N | 0 | 0 | 0 | 0 | 1 | 0 | 1 | 0 | 0 | 0 | 0 | 0 | 0 | 0 | 0 | 0 |
| A | H | Q | 0 | 0 | 0 | 0 | 0 | 0 | 1 | 0 | 0 | 0 | 0 | 0 | 0 | 0 | 0 | 0 |
| A | H | R | 0 | 0 | 0 | 0 | 0 | 0 | 0 | 1 | 0 | 0 | 0 | 0 | 0 | 0 | 0 | 0 |
| A | H | S | 0 | 0 | 0 | 0 | 0 | 0 | 1 | 0 | 0 | 0 | 0 | 0 | 0 | 0 | 0 | 0 |
| A | H | T | 0 | 0 | 0 | 0 | 0 | 0 | 1 | 0 | 0 | 0 | 0 | 0 | 0 | 0 | 0 | 0 |
| A | K | A | 0 | 0 | 0 | 0 | 0 | 0 | 1 | 0 | 0 | 0 | 0 | 0 | 0 | 0 | 0 | 0 |
| A | K | G | 0 | 0 | 0 | 0 | 0 | 0 | 1 | 0 | 0 | 0 | 0 | 0 | 0 | 0 | 0 | 0 |
| A | K | H | 0 | 0 | 0 | 0 | 1 | 0 | 1 | 1 | 0 | 0 | 0 | 0 | 0 | 0 | 0 | 0 |
| A | K | K | 0 | 0 | 0 | 0 | 0 | 0 | 0 | 0 | 0 | 0 | 0 | 0 | 0 | 0 | 0 | 0 |
| A | K | N | 0 | 0 | 0 | 0 | 0 | 0 | 1 | 0 | 0 | 0 | 0 | 0 | 0 | 0 | 0 | 0 |
| A | K | Q | 0 | 0 | 0 | 0 | 0 | 0 | 1 | 0 | 0 | 0 | 0 | 0 | 0 | 0 | 0 | 0 |
| A | K | R | 0 | 0 | 0 | 0 | 0 | 0 | 0 | 1 | 0 | 0 | 0 | 0 | 0 | 0 | 0 | 0 |
| A | K | S | 0 | 0 | 0 | 0 | 0 | 0 | 1 | 0 | 0 | 0 | 0 | 0 | 0 | 0 | 0 | 0 |
| A | K | T | 0 | 0 | 0 | 0 | 0 | 0 | 1 | 0 | 0 | 0 | 0 | 0 | 0 | 0 | 0 | 0 |

*Fig. 7.1c*

|   |   |   | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| 44 | 68 | 70 |   |   |   |   |   |   |   |   |   |   |   |   |   |   |   |   |
| A | N | A | 0 | 0 | 0 | 0 | 1 | 0 | 1 | 0 | 0 | 0 | 0 | 0 | 0 | 0 | 0 | 0 |
| A | N | E | 0 | 0 | 0 | 0 | 1 | 0 | 1 | 0 | 0 | 0 | 0 | 0 | 0 | 0 | 0 | 0 |
| A | N | G | 0 | 0 | 0 | 0 | 1 | 0 | 1 | 0 | 0 | 0 | 0 | 0 | 0 | 0 | 0 | 0 |
| A | N | H | 0 | 0 | 0 | 0 | 1 | 0 | 1 | 0 | 0 | 0 | 0 | 0 | 0 | 0 | 0 | 0 |
| A | N | K | 0 | 0 | 0 | 0 | 0 | 0 | 0 | 0 | 0 | 0 | 0 | 0 | 0 | 0 | 0 | 0 |
| A | N | N | 0 | 0 | 0 | 0 | 1 | 0 | 1 | 0 | 0 | 0 | 0 | 0 | 0 | 0 | 0 | 0 |
| A | N | Q | 0 | 0 | 0 | 0 | 1 | 0 | 1 | 0 | 0 | 0 | 0 | 0 | 0 | 0 | 0 | 0 |
| A | N | R | 0 | 0 | 0 | 0 | 0 | 0 | 0 | 1 | 0 | 0 | 0 | 0 | 0 | 0 | 0 | 0 |
| A | N | S | 0 | 0 | 0 | 0 | 0 | 0 | 1 | 0 | 0 | 0 | 0 | 0 | 0 | 0 | 0 | 0 |
| A | N | T | 0 | 0 | 0 | 0 | 0 | 0 | 1 | 0 | 0 | 0 | 0 | 0 | 0 | 0 | 0 | 0 |
| A | Q | A | 0 | 0 | 0 | 0 | 0 | 0 | 1 | 0 | 0 | 0 | 0 | 0 | 0 | 0 | 0 | 0 |
| A | Q | D | 0 | 0 | 0 | 0 | 0 | 0 | 1 | 0 | 0 | 0 | 0 | 0 | 0 | 0 | 0 | 0 |
| A | Q | G | 0 | 0 | 0 | 0 | 0 | 0 | 1 | 0 | 0 | 0 | 0 | 0 | 0 | 0 | 0 | 0 |
| A | Q | H | 0 | 0 | 0 | 0 | 0 | 0 | 1 | 0 | 0 | 0 | 0 | 0 | 0 | 0 | 0 | 0 |
| A | Q | N | 0 | 0 | 0 | 0 | 1 | 0 | 1 | 1 | 0 | 0 | 0 | 0 | 0 | 0 | 0 | 0 |
| A | Q | R | 0 | 0 | 0 | 0 | 0 | 0 | 0 | 1 | 0 | 0 | 0 | 0 | 0 | 0 | 0 | 0 |
| A | Q | S | 0 | 0 | 0 | 0 | 0 | 0 | 1 | 0 | 0 | 0 | 0 | 0 | 0 | 0 | 0 | 0 |
| A | R | A | 0 | 0 | 0 | 0 | 1 | 0 | 1 | 1 | 0 | 0 | 0 | 0 | 0 | 0 | 0 | 0 |
| A | R | D | 0 | 0 | 0 | 0 | 1 | 0 | 1 | 1 | 0 | 0 | 0 | 0 | 0 | 0 | 0 | 0 |
| A | R | E | 0 | 0 | 0 | 0 | 1 | 0 | 1 | 1 | 0 | 0 | 0 | 0 | 0 | 0 | 0 | 0 |
| A | R | G | 0 | 0 | 0 | 0 | 1 | 0 | 1 | 1 | 0 | 0 | 0 | 0 | 0 | 0 | 0 | 0 |
| A | R | H | 0 | 0 | 0 | 0 | 1 | 0 | 1 | 1 | 0 | 0 | 0 | 0 | 0 | 0 | 0 | 0 |
| A | R | K | 0 | 0 | 0 | 0 | 0 | 0 | 1 | 1 | 0 | 0 | 0 | 0 | 0 | 0 | 0 | 0 |
| A | R | L | 0 | 0 | 0 | 0 | 0 | 0 | 1 | 1 | 0 | 0 | 0 | 0 | 0 | 0 | 0 | 0 |
| A | R | N | 0 | 0 | 0 | 0 | 1 | 0 | 1 | 1 | 0 | 0 | 0 | 0 | 0 | 0 | 0 | 0 |
| A | R | R | 0 | 0 | 0 | 0 | 0 | 0 | 1 | 1 | 0 | 0 | 0 | 0 | 0 | 0 | 0 | 0 |
| A | R | S | 0 | 0 | 0 | 0 | 1 | 0 | 1 | 1 | 0 | 0 | 0 | 0 | 0 | 0 | 0 | 0 |
| A | R | T | 0 | 0 | 0 | 0 | 1 | 0 | 1 | 1 | 0 | 0 | 0 | 0 | 0 | 0 | 0 | 0 |
| A | S | A | 0 | 0 | 0 | 0 | 0 | 0 | 1 | 0 | 0 | 0 | 0 | 0 | 0 | 0 | 0 | 0 |
| A | S | G | 0 | 0 | 0 | 0 | 0 | 0 | 1 | 0 | 0 | 0 | 0 | 0 | 0 | 0 | 0 | 0 |
| A | S | K | 0 | 0 | 0 | 0 | 0 | 0 | 1 | 0 | 0 | 0 | 0 | 0 | 0 | 0 | 0 | 0 |
| A | S | N | 0 | 0 | 0 | 0 | 1 | 0 | 1 | 0 | 0 | 0 | 0 | 0 | 0 | 0 | 0 | 0 |
| A | S | Q | 0 | 0 | 0 | 0 | 0 | 0 | 1 | 0 | 0 | 0 | 0 | 0 | 0 | 0 | 0 | 0 |
| A | S | R | 0 | 0 | 0 | 0 | 1 | 0 | 1 | 1 | 0 | 0 | 0 | 0 | 0 | 0 | 0 | 0 |

*Fig. 7.1d*

| 44 | 68 | 70 | AGG | AGA | AGT | AGC | AAG | AAA | AAT | AAC | ATG | ATA | ATT | ATC | ACG | ACA | ACT | ACC |
|----|----|----|-----|-----|-----|-----|-----|-----|-----|-----|-----|-----|-----|-----|-----|-----|-----|-----|
| A | A | A | 0 | 0 | 0 | 0 | 0 | 0 | 0 | 0 | 0 | 0 | 0 | 0 | 0 | 0 | 0 | 0 |
| A | A | G | 0 | 0 | 0 | 0 | 0 | 0 | 0 | 0 | 0 | 0 | 0 | 0 | 0 | 0 | 0 | 0 |
| A | A | H | 0 | 0 | 0 | 0 | 0 | 0 | 0 | 0 | 0 | 0 | 0 | 0 | 0 | 0 | 0 | 0 |
| A | A | K | 0 | 0 | 0 | 0 | 0 | 0 | 0 | 0 | 0 | 0 | 0 | 0 | 0 | 0 | 0 | 0 |
| A | A | N | 0 | 0 | 0 | 0 | 0 | 0 | 0 | 0 | 0 | 0 | 0 | 0 | 0 | 0 | 0 | 0 |
| A | A | Q | 0 | 0 | 0 | 0 | 0 | 0 | 0 | 0 | 0 | 0 | 0 | 0 | 0 | 0 | 0 | 0 |
| A | A | R | 0 | 0 | 0 | 0 | 0 | 0 | 0 | 1 | 0 | 0 | 0 | 0 | 0 | 0 | 0 | 0 |
| A | A | S | 0 | 0 | 0 | 0 | 0 | 0 | 0 | 0 | 0 | 0 | 0 | 0 | 0 | 0 | 0 | 0 |
| A | A | T | 0 | 0 | 0 | 0 | 0 | 0 | 0 | 0 | 0 | 0 | 0 | 0 | 0 | 0 | 0 | 0 |
| A | D | H | 0 | 0 | 0 | 0 | 0 | 0 | 0 | 0 | 0 | 0 | 0 | 0 | 0 | 0 | 0 | 0 |
| A | D | K | 0 | 0 | 0 | 0 | 0 | 0 | 0 | 0 | 0 | 0 | 0 | 0 | 0 | 0 | 0 | 0 |
| A | D | R | 0 | 0 | 0 | 0 | 0 | 0 | 0 | 0 | 0 | 0 | 0 | 0 | 0 | 0 | 0 | 0 |
| A | G | H | 0 | 0 | 0 | 0 | 0 | 0 | 0 | 0 | 0 | 0 | 0 | 0 | 0 | 0 | 0 | 0 |
| A | G | K | 0 | 0 | 0 | 0 | 0 | 0 | 0 | 0 | 0 | 0 | 0 | 0 | 0 | 0 | 0 | 0 |
| A | G | N | 0 | 0 | 0 | 0 | 0 | 0 | 0 | 0 | 0 | 0 | 0 | 0 | 0 | 0 | 0 | 0 |
| A | G | P | 0 | 0 | 0 | 0 | 0 | 0 | 0 | 0 | 0 | 0 | 0 | 0 | 0 | 0 | 0 | 0 |
| A | G | R | 0 | 0 | 0 | 0 | 0 | 0 | 0 | 1 | 0 | 0 | 0 | 0 | 0 | 0 | 0 | 0 |
| A | H | A | 0 | 0 | 0 | 0 | 0 | 0 | 1 | 0 | 0 | 0 | 0 | 0 | 0 | 0 | 0 | 0 |
| A | H | G | 0 | 0 | 0 | 0 | 0 | 0 | 0 | 0 | 0 | 0 | 0 | 0 | 0 | 0 | 0 | 0 |
| A | H | H | 0 | 0 | 0 | 0 | 0 | 0 | 0 | 0 | 0 | 0 | 0 | 0 | 0 | 0 | 0 | 0 |
| A | H | K | 0 | 0 | 0 | 0 | 0 | 0 | 0 | 0 | 0 | 0 | 0 | 0 | 0 | 0 | 0 | 0 |
| A | H | N | 0 | 0 | 0 | 0 | 0 | 0 | 0 | 0 | 0 | 0 | 0 | 0 | 0 | 0 | 0 | 0 |
| A | H | Q | 0 | 0 | 0 | 0 | 0 | 0 | 1 | 0 | 0 | 0 | 0 | 0 | 0 | 0 | 0 | 0 |
| A | H | R | 0 | 0 | 0 | 0 | 0 | 0 | 1 | 0 | 0 | 0 | 0 | 0 | 0 | 0 | 0 | 0 |
| A | H | S | 0 | 0 | 0 | 0 | 0 | 0 | 0 | 0 | 0 | 0 | 0 | 0 | 0 | 0 | 0 | 0 |
| A | H | T | 0 | 0 | 0 | 0 | 0 | 0 | 0 | 0 | 0 | 0 | 0 | 0 | 0 | 0 | 0 | 0 |
| A | K | A | 0 | 0 | 0 | 0 | 0 | 0 | 0 | 0 | 0 | 0 | 0 | 0 | 0 | 0 | 0 | 0 |
| A | K | G | 0 | 0 | 0 | 0 | 0 | 0 | 0 | 0 | 0 | 0 | 0 | 0 | 0 | 0 | 0 | 0 |
| A | K | H | 0 | 0 | 0 | 0 | 0 | 0 | 0 | 0 | 0 | 0 | 0 | 0 | 0 | 0 | 0 | 0 |
| A | K | K | 0 | 0 | 0 | 0 | 0 | 0 | 0 | 0 | 0 | 0 | 0 | 0 | 0 | 0 | 0 | 0 |
| A | K | N | 0 | 0 | 0 | 0 | 0 | 0 | 0 | 0 | 0 | 0 | 0 | 0 | 0 | 0 | 0 | 0 |
| A | K | Q | 0 | 0 | 0 | 0 | 0 | 0 | 0 | 0 | 0 | 0 | 0 | 0 | 0 | 0 | 0 | 0 |
| A | K | R | 0 | 0 | 0 | 0 | 0 | 0 | 0 | 0 | 0 | 0 | 0 | 0 | 0 | 0 | 0 | 0 |
| A | K | S | 0 | 0 | 0 | 0 | 0 | 0 | 0 | 0 | 0 | 0 | 0 | 0 | 0 | 0 | 0 | 0 |
| A | K | T | 0 | 0 | 0 | 0 | 0 | 0 | 0 | 0 | 0 | 0 | 0 | 0 | 0 | 0 | 0 | 0 |

*Fig. 7.1e*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| A | N | A | 0 | 0 | 0 | 0 | 0 | 0 | 0 | 0 | 0 | 0 | 0 | 0 | 0 | 0 | 0 | 0 |
| A | N | E | 0 | 0 | 0 | 0 | 0 | 0 | 0 | 0 | 0 | 0 | 0 | 0 | 0 | 0 | 0 | 0 |
| A | N | G | 0 | 0 | 0 | 0 | 0 | 0 | 0 | 0 | 0 | 0 | 0 | 0 | 0 | 0 | 0 | 0 |
| A | N | H | 0 | 0 | 0 | 0 | 0 | 0 | 0 | 0 | 0 | 0 | 0 | 0 | 0 | 0 | 0 | 0 |
| A | N | K | 0 | 0 | 0 | 0 | 0 | 0 | 0 | 0 | 0 | 0 | 0 | 0 | 0 | 0 | 0 | 0 |
| A | N | N | 0 | 0 | 0 | 0 | 1 | 0 | 0 | 0 | 0 | 0 | 0 | 0 | 0 | 0 | 0 | 0 |
| A | N | Q | 0 | 0 | 0 | 0 | 0 | 0 | 0 | 0 | 0 | 0 | 0 | 0 | 0 | 0 | 0 | 0 |
| A | N | R | 0 | 0 | 0 | 0 | 0 | 0 | 1 | 0 | 0 | 0 | 0 | 0 | 0 | 0 | 0 | 0 |
| A | N | S | 0 | 0 | 0 | 0 | 0 | 0 | 0 | 0 | 0 | 0 | 0 | 0 | 0 | 0 | 0 | 0 |
| A | N | T | 0 | 0 | 0 | 0 | 0 | 0 | 0 | 0 | 0 | 0 | 0 | 0 | 0 | 0 | 0 | 0 |
| A | Q | A | 0 | 0 | 0 | 0 | 0 | 0 | 0 | 0 | 0 | 0 | 0 | 0 | 0 | 0 | 0 | 0 |
| A | Q | D | 0 | 0 | 0 | 0 | 0 | 0 | 0 | 0 | 0 | 0 | 0 | 0 | 0 | 0 | 0 | 0 |
| A | Q | G | 0 | 0 | 0 | 0 | 0 | 0 | 0 | 0 | 0 | 0 | 0 | 0 | 0 | 0 | 0 | 0 |
| A | Q | H | 0 | 0 | 0 | 0 | 0 | 0 | 0 | 0 | 0 | 0 | 0 | 0 | 0 | 0 | 0 | 0 |
| A | Q | N | 0 | 0 | 0 | 0 | 1 | 0 | 0 | 0 | 0 | 0 | 0 | 0 | 0 | 0 | 0 | 0 |
| A | Q | R | 0 | 0 | 0 | 0 | 0 | 0 | 1 | 0 | 0 | 0 | 0 | 0 | 0 | 0 | 0 | 0 |
| A | Q | S | 0 | 0 | 0 | 0 | 0 | 0 | 0 | 0 | 0 | 0 | 0 | 0 | 0 | 0 | 0 | 0 |
| A | R | A | 0 | 0 | 0 | 0 | 1 | 0 | 1 | 1 | 0 | 0 | 0 | 0 | 0 | 0 | 0 | 0 |
| A | R | D | 0 | 0 | 0 | 0 | 1 | 0 | 1 | 1 | 0 | 0 | 0 | 0 | 0 | 0 | 0 | 0 |
| A | R | E | 0 | 0 | 0 | 0 | 0 | 0 | 1 | 1 | 0 | 0 | 0 | 0 | 0 | 0 | 0 | 0 |
| A | R | G | 0 | 0 | 0 | 0 | 1 | 0 | 1 | 1 | 0 | 0 | 0 | 0 | 0 | 0 | 0 | 0 |
| A | R | H | 0 | 0 | 0 | 0 | 0 | 0 | 0 | 1 | 0 | 0 | 0 | 0 | 0 | 0 | 0 | 0 |
| A | R | K | 0 | 0 | 0 | 0 | 0 | 0 | 0 | 0 | 0 | 0 | 0 | 0 | 0 | 0 | 0 | 0 |
| A | R | L | 0 | 0 | 0 | 0 | 0 | 0 | 1 | 0 | 0 | 0 | 0 | 0 | 0 | 0 | 0 | 0 |
| A | R | N | 1 | 0 | 0 | 0 | 1 | 0 | 1 | 1 | 0 | 0 | 0 | 0 | 0 | 0 | 0 | 0 |
| A | R | R | 0 | 0 | 0 | 0 | 0 | 0 | 1 | 1 | 0 | 0 | 0 | 0 | 0 | 0 | 0 | 0 |
| A | R | S | 0 | 0 | 0 | 0 | 1 | 0 | 1 | 1 | 0 | 0 | 0 | 0 | 0 | 0 | 0 | 0 |
| A | R | T | 0 | 0 | 0 | 0 | 0 | 0 | 1 | 1 | 0 | 0 | 0 | 0 | 0 | 0 | 0 | 0 |
| A | S | A | 0 | 0 | 0 | 0 | 0 | 0 | 1 | 0 | 0 | 0 | 0 | 0 | 0 | 0 | 0 | 0 |
| A | S | G | 0 | 0 | 0 | 0 | 0 | 0 | 0 | 0 | 0 | 0 | 0 | 0 | 0 | 0 | 0 | 0 |
| A | S | K | 0 | 0 | 0 | 0 | 0 | 0 | 0 | 0 | 0 | 0 | 0 | 0 | 0 | 0 | 0 | 0 |
| A | S | N | 0 | 0 | 0 | 0 | 0 | 0 | 0 | 0 | 0 | 0 | 0 | 0 | 0 | 0 | 0 | 0 |
| A | S | Q | 0 | 0 | 0 | 0 | 0 | 0 | 0 | 0 | 0 | 0 | 0 | 0 | 0 | 0 | 0 | 0 |
| A | S | R | 0 | 0 | 0 | 0 | 0 | 1 | 0 | 0 | 0 | 0 | 0 | 0 | 0 | 0 | 0 | 0 |

*Fig. 7.1f*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| A | A | A | 0 | 0 | 0 | 0 | 0 | 0 | 0 | 0 | 0 | 0 | 0 | 0 | 0 | 0 | 0 | 0 |
| A | A | G | 0 | 0 | 0 | 0 | 0 | 0 | 0 | 0 | 0 | 0 | 0 | 0 | 0 | 0 | 0 | 0 |
| A | A | H | 0 | 0 | 0 | 0 | 0 | 0 | 0 | 0 | 0 | 0 | 0 | 0 | 0 | 0 | 0 | 0 |
| A | A | K | 0 | 0 | 0 | 0 | 0 | 0 | 0 | 0 | 0 | 0 | 0 | 0 | 0 | 0 | 0 | 0 |
| A | A | N | 0 | 0 | 0 | 0 | 0 | 0 | 0 | 0 | 0 | 0 | 0 | 0 | 0 | 0 | 0 | 0 |
| A | A | Q | 0 | 0 | 0 | 0 | 0 | 0 | 1 | 0 | 0 | 0 | 0 | 0 | 0 | 0 | 0 | 0 |
| A | A | R | 0 | 0 | 0 | 0 | 0 | 0 | 0 | 1 | 0 | 0 | 0 | 0 | 0 | 0 | 0 | 0 |
| A | A | S | 0 | 0 | 0 | 0 | 0 | 0 | 1 | 0 | 0 | 0 | 0 | 0 | 0 | 0 | 0 | 0 |
| A | A | T | 0 | 0 | 0 | 0 | 0 | 0 | 0 | 0 | 0 | 0 | 0 | 0 | 0 | 0 | 0 | 0 |
| A | D | H | 0 | 0 | 0 | 0 | 0 | 0 | 0 | 0 | 0 | 0 | 0 | 0 | 0 | 0 | 0 | 0 |
| A | D | K | 0 | 0 | 0 | 0 | 0 | 0 | 0 | 0 | 0 | 0 | 0 | 0 | 0 | 0 | 0 | 0 |
| A | D | R | 0 | 0 | 0 | 0 | 0 | 0 | 0 | 0 | 0 | 0 | 0 | 0 | 0 | 0 | 0 | 0 |
| A | G | H | 0 | 0 | 0 | 0 | 0 | 0 | 0 | 0 | 0 | 0 | 0 | 0 | 0 | 0 | 0 | 0 |
| A | G | K | 0 | 0 | 0 | 0 | 0 | 0 | 0 | 0 | 0 | 0 | 0 | 0 | 0 | 0 | 0 | 0 |
| A | G | N | 0 | 0 | 0 | 0 | 0 | 0 | 0 | 0 | 0 | 0 | 0 | 0 | 0 | 0 | 0 | 0 |
| A | G | P | 0 | 0 | 0 | 0 | 0 | 0 | 0 | 0 | 0 | 0 | 0 | 0 | 0 | 0 | 0 | 0 |
| A | G | R | 0 | 0 | 0 | 0 | 0 | 0 | 0 | 0 | 0 | 0 | 0 | 0 | 0 | 0 | 0 | 0 |
| A | H | A | 0 | 0 | 0 | 0 | 0 | 0 | 0 | 0 | 0 | 0 | 0 | 0 | 0 | 0 | 0 | 0 |
| A | H | G | 0 | 0 | 0 | 0 | 0 | 0 | 0 | 0 | 0 | 0 | 0 | 0 | 0 | 0 | 0 | 0 |
| A | H | H | 0 | 0 | 0 | 0 | 0 | 0 | 0 | 0 | 0 | 0 | 0 | 0 | 0 | 0 | 0 | 0 |
| A | H | K | 0 | 0 | 0 | 0 | 0 | 0 | 0 | 0 | 0 | 0 | 0 | 0 | 0 | 0 | 0 | 0 |
| A | H | N | 0 | 0 | 0 | 0 | 0 | 0 | 0 | 0 | 0 | 0 | 0 | 0 | 0 | 0 | 0 | 0 |
| A | H | Q | 0 | 0 | 0 | 0 | 0 | 0 | 0 | 0 | 0 | 0 | 0 | 0 | 0 | 0 | 0 | 0 |
| A | H | R | 0 | 0 | 0 | 0 | 0 | 0 | 0 | 0 | 0 | 0 | 0 | 0 | 0 | 0 | 0 | 0 |
| A | H | S | 0 | 0 | 0 | 0 | 0 | 0 | 0 | 0 | 0 | 0 | 0 | 0 | 0 | 0 | 0 | 0 |
| A | H | T | 0 | 0 | 0 | 0 | 0 | 0 | 0 | 0 | 0 | 0 | 0 | 0 | 0 | 0 | 0 | 0 |
| A | K | A | 0 | 0 | 0 | 0 | 0 | 0 | 0 | 0 | 0 | 0 | 0 | 0 | 0 | 0 | 0 | 0 |
| A | K | G | 0 | 0 | 0 | 0 | 0 | 0 | 0 | 0 | 0 | 0 | 0 | 0 | 0 | 0 | 0 | 0 |
| A | K | H | 0 | 0 | 0 | 0 | 0 | 0 | 0 | 0 | 0 | 0 | 0 | 0 | 0 | 0 | 0 | 0 |
| A | K | K | 0 | 0 | 0 | 0 | 0 | 0 | 0 | 0 | 0 | 0 | 0 | 0 | 0 | 0 | 0 | 0 |
| A | K | N | 0 | 0 | 0 | 0 | 0 | 0 | 0 | 0 | 0 | 0 | 0 | 0 | 0 | 0 | 0 | 0 |
| A | K | Q | 0 | 0 | 0 | 0 | 0 | 0 | 0 | 0 | 0 | 0 | 0 | 0 | 0 | 0 | 0 | 0 |
| A | K | R | 0 | 0 | 0 | 0 | 0 | 0 | 0 | 0 | 0 | 0 | 0 | 0 | 0 | 0 | 0 | 0 |
| A | K | S | 0 | 0 | 0 | 0 | 0 | 0 | 0 | 0 | 0 | 0 | 0 | 0 | 0 | 0 | 0 | 0 |
| A | K | T | 0 | 0 | 0 | 0 | 0 | 0 | 0 | 0 | 0 | 0 | 0 | 0 | 0 | 0 | 0 | 0 |

*Fig. 7.1g*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| A | N | A | 0 | 0 | 0 | 0 | 0 | 0 | 0 | 0 | 0 | 0 | 0 | 0 | 0 | 0 | 0 | 0 |
| A | N | E | 0 | 0 | 0 | 0 | 0 | 0 | 0 | 0 | 0 | 0 | 0 | 0 | 0 | 0 | 0 | 0 |
| A | N | G | 0 | 0 | 0 | 0 | 0 | 0 | 0 | 0 | 0 | 0 | 0 | 0 | 0 | 0 | 0 | 0 |
| A | N | H | 0 | 0 | 0 | 0 | 0 | 0 | 0 | 0 | 0 | 0 | 0 | 0 | 0 | 0 | 0 | 0 |
| A | N | K | 0 | 0 | 0 | 0 | 0 | 0 | 0 | 0 | 0 | 0 | 0 | 0 | 0 | 0 | 0 | 0 |
| A | N | N | 0 | 0 | 0 | 0 | 0 | 0 | 0 | 0 | 0 | 0 | 0 | 0 | 0 | 0 | 0 | 0 |
| A | N | Q | 0 | 0 | 0 | 0 | 0 | 0 | 1 | 0 | 0 | 0 | 0 | 0 | 0 | 0 | 0 | 0 |
| A | N | R | 0 | 0 | 0 | 0 | 0 | 0 | 0 | 0 | 0 | 0 | 0 | 0 | 0 | 0 | 0 | 0 |
| A | N | S | 0 | 0 | 0 | 0 | 0 | 0 | 0 | 0 | 0 | 0 | 0 | 0 | 0 | 0 | 0 | 0 |
| A | N | T | 0 | 0 | 0 | 0 | 0 | 0 | 0 | 0 | 0 | 0 | 0 | 0 | 0 | 0 | 0 | 0 |
| A | Q | A | 0 | 0 | 0 | 0 | 0 | 0 | 0 | 0 | 0 | 0 | 0 | 0 | 0 | 0 | 0 | 0 |
| A | Q | D | 0 | 0 | 0 | 0 | 0 | 0 | 0 | 0 | 0 | 0 | 0 | 0 | 0 | 0 | 0 | 0 |
| A | Q | G | 0 | 0 | 0 | 0 | 0 | 0 | 0 | 0 | 0 | 0 | 0 | 0 | 0 | 0 | 0 | 0 |
| A | Q | H | 0 | 0 | 0 | 0 | 0 | 0 | 0 | 0 | 0 | 0 | 0 | 0 | 0 | 0 | 0 | 0 |
| A | Q | N | 0 | 0 | 0 | 0 | 0 | 0 | 0 | 0 | 0 | 0 | 0 | 0 | 0 | 0 | 0 | 0 |
| A | Q | R | 0 | 0 | 0 | 0 | 0 | 0 | 1 | 0 | 0 | 0 | 0 | 0 | 0 | 0 | 0 | 0 |
| A | Q | S | 0 | 0 | 0 | 0 | 0 | 0 | 0 | 0 | 0 | 0 | 0 | 0 | 0 | 0 | 0 | 0 |
| A | R | A | 0 | 0 | 0 | 0 | 1 | 0 | 1 | 1 | 0 | 0 | 0 | 0 | 0 | 0 | 0 | 0 |
| A | R | D | 0 | 0 | 0 | 0 | 1 | 0 | 1 | 1 | 0 | 0 | 0 | 0 | 0 | 0 | 0 | 0 |
| A | R | E | 0 | 0 | 0 | 0 | 1 | 0 | 1 | 1 | 0 | 0 | 0 | 0 | 0 | 0 | 0 | 0 |
| A | R | G | 0 | 0 | 0 | 0 | 1 | 0 | 1 | 1 | 0 | 0 | 0 | 0 | 0 | 0 | 0 | 0 |
| A | R | H | 0 | 0 | 0 | 0 | 0 | 0 | 1 | 0 | 0 | 0 | 0 | 0 | 0 | 0 | 0 | 0 |
| A | R | K | 0 | 0 | 0 | 0 | 0 | 0 | 0 | 0 | 0 | 0 | 0 | 0 | 0 | 0 | 0 | 0 |
| A | R | L | 0 | 0 | 0 | 0 | 0 | 0 | 1 | 0 | 0 | 0 | 0 | 0 | 0 | 0 | 0 | 0 |
| A | R | N | 0 | 0 | 0 | 0 | 1 | 0 | 1 | 1 | 0 | 0 | 0 | 0 | 0 | 0 | 0 | 0 |
| A | R | R | 0 | 0 | 0 | 0 | 0 | 0 | 1 | 1 | 0 | 0 | 0 | 0 | 0 | 0 | 0 | 0 |
| A | R | S | 0 | 0 | 0 | 0 | 1 | 0 | 1 | 1 | 0 | 0 | 0 | 0 | 0 | 0 | 0 | 0 |
| A | R | T | 0 | 0 | 0 | 0 | 0 | 0 | 1 | 0 | 0 | 0 | 0 | 0 | 0 | 0 | 0 | 0 |
| A | S | A | 0 | 0 | 0 | 0 | 0 | 0 | 1 | 0 | 0 | 0 | 0 | 0 | 0 | 0 | 0 | 0 |
| A | S | G | 0 | 0 | 0 | 0 | 0 | 0 | 1 | 0 | 0 | 0 | 0 | 0 | 0 | 0 | 0 | 0 |
| A | S | K | 0 | 0 | 0 | 0 | 0 | 0 | 0 | 0 | 0 | 0 | 0 | 0 | 0 | 0 | 0 | 0 |
| A | S | N | 0 | 0 | 0 | 0 | 0 | 0 | 0 | 0 | 0 | 0 | 0 | 0 | 0 | 0 | 0 | 0 |
| A | S | Q | 0 | 0 | 0 | 0 | 0 | 0 | 0 | 0 | 0 | 0 | 0 | 0 | 0 | 0 | 0 | 0 |
| A | S | R | 0 | 0 | 0 | 0 | 0 | 0 | 1 | 1 | 0 | 0 | 0 | 0 | 0 | 0 | 0 | 0 |

*Fig. 7.1h*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| A | S | S | 0 | 0 | 0 | 0 | 1 | 0 | 1 | 0 | 0 | 0 | 0 | 0 | 0 | 0 | 0 | 0 |
| A | S | T | 0 | 0 | 0 | 0 | 1 | 0 | 1 | 0 | 0 | 0 | 0 | 0 | 0 | 0 | 0 | 0 |
| A | T | A | 0 | 0 | 0 | 0 | 1 | 0 | 1 | 0 | 0 | 0 | 0 | 0 | 0 | 0 | 0 | 0 |
| A | T | G | 0 | 0 | 0 | 0 | 1 | 0 | 1 | 0 | 0 | 0 | 0 | 0 | 0 | 0 | 0 | 0 |
| A | T | H | 0 | 0 | 0 | 0 | 1 | 0 | 1 | 0 | 0 | 0 | 0 | 0 | 0 | 0 | 0 | 0 |
| A | T | K | 0 | 0 | 0 | 0 | 1 | 0 | 1 | 1 | 0 | 0 | 0 | 0 | 0 | 0 | 0 | 0 |
| A | T | N | 0 | 0 | 0 | 0 | 1 | 0 | 1 | 0 | 0 | 0 | 0 | 0 | 0 | 0 | 0 | 0 |
| A | T | Q | 0 | 0 | 0 | 0 | 0 | 0 | 1 | 0 | 0 | 0 | 0 | 0 | 0 | 0 | 0 | 0 |
| A | T | R | 0 | 0 | 0 | 0 | 1 | 0 | 1 | 1 | 0 | 0 | 0 | 0 | 0 | 0 | 0 | 0 |
| A | T | S | 0 | 0 | 0 | 0 | 1 | 0 | 1 | 0 | 0 | 0 | 0 | 0 | 0 | 0 | 0 | 0 |
| A | T | T | 0 | 0 | 0 | 0 | 0 | 0 | 1 | 0 | 0 | 0 | 0 | 0 | 0 | 0 | 0 | 0 |
| D | D | H | 0 | 0 | 0 | 0 | 1 | 0 | 1 | 1 | 0 | 0 | 0 | 0 | 0 | 0 | 0 | 0 |
| D | N | S | 0 | 0 | 0 | 0 | 1 | 0 | 1 | 0 | 0 | 0 | 0 | 0 | 0 | 0 | 0 | 0 |
| D | R | A | 0 | 0 | 0 | 0 | 0 | 0 | 1 | 0 | 0 | 0 | 0 | 0 | 0 | 0 | 0 | 0 |
| D | R | K | 1 | 0 | 0 | 0 | 0 | 0 | 0 | 0 | 0 | 0 | 0 | 0 | 0 | 0 | 0 | 0 |
| D | R | N | 1 | 0 | 0 | 0 | 1 | 0 | 1 | 1 | 0 | 0 | 0 | 1 | 0 | 0 | 0 | 0 |
| D | R | Q | 0 | 0 | 0 | 0 | 1 | 0 | 1 | 1 | 0 | 0 | 0 | 0 | 0 | 0 | 0 | 0 |
| D | R | R | 0 | 0 | 0 | 0 | 0 | 0 | 0 | 1 | 0 | 0 | 0 | 0 | 0 | 0 | 0 | 0 |
| D | R | S | 0 | 0 | 0 | 0 | 1 | 0 | 1 | 1 | 0 | 0 | 0 | 0 | 0 | 0 | 0 | 0 |
| D | R | T | 0 | 0 | 0 | 0 | 0 | 0 | 1 | 0 | 0 | 0 | 0 | 0 | 0 | 0 | 0 | 0 |
| E | H | H | 0 | 0 | 0 | 0 | 0 | 0 | 1 | 0 | 0 | 0 | 0 | 0 | 0 | 0 | 0 | 0 |
| E | R | A | 0 | 0 | 0 | 0 | 1 | 0 | 1 | 1 | 1 | 1 | 1 | 0 | 0 | 1 | 0 | 0 |
| E | R | H | 1 | 0 | 0 | 0 | 0 | 0 | 0 | 1 | 0 | 0 | 0 | 0 | 0 | 0 | 0 | 0 |
| E | R | N | 0 | 0 | 0 | 0 | 1 | 0 | 1 | 1 | 1 | 0 | 1 | 1 | 0 | 0 | 1 | 1 |
| E | R | S | 0 | 0 | 0 | 0 | 1 | 0 | 1 | 0 | 1 | 0 | 1 | 1 | 0 | 0 | 1 | 1 |
| E | R | T | 0 | 0 | 0 | 0 | 0 | 0 | 1 | 1 | 0 | 1 | 1 | 1 | 0 | 0 | 1 | 1 |
| E | S | T | 0 | 0 | 0 | 0 | 0 | 0 | 0 | 0 | 0 | 0 | 0 | 0 | 0 | 0 | 1 | 1 |
| G | H | K | 0 | 0 | 0 | 0 | 1 | 0 | 1 | 0 | 0 | 0 | 0 | 0 | 0 | 0 | 0 | 0 |
| G | Q | H | 0 | 0 | 0 | 0 | 1 | 0 | 1 | 0 | 0 | 0 | 0 | 0 | 0 | 0 | 0 | 0 |
| G | R | Q | 0 | 0 | 0 | 0 | 0 | 0 | 1 | 0 | 0 | 0 | 0 | 0 | 0 | 0 | 0 | 0 |
| G | R | R | 0 | 0 | 0 | 0 | 0 | 0 | 0 | 1 | 0 | 0 | 0 | 1 | 0 | 0 | 0 | 0 |
| G | T | D | 0 | 0 | 0 | 0 | 0 | 0 | 0 | 1 | 0 | 0 | 0 | 0 | 0 | 0 | 0 | 0 |
| G | T | P | 0 | 0 | 0 | 0 | 0 | 0 | 1 | 0 | 1 | 0 | 0 | 0 | 0 | 0 | 1 | 1 |
| G | T | R | 0 | 0 | 0 | 0 | 0 | 0 | 1 | 0 | 0 | 0 | 0 | 0 | 0 | 0 | 0 | 0 |
| H | A | S | 0 | 0 | 0 | 0 | 0 | 0 | 0 | 0 | 0 | 0 | 0 | 1 | 0 | 0 | 0 | 0 |
| H | A | T | 0 | 0 | 0 | 0 | 0 | 0 | 0 | 0 | 0 | 0 | 0 | 0 | 0 | 0 | 0 | 0 |

*Fig. 7.2a*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| H | R | A | 0 | 0 | 0 | 0 | 0 | 0 | 1 | 1 | 0 | 0 | 0 | 0 | 0 | 0 | 0 | 0 |
| H | R | D | 0 | 0 | 0 | 0 | 0 | 0 | 0 | 0 | 0 | 0 | 0 | 0 | 0 | 0 | 0 | 0 |
| H | R | E | 0 | 0 | 0 | 0 | 0 | 0 | 1 | 0 | 0 | 0 | 0 | 0 | 0 | 0 | 0 | 0 |
| H | R | G | 0 | 0 | 0 | 0 | 1 | 0 | 1 | 1 | 0 | 0 | 0 | 0 | 0 | 0 | 1 | 1 |
| H | R | N | 0 | 0 | 0 | 0 | 1 | 0 | 1 | 1 | 0 | 0 | 0 | 0 | 0 | 0 | 0 | 0 |
| H | R | R | 0 | 0 | 0 | 0 | 0 | 0 | 1 | 1 | 0 | 0 | 0 | 1 | 0 | 0 | 0 | 0 |
| H | R | S | 0 | 0 | 0 | 0 | 1 | 0 | 1 | 1 | 0 | 0 | 0 | 1 | 0 | 0 | 0 | 0 |
| H | R | T | 0 | 0 | 0 | 0 | 1 | 0 | 1 | 1 | 0 | 0 | 0 | 0 | 0 | 0 | 0 | 0 |
| H | S | G | 0 | 0 | 0 | 0 | 0 | 0 | 0 | 0 | 0 | 0 | 0 | 0 | 0 | 0 | 0 | 0 |
| H | S | S | 0 | 0 | 0 | 0 | 0 | 0 | 0 | 0 | 1 | 0 | 1 | 1 | 0 | 0 | 1 | 0 |
| H | S | T | 0 | 0 | 0 | 0 | 0 | 0 | 0 | 0 | 0 | 0 | 0 | 0 | 0 | 0 | 0 | 0 |
| H | T | S | 0 | 0 | 0 | 0 | 0 | 0 | 0 | 0 | 1 | 0 | 1 | 1 | 0 | 0 | 1 | 1 |
| H | T | T | 0 | 0 | 0 | 0 | 0 | 0 | 0 | 0 | 0 | 0 | 0 | 0 | 0 | 0 | 0 | 0 |
| K | A | A | 0 | 0 | 0 | 0 | 0 | 0 | 0 | 0 | 0 | 0 | 0 | 0 | 0 | 0 | 1 | 1 |
| K | A | D | 0 | 0 | 0 | 0 | 0 | 0 | 0 | 0 | 0 | 0 | 0 | 0 | 0 | 0 | 1 | 1 |
| K | A | E | 0 | 0 | 0 | 0 | 0 | 0 | 0 | 0 | 0 | 0 | 0 | 0 | 0 | 0 | 0 | 0 |
| K | A | G | 0 | 0 | 0 | 0 | 0 | 0 | 0 | 0 | 0 | 0 | 0 | 0 | 0 | 0 | 1 | 1 |
| K | A | H | 0 | 0 | 0 | 0 | 0 | 0 | 0 | 0 | 0 | 0 | 0 | 0 | 0 | 0 | 0 | 0 |
| K | A | N | 0 | 0 | 0 | 0 | 0 | 0 | 0 | 0 | 0 | 0 | 0 | 0 | 0 | 0 | 1 | 1 |
| K | A | Q | 0 | 0 | 0 | 0 | 0 | 0 | 0 | 0 | 0 | 0 | 0 | 0 | 0 | 0 | 1 | 1 |
| K | A | S | 0 | 0 | 0 | 0 | 0 | 0 | 0 | 0 | 0 | 0 | 0 | 0 | 0 | 0 | 1 | 1 |
| K | A | T | 0 | 0 | 0 | 0 | 0 | 0 | 1 | 0 | 0 | 0 | 0 | 0 | 0 | 0 | 0 | 0 |
| K | D | A | 0 | 0 | 0 | 0 | 0 | 0 | 0 | 0 | 0 | 0 | 0 | 0 | 0 | 0 | 0 | 0 |
| K | D | T | 0 | 0 | 0 | 0 | 0 | 0 | 0 | 0 | 0 | 0 | 0 | 0 | 0 | 0 | 0 | 0 |
| K | E | G | 0 | 0 | 0 | 0 | 0 | 0 | 0 | 0 | 0 | 0 | 0 | 0 | 0 | 0 | 1 | 1 |
| K | E | N | 0 | 0 | 0 | 0 | 0 | 0 | 0 | 0 | 0 | 0 | 0 | 0 | 0 | 0 | 1 | 0 |
| K | E | S | 0 | 0 | 0 | 0 | 0 | 0 | 0 | 0 | 0 | 0 | 0 | 0 | 0 | 0 | 1 | 0 |
| K | G | A | 0 | 0 | 0 | 0 | 0 | 0 | 0 | 0 | 0 | 0 | 0 | 0 | 0 | 0 | 1 | 0 |
| K | G | G | 0 | 0 | 0 | 0 | 0 | 0 | 0 | 0 | 0 | 0 | 0 | 0 | 0 | 0 | 1 | 1 |
| K | G | N | 0 | 0 | 0 | 0 | 0 | 0 | 0 | 0 | 0 | 0 | 0 | 0 | 0 | 0 | 1 | 1 |
| K | G | S | 0 | 0 | 0 | 0 | 0 | 0 | 0 | 0 | 0 | 0 | 0 | 0 | 0 | 0 | 1 | 1 |
| K | G | T | 0 | 0 | 0 | 0 | 0 | 0 | 0 | 0 | 0 | 0 | 0 | 0 | 0 | 0 | 1 | 0 |
| K | H | D | 0 | 0 | 0 | 0 | 0 | 0 | 0 | 0 | 0 | 0 | 0 | 0 | 0 | 0 | 0 | 1 |
| K | H | E | 0 | 0 | 0 | 0 | 0 | 0 | 0 | 0 | 0 | 0 | 0 | 0 | 0 | 0 | 0 | 0 |
| K | H | G | 0 | 0 | 0 | 0 | 0 | 0 | 0 | 0 | 0 | 0 | 0 | 0 | 0 | 0 | 1 | 0 |
| K | H | N | 0 | 0 | 0 | 0 | 0 | 0 | 0 | 0 | 0 | 0 | 0 | 0 | 0 | 0 | 0 | 0 |

*Fig. 7.2b*

|   |   |   | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
|   |   |   | 44 | 68 | 70 |   |   |   |   |   |   |   |   |   |   |   |   |   |
| A | S | S | 0 | 0 | 0 | 0 | 1 | 0 | 1 | 0 | 0 | 0 | 0 | 0 | 0 | 0 | 0 | 0 |
| A | S | T | 0 | 0 | 0 | 0 | 0 | 0 | 1 | 0 | 0 | 0 | 0 | 0 | 0 | 0 | 0 | 0 |
| A | T | A | 0 | 0 | 0 | 0 | 1 | 0 | 1 | 0 | 0 | 0 | 0 | 0 | 0 | 0 | 0 | 0 |
| A | T | G | 0 | 0 | 0 | 0 | 0 | 0 | 1 | 0 | 0 | 0 | 0 | 0 | 0 | 0 | 0 | 0 |
| A | T | H | 0 | 0 | 0 | 0 | 0 | 0 | 1 | 0 | 0 | 0 | 0 | 0 | 0 | 0 | 0 | 0 |
| A | T | K | 0 | 0 | 0 | 0 | 0 | 0 | 0 | 0 | 0 | 0 | 0 | 0 | 0 | 0 | 0 | 0 |
| A | T | N | 0 | 0 | 0 | 0 | 1 | 0 | 1 | 0 | 0 | 0 | 0 | 0 | 0 | 0 | 0 | 0 |
| A | T | Q | 0 | 0 | 0 | 0 | 0 | 0 | 1 | 0 | 0 | 0 | 0 | 0 | 0 | 0 | 0 | 0 |
| A | T | R | 0 | 0 | 0 | 0 | 0 | 0 | 1 | 1 | 0 | 0 | 0 | 0 | 0 | 0 | 0 | 0 |
| A | T | S | 0 | 0 | 0 | 0 | 1 | 0 | 1 | 0 | 0 | 0 | 0 | 0 | 0 | 0 | 0 | 0 |
| A | T | T | 0 | 0 | 0 | 0 | 0 | 0 | 1 | 0 | 0 | 0 | 0 | 0 | 0 | 0 | 0 | 0 |
| D | D | H | 0 | 0 | 0 | 0 | 1 | 0 | 1 | 1 | 0 | 0 | 0 | 0 | 0 | 0 | 0 | 0 |
| D | N | S | 0 | 0 | 0 | 0 | 0 | 0 | 1 | 0 | 0 | 0 | 0 | 0 | 0 | 0 | 0 | 0 |
| D | R | A | 0 | 0 | 0 | 0 | 0 | 0 | 0 | 0 | 0 | 0 | 0 | 0 | 0 | 0 | 0 | 0 |
| D | R | K | 0 | 0 | 0 | 0 | 0 | 0 | 0 | 0 | 0 | 0 | 0 | 0 | 0 | 0 | 0 | 0 |
| D | R | N | 0 | 0 | 0 | 0 | 1 | 0 | 1 | 1 | 0 | 0 | 0 | 0 | 0 | 0 | 0 | 0 |
| D | R | Q | 0 | 0 | 0 | 0 | 0 | 0 | 1 | 0 | 0 | 0 | 0 | 0 | 0 | 0 | 0 | 0 |
| D | R | R | 0 | 0 | 0 | 0 | 0 | 0 | 0 | 0 | 0 | 0 | 0 | 0 | 0 | 0 | 0 | 0 |
| D | R | S | 0 | 0 | 0 | 0 | 0 | 0 | 1 | 0 | 0 | 0 | 0 | 0 | 0 | 0 | 0 | 0 |
| D | R | T | 0 | 0 | 0 | 0 | 0 | 0 | 0 | 0 | 0 | 0 | 0 | 0 | 0 | 0 | 0 | 0 |
| E | H | H | 0 | 0 | 0 | 0 | 1 | 0 | 1 | 0 | 0 | 0 | 0 | 0 | 0 | 0 | 0 | 0 |
| E | R | A | 0 | 0 | 0 | 0 | 0 | 0 | 0 | 0 | 0 | 0 | 0 | 0 | 0 | 0 | 0 | 0 |
| E | R | H | 0 | 0 | 0 | 0 | 0 | 0 | 0 | 0 | 0 | 0 | 0 | 0 | 0 | 0 | 0 | 0 |
| E | R | N | 0 | 0 | 0 | 0 | 0 | 0 | 0 | 0 | 0 | 0 | 0 | 0 | 0 | 0 | 0 | 0 |
| E | R | S | 0 | 0 | 0 | 0 | 0 | 0 | 0 | 0 | 0 | 0 | 1 | 0 | 0 | 0 | 1 | 0 |
| E | R | T | 0 | 0 | 0 | 0 | 0 | 0 | 0 | 0 | 0 | 0 | 1 | 0 | 0 | 0 | 0 | 0 |
| E | S | T | 0 | 0 | 0 | 0 | 0 | 0 | 0 | 0 | 0 | 0 | 1 | 0 | 0 | 0 | 1 | 1 |
| G | H | K | 0 | 0 | 0 | 0 | 0 | 0 | 1 | 1 | 0 | 0 | 0 | 0 | 0 | 0 | 0 | 0 |
| G | Q | H | 0 | 0 | 0 | 0 | 0 | 0 | 1 | 0 | 0 | 0 | 0 | 0 | 0 | 0 | 0 | 0 |
| G | R | Q | 0 | 0 | 0 | 0 | 0 | 0 | 0 | 0 | 0 | 0 | 0 | 0 | 0 | 0 | 0 | 0 |
| G | R | R | 0 | 0 | 0 | 0 | 0 | 0 | 0 | 0 | 0 | 0 | 0 | 0 | 0 | 0 | 0 | 0 |
| G | T | D | 0 | 0 | 0 | 0 | 0 | 0 | 1 | 0 | 0 | 0 | 0 | 0 | 0 | 0 | 0 | 0 |
| G | T | P | 0 | 0 | 0 | 0 | 1 | 0 | 0 | 0 | 1 | 0 | 0 | 0 | 0 | 1 | 0 | 0 |
| G | T | R | 0 | 0 | 0 | 0 | 0 | 0 | 0 | 0 | 0 | 0 | 0 | 0 | 0 | 0 | 0 | 0 |
| H | A | S | 0 | 0 | 0 | 0 | 0 | 0 | 0 | 0 | 0 | 0 | 0 | 0 | 0 | 0 | 0 | 0 |
| H | A | T | 0 | 0 | 0 | 0 | 0 | 0 | 0 | 0 | 0 | 0 | 0 | 0 | 0 | 0 | 0 | 0 |

*Fig. 7.2c*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| H | R | A | 0 | 0 | 0 | 0 | 0 | 0 | 0 | 0 | 0 | 0 | 0 | 0 | 0 | 0 | 0 | 0 |
| H | R | D | 0 | 0 | 0 | 0 | 0 | 0 | 0 | 0 | 0 | 0 | 0 | 0 | 0 | 0 | 0 | 0 |
| H | R | E | 0 | 0 | 0 | 0 | 0 | 0 | 0 | 0 | 0 | 0 | 0 | 0 | 0 | 0 | 0 | 0 |
| H | R | G | 0 | 0 | 0 | 0 | 0 | 0 | 0 | 0 | 0 | 0 | 0 | 0 | 0 | 0 | 0 | 0 |
| H | R | N | 0 | 0 | 0 | 0 | 0 | 0 | 0 | 0 | 0 | 0 | 0 | 0 | 0 | 0 | 0 | 0 |
| H | R | R | 0 | 0 | 0 | 0 | 0 | 0 | 0 | 0 | 0 | 0 | 0 | 0 | 0 | 0 | 0 | 0 |
| H | R | S | 0 | 0 | 0 | 0 | 0 | 0 | 0 | 0 | 0 | 0 | 0 | 0 | 0 | 0 | 0 | 0 |
| H | R | T | 0 | 0 | 0 | 0 | 0 | 0 | 0 | 0 | 0 | 0 | 0 | 0 | 0 | 0 | 0 | 0 |
| H | S | G | 0 | 0 | 0 | 0 | 0 | 0 | 0 | 0 | 0 | 0 | 0 | 0 | 0 | 0 | 0 | 0 |
| H | S | S | 0 | 0 | 0 | 0 | 0 | 0 | 0 | 0 | 0 | 1 | 0 | 0 | 0 | 0 | 0 | 0 |
| H | S | T | 0 | 0 | 0 | 0 | 0 | 0 | 0 | 0 | 0 | 0 | 0 | 0 | 0 | 0 | 0 | 0 |
| H | T | S | 0 | 0 | 0 | 0 | 0 | 0 | 0 | 0 | 0 | 1 | 0 | 0 | 1 | 0 | 0 | 0 |
| H | T | T | 0 | 0 | 0 | 0 | 0 | 0 | 0 | 0 | 0 | 0 | 0 | 0 | 0 | 0 | 0 | 0 |
| K | A | A | 0 | 0 | 0 | 0 | 0 | 0 | 0 | 0 | 0 | 1 | 1 | 0 | 0 | 1 | 1 | 1 |
| K | A | D | 0 | 0 | 0 | 0 | 0 | 0 | 0 | 0 | 0 | 0 | 0 | 1 | 0 | 1 | 1 | 1 |
| K | A | E | 0 | 0 | 0 | 0 | 0 | 0 | 0 | 0 | 0 | 0 | 0 | 1 | 0 | 1 | 1 | 1 |
| K | A | G | 0 | 0 | 0 | 0 | 0 | 0 | 0 | 0 | 0 | 1 | 1 | 0 | 0 | 1 | 1 | 1 |
| K | A | H | 0 | 0 | 0 | 0 | 0 | 0 | 0 | 0 | 0 | 0 | 1 | 0 | 0 | 1 | 1 | 1 |
| K | A | N | 0 | 0 | 0 | 0 | 0 | 0 | 0 | 0 | 0 | 0 | 1 | 0 | 0 | 1 | 1 | 1 |
| K | A | Q | 0 | 0 | 0 | 0 | 0 | 0 | 0 | 0 | 0 | 0 | 1 | 0 | 0 | 1 | 1 | 1 |
| K | A | S | 0 | 0 | 0 | 0 | 0 | 0 | 0 | 0 | 0 | 1 | 1 | 0 | 0 | 1 | 1 | 1 |
| K | A | T | 0 | 0 | 0 | 0 | 0 | 0 | 0 | 0 | 0 | 0 | 1 | 0 | 0 | 1 | 1 | 1 |
| K | D | A | 0 | 0 | 0 | 0 | 0 | 0 | 0 | 0 | 0 | 0 | 0 | 0 | 0 | 1 | 1 | 0 |
| K | D | T | 0 | 0 | 0 | 0 | 0 | 0 | 0 | 0 | 0 | 0 | 0 | 0 | 0 | 1 | 1 | 0 |
| K | E | G | 0 | 0 | 0 | 0 | 0 | 0 | 0 | 0 | 0 | 0 | 0 | 0 | 0 | 1 | 1 | 1 |
| K | E | N | 0 | 0 | 0 | 0 | 0 | 0 | 0 | 0 | 0 | 0 | 0 | 0 | 0 | 0 | 0 | 0 |
| K | E | S | 0 | 0 | 0 | 0 | 0 | 0 | 0 | 0 | 0 | 0 | 0 | 0 | 0 | 1 | 1 | 0 |
| K | G | A | 0 | 0 | 0 | 0 | 0 | 0 | 0 | 0 | 0 | 1 | 1 | 0 | 0 | 1 | 1 | 1 |
| K | G | G | 0 | 0 | 0 | 0 | 0 | 0 | 0 | 0 | 0 | 0 | 0 | 0 | 0 | 1 | 1 | 1 |
| K | G | N | 0 | 0 | 0 | 0 | 0 | 0 | 0 | 0 | 0 | 0 | 0 | 0 | 0 | 1 | 1 | 1 |
| K | G | S | 0 | 0 | 0 | 0 | 0 | 0 | 0 | 0 | 0 | 1 | 1 | 1 | 0 | 1 | 1 | 1 |
| K | G | T | 0 | 0 | 0 | 0 | 0 | 0 | 0 | 0 | 0 | 1 | 1 | 0 | 0 | 1 | 1 | 1 |
| K | H | D | 0 | 0 | 0 | 0 | 0 | 0 | 0 | 0 | 0 | 0 | 0 | 1 | 0 | 1 | 1 | 1 |
| K | H | E | 0 | 0 | 0 | 0 | 0 | 0 | 0 | 0 | 0 | 0 | 0 | 1 | 0 | 1 | 1 | 1 |
| K | H | G | 0 | 0 | 0 | 0 | 0 | 0 | 0 | 0 | 0 | 1 | 1 | 0 | 0 | 1 | 1 | 1 |
| K | H | N | 0 | 0 | 0 | 0 | 0 | 0 | 0 | 0 | 0 | 0 | 0 | 0 | 0 | 0 | 1 | 1 |

*Fig. 7.2d*

| | 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|---|
| | A | S | S | 0 | 0 | 0 | 0 | 0 | 0 | 0 | 0 | 0 | 0 | 0 | 0 | 0 | 0 | 0 | 0 |
| | A | S | T | 0 | 0 | 0 | 0 | 0 | 0 | 0 | 0 | 0 | 0 | 0 | 0 | 0 | 0 | 0 | 0 |
| | A | T | A | 0 | 0 | 0 | 0 | 0 | 0 | 0 | 0 | 0 | 0 | 0 | 0 | 0 | 0 | 0 | 0 |
| | A | T | G | 0 | 0 | 0 | 0 | 0 | 0 | 0 | 0 | 0 | 0 | 0 | 0 | 0 | 0 | 0 | 0 |
| | A | T | H | 0 | 0 | 0 | 0 | 0 | 0 | 0 | 0 | 0 | 0 | 0 | 0 | 0 | 0 | 0 | 0 |
| | A | T | K | 0 | 0 | 0 | 0 | 0 | 0 | 0 | 0 | 0 | 0 | 0 | 0 | 0 | 0 | 0 | 0 |
| | A | T | N | 0 | 0 | 0 | 0 | 0 | 0 | 0 | 0 | 0 | 0 | 0 | 0 | 0 | 0 | 0 | 0 |
| | A | T | Q | 0 | 0 | 0 | 0 | 0 | 0 | 0 | 0 | 0 | 0 | 0 | 0 | 0 | 0 | 0 | 0 |
| | A | T | R | 0 | 0 | 0 | 0 | 0 | 0 | 0 | 0 | 0 | 0 | 0 | 0 | 0 | 0 | 0 | 0 |
| | A | T | S | 0 | 0 | 0 | 0 | 0 | 0 | 0 | 0 | 0 | 0 | 0 | 0 | 0 | 0 | 0 | 0 |
| | A | T | T | 0 | 0 | 0 | 0 | 0 | 0 | 0 | 0 | 0 | 0 | 0 | 0 | 0 | 0 | 0 | 0 |
| | D | D | H | 0 | 0 | 0 | 0 | 0 | 0 | 0 | 0 | 0 | 0 | 0 | 0 | 0 | 0 | 0 | 0 |
| | D | N | S | 0 | 0 | 0 | 0 | 0 | 0 | 0 | 0 | 0 | 0 | 0 | 0 | 0 | 0 | 0 | 0 |
| | D | R | A | 0 | 0 | 0 | 0 | 0 | 0 | 0 | 0 | 0 | 0 | 0 | 0 | 0 | 0 | 0 | 0 |
| | D | R | K | 0 | 0 | 0 | 0 | 0 | 0 | 0 | 0 | 0 | 0 | 0 | 0 | 0 | 0 | 0 | 0 |
| | D | R | N | 0 | 0 | 0 | 0 | 0 | 0 | 0 | 0 | 0 | 0 | 0 | 0 | 0 | 0 | 0 | 0 |
| | D | R | Q | 0 | 0 | 0 | 0 | 0 | 0 | 0 | 0 | 0 | 0 | 0 | 0 | 0 | 0 | 0 | 0 |
| | D | R | R | 0 | 0 | 0 | 0 | 0 | 0 | 0 | 0 | 0 | 0 | 0 | 0 | 0 | 0 | 0 | 0 |
| | D | R | S | 0 | 0 | 0 | 0 | 0 | 0 | 0 | 0 | 0 | 0 | 0 | 0 | 0 | 0 | 0 | 0 |
| | D | R | T | 0 | 0 | 0 | 0 | 0 | 0 | 0 | 0 | 0 | 0 | 0 | 0 | 0 | 0 | 0 | 0 |
| | E | H | H | 0 | 0 | 0 | 0 | 0 | 0 | 0 | 0 | 0 | 0 | 0 | 0 | 0 | 0 | 0 | 0 |
| | E | R | A | 0 | 0 | 0 | 0 | 0 | 0 | 0 | 0 | 0 | 0 | 0 | 0 | 0 | 0 | 0 | 0 |
| | E | R | H | 0 | 0 | 0 | 0 | 0 | 0 | 0 | 0 | 0 | 0 | 0 | 0 | 0 | 0 | 0 | 0 |
| | E | R | N | 0 | 0 | 0 | 0 | 0 | 0 | 0 | 0 | 0 | 0 | 0 | 0 | 0 | 0 | 0 | 0 |
| | E | R | S | 0 | 0 | 0 | 0 | 0 | 0 | 0 | 0 | 0 | 0 | 0 | 0 | 0 | 0 | 0 | 0 |
| | E | R | T | 0 | 0 | 0 | 0 | 0 | 0 | 0 | 0 | 0 | 0 | 0 | 0 | 0 | 0 | 0 | 0 |
| | E | S | T | 0 | 0 | 0 | 0 | 0 | 0 | 0 | 0 | 0 | 0 | 0 | 0 | 0 | 0 | 0 | 0 |
| | G | H | K | 0 | 0 | 0 | 0 | 0 | 0 | 0 | 0 | 0 | 0 | 0 | 0 | 0 | 0 | 0 | 0 |
| | G | Q | H | 0 | 0 | 0 | 0 | 0 | 0 | 0 | 0 | 0 | 0 | 0 | 0 | 0 | 0 | 0 | 0 |
| | G | R | Q | 0 | 0 | 0 | 0 | 0 | 0 | 0 | 0 | 0 | 0 | 0 | 0 | 0 | 0 | 0 | 0 |
| | G | R | R | 0 | 0 | 0 | 0 | 0 | 0 | 0 | 0 | 0 | 0 | 0 | 0 | 0 | 0 | 0 | 0 |
| | G | T | D | 0 | 0 | 0 | 0 | 0 | 0 | 0 | 0 | 0 | 0 | 0 | 0 | 0 | 0 | 0 | 0 |
| | G | T | P | 0 | 0 | 0 | 0 | 0 | 0 | 0 | 0 | 0 | 0 | 0 | 0 | 0 | 0 | 0 | 0 |
| | G | T | R | 0 | 0 | 0 | 0 | 0 | 0 | 0 | 0 | 0 | 0 | 0 | 0 | 0 | 0 | 0 | 0 |
| | H | A | S | 0 | 0 | 0 | 0 | 0 | 0 | 0 | 0 | 0 | 0 | 0 | 0 | 0 | 0 | 1 | 0 |
| | H | A | T | 0 | 0 | 0 | 0 | 0 | 0 | 0 | 0 | 0 | 0 | 0 | 0 | 0 | 0 | 1 | 0 |

*Fig. 7.2e*

| | | | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| 44 | 68 | 70 | | | | | | | | | | | | | | | | |
| H | R | A | 0 | 0 | 0 | 0 | 0 | 0 | 0 | 0 | 0 | 0 | 0 | 0 | 0 | 0 | 0 | 0 |
| H | R | D | 0 | 0 | 0 | 0 | 0 | 0 | 0 | 0 | 0 | 0 | 0 | 0 | 0 | 0 | 1 | 0 |
| H | R | E | 0 | 0 | 0 | 0 | 0 | 0 | 0 | 0 | 0 | 0 | 0 | 0 | 0 | 1 | 1 | 1 |
| H | R | G | 0 | 0 | 0 | 0 | 0 | 0 | 0 | 0 | 0 | 0 | 0 | 0 | 0 | 1 | 1 | 1 |
| H | R | N | 0 | 0 | 0 | 0 | 0 | 0 | 0 | 0 | 0 | 0 | 0 | 0 | 0 | 0 | 0 | 0 |
| H | R | R | 0 | 0 | 0 | 0 | 0 | 0 | 0 | 0 | 0 | 0 | 0 | 0 | 0 | 0 | 0 | 0 |
| H | R | S | 0 | 0 | 0 | 0 | 0 | 0 | 0 | 0 | 0 | 1 | 0 | 0 | 0 | 1 | 1 | 1 |
| H | R | T | 0 | 0 | 0 | 0 | 0 | 0 | 0 | 0 | 0 | 0 | 0 | 0 | 0 | 0 | 0 | 0 |
| H | S | G | 0 | 0 | 0 | 0 | 0 | 0 | 0 | 0 | 0 | 0 | 0 | 0 | 0 | 0 | 1 | 0 |
| H | S | S | 0 | 0 | 0 | 0 | 0 | 0 | 0 | 0 | 0 | 0 | 0 | 0 | 0 | 0 | 0 | 0 |
| H | S | T | 0 | 0 | 0 | 0 | 0 | 0 | 0 | 0 | 0 | 0 | 0 | 0 | 0 | 0 | 1 | 0 |
| H | T | S | 0 | 0 | 0 | 0 | 0 | 0 | 0 | 0 | 0 | 1 | 0 | 0 | 0 | 0 | 1 | 0 |
| H | T | T | 0 | 0 | 0 | 0 | 0 | 0 | 0 | 0 | 0 | 0 | 0 | 0 | 0 | 0 | 0 | 0 |
| K | A | A | 0 | 0 | 0 | 0 | 0 | 0 | 0 | 0 | 0 | 0 | 0 | 0 | 0 | 0 | 1 | 1 |
| K | A | D | 0 | 0 | 0 | 0 | 0 | 0 | 0 | 0 | 0 | 0 | 0 | 0 | 0 | 0 | 0 | 0 |
| K | A | E | 0 | 0 | 0 | 0 | 0 | 0 | 0 | 0 | 0 | 0 | 0 | 0 | 0 | 0 | 0 | 0 |
| K | A | G | 0 | 0 | 0 | 0 | 0 | 0 | 0 | 0 | 0 | 0 | 0 | 0 | 0 | 0 | 1 | 1 |
| K | A | H | 0 | 0 | 0 | 0 | 0 | 0 | 0 | 0 | 0 | 0 | 0 | 0 | 0 | 0 | 0 | 0 |
| K | A | N | 0 | 0 | 0 | 0 | 0 | 0 | 0 | 0 | 0 | 0 | 0 | 0 | 0 | 0 | 1 | 1 |
| K | A | Q | 0 | 0 | 0 | 0 | 0 | 0 | 0 | 0 | 0 | 0 | 0 | 0 | 0 | 0 | 1 | 0 |
| K | A | S | 0 | 0 | 0 | 0 | 0 | 0 | 0 | 0 | 0 | 0 | 0 | 0 | 0 | 0 | 1 | 1 |
| K | A | T | 0 | 0 | 0 | 0 | 0 | 0 | 0 | 0 | 0 | 0 | 0 | 0 | 0 | 0 | 0 | 0 |
| K | D | A | 0 | 0 | 0 | 0 | 0 | 0 | 0 | 0 | 0 | 0 | 0 | 0 | 0 | 0 | 0 | 0 |
| K | D | T | 0 | 0 | 0 | 0 | 0 | 0 | 0 | 0 | 0 | 0 | 0 | 0 | 0 | 0 | 0 | 0 |
| K | E | G | 0 | 0 | 0 | 0 | 0 | 0 | 0 | 0 | 0 | 0 | 0 | 0 | 0 | 0 | 1 | 0 |
| K | E | N | 0 | 0 | 0 | 0 | 0 | 0 | 0 | 0 | 0 | 0 | 0 | 0 | 0 | 0 | 0 | 0 |
| K | E | S | 0 | 0 | 0 | 0 | 0 | 0 | 0 | 0 | 0 | 0 | 0 | 0 | 0 | 0 | 0 | 0 |
| K | G | A | 0 | 0 | 0 | 0 | 0 | 0 | 0 | 0 | 0 | 0 | 0 | 0 | 0 | 0 | 0 | 0 |
| K | G | G | 0 | 0 | 0 | 0 | 0 | 0 | 0 | 0 | 0 | 0 | 0 | 0 | 0 | 0 | 0 | 0 |
| K | G | N | 0 | 0 | 0 | 0 | 0 | 0 | 0 | 0 | 0 | 0 | 0 | 0 | 0 | 0 | 0 | 0 |
| K | G | S | 0 | 0 | 0 | 0 | 0 | 0 | 0 | 0 | 0 | 0 | 0 | 0 | 0 | 0 | 1 | 1 |
| K | G | T | 0 | 0 | 0 | 0 | 0 | 0 | 0 | 0 | 0 | 0 | 0 | 0 | 0 | 0 | 1 | 1 |
| K | H | D | 0 | 0 | 0 | 0 | 0 | 0 | 0 | 0 | 0 | 0 | 0 | 0 | 0 | 1 | 1 | 1 |
| K | H | E | 0 | 0 | 0 | 0 | 0 | 0 | 0 | 0 | 0 | 0 | 0 | 0 | 0 | 0 | 0 | 0 |
| K | H | G | 0 | 0 | 0 | 0 | 0 | 0 | 0 | 0 | 0 | 0 | 0 | 0 | 0 | 0 | 0 | 0 |
| K | H | N | 0 | 0 | 0 | 0 | 0 | 0 | 0 | 0 | 0 | 0 | 0 | 0 | 0 | 0 | 0 | 0 |

*Fig. 7.2f*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| A | S | S | 0 | 0 | 0 | 0 | 0 | 0 | 0 | 0 | 0 | 0 | 0 | 0 | 0 | 0 | 0 | 0 |
| A | S | T | 0 | 0 | 0 | 0 | 0 | 0 | 0 | 0 | 0 | 0 | 0 | 0 | 0 | 0 | 0 | 0 |
| A | T | A | 0 | 0 | 0 | 0 | 0 | 0 | 0 | 0 | 0 | 0 | 0 | 0 | 0 | 0 | 0 | 0 |
| A | T | G | 0 | 0 | 0 | 0 | 0 | 0 | 0 | 0 | 0 | 0 | 0 | 0 | 0 | 0 | 0 | 0 |
| A | T | H | 0 | 0 | 0 | 0 | 0 | 0 | 0 | 0 | 0 | 0 | 0 | 0 | 0 | 0 | 0 | 0 |
| A | T | K | 0 | 0 | 0 | 0 | 0 | 0 | 0 | 0 | 0 | 0 | 0 | 0 | 0 | 0 | 0 | 0 |
| A | T | N | 0 | 0 | 0 | 0 | 0 | 0 | 1 | 0 | 0 | 0 | 0 | 0 | 0 | 0 | 0 | 0 |
| A | T | Q | 0 | 0 | 0 | 0 | 0 | 0 | 1 | 0 | 0 | 0 | 0 | 0 | 0 | 0 | 0 | 0 |
| A | T | R | 0 | 0 | 0 | 0 | 0 | 0 | 0 | 1 | 0 | 0 | 0 | 0 | 0 | 0 | 0 | 0 |
| A | T | S | 0 | 0 | 0 | 0 | 0 | 0 | 1 | 0 | 0 | 0 | 0 | 0 | 0 | 0 | 0 | 0 |
| A | T | T | 0 | 0 | 0 | 0 | 0 | 0 | 0 | 0 | 0 | 0 | 0 | 0 | 0 | 0 | 0 | 0 |
| D | D | H | 0 | 0 | 0 | 0 | 0 | 0 | 1 | 0 | 0 | 0 | 0 | 0 | 0 | 0 | 0 | 0 |
| D | N | S | 0 | 0 | 0 | 0 | 0 | 0 | 0 | 0 | 0 | 0 | 0 | 0 | 0 | 0 | 0 | 0 |
| D | R | A | 0 | 0 | 0 | 0 | 0 | 0 | 0 | 0 | 0 | 0 | 0 | 0 | 0 | 0 | 0 | 0 |
| D | R | K | 0 | 0 | 0 | 0 | 0 | 0 | 0 | 0 | 0 | 0 | 0 | 0 | 0 | 0 | 0 | 0 |
| D | R | N | 0 | 0 | 0 | 0 | 0 | 0 | 0 | 0 | 0 | 0 | 0 | 0 | 0 | 0 | 0 | 0 |
| D | R | Q | 0 | 0 | 0 | 0 | 0 | 0 | 0 | 0 | 0 | 0 | 0 | 0 | 0 | 0 | 0 | 0 |
| D | R | R | 0 | 0 | 0 | 0 | 0 | 0 | 0 | 0 | 0 | 0 | 0 | 0 | 0 | 0 | 0 | 0 |
| D | R | S | 0 | 0 | 0 | 0 | 0 | 0 | 0 | 0 | 0 | 0 | 0 | 0 | 0 | 0 | 0 | 0 |
| D | R | T | 0 | 0 | 0 | 0 | 0 | 0 | 0 | 0 | 0 | 0 | 0 | 0 | 0 | 0 | 0 | 0 |
| E | H | H | 0 | 0 | 0 | 0 | 0 | 0 | 0 | 0 | 0 | 0 | 0 | 0 | 0 | 0 | 0 | 0 |
| E | R | A | 0 | 0 | 0 | 0 | 0 | 0 | 0 | 0 | 0 | 0 | 0 | 0 | 0 | 0 | 0 | 0 |
| E | R | H | 0 | 0 | 0 | 0 | 0 | 0 | 0 | 0 | 0 | 0 | 0 | 0 | 0 | 0 | 0 | 0 |
| E | R | N | 0 | 0 | 0 | 0 | 0 | 0 | 0 | 0 | 0 | 0 | 0 | 0 | 0 | 0 | 0 | 0 |
| E | R | S | 0 | 0 | 0 | 0 | 0 | 0 | 0 | 0 | 0 | 0 | 0 | 0 | 0 | 0 | 0 | 0 |
| E | R | T | 0 | 0 | 0 | 0 | 0 | 0 | 0 | 0 | 0 | 0 | 0 | 0 | 0 | 0 | 0 | 0 |
| E | S | T | 0 | 0 | 0 | 0 | 0 | 0 | 0 | 0 | 0 | 0 | 1 | 1 | 0 | 0 | 1 | 1 |
| G | H | K | 0 | 0 | 0 | 0 | 0 | 0 | 0 | 0 | 0 | 0 | 0 | 0 | 0 | 0 | 0 | 0 |
| G | Q | H | 0 | 0 | 0 | 0 | 0 | 0 | 0 | 0 | 0 | 0 | 0 | 0 | 0 | 0 | 0 | 0 |
| G | R | Q | 0 | 0 | 0 | 0 | 0 | 0 | 0 | 0 | 0 | 0 | 0 | 0 | 0 | 0 | 0 | 0 |
| G | R | R | 0 | 0 | 0 | 0 | 0 | 0 | 0 | 0 | 0 | 0 | 0 | 0 | 0 | 0 | 0 | 0 |
| G | T | D | 0 | 0 | 0 | 0 | 0 | 0 | 0 | 0 | 0 | 0 | 0 | 0 | 0 | 0 | 0 | 0 |
| G | T | P | 0 | 0 | 0 | 0 | 0 | 0 | 0 | 0 | 0 | 0 | 0 | 0 | 0 | 0 | 0 | 0 |
| G | T | R | 0 | 0 | 0 | 0 | 0 | 0 | 0 | 0 | 0 | 0 | 0 | 0 | 0 | 0 | 0 | 0 |
| H | A | S | 0 | 0 | 0 | 0 | 0 | 0 | 0 | 0 | 0 | 0 | 0 | 0 | 0 | 1 | 0 | 0 |
| H | A | T | 0 | 0 | 0 | 0 | 0 | 0 | 0 | 0 | 0 | 0 | 0 | 0 | 0 | 1 | 0 | 0 |

*Fig. 7.2g*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| H | R | A | 0 | 0 | 0 | 0 | 0 | 0 | 0 | 0 | 0 | 0 | 0 | 0 | 0 | 0 | 0 | 0 |
| H | R | D | 0 | 0 | 0 | 0 | 0 | 0 | 0 | 0 | 0 | 0 | 0 | 1 | 0 | 0 | 1 | 1 |
| H | R | E | 0 | 0 | 0 | 0 | 0 | 0 | 0 | 0 | 0 | 0 | 0 | 0 | 0 | 0 | 1 | 1 |
| H | R | G | 0 | 0 | 0 | 0 | 0 | 0 | 0 | 0 | 0 | 0 | 0 | 0 | 0 | 0 | 1 | 1 |
| H | R | N | 0 | 0 | 0 | 0 | 0 | 0 | 0 | 0 | 0 | 0 | 0 | 0 | 0 | 0 | 1 | 0 |
| H | R | R | 0 | 0 | 0 | 0 | 0 | 0 | 0 | 0 | 0 | 0 | 0 | 0 | 0 | 0 | 0 | 0 |
| H | R | S | 0 | 0 | 0 | 0 | 0 | 0 | 0 | 0 | 0 | 0 | 0 | 0 | 0 | 0 | 1 | 1 |
| H | R | T | 0 | 0 | 0 | 0 | 0 | 0 | 0 | 0 | 0 | 0 | 0 | 0 | 0 | 0 | 1 | 1 |
| H | S | G | 0 | 0 | 0 | 0 | 0 | 0 | 0 | 0 | 0 | 0 | 0 | 0 | 0 | 0 | 1 | 0 |
| H | S | S | 0 | 0 | 0 | 0 | 0 | 0 | 0 | 0 | 0 | 0 | 0 | 0 | 0 | 0 | 0 | 0 |
| H | S | T | 0 | 0 | 0 | 0 | 0 | 0 | 0 | 0 | 0 | 0 | 0 | 0 | 0 | 0 | 1 | 0 |
| H | T | S | 0 | 0 | 0 | 0 | 0 | 0 | 0 | 0 | 0 | 0 | 0 | 0 | 0 | 0 | 1 | 0 |
| H | T | T | 0 | 0 | 0 | 0 | 0 | 0 | 0 | 0 | 0 | 0 | 0 | 0 | 0 | 0 | 1 | 0 |
| K | A | A | 0 | 0 | 0 | 0 | 0 | 0 | 0 | 0 | 0 | 0 | 1 | 0 | 0 | 0 | 1 | 1 |
| K | A | D | 0 | 0 | 0 | 0 | 0 | 0 | 0 | 0 | 0 | 0 | 0 | 0 | 0 | 0 | 1 | 1 |
| K | A | E | 0 | 0 | 0 | 0 | 0 | 0 | 0 | 0 | 0 | 0 | 0 | 0 | 0 | 0 | 1 | 1 |
| K | A | G | 0 | 0 | 0 | 0 | 0 | 0 | 1 | 0 | 0 | 0 | 1 | 1 | 0 | 0 | 1 | 1 |
| K | A | H | 0 | 0 | 0 | 0 | 0 | 0 | 0 | 0 | 0 | 0 | 0 | 0 | 0 | 0 | 1 | 1 |
| K | A | N | 0 | 0 | 0 | 0 | 0 | 0 | 0 | 0 | 0 | 0 | 0 | 0 | 0 | 0 | 1 | 1 |
| K | A | Q | 0 | 0 | 0 | 0 | 0 | 0 | 1 | 0 | 0 | 0 | 1 | 1 | 0 | 0 | 1 | 1 |
| K | A | S | 0 | 0 | 0 | 0 | 0 | 0 | 0 | 0 | 0 | 0 | 1 | 1 | 0 | 0 | 1 | 1 |
| K | A | T | 0 | 0 | 0 | 0 | 0 | 0 | 0 | 0 | 0 | 0 | 1 | 0 | 0 | 0 | 1 | 1 |
| K | D | A | 0 | 0 | 0 | 0 | 0 | 0 | 0 | 0 | 0 | 0 | 1 | 0 | 0 | 0 | 1 | 0 |
| K | D | T | 0 | 0 | 0 | 0 | 0 | 0 | 0 | 0 | 0 | 0 | 1 | 0 | 0 | 0 | 1 | 0 |
| K | E | G | 0 | 0 | 0 | 0 | 0 | 0 | 0 | 0 | 0 | 0 | 0 | 0 | 0 | 0 | 1 | 1 |
| K | E | N | 0 | 0 | 0 | 0 | 0 | 0 | 0 | 0 | 0 | 0 | 0 | 0 | 0 | 0 | 1 | 0 |
| K | E | S | 0 | 0 | 0 | 0 | 0 | 0 | 0 | 0 | 0 | 0 | 0 | 0 | 0 | 0 | 1 | 1 |
| K | G | A | 0 | 0 | 0 | 0 | 0 | 0 | 0 | 0 | 0 | 0 | 1 | 0 | 0 | 0 | 1 | 1 |
| K | G | G | 0 | 0 | 0 | 0 | 0 | 0 | 0 | 0 | 0 | 0 | 0 | 0 | 0 | 0 | 1 | 1 |
| K | G | N | 0 | 0 | 0 | 0 | 0 | 0 | 0 | 0 | 0 | 0 | 0 | 0 | 0 | 0 | 1 | 1 |
| K | G | S | 0 | 0 | 0 | 0 | 0 | 0 | 0 | 0 | 0 | 0 | 1 | 0 | 0 | 0 | 1 | 1 |
| K | G | T | 0 | 0 | 0 | 0 | 0 | 0 | 0 | 0 | 0 | 0 | 1 | 0 | 0 | 0 | 1 | 1 |
| K | H | D | 0 | 0 | 0 | 0 | 0 | 0 | 0 | 0 | 0 | 0 | 0 | 0 | 0 | 0 | 1 | 0 |
| K | H | E | 0 | 0 | 0 | 0 | 0 | 0 | 0 | 0 | 0 | 0 | 0 | 0 | 0 | 0 | 1 | 1 |
| K | H | G | 0 | 0 | 0 | 0 | 0 | 0 | 0 | 0 | 0 | 0 | 0 | 0 | 0 | 0 | 1 | 1 |
| K | H | N | 0 | 0 | 0 | 0 | 0 | 0 | 0 | 0 | 0 | 0 | 0 | 0 | 0 | 0 | 1 | 0 |

*Fig. 7.2h*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| K | H | S | 0 | 0 | 0 | 0 | 0 | 0 | 0 | 0 | 0 | 0 | 0 | 0 | 0 | 0 | 1 | 1 |
| K | H | T | 0 | 0 | 0 | 0 | 0 | 0 | 0 | 0 | 0 | 0 | 0 | 0 | 0 | 0 | 0 | 0 |
| K | K | A | 0 | 0 | 0 | 0 | 0 | 0 | 0 | 0 | 0 | 0 | 0 | 0 | 0 | 0 | 0 | 0 |
| K | K | D | 0 | 0 | 0 | 0 | 0 | 0 | 0 | 0 | 0 | 0 | 0 | 0 | 0 | 0 | 0 | 0 |
| K | K | H | 0 | 0 | 0 | 0 | 0 | 0 | 0 | 0 | 0 | 0 | 0 | 0 | 0 | 0 | 0 | 0 |
| K | K | T | 0 | 0 | 0 | 0 | 0 | 0 | 0 | 0 | 0 | 0 | 0 | 0 | 0 | 0 | 0 | 0 |
| K | N | A | 0 | 0 | 0 | 0 | 0 | 0 | 0 | 0 | 0 | 0 | 0 | 0 | 0 | 0 | 0 | 0 |
| K | N | D | 0 | 0 | 0 | 0 | 0 | 0 | 0 | 0 | 0 | 0 | 0 | 0 | 0 | 0 | 0 | 0 |
| K | N | E | 0 | 0 | 0 | 0 | 0 | 0 | 0 | 0 | 0 | 0 | 0 | 0 | 0 | 0 | 0 | 0 |
| K | N | G | 0 | 0 | 0 | 0 | 0 | 0 | 0 | 0 | 0 | 0 | 0 | 0 | 0 | 0 | 1 | 1 |
| K | N | H | 0 | 0 | 0 | 0 | 0 | 0 | 0 | 0 | 0 | 0 | 0 | 0 | 0 | 0 | 0 | 0 |
| K | N | N | 0 | 0 | 0 | 0 | 0 | 0 | 0 | 0 | 0 | 0 | 0 | 0 | 0 | 0 | 1 | 1 |
| K | N | Q | 0 | 0 | 0 | 0 | 0 | 0 | 0 | 0 | 0 | 0 | 0 | 0 | 0 | 1 | 1 | 0 |
| K | N | S | 0 | 0 | 0 | 0 | 0 | 0 | 0 | 0 | 0 | 0 | 0 | 0 | 0 | 0 | 1 | 1 |
| K | N | T | 0 | 0 | 0 | 0 | 0 | 0 | 0 | 0 | 0 | 0 | 0 | 0 | 0 | 0 | 0 | 0 |
| K | P | H | 0 | 0 | 0 | 0 | 0 | 0 | 0 | 0 | 0 | 0 | 0 | 0 | 0 | 0 | 0 | 0 |
| K | Q | A | 0 | 0 | 0 | 0 | 0 | 0 | 0 | 0 | 0 | 0 | 0 | 0 | 0 | 0 | 1 | 1 |
| K | Q | D | 0 | 0 | 0 | 0 | 0 | 0 | 0 | 0 | 0 | 0 | 0 | 0 | 0 | 0 | 1 | 1 |
| K | Q | E | 0 | 0 | 0 | 0 | 0 | 0 | 0 | 0 | 0 | 0 | 0 | 0 | 0 | 0 | 0 | 0 |
| K | Q | S | 0 | 0 | 0 | 0 | 0 | 0 | 0 | 0 | 0 | 0 | 0 | 0 | 0 | 0 | 1 | 1 |
| K | Q | T | 0 | 0 | 0 | 0 | 0 | 0 | 0 | 0 | 0 | 0 | 0 | 0 | 0 | 0 | 1 | 1 |
| K | R | A | 0 | 0 | 0 | 0 | 0 | 0 | 0 | 0 | 0 | 0 | 0 | 0 | 0 | 0 | 1 | 1 |
| K | R | D | 0 | 0 | 0 | 0 | 0 | 0 | 0 | 0 | 0 | 0 | 0 | 0 | 0 | 0 | 1 | 1 |
| K | R | E | 0 | 0 | 0 | 0 | 0 | 0 | 0 | 0 | 0 | 0 | 0 | 0 | 1 | 0 | 1 | 1 |
| K | R | G | 0 | 0 | 0 | 0 | 0 | 0 | 0 | 0 | 0 | 0 | 0 | 0 | 0 | 0 | 1 | 1 |
| K | R | H | 0 | 0 | 0 | 0 | 0 | 0 | 0 | 0 | 0 | 0 | 0 | 0 | 0 | 0 | 0 | 1 |
| K | R | N | 0 | 0 | 0 | 0 | 0 | 0 | 0 | 0 | 0 | 0 | 0 | 0 | 0 | 0 | 1 | 1 |
| K | R | Q | 0 | 0 | 0 | 0 | 0 | 0 | 0 | 0 | 0 | 0 | 0 | 0 | 0 | 0 | 1 | 1 |
| K | R | S | 0 | 0 | 0 | 0 | 0 | 0 | 0 | 0 | 0 | 0 | 0 | 0 | 0 | 0 | 1 | 1 |
| K | R | T | 0 | 0 | 0 | 0 | 0 | 0 | 0 | 0 | 0 | 0 | 0 | 0 | 0 | 0 | 1 | 1 |
| K | S | A | 0 | 0 | 0 | 0 | 0 | 0 | 0 | 0 | 0 | 0 | 0 | 0 | 0 | 0 | 1 | 1 |
| K | S | D | 0 | 0 | 0 | 0 | 0 | 0 | 0 | 0 | 0 | 0 | 0 | 0 | 0 | 0 | 0 | 0 |
| K | S | H | 0 | 0 | 0 | 0 | 0 | 0 | 0 | 0 | 0 | 0 | 0 | 0 | 0 | 0 | 0 | 0 |
| K | S | N | 0 | 0 | 0 | 0 | 0 | 0 | 0 | 0 | 0 | 0 | 0 | 0 | 0 | 0 | 1 | 1 |
| K | S | S | 0 | 0 | 0 | 0 | 0 | 0 | 0 | 0 | 0 | 0 | 0 | 0 | 0 | 0 | 1 | 1 |
| K | S | T | 0 | 0 | 0 | 0 | 0 | 0 | 0 | 0 | 0 | 0 | 0 | 0 | 0 | 0 | 1 | 1 |

*Fig. 7.3a*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| K | T | A | 0 | 0 | 0 | 0 | 0 | 0 | 0 | 0 | 0 | 0 | 0 | 0 | 0 | 0 | 1 | 1 |
| K | T | D | 0 | 0 | 0 | 0 | 0 | 0 | 0 | 0 | 0 | 0 | 0 | 0 | 0 | 0 | 1 | 1 |
| K | T | E | 0 | 0 | 0 | 0 | 0 | 0 | 0 | 0 | 0 | 0 | 0 | 0 | 0 | 0 | 0 | 0 |
| K | T | G | 0 | 0 | 0 | 0 | 0 | 0 | 0 | 0 | 0 | 0 | 0 | 0 | 0 | 0 | 1 | 1 |
| K | T | H | 0 | 0 | 0 | 0 | 0 | 0 | 0 | 0 | 0 | 0 | 0 | 0 | 0 | 0 | 0 | 0 |
| K | T | N | 0 | 0 | 0 | 0 | 0 | 0 | 0 | 0 | 0 | 0 | 0 | 0 | 0 | 0 | 1 | 1 |
| K | T | Q | 0 | 0 | 0 | 0 | 0 | 0 | 0 | 0 | 0 | 0 | 0 | 0 | 0 | 0 | 0 | 0 |
| K | T | S | 0 | 0 | 0 | 0 | 0 | 0 | 0 | 0 | 0 | 0 | 0 | 0 | 0 | 0 | 1 | 1 |
| K | T | T | 0 | 0 | 0 | 0 | 0 | 0 | 0 | 0 | 0 | 0 | 0 | 0 | 0 | 0 | 0 | 0 |
| N | A | H | 0 | 0 | 0 | 0 | 0 | 0 | 0 | 0 | 0 | 0 | 0 | 0 | 0 | 0 | 0 | 0 |
| N | A | R | 0 | 0 | 0 | 0 | 0 | 0 | 0 | 1 | 0 | 0 | 0 | 0 | 0 | 0 | 0 | 0 |
| N | H | N | 0 | 0 | 0 | 0 | 0 | 0 | 1 | 0 | 0 | 0 | 0 | 0 | 0 | 0 | 0 | 0 |
| N | H | R | 0 | 0 | 0 | 0 | 0 | 0 | 0 | 1 | 0 | 0 | 0 | 0 | 0 | 0 | 0 | 0 |
| N | K | G | 0 | 0 | 0 | 0 | 0 | 0 | 1 | 0 | 0 | 0 | 0 | 0 | 0 | 0 | 0 | 0 |
| N | K | H | 0 | 0 | 0 | 0 | 0 | 0 | 0 | 0 | 0 | 0 | 0 | 0 | 0 | 0 | 0 | 0 |
| N | K | R | 0 | 0 | 0 | 0 | 0 | 0 | 0 | 1 | 0 | 0 | 0 | 0 | 0 | 0 | 0 | 0 |
| N | K | S | 0 | 0 | 0 | 0 | 0 | 1 | 0 | 1 | 0 | 0 | 0 | 0 | 0 | 0 | 0 | 0 |
| N | N | R | 0 | 0 | 0 | 0 | 0 | 0 | 0 | 1 | 0 | 0 | 0 | 0 | 0 | 0 | 0 | 0 |
| N | P | D | 0 | 0 | 0 | 0 | 0 | 0 | 0 | 0 | 0 | 0 | 0 | 0 | 0 | 0 | 0 | 0 |
| N | Q | H | 0 | 0 | 0 | 0 | 0 | 0 | 0 | 1 | 0 | 0 | 0 | 1 | 0 | 0 | 0 | 0 |
| N | Q | R | 0 | 0 | 0 | 0 | 0 | 0 | 1 | 1 | 0 | 0 | 0 | 0 | 0 | 0 | 0 | 0 |
| N | R | A | 0 | 0 | 0 | 0 | 1 | 0 | 1 | 1 | 0 | 0 | 1 | 0 | 0 | 0 | 0 | 0 |
| N | R | D | 0 | 0 | 0 | 0 | 0 | 0 | 0 | 0 | 0 | 0 | 0 | 0 | 0 | 0 | 0 | 0 |
| N | R | E | 0 | 0 | 0 | 0 | 0 | 1 | 0 | 0 | 0 | 0 | 0 | 0 | 0 | 0 | 0 | 0 |
| N | R | G | 0 | 0 | 0 | 0 | 0 | 1 | 1 | 1 | 0 | 0 | 0 | 0 | 0 | 0 | 0 | 0 |
| N | R | H | 0 | 0 | 0 | 0 | 1 | 0 | 1 | 1 | 0 | 0 | 0 | 0 | 0 | 0 | 0 | 0 |
| N | R | K | 0 | 0 | 1 | 1 | 1 | 0 | 1 | 1 | 0 | 0 | 0 | 1 | 0 | 0 | 0 | 0 |
| N | R | N | 0 | 0 | 0 | 0 | 1 | 1 | 1 | 1 | 0 | 0 | 0 | 0 | 0 | 0 | 0 | 0 |
| N | R | R | 0 | 0 | 0 | 0 | 1 | 0 | 1 | 1 | 0 | 0 | 0 | 1 | 0 | 0 | 0 | 0 |
| N | R | S | 0 | 0 | 0 | 0 | 1 | 0 | 1 | 1 | 0 | 0 | 0 | 0 | 0 | 0 | 0 | 0 |
| N | R | T | 0 | 0 | 0 | 0 | 1 | 0 | 1 | 1 | 0 | 0 | 1 | 0 | 0 | 0 | 0 | 0 |
| N | S | G | 0 | 0 | 0 | 0 | 0 | 0 | 1 | 0 | 0 | 0 | 0 | 0 | 0 | 0 | 0 | 0 |
| N | S | H | 0 | 0 | 0 | 0 | 1 | 0 | 1 | 0 | 0 | 0 | 0 | 0 | 0 | 0 | 0 | 0 |
| N | S | K | 0 | 0 | 0 | 0 | 0 | 0 | 1 | 1 | 0 | 0 | 0 | 0 | 0 | 0 | 0 | 0 |
| N | S | R | 0 | 0 | 0 | 0 | 1 | 0 | 1 | 1 | 0 | 0 | 0 | 0 | 0 | 0 | 0 | 0 |
| N | T | H | 0 | 0 | 0 | 0 | 0 | 0 | 0 | 0 | 0 | 0 | 0 | 0 | 0 | 0 | 0 | 0 |

*Fig. 7.3b*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| K | H | S | 0 | 0 | 0 | 0 | 0 | 0 | 0 | 0 | 0 | 1 | 1 | 0 | 0 | 1 | 1 | 1 |
| K | H | T | 0 | 0 | 0 | 0 | 0 | 0 | 0 | 0 | 0 | 0 | 0 | 0 | 0 | 0 | 1 | 1 |
| K | K | A | 0 | 0 | 0 | 0 | 0 | 0 | 0 | 0 | 0 | 0 | 0 | 0 | 0 | 0 | 1 | 1 |
| K | K | D | 0 | 0 | 0 | 0 | 0 | 0 | 0 | 0 | 0 | 0 | 0 | 0 | 0 | 0 | 1 | 0 |
| K | K | H | 0 | 0 | 0 | 0 | 0 | 0 | 0 | 0 | 0 | 0 | 0 | 0 | 0 | 0 | 1 | 1 |
| K | K | T | 0 | 0 | 0 | 0 | 0 | 0 | 0 | 0 | 0 | 0 | 0 | 0 | 0 | 0 | 1 | 1 |
| K | N | A | 0 | 0 | 0 | 0 | 0 | 0 | 0 | 0 | 0 | 1 | 1 | 0 | 0 | 1 | 1 | 1 |
| K | N | D | 0 | 0 | 0 | 0 | 0 | 0 | 0 | 0 | 0 | 0 | 0 | 1 | 0 | 1 | 1 | 1 |
| K | N | E | 0 | 0 | 0 | 0 | 0 | 0 | 0 | 0 | 0 | 0 | 0 | 1 | 0 | 1 | 1 | 1 |
| K | N | G | 0 | 0 | 0 | 0 | 0 | 0 | 0 | 0 | 0 | 1 | 1 | 0 | 0 | 1 | 1 | 1 |
| K | N | H | 0 | 0 | 0 | 0 | 0 | 0 | 0 | 0 | 0 | 0 | 0 | 0 | 0 | 1 | 1 | 1 |
| K | N | N | 0 | 0 | 0 | 0 | 0 | 0 | 0 | 0 | 0 | 0 | 0 | 0 | 0 | 1 | 1 | 1 |
| K | N | Q | 0 | 0 | 0 | 0 | 0 | 0 | 0 | 0 | 0 | 1 | 1 | 0 | 0 | 1 | 1 | 1 |
| K | N | S | 0 | 0 | 0 | 0 | 0 | 0 | 0 | 0 | 0 | 1 | 1 | 1 | 0 | 1 | 1 | 1 |
| K | N | T | 0 | 0 | 0 | 0 | 0 | 0 | 0 | 0 | 0 | 1 | 1 | 0 | 0 | 1 | 1 | 1 |
| K | P | H | 0 | 0 | 0 | 0 | 0 | 0 | 0 | 0 | 0 | 0 | 0 | 0 | 0 | 0 | 1 | 1 |
| K | Q | A | 0 | 0 | 0 | 0 | 0 | 0 | 0 | 0 | 0 | 1 | 1 | 1 | 0 | 1 | 1 | 1 |
| K | Q | D | 0 | 0 | 0 | 0 | 0 | 0 | 0 | 0 | 0 | 0 | 0 | 1 | 0 | 1 | 1 | 1 |
| K | Q | E | 0 | 0 | 0 | 0 | 0 | 0 | 0 | 0 | 0 | 0 | 0 | 1 | 0 | 1 | 1 | 1 |
| K | Q | S | 0 | 0 | 0 | 0 | 0 | 0 | 0 | 0 | 0 | 1 | 1 | 1 | 0 | 1 | 1 | 1 |
| K | Q | T | 0 | 0 | 0 | 0 | 0 | 0 | 0 | 0 | 0 | 1 | 1 | 0 | 0 | 1 | 1 | 1 |
| K | R | A | 0 | 0 | 0 | 0 | 0 | 0 | 0 | 0 | 0 | 0 | 1 | 0 | 0 | 1 | 1 | 1 |
| K | R | D | 0 | 0 | 0 | 0 | 0 | 0 | 0 | 0 | 0 | 1 | 1 | 1 | 0 | 1 | 1 | 1 |
| K | R | E | 0 | 0 | 0 | 0 | 0 | 0 | 0 | 0 | 0 | 0 | 1 | 1 | 0 | 1 | 1 | 1 |
| K | R | G | 0 | 0 | 0 | 0 | 0 | 0 | 0 | 0 | 0 | 0 | 1 | 0 | 0 | 1 | 1 | 1 |
| K | R | H | 0 | 0 | 0 | 0 | 0 | 0 | 0 | 0 | 0 | 1 | 1 | 1 | 0 | 1 | 1 | 1 |
| K | R | N | 0 | 0 | 0 | 0 | 0 | 0 | 0 | 0 | 0 | 0 | 1 | 0 | 0 | 1 | 1 | 1 |
| K | R | Q | 0 | 0 | 0 | 0 | 0 | 0 | 1 | 0 | 0 | 0 | 1 | 1 | 0 | 1 | 1 | 1 |
| K | R | S | 0 | 0 | 0 | 0 | 0 | 0 | 0 | 0 | 0 | 1 | 1 | 1 | 0 | 1 | 1 | 1 |
| K | R | T | 0 | 0 | 0 | 0 | 0 | 0 | 0 | 0 | 0 | 0 | 1 | 1 | 0 | 1 | 1 | 1 |
| K | S | A | 0 | 0 | 0 | 0 | 0 | 0 | 0 | 0 | 0 | 1 | 1 | 0 | 0 | 1 | 1 | 1 |
| K | S | D | 0 | 0 | 0 | 0 | 0 | 0 | 0 | 0 | 0 | 0 | 0 | 1 | 0 | 1 | 1 | 1 |
| K | S | H | 0 | 0 | 0 | 0 | 0 | 0 | 0 | 0 | 0 | 0 | 0 | 0 | 0 | 0 | 1 | 1 |
| K | S | N | 0 | 0 | 0 | 0 | 0 | 0 | 0 | 0 | 0 | 1 | 1 | 1 | 0 | 1 | 1 | 1 |
| K | S | S | 0 | 0 | 0 | 0 | 0 | 0 | 0 | 0 | 0 | 1 | 1 | 0 | 0 | 1 | 1 | 1 |
| K | S | T | 0 | 0 | 0 | 0 | 0 | 0 | 0 | 0 | 0 | 0 | 1 | 0 | 0 | 1 | 1 | 1 |

*Fig. 7.3c*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| K | T | A | 0 | 0 | 0 | 0 | 0 | 0 | 0 | 0 | 0 | 1 | 1 | 0 | 0 | 1 | 1 |
| K | T | D | 0 | 0 | 0 | 0 | 0 | 0 | 0 | 0 | 0 | 0 | 0 | 0 | 0 | 1 | 1 |
| K | T | E | 0 | 0 | 0 | 0 | 0 | 0 | 0 | 0 | 0 | 0 | 0 | 1 | 0 | 1 | 1 |
| K | T | G | 0 | 0 | 0 | 0 | 0 | 0 | 0 | 0 | 0 | 0 | 0 | 0 | 0 | 1 | 1 |
| K | T | H | 0 | 0 | 0 | 0 | 0 | 0 | 0 | 0 | 0 | 0 | 0 | 0 | 0 | 1 | 1 |
| K | T | N | 0 | 0 | 0 | 0 | 0 | 0 | 0 | 0 | 0 | 0 | 1 | 0 | 0 | 1 | 1 |
| K | T | Q | 0 | 0 | 0 | 0 | 0 | 0 | 0 | 0 | 0 | 0 | 0 | 0 | 0 | 1 | 1 |
| K | T | S | 0 | 0 | 0 | 0 | 0 | 0 | 0 | 0 | 0 | 1 | 1 | 0 | 0 | 1 | 1 |
| K | T | T | 0 | 0 | 0 | 0 | 0 | 0 | 0 | 0 | 0 | 0 | 0 | 0 | 0 | 1 | 1 |
| N | A | H | 0 | 0 | 0 | 0 | 0 | 0 | 1 | 0 | 0 | 0 | 0 | 0 | 0 | 0 | 0 |
| N | A | R | 0 | 0 | 0 | 0 | 0 | 0 | 0 | 1 | 0 | 0 | 0 | 0 | 0 | 0 | 0 |
| N | H | N | 0 | 0 | 0 | 0 | 0 | 0 | 0 | 0 | 0 | 0 | 0 | 0 | 0 | 0 | 0 |
| N | H | R | 0 | 0 | 0 | 0 | 0 | 0 | 0 | 1 | 0 | 0 | 0 | 0 | 0 | 0 | 0 |
| N | K | G | 0 | 0 | 0 | 0 | 0 | 0 | 0 | 0 | 0 | 0 | 0 | 0 | 0 | 0 | 0 |
| N | K | H | 0 | 0 | 0 | 0 | 0 | 0 | 1 | 0 | 0 | 0 | 0 | 0 | 0 | 0 | 0 |
| N | K | R | 0 | 0 | 0 | 0 | 0 | 0 | 1 | 1 | 0 | 0 | 0 | 0 | 0 | 0 | 0 |
| N | K | S | 0 | 0 | 0 | 0 | 0 | 0 | 0 | 0 | 0 | 0 | 0 | 0 | 0 | 0 | 0 |
| N | N | R | 0 | 0 | 0 | 0 | 0 | 0 | 0 | 8 | 0 | 0 | 0 | 0 | 0 | 0 | 1 | 0 |
| N | P | D | 0 | 0 | 0 | 0 | 0 | 0 | 0 | 0 | 0 | 0 | 0 | 0 | 0 | 0 | 1 | 1 |
| N | Q | H | 0 | 0 | 0 | 0 | 0 | 0 | 0 | 1 | 0 | 0 | 0 | 1 | 0 | 0 | 0 |
| N | Q | R | 0 | 0 | 0 | 0 | 0 | 0 | 1 | 1 | 0 | 0 | 0 | 0 | 0 | 0 | 0 |
| N | R | A | 0 | 0 | 0 | 0 | 1 | 0 | 1 | 1 | 0 | 0 | 0 | 0 | 0 | 0 | 0 |
| N | R | D | 0 | 0 | 0 | 0 | 0 | 0 | 1 | 0 | 0 | 0 | 0 | 0 | 0 | 0 | 0 |
| N | R | E | 0 | 0 | 0 | 0 | 0 | 0 | 1 | 0 | 0 | 0 | 0 | 0 | 0 | 0 | 0 |
| N | R | G | 0 | 0 | 0 | 0 | 0 | 1 | 1 | 1 | 0 | 0 | 0 | 0 | 0 | 0 | 0 |
| N | R | H | 0 | 0 | 0 | 0 | 1 | 0 | 1 | 1 | 0 | 0 | 0 | 0 | 0 | 0 | 0 |
| N | R | K | 0 | 0 | 0 | 0 | 0 | 0 | 1 | 0 | 0 | 0 | 0 | 0 | 0 | 0 | 0 |
| N | R | N | 0 | 0 | 0 | 0 | 0 | 1 | 1 | 1 | 0 | 0 | 0 | 0 | 0 | 0 | 0 |
| N | R | R | 0 | 0 | 0 | 0 | 0 | 1 | 1 | 1 | 0 | 0 | 0 | 1 | 0 | 0 | 0 |
| N | R | S | 0 | 0 | 0 | 0 | 0 | 0 | 1 | 0 | 0 | 0 | 0 | 0 | 0 | 0 | 0 |
| N | R | T | 0 | 0 | 0 | 0 | 1 | 0 | 1 | 1 | 0 | 0 | 0 | 0 | 0 | 0 | 0 |
| N | S | G | 0 | 0 | 0 | 0 | 0 | 0 | 0 | 0 | 0 | 0 | 0 | 0 | 0 | 0 | 0 |
| N | S | H | 0 | 0 | 0 | 0 | 1 | 0 | 1 | 1 | 0 | 0 | 0 | 0 | 0 | 0 | 0 |
| N | S | K | 0 | 0 | 0 | 0 | 0 | 0 | 0 | 0 | 0 | 0 | 0 | 0 | 0 | 0 | 0 |
| N | S | R | 0 | 0 | 0 | 0 | 0 | 0 | 1 | 1 | 0 | 0 | 0 | 0 | 0 | 0 | 0 |
| N | T | H | 0 | 0 | 0 | 0 | 0 | 0 | 1 | 0 | 0 | 0 | 0 | 0 | 0 | 0 | 0 |

*Fig. 7.3d*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| K | H | S | 0 | 0 | 0 | 0 | 0 | 0 | 0 | 0 | 0 | 0 | 0 | 0 | 0 | 0 | 1 | 1 |
| K | H | T | 0 | 0 | 0 | 0 | 0 | 0 | 0 | 0 | 0 | 0 | 0 | 0 | 0 | 0 | 0 | 0 |
| K | K | A | 0 | 0 | 0 | 0 | 0 | 0 | 0 | 0 | 0 | 0 | 0 | 0 | 0 | 0 | 0 | 0 |
| K | K | D | 0 | 0 | 0 | 0 | 0 | 0 | 0 | 0 | 0 | 0 | 0 | 0 | 0 | 0 | 0 | 0 |
| K | K | H | 0 | 0 | 0 | 0 | 0 | 0 | 0 | 0 | 0 | 0 | 0 | 0 | 0 | 0 | 0 | 0 |
| K | K | T | 0 | 0 | 0 | 0 | 0 | 0 | 0 | 0 | 0 | 0 | 0 | 0 | 0 | 0 | 0 | 0 |
| K | N | A | 0 | 0 | 0 | 0 | 0 | 0 | 0 | 0 | 0 | 0 | 0 | 0 | 0 | 0 | 0 | 0 |
| K | N | D | 0 | 0 | 0 | 0 | 0 | 0 | 0 | 0 | 0 | 0 | 0 | 0 | 0 | 0 | 1 | 0 |
| K | N | E | 0 | 0 | 0 | 0 | 0 | 0 | 0 | 0 | 0 | 0 | 0 | 0 | 0 | 0 | 0 | 0 |
| K | N | G | 0 | 0 | 0 | 0 | 0 | 0 | 0 | 0 | 0 | 0 | 0 | 0 | 0 | 0 | 1 | 0 |
| K | N | H | 0 | 0 | 0 | 0 | 0 | 0 | 0 | 0 | 0 | 0 | 0 | 0 | 0 | 0 | 0 | 0 |
| K | N | N | 0 | 0 | 0 | 0 | 0 | 0 | 0 | 0 | 0 | 0 | 0 | 0 | 0 | 0 | 1 | 0 |
| K | N | Q | 0 | 0 | 0 | 0 | 0 | 0 | 0 | 0 | 0 | 0 | 0 | 0 | 0 | 0 | 1 | 0 |
| K | N | S | 0 | 0 | 0 | 0 | 0 | 0 | 0 | 0 | 0 | 0 | 0 | 0 | 0 | 0 | 1 | 1 |
| K | N | T | 0 | 0 | 0 | 0 | 0 | 0 | 0 | 0 | 0 | 0 | 0 | 0 | 0 | 0 | 0 | 0 |
| K | P | H | 0 | 0 | 0 | 0 | 0 | 0 | 0 | 0 | 0 | 0 | 0 | 0 | 0 | 0 | 0 | 0 |
| K | Q | A | 0 | 0 | 0 | 0 | 0 | 0 | 0 | 0 | 0 | 0 | 0 | 0 | 0 | 0 | 1 | 0 |
| K | Q | D | 0 | 0 | 0 | 0 | 0 | 0 | 0 | 0 | 0 | 0 | 0 | 0 | 0 | 0 | 0 | 0 |
| K | Q | E | 0 | 0 | 0 | 0 | 0 | 0 | 0 | 0 | 0 | 0 | 0 | 0 | 0 | 0 | 0 | 0 |
| K | Q | S | 0 | 0 | 0 | 0 | 0 | 0 | 0 | 0 | 0 | 0 | 0 | 0 | 0 | 0 | 1 | 1 |
| K | Q | T | 0 | 0 | 0 | 0 | 0 | 0 | 0 | 0 | 0 | 0 | 0 | 0 | 0 | 0 | 0 | 0 |
| K | R | A | 0 | 0 | 0 | 0 | 0 | 0 | 0 | 0 | 0 | 0 | 0 | 0 | 0 | 0 | 0 | 0 |
| K | R | D | 0 | 0 | 0 | 0 | 0 | 0 | 0 | 0 | 0 | 0 | 0 | 0 | 0 | 0 | 1 | 1 |
| K | R | E | 0 | 0 | 0 | 0 | 0 | 0 | 0 | 0 | 0 | 0 | 0 | 0 | 0 | 0 | 1 | 1 |
| K | R | G | 0 | 0 | 0 | 0 | 0 | 0 | 0 | 0 | 0 | 0 | 0 | 0 | 0 | 0 | 1 | 1 |
| K | R | H | 0 | 0 | 0 | 0 | 0 | 0 | 0 | 0 | 0 | 0 | 0 | 0 | 0 | 0 | 0 | 0 |
| K | R | N | 0 | 0 | 0 | 0 | 0 | 0 | 0 | 0 | 0 | 0 | 0 | 0 | 0 | 0 | 1 | 1 |
| K | R | Q | 0 | 0 | 0 | 0 | 0 | 0 | 0 | 0 | 0 | 0 | 0 | 0 | 0 | 0 | 1 | 1 |
| K | R | S | 0 | 0 | 0 | 0 | 0 | 0 | 0 | 0 | 0 | 0 | 0 | 0 | 0 | 0 | 1 | 1 |
| K | R | T | 0 | 0 | 0 | 0 | 0 | 0 | 0 | 0 | 0 | 0 | 0 | 0 | 0 | 0 | 1 | 1 |
| K | S | A | 0 | 0 | 0 | 0 | 0 | 0 | 0 | 0 | 0 | 0 | 0 | 0 | 0 | 0 | 1 | 1 |
| K | S | D | 0 | 0 | 0 | 0 | 0 | 0 | 0 | 0 | 0 | 0 | 0 | 0 | 0 | 0 | 0 | 0 |
| K | S | H | 0 | 0 | 0 | 0 | 0 | 0 | 0 | 0 | 0 | 0 | 0 | 0 | 0 | 0 | 0 | 0 |
| K | S | N | 0 | 0 | 0 | 0 | 0 | 0 | 0 | 0 | 0 | 0 | 0 | 0 | 0 | 0 | 1 | 1 |
| K | S | S | 0 | 0 | 0 | 0 | 0 | 0 | 0 | 0 | 0 | 0 | 0 | 0 | 0 | 0 | 1 | 1 |
| K | S | T | 0 | 0 | 0 | 0 | 0 | 0 | 0 | 0 | 0 | 0 | 0 | 0 | 0 | 0 | 1 | 1 |

*Fig. 7.3e*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| K | T | A | 0 | 0 | 0 | 0 | 0 | 0 | 0 | 0 | 0 | 0 | 0 | 0 | 0 | 0 | 0 | 0 |
| K | T | D | 0 | 0 | 0 | 0 | 0 | 0 | 0 | 0 | 0 | 0 | 0 | 0 | 0 | 0 | 0 | 0 |
| K | T | E | 0 | 0 | 0 | 0 | 0 | 0 | 0 | 0 | 0 | 0 | 0 | 0 | 0 | 0 | 0 | 0 |
| K | T | G | 0 | 0 | 0 | 0 | 0 | 0 | 0 | 0 | 0 | 0 | 0 | 0 | 0 | 0 | 1 | 1 |
| K | T | H | 0 | 0 | 0 | 0 | 0 | 0 | 0 | 0 | 0 | 0 | 0 | 0 | 0 | 0 | 0 | 0 |
| K | T | N | 0 | 0 | 0 | 0 | 0 | 0 | 0 | 0 | 0 | 0 | 0 | 0 | 0 | 0 | 1 | 1 |
| K | T | Q | 0 | 0 | 0 | 0 | 0 | 0 | 0 | 0 | 0 | 0 | 0 | 0 | 0 | 0 | 0 | 0 |
| K | T | S | 0 | 0 | 0 | 0 | 0 | 0 | 0 | 0 | 0 | 0 | 0 | 0 | 0 | 0 | 1 | 0 |
| K | T | T | 0 | 0 | 0 | 0 | 0 | 0 | 0 | 0 | 0 | 0 | 0 | 0 | 0 | 0 | 0 | 0 |
| N | A | H | 0 | 0 | 0 | 0 | 0 | 0 | 0 | 0 | 0 | 0 | 0 | 0 | 0 | 0 | 0 | 0 |
| N | A | R | 0 | 0 | 0 | 0 | 0 | 0 | 0 | 0 | 0 | 0 | 0 | 0 | 0 | 0 | 0 | 0 |
| N | H | N | 0 | 0 | 0 | 0 | 0 | 0 | 0 | 0 | 0 | 0 | 0 | 0 | 0 | 0 | 0 | 0 |
| N | H | R | 0 | 0 | 0 | 0 | 0 | 0 | 0 | 0 | 0 | 0 | 0 | 0 | 0 | 0 | 0 | 0 |
| N | K | G | 0 | 0 | 0 | 0 | 0 | 0 | 0 | 0 | 0 | 0 | 0 | 0 | 0 | 0 | 0 | 0 |
| N | K | H | 0 | 0 | 0 | 0 | 0 | 0 | 0 | 0 | 0 | 0 | 0 | 0 | 0 | 0 | 0 | 0 |
| N | K | R | 0 | 0 | 0 | 0 | 0 | 0 | 0 | 0 | 0 | 0 | 0 | 0 | 0 | 0 | 0 | 0 |
| N | K | S | 0 | 0 | 0 | 0 | 0 | 0 | 0 | 0 | 0 | 0 | 0 | 0 | 0 | 0 | 0 | 0 |
| N | N | R | 0 | 0 | 0 | 0 | 0 | 0 | 0 | 0 | 0 | 0 | 0 | 0 | 0 | 0 | 0 | 0 |
| N | P | D | 0 | 0 | 0 | 0 | 0 | 0 | 0 | 0 | 0 | 0 | 0 | 0 | 0 | 0 | 0 | 0 |
| N | Q | H | 0 | 0 | 0 | 0 | 0 | 0 | 0 | 0 | 0 | 0 | 0 | 0 | 0 | 0 | 0 | 0 |
| N | Q | R | 0 | 0 | 0 | 0 | 0 | 0 | 0 | 0 | 0 | 0 | 0 | 0 | 0 | 0 | 0 | 0 |
| N | R | A | 0 | 0 | 0 | 0 | 0 | 1 | 0 | 0 | 0 | 0 | 0 | 0 | 0 | 0 | 0 | 0 |
| N | R | D | 0 | 0 | 0 | 0 | 0 | 0 | 0 | 0 | 0 | 0 | 0 | 0 | 0 | 0 | 0 | 0 |
| N | R | E | 0 | 0 | 0 | 0 | 0 | 0 | 0 | 0 | 0 | 0 | 0 | 0 | 0 | 0 | 0 | 0 |
| N | R | G | 0 | 0 | 0 | 0 | 0 | 0 | 0 | 0 | 0 | 0 | 0 | 0 | 0 | 0 | 0 | 0 |
| N | R | H | 0 | 0 | 0 | 0 | 0 | 0 | 0 | 0 | 0 | 0 | 0 | 0 | 0 | 0 | 0 | 0 |
| N | R | K | 0 | 0 | 0 | 0 | 0 | 0 | 0 | 0 | 0 | 0 | 0 | 0 | 0 | 0 | 0 | 0 |
| N | R | N | 0 | 0 | 0 | 0 | 0 | 0 | 0 | 0 | 0 | 0 | 0 | 0 | 0 | 0 | 0 | 0 |
| N | R | R | 0 | 0 | 0 | 0 | 0 | 1 | 0 | 0 | 0 | 0 | 0 | 0 | 0 | 0 | 0 | 0 |
| N | R | S | 0 | 0 | 0 | 0 | 0 | 0 | 0 | 0 | 0 | 0 | 0 | 0 | 0 | 0 | 0 | 0 |
| N | R | T | 0 | 0 | 0 | 0 | 0 | 0 | 0 | 0 | 0 | 0 | 0 | 0 | 0 | 0 | 0 | 0 |
| N | S | G | 0 | 0 | 0 | 0 | 0 | 0 | 0 | 0 | 0 | 0 | 0 | 0 | 0 | 0 | 0 | 0 |
| N | S | H | 0 | 0 | 0 | 0 | 0 | 0 | 0 | 0 | 0 | 0 | 0 | 0 | 0 | 0 | 0 | 0 |
| N | S | K | 0 | 0 | 0 | 0 | 0 | 0 | 0 | 0 | 0 | 0 | 0 | 0 | 0 | 0 | 0 | 0 |
| N | S | R | 0 | 0 | 0 | 0 | 0 | 0 | 0 | 0 | 0 | 0 | 0 | 0 | 0 | 0 | 0 | 0 |
| N | T | H | 0 | 0 | 0 | 0 | 0 | 0 | 0 | 0 | 0 | 0 | 0 | 0 | 0 | 0 | 0 | 0 |

*Fig. 7.3f*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| K | H | S | 0 | 0 | 0 | 0 | 0 | 0 | 0 | 0 | 0 | 0 | 1 | 0 | 0 | 0 | 1 | 1 |
| K | H | T | 0 | 0 | 0 | 0 | 0 | 0 | 0 | 0 | 0 | 0 | 0 | 0 | 0 | 0 | 1 | 0 |
| K | K | A | 0 | 0 | 0 | 0 | 0 | 0 | 0 | 0 | 0 | 0 | 0 | 0 | 0 | 0 | 1 | 0 |
| K | K | D | 0 | 0 | 0 | 0 | 0 | 0 | 0 | 0 | 0 | 0 | 0 | 0 | 0 | 0 | 1 | 0 |
| K | K | H | 0 | 0 | 0 | 0 | 0 | 0 | 0 | 0 | 0 | 0 | 0 | 0 | 0 | 0 | 1 | 0 |
| K | K | T | 0 | 0 | 0 | 0 | 0 | 0 | 0 | 0 | 0 | 0 | 0 | 0 | 0 | 0 | 1 | 1 |
| K | N | A | 0 | 0 | 0 | 0 | 0 | 0 | 0 | 0 | 0 | 0 | 0 | 0 | 0 | 0 | 1 | 1 |
| K | N | D | 0 | 0 | 0 | 0 | 0 | 0 | 0 | 0 | 0 | 0 | 0 | 0 | 0 | 0 | 1 | 1 |
| K | N | E | 0 | 0 | 0 | 0 | 0 | 0 | 0 | 0 | 0 | 0 | 0 | 0 | 0 | 1 | 0 | 1 | 1 |
| K | N | G | 0 | 0 | 0 | 0 | 0 | 0 | 0 | 0 | 0 | 0 | 0 | 0 | 0 | 0 | 1 | 1 |
| K | N | H | 0 | 0 | 0 | 0 | 0 | 0 | 0 | 0 | 0 | 0 | 0 | 0 | 0 | 0 | 1 | 1 |
| K | N | N | 0 | 0 | 0 | 0 | 0 | 0 | 0 | 0 | 0 | 0 | 0 | 0 | 0 | 0 | 1 | 1 |
| K | N | Q | 0 | 0 | 0 | 0 | 0 | 0 | 0 | 0 | 0 | 0 | 1 | 0 | 0 | 0 | 1 | 1 |
| K | N | S | 0 | 0 | 0 | 0 | 0 | 0 | 0 | 0 | 0 | 0 | 0 | 1 | 0 | 0 | 1 | 1 |
| K | N | T | 0 | 0 | 0 | 0 | 0 | 0 | 0 | 0 | 0 | 0 | 1 | 0 | 0 | 0 | 1 | 1 |
| K | P | H | 0 | 0 | 0 | 0 | 0 | 0 | 0 | 0 | 0 | 0 | 0 | 0 | 0 | 0 | 1 | 1 |
| K | Q | A | 0 | 0 | 0 | 0 | 0 | 0 | 0 | 0 | 0 | 0 | 0 | 0 | 0 | 0 | 1 | 1 |
| K | Q | D | 0 | 0 | 0 | 0 | 0 | 0 | 0 | 0 | 0 | 0 | 0 | 0 | 0 | 0 | 1 | 1 |
| K | Q | E | 0 | 0 | 0 | 0 | 0 | 0 | 0 | 0 | 0 | 0 | 0 | 0 | 0 | 0 | 1 | 0 |
| K | Q | S | 0 | 0 | 0 | 0 | 0 | 0 | 0 | 0 | 0 | 0 | 1 | 0 | 0 | 0 | 1 | 1 |
| K | Q | T | 0 | 0 | 0 | 0 | 0 | 0 | 0 | 0 | 0 | 0 | 0 | 0 | 0 | 0 | 1 | 1 |
| K | R | A | 0 | 0 | 0 | 0 | 0 | 0 | 0 | 0 | 0 | 0 | 0 | 0 | 0 | 0 | 1 | 1 |
| K | R | D | 0 | 0 | 0 | 0 | 0 | 0 | 0 | 0 | 0 | 0 | 1 | 1 | 1 | 0 | 1 | 0 |
| K | R | E | 0 | 0 | 0 | 0 | 0 | 0 | 1 | 0 | 0 | 0 | 1 | 1 | 1 | 0 | 1 | 1 |
| K | R | G | 0 | 0 | 0 | 0 | 0 | 0 | 0 | 0 | 0 | 0 | 0 | 0 | 0 | 0 | 1 | 1 |
| K | R | H | 0 | 0 | 0 | 0 | 0 | 0 | 0 | 0 | 0 | 0 | 1 | 0 | 0 | 0 | 1 | 1 |
| K | R | N | 0 | 0 | 0 | 0 | 0 | 0 | 0 | 0 | 0 | 0 | 0 | 1 | 0 | 0 | 1 | 1 |
| K | R | Q | 0 | 0 | 0 | 0 | 0 | 0 | 1 | 0 | 0 | 0 | 1 | 1 | 0 | 0 | 1 | 1 |
| K | R | S | 0 | 0 | 0 | 0 | 0 | 0 | 0 | 0 | 0 | 0 | 1 | 1 | 0 | 0 | 1 | 1 |
| K | R | T | 0 | 0 | 0 | 0 | 0 | 0 | 0 | 0 | 0 | 0 | 1 | 1 | 0 | 0 | 1 | 1 |
| K | S | A | 0 | 0 | 0 | 0 | 0 | 0 | 0 | 0 | 0 | 0 | 1 | 1 | 0 | 0 | 1 | 1 |
| K | S | D | 0 | 0 | 0 | 0 | 0 | 0 | 0 | 0 | 0 | 0 | 0 | 0 | 0 | 0 | 1 | 0 |
| K | S | H | 0 | 0 | 0 | 0 | 0 | 0 | 0 | 0 | 0 | 0 | 0 | 0 | 0 | 0 | 1 | 1 |
| K | S | N | 0 | 0 | 0 | 0 | 0 | 0 | 0 | 0 | 0 | 0 | 1 | 1 | 0 | 0 | 1 | 1 |
| K | S | S | 0 | 0 | 0 | 0 | 0 | 0 | 0 | 0 | 0 | 0 | 1 | 1 | 0 | 0 | 1 | 1 |
| K | S | T | 0 | 0 | 0 | 0 | 0 | 0 | 0 | 0 | 0 | 0 | 1 | 1 | 0 | 0 | 1 | 1 |

*Fig. 7.3g*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| K | T | A | 0 | 0 | 0 | 0 | 0 | 0 | 0 | 0 | 0 | 0 | 1 | 0 | 0 | 0 | 1 | 1 |
| K | T | D | 0 | 0 | 0 | 0 | 0 | 0 | 0 | 0 | 0 | 0 | 0 | 0 | 0 | 0 | 1 | 1 |
| K | T | E | 0 | 0 | 0 | 0 | 0 | 0 | 0 | 0 | 0 | 0 | 0 | 1 | 0 | 0 | 1 | 1 |
| K | T | G | 0 | 0 | 0 | 0 | 0 | 0 | 0 | 0 | 0 | 0 | 0 | 0 | 0 | 0 | 1 | 1 |
| K | T | H | 0 | 0 | 0 | 0 | 0 | 0 | 0 | 0 | 0 | 0 | 0 | 0 | 0 | 0 | 1 | 1 |
| K | T | N | 0 | 0 | 0 | 0 | 0 | 0 | 0 | 0 | 0 | 1 | 1 | 0 | 0 | 0 | 1 | 1 |
| K | T | Q | 0 | 0 | 0 | 0 | 0 | 0 | 0 | 0 | 0 | 1 | 1 | 0 | 0 | 0 | 1 | 1 |
| K | T | S | 0 | 0 | 0 | 0 | 0 | 0 | 0 | 0 | 0 | 1 | 1 | 0 | 0 | 0 | 1 | 1 |
| K | T | T | 0 | 0 | 0 | 0 | 0 | 0 | 0 | 0 | 0 | 1 | 0 | 0 | 0 | 0 | 1 | 1 |
| N | A | H | 0 | 0 | 0 | 0 | 0 | 0 | 0 | 0 | 0 | 0 | 0 | 0 | 0 | 0 | 0 | 0 |
| N | A | R | 0 | 0 | 0 | 0 | 0 | 1 | 0 | 0 | 0 | 0 | 0 | 0 | 0 | 0 | 0 | 0 |
| N | H | N | 0 | 0 | 0 | 0 | 0 | 0 | 0 | 0 | 0 | 0 | 0 | 0 | 0 | 0 | 0 | 0 |
| N | H | R | 0 | 0 | 0 | 0 | 0 | 0 | 0 | 0 | 0 | 0 | 0 | 0 | 0 | 0 | 0 | 0 |
| N | K | G | 0 | 0 | 0 | 0 | 0 | 0 | 0 | 0 | 0 | 0 | 0 | 0 | 0 | 0 | 0 | 0 |
| N | K | H | 0 | 0 | 0 | 0 | 0 | 0 | 0 | 0 | 0 | 0 | 0 | 0 | 0 | 0 | 0 | 0 |
| N | K | R | 0 | 0 | 0 | 0 | 0 | 0 | 0 | 0 | 0 | 0 | 0 | 0 | 0 | 0 | 0 | 0 |
| N | K | S | 0 | 0 | 0 | 0 | 0 | 0 | 0 | 0 | 0 | 0 | 0 | 0 | 0 | 0 | 0 | 0 |
| N | N | R | 0 | 0 | 0 | 0 | 0 | 0 | 0 | 0 | 0 | 0 | 0 | 0 | 0 | 0 | 1 | 0 |
| N | P | D | 0 | 0 | 0 | 0 | 0 | 0 | 0 | 0 | 0 | 0 | 0 | 0 | 0 | 0 | 1 | 0 |
| N | Q | H | 0 | 0 | 0 | 0 | 0 | 0 | 0 | 0 | 0 | 0 | 0 | 0 | 0 | 0 | 0 | 0 |
| N | Q | R | 0 | 0 | 0 | 0 | 0 | 0 | 0 | 0 | 0 | 0 | 0 | 0 | 0 | 0 | 0 | 0 |
| N | R | A | 0 | 0 | 0 | 0 | 0 | 1 | 0 | 0 | 0 | 0 | 0 | 0 | 0 | 0 | 0 | 0 |
| N | R | D | 0 | 0 | 0 | 0 | 0 | 0 | 0 | 0 | 0 | 0 | 0 | 0 | 0 | 0 | 0 | 0 |
| N | R | E | 0 | 0 | 0 | 0 | 0 | 0 | 0 | 0 | 0 | 0 | 0 | 0 | 0 | 0 | 0 | 0 |
| N | R | G | 0 | 0 | 0 | 0 | 0 | 1 | 0 | 0 | 0 | 0 | 0 | 0 | 0 | 0 | 0 | 0 |
| N | R | H | 0 | 0 | 0 | 0 | 0 | 0 | 0 | 0 | 0 | 0 | 0 | 0 | 0 | 0 | 0 | 0 |
| N | R | K | 0 | 0 | 0 | 0 | 0 | 0 | 0 | 0 | 0 | 0 | 0 | 0 | 0 | 0 | 0 | 0 |
| N | R | N | 0 | 0 | 0 | 0 | 0 | 1 | 0 | 0 | 0 | 0 | 0 | 0 | 0 | 0 | 0 | 0 |
| N | R | R | 0 | 0 | 0 | 0 | 0 | 0 | 1 | 0 | 0 | 0 | 0 | 0 | 0 | 0 | 0 | 0 |
| N | R | S | 0 | 0 | 0 | 0 | 0 | 0 | 0 | 0 | 0 | 0 | 0 | 0 | 0 | 0 | 0 | 0 |
| N | R | T | 0 | 0 | 0 | 0 | 0 | 0 | 0 | 0 | 0 | 0 | 0 | 0 | 0 | 0 | 0 | 0 |
| N | S | G | 0 | 0 | 0 | 0 | 0 | 0 | 0 | 0 | 0 | 0 | 0 | 0 | 0 | 0 | 0 | 0 |
| N | S | H | 0 | 0 | 0 | 0 | 0 | 0 | 0 | 0 | 0 | 0 | 0 | 0 | 0 | 0 | 0 | 0 |
| N | S | K | 0 | 0 | 0 | 0 | 0 | 0 | 0 | 0 | 0 | 0 | 0 | 0 | 0 | 0 | 0 | 0 |
| N | S | R | 0 | 0 | 0 | 0 | 0 | 0 | 1 | 0 | 0 | 0 | 0 | 0 | 0 | 0 | 0 | 0 |
| N | T | H | 0 | 0 | 0 | 0 | 0 | 0 | 0 | 0 | 0 | 0 | 0 | 0 | 0 | 0 | 0 | 0 |

*Fig. 7.3h*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| N | T | K | 0 | 0 | 0 | 0 | 1 | 0 | 1 | 1 | 0 | 0 | 0 | 0 | 0 | 0 | 0 | 0 |
| N | T | Q | 0 | 0 | 0 | 0 | 1 | 0 | 1 | 0 | 0 | 0 | 0 | 0 | 0 | 0 | 0 | 0 |
| N | T | R | 0 | 0 | 0 | 0 | 1 | 0 | 1 | 1 | 0 | 0 | 0 | 0 | 0 | 0 | 0 | 0 |
| N | T | S | 0 | 0 | 0 | 0 | 1 | 0 | 1 | 0 | 0 | 0 | 0 | 0 | 0 | 0 | 0 | 0 |
| P | N | D | 0 | 0 | 0 | 0 | 0 | 0 | 0 | 0 | 0 | 0 | 0 | 0 | 0 | 0 | 1 | 1 |
| P | T | T | 0 | 0 | 0 | 0 | 0 | 0 | 0 | 0 | 0 | 0 | 0 | 0 | 0 | 0 | 0 | 0 |
| Q | A | A | 0 | 0 | 0 | 0 | 0 | 0 | 0 | 0 | 1 | 0 | 1 | 0 | 0 | 0 | 0 | 0 |
| Q | A | H | 0 | 0 | 0 | 0 | 0 | 0 | 0 | 0 | 1 | 0 | 1 | 0 | 0 | 0 | 0 | 0 |
| Q | A | R | 0 | 0 | 0 | 0 | 0 | 0 | 0 | 0 | 1 | 0 | 1 | 0 | 0 | 0 | 1 | 1 |
| Q | G | K | 0 | 0 | 0 | 0 | 1 | 0 | 1 | 0 | 0 | 0 | 0 | 0 | 0 | 0 | 0 | 0 |
| Q | G | R | 0 | 0 | 0 | 0 | 0 | 0 | 0 | 0 | 1 | 0 | 1 | 1 | 0 | 0 | 0 | 0 |
| Q | K | G | 0 | 0 | 0 | 0 | 0 | 0 | 0 | 0 | 1 | 0 | 1 | 1 | 0 | 0 | 1 | 1 |
| Q | N | A | 0 | 0 | 0 | 0 | 0 | 0 | 0 | 0 | 1 | 0 | 1 | 0 | 0 | 0 | 0 | 0 |
| Q | N | H | 0 | 0 | 0 | 0 | 0 | 0 | 0 | 0 | 1 | 0 | 1 | 0 | 0 | 0 | 0 | 0 |
| Q | N | S | 0 | 0 | 0 | 0 | 0 | 0 | 0 | 0 | 1 | 0 | 1 | 0 | 0 | 0 | 1 | 0 |
| Q | P | P | 0 | 0 | 0 | 0 | 0 | 0 | 0 | 0 | 0 | 0 | 0 | 0 | 0 | 0 | 0 | 0 |
| Q | Q | G | 0 | 0 | 0 | 0 | 0 | 0 | 0 | 0 | 1 | 0 | 1 | 0 | 0 | 0 | 1 | 0 |
| Q | R | A | 0 | 0 | 0 | 0 | 1 | 0 | 1 | 0 | 1 | 1 | 1 | 1 | 0 | 0 | 1 | 1 |
| Q | R | D | 0 | 0 | 0 | 0 | 0 | 0 | 0 | 0 | 1 | 0 | 1 | 1 | 0 | 0 | 1 | 0 |
| Q | R | E | 0 | 0 | 0 | 0 | 0 | 0 | 0 | 0 | 1 | 0 | 1 | 1 | 0 | 0 | 1 | 1 |
| Q | R | G | 0 | 0 | 0 | 0 | 1 | 1 | 1 | 0 | 1 | 1 | 1 | 1 | 0 | 0 | 1 | 1 |
| Q | R | H | 0 | 0 | 0 | 0 | 0 | 0 | 0 | 0 | 1 | 0 | 1 | 1 | 0 | 0 | 1 | 1 |
| Q | R | N | 0 | 0 | 0 | 0 | 1 | 0 | 1 | 0 | 1 | 1 | 1 | 1 | 0 | 0 | 1 | 1 |
| Q | R | Q | 0 | 0 | 0 | 0 | 0 | 0 | 0 | 0 | 1 | 1 | 1 | 1 | 0 | 1 | 0 | 1 |
| Q | R | S | 0 | 0 | 0 | 0 | 1 | 0 | 1 | 1 | 1 | 1 | 1 | 1 | 0 | 0 | 1 | 1 |
| Q | S | H | 0 | 0 | 0 | 0 | 0 | 0 | 0 | 0 | 0 | 0 | 1 | 0 | 0 | 0 | 0 | 0 |
| Q | S | R | 0 | 0 | 0 | 0 | 0 | 0 | 0 | 0 | 1 | 0 | 1 | 1 | 0 | 0 | 1 | 1 |
| Q | S | S | 0 | 0 | 0 | 0 | 0 | 0 | 0 | 0 | 1 | 0 | 1 | 1 | 0 | 0 | 1 | 0 |
| Q | T | A | 0 | 0 | 0 | 0 | 0 | 0 | 0 | 0 | 1 | 0 | 1 | 0 | 0 | 0 | 0 | 0 |
| Q | T | G | 0 | 0 | 0 | 0 | 0 | 0 | 0 | 0 | 1 | 0 | 1 | 0 | 0 | 0 | 1 | 0 |
| Q | T | H | 0 | 0 | 0 | 0 | 0 | 0 | 0 | 0 | 1 | 0 | 1 | 0 | 0 | 0 | 0 | 0 |
| Q | T | R | 0 | 0 | 0 | 0 | 0 | 0 | 0 | 0 | 1 | 0 | 1 | 0 | 0 | 0 | 1 | 1 |
| R | A | G | 0 | 0 | 0 | 0 | 0 | 0 | 0 | 0 | 0 | 0 | 0 | 0 | 0 | 0 | 0 | 0 |
| R | A | T | 0 | 0 | 0 | 0 | 0 | 0 | 0 | 0 | 0 | 0 | 0 | 0 | 0 | 0 | 0 | 0 |
| R | G | T | 0 | 0 | 0 | 0 | 0 | 0 | 0 | 0 | 0 | 0 | 0 | 0 | 0 | 0 | 0 | 0 |
| R | H | D | 0 | 0 | 0 | 0 | 0 | 0 | 0 | 0 | 0 | 0 | 0 | 0 | 0 | 0 | 0 | 1 |

*Fig. 7.4a*

| 44 | 68 | 70 | GGG | GGA | GGT | GGC | GAG | GAA | GAT | GAC | GTG | GTA | GTT | GTC | GCG | GCA | GCT | GCC |
|---|---|---|---|---|---|---|---|---|---|---|---|---|---|---|---|---|---|---|
| R | H | T | 0 | 0 | 0 | 0 | 1 | 0 | 1 | 1 | 0 | 0 | 1 | 1 | 0 | 0 | 1 | 0 |
| R | N | T | 0 | 0 | 0 | 0 | 0 | 0 | 0 | 0 | 0 | 0 | 0 | 0 | 0 | 0 | 0 | 0 |
| R | R | A | 0 | 0 | 0 | 0 | 0 | 0 | 0 | 0 | 0 | 0 | 0 | 0 | 0 | 0 | 0 | 0 |
| R | R | D | 0 | 0 | 0 | 0 | 0 | 0 | 0 | 0 | 0 | 0 | 0 | 0 | 0 | 0 | 1 | 1 |
| R | R | E | 0 | 0 | 0 | 0 | 0 | 0 | 0 | 0 | 0 | 0 | 0 | 0 | 0 | 0 | 0 | 0 |
| R | R | G | 0 | 0 | 0 | 0 | 0 | 0 | 0 | 0 | 0 | 0 | 0 | 0 | 0 | 0 | 0 | 0 |
| R | R | N | 0 | 0 | 0 | 0 | 0 | 0 | 0 | 0 | 0 | 0 | 0 | 0 | 0 | 0 | 0 | 0 |
| R | R | Q | 0 | 0 | 0 | 0 | 0 | 0 | 0 | 0 | 0 | 0 | 0 | 0 | 0 | 0 | 0 | 0 |
| R | R | S | 0 | 0 | 0 | 0 | 0 | 0 | 0 | 0 | 0 | 0 | 0 | 1 | 0 | 0 | 0 | 0 |
| R | R | T | 0 | 0 | 0 | 0 | 0 | 0 | 0 | 0 | 0 | 0 | 1 | 0 | 0 | 0 | 0 | 0 |
| R | S | G | 0 | 0 | 0 | 0 | 0 | 0 | 0 | 0 | 0 | 0 | 0 | 0 | 0 | 0 | 0 | 0 |
| R | S | N | 0 | 0 | 0 | 0 | 0 | 0 | 0 | 0 | 0 | 0 | 0 | 0 | 0 | 0 | 0 | 0 |
| R | S | S | 0 | 0 | 0 | 0 | 0 | 0 | 0 | 0 | 0 | 0 | 0 | 0 | 0 | 0 | 0 | 0 |
| R | S | T | 0 | 0 | 0 | 0 | 0 | 0 | 0 | 0 | 0 | 0 | 0 | 0 | 0 | 0 | 0 | 0 |
| S | D | K | 0 | 0 | 0 | 0 | 0 | 0 | 0 | 1 | 0 | 1 | 1 | 0 | 0 | 0 | 1 | 0 |
| S | H | R | 0 | 0 | 0 | 0 | 0 | 0 | 0 | 1 | 0 | 0 | 0 | 0 | 0 | 0 | 0 | 0 |
| S | R | G | 0 | 0 | 0 | 0 | 0 | 0 | 0 | 1 | 0 | 0 | 0 | 0 | 0 | 0 | 0 | 0 |
| S | R | N | 0 | 0 | 0 | 0 | 1 | 0 | 0 | 1 | 0 | 0 | 1 | 0 | 0 | 0 | 1 | 1 |
| S | R | R | 0 | 0 | 0 | 0 | 0 | 0 | 0 | 1 | 0 | 0 | 0 | 0 | 0 | 0 | 0 | 0 |
| S | R | S | 0 | 0 | 0 | 0 | 1 | 0 | 0 | 1 | 0 | 0 | 0 | 0 | 0 | 0 | 0 | 0 |
| T | A | K | 0 | 0 | 0 | 0 | 0 | 0 | 1 | 1 | 0 | 0 | 1 | 0 | 0 | 0 | 0 | 0 |
| T | A | R | 0 | 0 | 0 | 0 | 0 | 0 | 0 | 1 | 0 | 0 | 0 | 1 | 0 | 0 | 0 | 0 |
| T | H | R | 0 | 0 | 0 | 0 | 0 | 0 | 0 | 1 | 0 | 0 | 0 | 0 | 0 | 0 | 0 | 0 |
| T | K | R | 0 | 0 | 0 | 0 | 0 | 0 | 0 | 1 | 0 | 0 | 0 | 0 | 0 | 0 | 0 | 0 |
| T | N | P | 0 | 0 | 0 | 0 | 0 | 0 | 0 | 0 | 0 | 0 | 0 | 0 | 0 | 0 | 0 | 1 |
| T | N | R | 0 | 0 | 0 | 0 | 1 | 0 | 0 | 1 | 0 | 0 | 1 | 0 | 0 | 0 | 0 | 0 |
| T | O | K | 0 | 0 | 0 | 0 | 0 | 0 | 1 | 0 | 0 | 0 | 1 | 0 | 0 | 0 | 0 | 0 |
| T | Q | R | 0 | 0 | 0 | 0 | 0 | 0 | 0 | 1 | 0 | 0 | 0 | 0 | 0 | 0 | 0 | 0 |
| T | R | A | 1 | 0 | 0 | 0 | 1 | 0 | 1 | 1 | 0 | 0 | 1 | 0 | 0 | 0 | 0 | 0 |
| T | R | D | 0 | 0 | 0 | 0 | 0 | 0 | 0 | 0 | 0 | 0 | 0 | 0 | 0 | 0 | 0 | 0 |
| T | R | E | 0 | 0 | 0 | 0 | 1 | 0 | 1 | 1 | 0 | 0 | 0 | 0 | 0 | 0 | 0 | 0 |
| T | R | G | 0 | 0 | 0 | 1 | 1 | 0 | 1 | 1 | 0 | 0 | 1 | 0 | 0 | 0 | 1 | 1 |
| T | R | H | 0 | 0 | 0 | 0 | 1 | 0 | 1 | 1 | 0 | 0 | 0 | 0 | 0 | 0 | 0 | 0 |
| T | R | K | 0 | 0 | 0 | 1 | 0 | 0 | 1 | 1 | 0 | 0 | 1 | 0 | 0 | 0 | 0 | 0 |
| T | R | N | 1 | 0 | 0 | 0 | 1 | 0 | 1 | 1 | 0 | 0 | 1 | 0 | 0 | 0 | 1 | 1 |
| T | R | Q | 1 | 0 | 0 | 0 | 1 | 0 | 1 | 1 | 0 | 1 | 1 | 0 | 0 | 0 | 1 | 1 |

*Fig. 7.4b*

| | | | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| 44 | 68 | 70 | | | | | | | | | | | | | | | | |
| N | T | K | 0 | 0 | 0 | 0 | 0 | 0 | 0 | 0 | 0 | 0 | 0 | 0 | 0 | 0 | 0 | 0 |
| N | T | Q | 0 | 0 | 0 | 0 | 0 | 0 | 1 | 0 | 0 | 0 | 0 | 0 | 0 | 0 | 0 | 0 |
| N | T | R | 0 | 0 | 0 | 0 | 0 | 0 | 0 | 1 | 0 | 0 | 0 | 0 | 0 | 0 | 0 | 0 |
| N | T | S | 0 | 0 | 0 | 0 | 0 | 0 | 1 | 0 | 0 | 0 | 0 | 0 | 0 | 0 | 0 | 0 |
| P | N | D | 0 | 0 | 0 | 0 | 0 | 0 | 0 | 0 | 0 | 0 | 1 | 1 | 0 | 0 | 1 | 1 |
| P | T | T | 0 | 0 | 0 | 0 | 0 | 0 | 0 | 0 | 0 | 0 | 0 | 0 | 0 | 0 | 1 | 0 |
| Q | A | A | 0 | 0 | 0 | 0 | 0 | 0 | 0 | 0 | 0 | 0 | 1 | 0 | 0 | 0 | 0 | 0 |
| Q | A | H | 0 | 0 | 0 | 0 | 0 | 0 | 0 | 0 | 0 | 0 | 1 | 0 | 0 | 0 | 0 | 0 |
| Q | A | R | 0 | 0 | 0 | 0 | 0 | 0 | 0 | 0 | 0 | 0 | 0 | 1 | 0 | 0 | 0 | 0 |
| Q | G | K | 0 | 0 | 0 | 0 | 1 | 0 | 1 | 1 | 0 | 0 | 0 | 0 | 0 | 0 | 0 | 0 |
| Q | G | R | 0 | 0 | 0 | 0 | 0 | 0 | 0 | 0 | 0 | 0 | 0 | 1 | 0 | 0 | 0 | 0 |
| Q | K | G | 0 | 0 | 0 | 0 | 0 | 0 | 0 | 0 | 0 | 0 | 0 | 0 | 0 | 0 | 0 | 0 |
| Q | N | A | 0 | 0 | 0 | 0 | 0 | 0 | 0 | 0 | 0 | 0 | 1 | 0 | 0 | 0 | 0 | 0 |
| Q | N | H | 0 | 0 | 0 | 0 | 0 | 0 | 0 | 0 | 0 | 0 | 1 | 0 | 0 | 0 | 0 | 0 |
| Q | N | S | 0 | 0 | 0 | 0 | 0 | 0 | 0 | 0 | 0 | 0 | 1 | 0 | 0 | 0 | 1 | 0 |
| Q | P | P | 0 | 0 | 0 | 0 | 0 | 0 | 0 | 0 | 0 | 0 | 0 | 0 | 0 | 0 | 0 | 0 |
| Q | Q | G | 0 | 0 | 0 | 0 | 0 | 0 | 0 | 0 | 0 | 0 | 1 | 0 | 0 | 0 | 1 | 1 |
| Q | R | A | 0 | 0 | 0 | 0 | 0 | 0 | 0 | 0 | 0 | 0 | 1 | 0 | 0 | 0 | 1 | 1 |
| Q | R | D | 0 | 0 | 0 | 0 | 0 | 0 | 0 | 0 | 0 | 0 | 1 | 0 | 0 | 0 | 1 | 1 |
| Q | R | E | 0 | 0 | 0 | 0 | 0 | 0 | 0 | 0 | 0 | 0 | 0 | 0 | 0 | 0 | 1 | 1 |
| Q | R | G | 0 | 0 | 0 | 0 | 0 | 0 | 0 | 0 | 0 | 1 | 1 | 1 | 0 | 0 | 1 | 1 |
| Q | R | H | 0 | 0 | 0 | 0 | 0 | 0 | 0 | 0 | 0 | 0 | 1 | 1 | 0 | 0 | 1 | 0 |
| Q | R | N | 0 | 0 | 0 | 0 | 0 | 0 | 0 | 0 | 0 | 0 | 1 | 1 | 0 | 0 | 1 | 0 |
| Q | R | Q | 0 | 0 | 0 | 0 | 0 | 0 | 0 | 0 | 0 | 0 | 1 | 1 | 0 | 0 | 1 | 1 |
| Q | R | S | 0 | 0 | 0 | 0 | 0 | 0 | 0 | 0 | 0 | 1 | 1 | 1 | 0 | 0 | 1 | 1 |
| Q | S | H | 0 | 0 | 0 | 0 | 0 | 0 | 0 | 0 | 0 | 0 | 1 | 0 | 0 | 0 | 0 | 0 |
| Q | S | R | 0 | 0 | 0 | 0 | 0 | 0 | 0 | 0 | 0 | 0 | 1 | 1 | 0 | 0 | 0 | 0 |
| Q | S | S | 0 | 0 | 0 | 0 | 0 | 0 | 0 | 0 | 0 | 0 | 1 | 0 | 0 | 0 | 1 | 0 |
| Q | T | A | 0 | 0 | 0 | 0 | 0 | 0 | 0 | 0 | 0 | 0 | 1 | 0 | 0 | 0 | 0 | 0 |
| Q | T | G | 0 | 0 | 0 | 0 | 0 | 0 | 0 | 0 | 0 | 0 | 1 | 0 | 0 | 0 | 0 | 0 |
| Q | T | H | 0 | 0 | 0 | 0 | 0 | 0 | 0 | 0 | 0 | 0 | 1 | 0 | 0 | 0 | 0 | 0 |
| Q | T | R | 0 | 0 | 0 | 0 | 0 | 0 | 0 | 0 | 0 | 0 | 1 | 1 | 0 | 0 | 0 | 0 |
| R | A | G | 0 | 0 | 0 | 0 | 0 | 0 | 0 | 0 | 0 | 0 | 0 | 0 | 0 | 0 | 0 | 0 |
| R | A | T | 0 | 0 | 0 | 0 | 0 | 0 | 0 | 0 | 0 | 0 | 0 | 0 | 0 | 0 | 0 | 0 |
| R | G | T | 0 | 0 | 0 | 0 | 0 | 0 | 0 | 0 | 0 | 0 | 0 | 0 | 0 | 0 | 0 | 0 |
| R | H | D | 0 | 0 | 0 | 0 | 0 | 0 | 0 | 0 | 0 | 0 | 1 | 0 | 0 | 0 | 1 | 1 |

*Fig. 7.4c*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| R | H | T | 0 | 0 | 0 | 0 | 1 | 0 | 1 | 1 | 0 | 0 | 0 | 0 | 0 | 0 | 0 | 0 |
| R | N | T | 0 | 0 | 0 | 0 | 0 | 0 | 0 | 0 | 0 | 0 | 0 | 0 | 0 | 0 | 0 | 0 |
| R | R | A | 0 | 0 | 0 | 0 | 0 | 0 | 0 | 0 | 0 | 0 | 0 | 0 | 0 | 0 | 0 | 0 |
| R | R | D | 0 | 0 | 0 | 0 | 0 | 0 | 0 | 0 | 1 | 1 | 1 | 0 | 1 | 1 |
| R | R | E | 0 | 0 | 0 | 0 | 0 | 0 | 0 | 0 | 0 | 0 | 0 | 0 | 0 | 0 | 0 | 0 |
| R | R | G | 0 | 0 | 0 | 0 | 0 | 0 | 0 | 0 | 0 | 0 | 0 | 0 | 0 | 0 | 0 | 0 |
| R | R | N | 0 | 0 | 0 | 0 | 0 | 0 | 0 | 0 | 0 | 0 | 0 | 0 | 0 | 0 | 0 | 0 |
| R | R | Q | 0 | 0 | 0 | 0 | 0 | 0 | 1 | 0 | 0 | 0 | 0 | 0 | 0 | 0 | 0 | 0 |
| R | R | S | 0 | 0 | 0 | 0 | 0 | 0 | 0 | 0 | 0 | 0 | 0 | 0 | 0 | 0 | 0 | 0 |
| R | R | T | 0 | 0 | 0 | 0 | 0 | 0 | 0 | 0 | 0 | 0 | 0 | 0 | 0 | 0 | 0 | 0 |
| R | S | G | 0 | 0 | 0 | 0 | 0 | 0 | 0 | 0 | 0 | 0 | 0 | 0 | 0 | 0 | 0 | 0 |
| R | S | N | 0 | 0 | 0 | 0 | 0 | 0 | 0 | 0 | 0 | 0 | 0 | 0 | 0 | 1 | 1 |
| R | S | S | 0 | 0 | 0 | 0 | 0 | 0 | 0 | 0 | 0 | 0 | 0 | 0 | 0 | 0 | 0 | 0 |
| R | S | T | 0 | 0 | 0 | 0 | 0 | 0 | 0 | 0 | 0 | 0 | 0 | 0 | 0 | 0 | 0 | 0 |
| S | D | K | 0 | 0 | 0 | 0 | 0 | 0 | 0 | 0 | 0 | 1 | 0 | 0 | 1 | 0 |
| S | H | R | 0 | 0 | 0 | 0 | 0 | 0 | 0 | 0 | 0 | 0 | 0 | 0 | 0 | 0 | 0 | 0 |
| S | R | G | 0 | 0 | 0 | 0 | 0 | 0 | 1 | 0 | 0 | 0 | 0 | 0 | 0 | 0 | 0 | 0 |
| S | R | N | 0 | 0 | 0 | 0 | 1 | 0 | 1 | 1 | 0 | 0 | 0 | 0 | 0 | 0 | 0 | 0 |
| S | R | R | 0 | 0 | 0 | 0 | 0 | 0 | 0 | 1 | 0 | 0 | 0 | 1 | 0 | 0 | 0 | 0 |
| S | R | S | 0 | 0 | 0 | 0 | 0 | 0 | 1 | 0 | 0 | 0 | 0 | 0 | 0 | 0 | 0 | 0 |
| T | A | K | 0 | 0 | 0 | 0 | 0 | 0 | 0 | 0 | 0 | 0 | 0 | 0 | 0 | 0 | 0 | 0 |
| T | A | R | 0 | 0 | 0 | 0 | 0 | 0 | 0 | 0 | 0 | 0 | 0 | 0 | 0 | 0 | 0 | 0 |
| T | H | R | 0 | 0 | 0 | 0 | 0 | 0 | 0 | 0 | 0 | 0 | 0 | 0 | 0 | 0 | 0 | 0 |
| T | K | R | 0 | 0 | 0 | 0 | 0 | 0 | 0 | 0 | 0 | 0 | 0 | 0 | 0 | 0 | 0 | 0 |
| T | N | P | 0 | 0 | 0 | 0 | 0 | 0 | 0 | 0 | 0 | 1 | 0 | 0 | 1 | 1 |
| T | N | R | 0 | 0 | 0 | 0 | 0 | 0 | 1 | 0 | 0 | 0 | 0 | 0 | 0 | 0 | 0 | 0 |
| T | Q | K | 0 | 0 | 0 | 0 | 0 | 0 | 0 | 0 | 0 | 0 | 0 | 0 | 0 | 0 | 0 | 0 |
| T | Q | R | 0 | 0 | 0 | 0 | 0 | 0 | 1 | 1 | 0 | 0 | 0 | 0 | 0 | 0 | 0 | 0 |
| T | R | A | 0 | 0 | 0 | 0 | 1 | 0 | 1 | 1 | 0 | 0 | 0 | 0 | 0 | 0 | 0 | 0 |
| T | R | D | 0 | 0 | 0 | 0 | 0 | 0 | 1 | 0 | 0 | 0 | 0 | 0 | 0 | 0 | 0 | 0 |
| T | R | E | 0 | 0 | 0 | 0 | 0 | 0 | 1 | 0 | 0 | 0 | 0 | 0 | 0 | 0 | 0 | 0 |
| T | R | G | 0 | 0 | 0 | 0 | 1 | 0 | 1 | 0 | 0 | 0 | 0 | 0 | 0 | 0 | 0 | 0 |
| T | R | H | 0 | 0 | 0 | 0 | 0 | 0 | 1 | 0 | 0 | 0 | 0 | 0 | 0 | 0 | 0 | 0 |
| T | R | K | 0 | 0 | 0 | 0 | 0 | 0 | 0 | 0 | 0 | 0 | 0 | 0 | 0 | 0 | 0 | 0 |
| T | R | N | 0 | 0 | 0 | 0 | 1 | 0 | 1 | 0 | 0 | 0 | 0 | 0 | 0 | 0 | 0 | 0 |
| T | R | Q | 0 | 0 | 0 | 0 | 1 | 0 | 1 | 1 | 0 | 0 | 0 | 0 | 0 | 0 | 0 | 0 |

*Fig. 7.4d*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| N | T | K | 0 | 0 | 0 | 0 | 0 | 0 | 0 | 0 | 0 | 0 | 0 | 0 | 0 | 0 | 0 | 0 |
| N | T | Q | 0 | 0 | 0 | 0 | 0 | 0 | 0 | 0 | 0 | 0 | 0 | 0 | 0 | 0 | 0 | 0 |
| N | T | R | 0 | 0 | 0 | 0 | 0 | 0 | 0 | 0 | 0 | 0 | 0 | 0 | 0 | 0 | 0 | 0 |
| N | T | S | 0 | 0 | 0 | 0 | 0 | 0 | 0 | 0 | 0 | 0 | 0 | 0 | 0 | 0 | 0 | 0 |
| P | N | D | 0 | 0 | 0 | 0 | 0 | 0 | 0 | 0 | 0 | 0 | 0 | 0 | 0 | 0 | 0 | 0 |
| P | T | T | 0 | 0 | 0 | 0 | 0 | 0 | 0 | 0 | 0 | 0 | 0 | 0 | 0 | 0 | 0 | 0 |
| Q | A | A | 0 | 0 | 0 | 0 | 0 | 0 | 0 | 0 | 0 | 0 | 0 | 0 | 0 | 0 | 0 | 0 |
| Q | A | H | 0 | 0 | 0 | 0 | 0 | 0 | 0 | 0 | 0 | 0 | 0 | 0 | 0 | 0 | 0 | 0 |
| Q | A | R | 0 | 0 | 0 | 0 | 0 | 0 | 0 | 0 | 0 | 0 | 0 | 0 | 0 | 0 | 0 | 0 |
| Q | G | K | 0 | 0 | 0 | 0 | 0 | 0 | 0 | 0 | 0 | 0 | 0 | 0 | 0 | 0 | 0 | 0 |
| Q | G | R | 0 | 0 | 0 | 0 | 0 | 0 | 0 | 0 | 0 | 0 | 0 | 0 | 0 | 0 | 0 | 0 |
| Q | K | G | 0 | 0 | 0 | 0 | 0 | 0 | 0 | 0 | 0 | 0 | 0 | 0 | 0 | 0 | 0 | 0 |
| Q | N | A | 0 | 0 | 0 | 0 | 0 | 0 | 0 | 0 | 0 | 0 | 0 | 0 | 0 | 0 | 0 | 0 |
| Q | N | H | 0 | 0 | 0 | 0 | 0 | 0 | 0 | 0 | 0 | 0 | 0 | 0 | 0 | 0 | 0 | 0 |
| Q | N | S | 0 | 0 | 0 | 0 | 0 | 0 | 0 | 0 | 0 | 0 | 0 | 0 | 0 | 0 | 0 | 0 |
| Q | P | P | 0 | 0 | 0 | 0 | 0 | 0 | 0 | 0 | 0 | 0 | 0 | 0 | 0 | 0 | 0 | 0 |
| Q | Q | G | 0 | 0 | 0 | 0 | 0 | 0 | 0 | 0 | 0 | 0 | 0 | 0 | 0 | 0 | 0 | 0 |
| Q | R | A | 0 | 0 | 0 | 0 | 0 | 0 | 0 | 0 | 0 | 1 | 0 | 0 | 0 | 0 | 0 | 0 |
| Q | R | D | 0 | 0 | 0 | 0 | 0 | 0 | 0 | 0 | 0 | 1 | 0 | 0 | 0 | 1 | 0 | 0 |
| Q | R | E | 0 | 0 | 0 | 0 | 0 | 0 | 0 | 0 | 0 | 0 | 0 | 0 | 0 | 0 | 0 | 0 |
| Q | R | G | 0 | 0 | 0 | 0 | 0 | 0 | 0 | 0 | 0 | 1 | 0 | 0 | 0 | 1 | 0 | 0 |
| Q | R | H | 0 | 0 | 0 | 0 | 0 | 0 | 0 | 0 | 0 | 0 | 0 | 0 | 0 | 0 | 0 | 0 |
| Q | R | N | 0 | 0 | 0 | 0 | 0 | 0 | 0 | 0 | 0 | 1 | 0 | 0 | 0 | 1 | 0 | 0 |
| Q | R | Q | 0 | 0 | 0 | 0 | 0 | 0 | 0 | 0 | 0 | 0 | 0 | 0 | 0 | 0 | 0 | 0 |
| Q | R | S | 0 | 0 | 0 | 0 | 0 | 0 | 0 | 0 | 0 | 1 | 0 | 0 | 0 | 1 | 0 | 0 |
| Q | S | H | 0 | 0 | 0 | 0 | 0 | 0 | 0 | 0 | 0 | 0 | 0 | 0 | 0 | 0 | 0 | 0 |
| Q | S | R | 0 | 0 | 0 | 0 | 0 | 0 | 0 | 0 | 0 | 0 | 0 | 0 | 0 | 0 | 0 | 0 |
| Q | S | S | 0 | 0 | 0 | 0 | 0 | 0 | 0 | 0 | 0 | 0 | 0 | 0 | 0 | 0 | 0 | 0 |
| Q | T | A | 0 | 0 | 0 | 0 | 0 | 0 | 0 | 0 | 0 | 0 | 0 | 0 | 0 | 0 | 0 | 0 |
| Q | T | G | 0 | 0 | 0 | 0 | 0 | 0 | 0 | 0 | 0 | 0 | 0 | 0 | 0 | 0 | 0 | 0 |
| Q | T | H | 0 | 0 | 0 | 0 | 0 | 0 | 0 | 0 | 0 | 0 | 0 | 0 | 0 | 0 | 0 | 0 |
| Q | T | R | 0 | 0 | 0 | 0 | 0 | 0 | 0 | 0 | 0 | 0 | 0 | 0 | 0 | 0 | 0 | 0 |
| R | A | G | 0 | 0 | 0 | 0 | 0 | 0 | 0 | 0 | 0 | 0 | 0 | 0 | 0 | 0 | 0 | 0 |
| R | A | T | 0 | 0 | 0 | 0 | 0 | 0 | 0 | 0 | 0 | 0 | 0 | 0 | 0 | 0 | 0 | 0 |
| R | G | T | 0 | 0 | 0 | 0 | 0 | 0 | 0 | 0 | 0 | 0 | 0 | 0 | 0 | 0 | 0 | 0 |
| R | H | D | 0 | 0 | 0 | 0 | 0 | 0 | 0 | 0 | 0 | 0 | 0 | 0 | 0 | 0 | 0 | 0 |

*Fig. 7.4e*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| R | H | T | 0 | 0 | 0 | 0 | 0 | 0 | 1 | 0 | 0 | 0 | 0 | 0 | 0 | 0 | 0 | 0 |
| R | N | T | 0 | 0 | 0 | 0 | 0 | 0 | 0 | 0 | 0 | 0 | 0 | 0 | 0 | 0 | 0 | 0 |
| R | R | A | 0 | 0 | 0 | 0 | 0 | 0 | 0 | 0 | 0 | 0 | 0 | 0 | 0 | 0 | 0 | 0 |
| R | R | D | 0 | 0 | 0 | 0 | 0 | 0 | 0 | 0 | 0 | 0 | 0 | 0 | 0 | 0 | 1 | 1 |
| R | R | E | 0 | 0 | 0 | 0 | 0 | 0 | 0 | 0 | 0 | 0 | 0 | 0 | 0 | 0 | 0 | 0 |
| R | R | G | 0 | 0 | 0 | 0 | 0 | 0 | 0 | 0 | 0 | 0 | 0 | 0 | 0 | 0 | 0 | 0 |
| R | R | N | 0 | 0 | 0 | 0 | 0 | 0 | 0 | 0 | 0 | 0 | 0 | 0 | 0 | 0 | 0 | 0 |
| R | R | Q | 0 | 0 | 0 | 0 | 0 | 0 | 0 | 0 | 0 | 0 | 0 | 0 | 0 | 0 | 0 | 0 |
| R | R | S | 0 | 0 | 0 | 0 | 0 | 0 | 0 | 0 | 0 | 0 | 0 | 0 | 0 | 0 | 0 | 0 |
| R | R | T | 0 | 0 | 0 | 0 | 0 | 0 | 0 | 0 | 0 | 0 | 0 | 0 | 0 | 0 | 0 | 0 |
| R | S | G | 0 | 0 | 0 | 0 | 0 | 0 | 0 | 0 | 0 | 0 | 0 | 0 | 0 | 0 | 0 | 0 |
| R | S | N | 0 | 0 | 0 | 0 | 0 | 0 | 0 | 0 | 0 | 0 | 0 | 0 | 0 | 0 | 0 | 0 |
| R | S | S | 0 | 0 | 0 | 0 | 0 | 0 | 0 | 0 | 0 | 0 | 0 | 0 | 0 | 0 | 0 | 0 |
| R | S | T | 0 | 0 | 0 | 0 | 0 | 0 | 0 | 0 | 0 | 0 | 0 | 0 | 0 | 0 | 0 | 0 |
| S | D | K | 0 | 0 | 0 | 0 | 0 | 0 | 0 | 0 | 0 | 0 | 0 | 0 | 0 | 0 | 0 | 0 |
| S | H | R | 0 | 0 | 0 | 0 | 0 | 0 | 0 | 0 | 0 | 0 | 0 | 0 | 0 | 0 | 0 | 0 |
| S | R | G | 0 | 0 | 0 | 0 | 0 | 0 | 0 | 0 | 0 | 0 | 0 | 0 | 0 | 0 | 0 | 0 |
| S | R | N | 0 | 0 | 0 | 0 | 0 | 0 | 0 | 0 | 0 | 0 | 0 | 0 | 0 | 0 | 0 | 0 |
| S | R | R | 0 | 0 | 0 | 0 | 0 | 0 | 0 | 0 | 0 | 0 | 0 | 0 | 0 | 0 | 0 | 0 |
| S | R | S | 0 | 0 | 0 | 0 | 0 | 0 | 0 | 0 | 0 | 0 | 0 | 0 | 0 | 0 | 0 | 0 |
| T | A | K | 0 | 0 | 0 | 0 | 0 | 0 | 0 | 0 | 0 | 0 | 0 | 0 | 0 | 0 | 0 | 0 |
| T | A | R | 0 | 0 | 0 | 0 | 0 | 0 | 0 | 0 | 0 | 0 | 0 | 0 | 0 | 0 | 0 | 0 |
| T | H | R | 0 | 0 | 0 | 0 | 0 | 0 | 0 | 0 | 0 | 0 | 0 | 0 | 0 | 0 | 0 | 0 |
| T | K | R | 0 | 0 | 0 | 0 | 0 | 0 | 0 | 0 | 0 | 0 | 0 | 0 | 0 | 0 | 0 | 0 |
| T | N | P | 0 | 0 | 0 | 0 | 0 | 0 | 0 | 0 | 0 | 0 | 0 | 0 | 0 | 0 | 0 | 1 |
| T | N | R | 0 | 0 | 0 | 0 | 0 | 0 | 0 | 0 | 0 | 0 | 0 | 0 | 0 | 0 | 0 | 0 |
| T | Q | K | 0 | 0 | 0 | 0 | 0 | 0 | 0 | 0 | 0 | 0 | 0 | 0 | 0 | 0 | 0 | 0 |
| T | Q | R | 0 | 0 | 0 | 0 | 0 | 0 | 0 | 0 | 0 | 0 | 0 | 0 | 0 | 0 | 0 | 0 |
| T | R | A | 0 | 0 | 0 | 0 | 0 | 0 | 0 | 0 | 0 | 0 | 0 | 0 | 0 | 0 | 0 | 0 |
| T | R | D | 0 | 0 | 0 | 0 | 0 | 0 | 0 | 0 | 0 | 0 | 0 | 0 | 0 | 0 | 0 | 0 |
| T | R | E | 0 | 0 | 0 | 0 | 0 | 0 | 0 | 0 | 0 | 0 | 0 | 0 | 0 | 0 | 0 | 0 |
| T | R | G | 0 | 0 | 0 | 0 | 0 | 0 | 0 | 0 | 0 | 0 | 0 | 0 | 0 | 0 | 0 | 0 |
| T | R | H | 0 | 0 | 0 | 0 | 0 | 0 | 0 | 0 | 0 | 0 | 0 | 0 | 0 | 0 | 0 | 0 |
| T | R | K | 0 | 0 | 0 | 0 | 0 | 0 | 0 | 0 | 0 | 0 | 0 | 0 | 0 | 0 | 0 | 0 |
| T | R | N | 0 | 0 | 0 | 0 | 0 | 0 | 0 | 0 | 0 | 0 | 0 | 0 | 0 | 0 | 0 | 0 |
| T | R | Q | 0 | 0 | 0 | 0 | 0 | 0 | 0 | 0 | 0 | 0 | 0 | 0 | 0 | 0 | 0 | 0 |

*Fig. 7.4f*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| N | T | K | 0 | 0 | 0 | 0 | 0 | 0 | 0 | 0 | 0 | 0 | 0 | 0 | 0 | 0 | 0 | 0 |
| N | T | Q | 0 | 0 | 0 | 0 | 0 | 0 | 0 | 0 | 0 | 0 | 0 | 0 | 0 | 0 | 0 | 0 |
| N | T | R | 0 | 0 | 0 | 0 | 0 | 0 | 1 | 0 | 0 | 0 | 0 | 0 | 0 | 0 | 0 | 0 |
| N | T | S | 0 | 0 | 0 | 0 | 0 | 0 | 0 | 0 | 0 | 0 | 0 | 0 | 0 | 0 | 0 | 0 |
| P | N | D | 0 | 0 | 0 | 0 | 0 | 0 | 0 | 0 | 0 | 1 | 0 | 0 | 0 | 1 | 1 | 0 |
| P | T | T | 0 | 0 | 0 | 0 | 0 | 0 | 0 | 0 | 0 | 0 | 0 | 0 | 0 | 0 | 1 | 0 |
| Q | A | A | 0 | 0 | 0 | 0 | 0 | 0 | 0 | 0 | 0 | 0 | 0 | 0 | 0 | 0 | 0 | 0 |
| Q | A | H | 0 | 0 | 0 | 0 | 0 | 0 | 0 | 0 | 0 | 0 | 0 | 0 | 0 | 0 | 0 | 0 |
| Q | A | R | 0 | 0 | 0 | 0 | 0 | 0 | 0 | 0 | 0 | 0 | 0 | 0 | 0 | 0 | 0 | 0 |
| Q | G | K | 0 | 0 | 0 | 0 | 0 | 0 | 0 | 0 | 0 | 0 | 0 | 0 | 0 | 0 | 0 | 0 |
| Q | G | R | 0 | 0 | 0 | 0 | 0 | 0 | 0 | 0 | 0 | 0 | 0 | 0 | 0 | 0 | 0 | 0 |
| Q | K | G | 0 | 0 | 0 | 0 | 0 | 0 | 0 | 0 | 0 | 0 | 0 | 0 | 0 | 0 | 0 | 0 |
| Q | N | A | 0 | 0 | 0 | 0 | 0 | 0 | 0 | 0 | 0 | 0 | 0 | 0 | 0 | 0 | 0 | 0 |
| Q | N | H | 0 | 0 | 0 | 0 | 0 | 0 | 0 | 0 | 0 | 0 | 0 | 0 | 0 | 0 | 0 | 0 |
| Q | N | S | 0 | 0 | 0 | 0 | 0 | 0 | 0 | 0 | 0 | 0 | 0 | 0 | 0 | 0 | 0 | 0 |
| Q | P | P | 0 | 0 | 0 | 0 | 0 | 0 | 0 | 0 | 0 | 0 | 0 | 0 | 0 | 0 | 1 | 1 |
| Q | Q | G | 0 | 0 | 0 | 0 | 0 | 0 | 0 | 0 | 0 | 0 | 0 | 0 | 0 | 0 | 0 | 0 |
| Q | R | A | 0 | 0 | 0 | 0 | 0 | 0 | 0 | 0 | 0 | 0 | 0 | 0 | 0 | 0 | 0 | 0 |
| Q | R | D | 0 | 0 | 0 | 0 | 0 | 0 | 0 | 0 | 0 | 1 | 0 | 0 | 0 | 1 | 1 | 0 |
| Q | R | E | 0 | 0 | 0 | 0 | 0 | 0 | 0 | 0 | 0 | 0 | 0 | 0 | 0 | 1 | 1 | 0 |
| Q | R | G | 0 | 0 | 0 | 0 | 0 | 0 | 0 | 0 | 0 | 0 | 0 | 0 | 0 | 0 | 1 | 0 |
| Q | R | H | 0 | 0 | 0 | 0 | 0 | 0 | 0 | 0 | 0 | 0 | 0 | 0 | 0 | 0 | 0 | 0 |
| Q | R | N | 0 | 0 | 0 | 0 | 0 | 0 | 0 | 0 | 0 | 0 | 0 | 0 | 0 | 0 | 0 | 0 |
| Q | R | Q | 0 | 0 | 0 | 0 | 0 | 0 | 0 | 0 | 0 | 0 | 0 | 0 | 0 | 0 | 0 | 0 |
| Q | R | S | 0 | 0 | 0 | 0 | 0 | 0 | 0 | 0 | 0 | 1 | 0 | 0 | 0 | 1 | 0 | 0 |
| Q | S | H | 0 | 0 | 0 | 0 | 0 | 0 | 0 | 0 | 0 | 0 | 0 | 0 | 0 | 0 | 0 | 0 |
| Q | S | R | 0 | 0 | 0 | 0 | 0 | 0 | 0 | 0 | 0 | 0 | 0 | 0 | 0 | 0 | 0 | 0 |
| Q | S | S | 0 | 0 | 0 | 0 | 0 | 0 | 0 | 0 | 0 | 0 | 0 | 0 | 0 | 0 | 0 | 0 |
| Q | T | A | 0 | 0 | 0 | 0 | 0 | 0 | 0 | 0 | 0 | 0 | 0 | 0 | 0 | 0 | 0 | 0 |
| Q | T | G | 0 | 0 | 0 | 0 | 0 | 0 | 0 | 0 | 0 | 0 | 0 | 0 | 0 | 0 | 0 | 0 |
| Q | T | H | 0 | 0 | 0 | 0 | 0 | 0 | 0 | 0 | 0 | 0 | 0 | 0 | 0 | 0 | 0 | 0 |
| Q | T | R | 0 | 0 | 0 | 0 | 0 | 0 | 0 | 0 | 0 | 0 | 0 | 0 | 0 | 0 | 0 | 0 |
| R | A | G | 0 | 0 | 0 | 0 | 0 | 0 | 0 | 0 | 0 | 0 | 0 | 0 | 0 | 0 | 1 | 0 |
| R | A | T | 0 | 0 | 0 | 0 | 0 | 0 | 0 | 0 | 0 | 0 | 0 | 0 | 0 | 1 | 1 | 0 |
| R | G | T | 0 | 0 | 0 | 0 | 0 | 0 | 0 | 0 | 0 | 0 | 0 | 0 | 0 | 0 | 1 | 0 |
| R | H | D | 0 | 0 | 0 | 0 | 0 | 0 | 0 | 0 | 0 | 1 | 0 | 0 | 0 | 1 | 1 | 1 |

*Fig. 7.4g*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| R | H | T | 0 | 0 | 0 | 0 | 0 | 0 | 1 | 0 | 0 | 0 | 0 | 0 | 0 | 0 | 0 | 0 |
| R | N | T | 0 | 0 | 0 | 0 | 0 | 0 | 0 | 0 | 0 | 0 | 0 | 0 | 0 | 0 | 1 | 0 |
| R | R | A | 0 | 0 | 0 | 0 | 0 | 0 | 1 | 1 | 0 | 0 | 0 | 1 | 0 | 0 | 0 | 0 |
| R | R | D | 0 | 0 | 0 | 0 | 0 | 0 | 0 | 0 | 0 | 0 | 1 | 1 | 0 | 0 | 1 | 1 |
| R | R | E | 0 | 0 | 0 | 0 | 0 | 0 | 1 | 0 | 0 | 0 | 1 | 1 | 0 | 0 | 1 | 0 |
| R | R | G | 0 | 0 | 0 | 0 | 0 | 0 | 1 | 1 | 0 | 0 | 0 | 1 | 0 | 0 | 1 | 1 |
| R | R | N | 0 | 0 | 0 | 0 | 0 | 0 | 1 | 0 | 0 | 0 | 0 | 0 | 0 | 0 | 0 | 0 |
| R | R | Q | 0 | 0 | 0 | 0 | 0 | 0 | 1 | 0 | 0 | 0 | 0 | 0 | 0 | 0 | 0 | 0 |
| R | R | S | 0 | 0 | 0 | 0 | 0 | 0 | 1 | 1 | 0 | 0 | 0 | 1 | 0 | 0 | 0 | 0 |
| R | R | T | 0 | 0 | 0 | 0 | 0 | 0 | 1 | 0 | 0 | 0 | 0 | 1 | 0 | 0 | 1 | 0 |
| R | S | G | 0 | 0 | 0 | 0 | 0 | 0 | 1 | 1 | 0 | 0 | 0 | 0 | 0 | 0 | 1 | 0 |
| R | S | N | 0 | 0 | 0 | 0 | 0 | 0 | 1 | 0 | 0 | 0 | 0 | 0 | 0 | 0 | 1 | 1 |
| R | S | S | 0 | 0 | 0 | 0 | 0 | 0 | 0 | 0 | 0 | 0 | 0 | 0 | 0 | 0 | 1 | 0 |
| R | S | T | 0 | 0 | 0 | 0 | 0 | 0 | 0 | 0 | 0 | 0 | 0 | 0 | 0 | 0 | 1 | 0 |
| S | D | K | 0 | 0 | 0 | 0 | 0 | 0 | 0 | 0 | 0 | 0 | 0 | 0 | 0 | 0 | 0 | 0 |
| S | H | R | 0 | 0 | 0 | 0 | 0 | 0 | 0 | 0 | 0 | 0 | 0 | 0 | 0 | 0 | 0 | 0 |
| S | R | G | 0 | 0 | 0 | 0 | 0 | 0 | 0 | 0 | 0 | 0 | 0 | 0 | 0 | 0 | 0 | 0 |
| S | R | N | 0 | 0 | 0 | 0 | 0 | 0 | 0 | 0 | 0 | 0 | 0 | 0 | 0 | 0 | 0 | 0 |
| S | R | R | 0 | 0 | 0 | 0 | 0 | 0 | 0 | 0 | 0 | 0 | 0 | 0 | 0 | 0 | 0 | 0 |
| S | R | S | 0 | 0 | 0 | 0 | 0 | 0 | 0 | 0 | 0 | 0 | 0 | 0 | 0 | 0 | 0 | 0 |
| T | A | K | 0 | 0 | 0 | 0 | 0 | 0 | 0 | 0 | 0 | 0 | 0 | 0 | 0 | 0 | 0 | 0 |
| T | A | R | 0 | 0 | 0 | 0 | 0 | 0 | 0 | 0 | 0 | 0 | 0 | 0 | 0 | 0 | 0 | 0 |
| T | H | R | 0 | 0 | 0 | 0 | 0 | 0 | 0 | 0 | 0 | 0 | 0 | 0 | 0 | 0 | 0 | 0 |
| T | K | R | 0 | 0 | 0 | 0 | 0 | 0 | 0 | 0 | 0 | 0 | 0 | 0 | 0 | 0 | 0 | 0 |
| T | N | P | 0 | 0 | 0 | 0 | 0 | 0 | 0 | 0 | 0 | 0 | 0 | 1 | 0 | 0 | 1 | 1 |
| T | N | R | 0 | 0 | 0 | 0 | 0 | 0 | 0 | 0 | 0 | 0 | 0 | 0 | 0 | 0 | 0 | 0 |
| T | Q | K | 0 | 0 | 0 | 0 | 0 | 0 | 0 | 0 | 0 | 0 | 0 | 0 | 0 | 0 | 0 | 0 |
| T | Q | R | 0 | 0 | 0 | 0 | 0 | 0 | 0 | 0 | 0 | 0 | 0 | 0 | 0 | 0 | 0 | 0 |
| T | R | A | 0 | 0 | 0 | 0 | 0 | 0 | 0 | 0 | 0 | 0 | 0 | 0 | 0 | 0 | 0 | 0 |
| T | R | D | 0 | 0 | 0 | 0 | 0 | 0 | 0 | 0 | 0 | 0 | 0 | 0 | 0 | 0 | 0 | 0 |
| T | R | E | 0 | 0 | 0 | 0 | 0 | 0 | 0 | 0 | 0 | 0 | 0 | 0 | 0 | 0 | 0 | 0 |
| T | R | G | 0 | 0 | 0 | 0 | 0 | 0 | 0 | 0 | 0 | 0 | 0 | 0 | 0 | 0 | 0 | 0 |
| T | R | H | 0 | 0 | 0 | 0 | 0 | 0 | 0 | 0 | 0 | 0 | 0 | 0 | 0 | 0 | 0 | 0 |
| T | R | K | 0 | 0 | 0 | 0 | 0 | 0 | 0 | 0 | 0 | 0 | 0 | 0 | 0 | 0 | 0 | 0 |
| T | R | N | 0 | 0 | 0 | 0 | 0 | 0 | 0 | 0 | 0 | 0 | 0 | 0 | 0 | 0 | 0 | 0 |
| T | R | Q | 0 | 0 | 0 | 0 | 0 | 0 | 1 | 0 | 0 | 0 | 0 | 0 | 0 | 0 | 0 | 0 |

*Fig. 7.4h*

| 44 | 68 | 70 | GGG | GGA | GGT | GGC | GAG | GAA | GAT | GAC | GTG | GTA | GTT | GTC | GCG | GCA | GCT | GCC |
|----|----|----|-----|-----|-----|-----|-----|-----|-----|-----|-----|-----|-----|-----|-----|-----|-----|-----|
| T | R | R | 0 | 0 | 0 | 0 | 0 | 0 | 1 | 0 | 0 | 0 | 1 | 0 | 0 | 0 | 1 |
| T | R | S | 0 | 0 | 0 | 0 | 1 | 0 | 1 | 1 | 0 | 0 | 1 | 1 | 0 | 0 | 0 | 1 |
| T | R | T | 0 | 0 | 0 | 0 | 1 | 0 | 1 | 1 | 0 | 0 | 1 | 1 | 0 | 0 | 1 | 1 |
| T | S | K | 0 | 0 | 0 | 0 | 0 | 0 | 1 | 0 | 0 | 0 | 0 | 0 | 0 | 0 | 0 | 0 |
| T | S | R | 0 | 0 | 0 | 0 | 0 | 0 | 0 | 0 | 0 | 0 | 0 | 0 | 0 | 0 | 0 | 0 |
| T | T | K | 0 | 0 | 0 | 0 | 0 | 0 | 1 | 0 | 0 | 0 | 1 | 0 | 0 | 0 | 0 | 0 |
| T | T | R | 0 | 0 | 0 | 0 | 0 | 0 | 1 | 0 | 0 | 0 | 0 | 0 | 0 | 0 | 0 | 0 |

*Fig. 7.5a*

| 44 | 68 | 70 | TGG | TGA | TGT | TGC | TAG | TAA | TAT | TAC | TTG | TTA | TTT | TTC | TCG | TCA | TCT | TCC |
|---|---|---|---|---|---|---|---|---|---|---|---|---|---|---|---|---|---|---|
| T | R | R | 0 | 0 | 0 | 0 | 0 | 0 | 0 | 1 | 0 | 0 | 0 | 1 | 0 | 0 | 0 | 0 |
| T | R | S | 0 | 0 | 0 | 0 | 1 | 0 | 1 | 0 | 0 | 0 | 0 | 0 | 0 | 0 | 0 | 0 |
| T | R | T | 0 | 0 | 0 | 0 | 1 | 0 | 1 | 1 | 0 | 0 | 0 | 0 | 0 | 0 | 0 | 0 |
| T | S | K | 0 | 0 | 0 | 0 | 0 | 0 | 0 | 0 | 0 | 0 | 0 | 0 | 0 | 0 | 0 | 0 |
| T | S | R | 0 | 0 | 0 | 0 | 0 | 0 | 0 | 1 | 0 | 0 | 0 | 0 | 0 | 0 | 0 | 0 |
| T | T | K | 0 | 0 | 0 | 0 | 0 | 0 | 0 | 0 | 0 | 0 | 0 | 0 | 0 | 0 | 0 | 0 |
| T | T | R | 0 | 0 | 0 | 0 | 0 | 0 | 0 | 1 | 0 | 0 | 0 | 0 | 0 | 0 | 0 | 0 |

*Fig. 7.5b*

| 44 | 68 | 70 | AGG | AGA | AGT | AGC | AAG | AAA | AAT | AAC | ATG | ATA | ATT | ATC | ACG | ACA | ACT | ACC |
|---|---|---|---|---|---|---|---|---|---|---|---|---|---|---|---|---|---|---|
| T | R | R | 0 | 0 | 0 | 0 | 0 | 0 | 0 | 0 | 0 | 0 | 0 | 0 | 0 | 0 | 0 | 0 |
| T | R | S | 0 | 0 | 0 | 0 | 0 | 0 | 0 | 0 | 0 | 0 | 0 | 0 | 0 | 0 | 0 | 0 |
| T | R | T | 0 | 0 | 0 | 0 | 0 | 0 | 0 | 0 | 0 | 0 | 0 | 0 | 0 | 0 | 0 | 0 |
| T | S | K | 0 | 0 | 0 | 0 | 0 | 0 | 0 | 0 | 0 | 0 | 0 | 0 | 0 | 0 | 0 | 0 |
| T | S | R | 0 | 0 | 0 | 0 | 0 | 0 | 0 | 0 | 0 | 0 | 0 | 0 | 0 | 0 | 0 | 0 |
| T | T | K | 0 | 0 | 0 | 0 | 0 | 0 | 0 | 0 | 0 | 0 | 0 | 0 | 0 | 0 | 0 | 0 |
| T | T | R | 0 | 0 | 0 | 0 | 0 | 0 | 0 | 0 | 0 | 0 | 0 | 0 | 0 | 0 | 0 | 0 |

*Fig. 7.5c*

| 44 | 68 | 70 | CGG | CGA | CGT | CGC | CAG | CAA | CAT | CAC | CTG | CTA | CTT | CTC | CCG | CCA | CCT | CCC |
|---|---|---|---|---|---|---|---|---|---|---|---|---|---|---|---|---|---|---|
| T | R | R | 0 | 0 | 0 | 0 | 0 | 0 | 0 | 1 | 0 | 0 | 0 | 1 | 0 | 0 | 0 | 0 |
| T | R | S | 0 | 0 | 0 | 0 | 0 | 0 | 0 | 0 | 0 | 0 | 0 | 0 | 0 | 0 | 0 | 0 |
| T | R | T | 0 | 0 | 0 | 0 | 0 | 0 | 0 | 0 | 0 | 0 | 0 | 0 | 0 | 0 | 0 | 0 |
| T | S | K | 0 | 0 | 0 | 0 | 0 | 0 | 0 | 0 | 0 | 0 | 0 | 0 | 0 | 0 | 0 | 0 |
| T | S | R | 0 | 0 | 0 | 0 | 0 | 0 | 0 | 0 | 0 | 0 | 0 | 0 | 0 | 0 | 0 | 0 |
| T | T | K | 0 | 0 | 0 | 0 | 0 | 0 | 0 | 0 | 0 | 0 | 0 | 0 | 0 | 0 | 0 | 0 |
| T | T | R | 0 | 0 | 0 | 0 | 0 | 0 | 0 | 0 | 0 | 0 | 0 | 0 | 0 | 0 | 0 | 0 |

| GGG 7 | GGA | GGT 1 | GGC 3 | AGG 1 | AGA | AGT | AGC |
|---|---|---|---|---|---|---|---|
| GAG 103 | GAA | GAT 146 | GAC 95 | AAG 7 | AAA | AAT 15 | AAC 15 |
| GTG 66 | GTA 5 | GTT 109 | GTC 99 | ATG | ATA | ATT 5 | ATC 6 |
| GCG 7 | GCA | GCT 100 | GCC 79 | ACG | ACA | ACT 45 | ACC 31 |
| TGG | TGA | TGT | TGC | CGG | CGA | CGT | CGC |
| TAG 48 | TAA | TAT 111 | TAC 53 | CAG 6 | CAA | CAT 38 | CAC 18 |
| TTG 2 | TTA | TTT 57 | TTC 58 | CTG | CTA | CTT 39 | CTC 26 |
| TCG 21 | TCA | TCT 91 | TCC 74 | CCG 4 | CCA | CCT 105 | CCC 70 |

*Fig.10a*

```
                    -12-11-10 -9 -8 -7 -6 -5 -4 -3 -2 -1  1  2  3  4  5  6  7  8  9 10 11 12
      GTT       5'   T  C  A  A  A  A  C  G  T  T  G  T  A  C  A  A  C  G  T  T  T  T  G  A   3'
(SEQ ID NO: 79) 3'   A  G  T  T  T  T  G  C  A  A  C  A  T  G  T  T  G  C  A  A  A  A  C  T   5'

CCT       5'   T  C  A  A  A  A  C  C  C  T  G  T  A  C  A  G  G  G  T  T  T  T  G  A   3'
(SEQ ID NO: 77) 3'   A  G  T  T  T  T  G  G  G  A  C  A  T  G  T  C  C  C  A  A  A  A  C  T   5'

GTT/CCT     5'   T  C  A  A  A  A  C  G  T  T  G  T  A  C  A  G  G  G  T  T  T  T  G  A   3'
(SEQ ID NO: 80) 3'   A  G  T  T  T  T  G  C  A  A  C  A  T  G  T  C  C  C  A  A  A  A  C  T   5'
```

*Fig. 11*

```
                            SEQUENCE LISTING

<160> NUMBER OF SEQ ID NOS: 92

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcaaaacggg gtaccccgtt ttga                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcaaaacgga gtactccgtt ttga                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcaaaacggt gtacaccgtt ttga                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcaaaacggc gtacgccgtt ttga                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcaaaacgag gtacctcgtt ttga                                              24

<210> SEQ ID NO 6
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 6
tcaaaacgaa gtacttcgtt ttga                                           24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcaaaacgat gtacatcgtt ttga                                           24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcaaaacgac gtacgtcgtt ttga                                           24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcaaaacgtg gtaccacgtt ttga                                           24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcaaaacgta gtactacgtt ttga                                           24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcaaaacgtt gtaaacgtt ttga                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic -continued

```
<400> SEQUENCE: 12
tcaaaacgtc gtacgacgtt ttga                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcaaaacgcg gtaccgcgtt ttga                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcaaaacgca gtactgcgtt ttga                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcaaaacgct gtacagcgtt ttga                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcaaaacgcc gtacggcgtt ttga                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcaaaacagg gtaccctgtt ttga                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 18
tcaaaacaga gtactctgtt ttga                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcaaaacagt gtacactgtt ttga                                              24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcaaaacagc gtacgctgtt ttga                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tcaaaacaag gtaccttgtt ttga                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcaaaacaaa gtactttgtt ttga                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcaaaacaat gtacattgtt ttga                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 24 tcaaacaac gtacgttgtt ttga                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcaaaacatg gtaccatgtt ttga                                         24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcaaaacata gtactatgtt ttga                                         24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcaaaacatt gtacaatgtt ttga                                         24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcaaaacatc gtacgatgtt ttga                                         24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcaaaacacg gtaccgtgtt ttga                                         24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
```

-continued tcaaaacaca gtactgtgtt ttga                                          24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tcaaaacact gtacagtgtt ttga                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcaaaacacc gtacggtgtt ttga                                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcaaaactgg gtacccagtt ttga                                          24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcaaaactga gtactcagtt ttga                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcaaaactgt gtacacagtt ttga                                          24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

-continued tcaaaactgc gtacgcagtt ttga                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcaaaactag gtacctagtt ttga                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcaaaactaa gtacttagtt ttga                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tcaaaactat gtacatagtt ttga                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcaaaactac gtacgtagtt ttga                                              24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcaaaacttg gtaccaagtt ttga                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcaaaactta gtactaagtt ttga                                              24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcaaaacttt gtacaaagtt ttga                                           24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcaaaacttc gtacgaagtt ttga                                           24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcaaaactcg gtaccgagtt ttga                                           24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tcaaaactca gtactgagtt ttga                                           24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tcaaaactct gtacagagtt ttga                                           24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcaaaactcc gtacggagtt ttga                                           24

```
<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcaaaaccgg gtacccggtt ttga                                          24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcaaaaccga gtactcggtt ttga                                          24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tcaaaaccgt gtacacggtt ttga                                          24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tcaaaaccgc gtacgcggtt ttga                                          24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tcaaaaccag gtacctggtt ttga                                          24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcaaaaccaa gtacttggtt ttga                                          24
```

```
<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tcaaaaccat gtacatggtt ttga                                            24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcaaaaccac gtacgtggtt ttga                                            24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tcaaaacctg gtaccaggtt ttga                                            24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcaaaaccta gtactaggtt ttga                                            24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tcaaaacctt gtacaaggtt ttga                                            24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tcaaaacctc gtacgaggtt ttga                                            24

<210> SEQ ID NO 61
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 tcaaacccg gtaccgggtt ttga                                              24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62 tcaaaccca gtactgggtt ttga                                              24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63 tcaaaccct gtacagggtt ttga                                              24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 tcaaacccc gtacggggtt ttga                                              24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65 tcaaacgtc gtgagacagt ttgg                                              24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccaaactgtc tcgagacagt ttgg                                             24

<210> SEQ ID NO 67
<211> LENGTH: 49
```

<210> SEQ ID NO 67
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gtttaaacat cagctaagct tgacctttvv kgtgactcaa aagacccag         49

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gatgtagttg gaaacggatc cmbbatcmbb tacgtaacca acgcc             45

<210> SEQ ID NO 69
<211> LENGTH: 501
<212> TYPE: DNA
<213> ORGANISM: Chlamydomonas reinhardtii
<220> FEATURE:
<221> NAME/KEY: CDS
<222> LOCATION: (1)..(501)

<400> SEQUENCE: 69

```
atg gcc aat acc aaa tat aac aaa gag ttc ctg ctg tac ctg gcc ggc      48
Met Ala Asn Thr Lys Tyr Asn Lys Glu Phe Leu Leu Tyr Leu Ala Gly
1               5                   10                  15 ttt gtg gac ggt gac ggt agc atc atc gct cag att aaa cca aac cag      96
Phe Val Asp Gly Asp Gly Ser Ile Ile Ala Gln Ile Lys Pro Asn Gln
            20                  25                  30 tct tat aag ttt aaa cat cag cta agc ttg acc ttt cag gtg act caa      144
Ser Tyr Lys Phe Lys His Gln Leu Ser Leu Thr Phe Gln Val Thr Gln
        35                  40                  45 aag acc cag cgc cgt tgg ttt ctg gac aaa cta gtg gat gaa att ggc      192
Lys Thr Gln Arg Arg Trp Phe Leu Asp Lys Leu Val Asp Glu Ile Gly
    50                  55                  60 gtt ggt tac gta cgt gat cgc gga tcc gtt tcc aac tac atc tta agc      240
Val Gly Tyr Val Arg Asp Arg Gly Ser Val Ser Asn Tyr Ile Leu Ser
65                  70                  75                  80 gaa atc aag ccg ctg cac aac ttc ctg act caa ctg cag ccg ttt ctg      288
Glu Ile Lys Pro Leu His Asn Phe Leu Thr Gln Leu Gln Pro Phe Leu
                85                  90                  95 aaa ctg aaa cag aaa cag gca aac ctg gtt ctg aaa att atc gaa cag      336
Lys Leu Lys Gln Lys Gln Ala Asn Leu Val Leu Lys Ile Ile Glu Gln
            100                 105                 110 ctg ccg tct gca aaa gaa tcc ccg gac aaa ttc ctg gaa gtt tgt acc      384
Leu Pro Ser Ala Lys Glu Ser Pro Asp Lys Phe Leu Glu Val Cys Thr
        115                 120                 125 tgg gtg gat cag att gca gct ctg aac gat tct aag acg cgt aaa acc      432
Trp Val Asp Gln Ile Ala Ala Leu Asn Asp Ser Lys Thr Arg Lys Thr
    130                 135                 140 act tct gaa acc gtt cgt gct gtg ctg gac agc ctg agc gag aag aag      480
Thr Ser Glu Thr Val Arg Ala Val Leu Asp Ser Leu Ser Glu Lys Lys
145                 150                 155                 160 aaa tcc tcc ccg gcg gcc gac                                          501
Lys Ser Ser Pro Ala Ala Asp
                165
```

-continued

```
<210> SEQ ID NO 70
<211> LENGTH: 167
<212> TYPE: PRT
<213> ORGANISM: Chlamydomonas reinhardtii

<400> SEQUENCE: 70

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caaaacgtcg tgagacagtt tg                                              22

<210> SEQ ID NO 72
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: a, c, t, g, unknown or other
<220> FEATURE:
<221> NAME/KEY: modified_base
<222> LOCATION: (27)..(29)
<223> OTHER INFORMATION: a, c, t, g, unknown or other

<400> SEQUENCE: 72
ggcatacaag tttcaaaacn nngtacnnng ttttgacaat cgtctgtca                 49

<210> SEQ ID NO 73
<211> LENGTH: 77
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 73
ggggacaagt ttgtacaaaa aagcaggctt cgaaggagat agaaccatgg ccaataccaa    60
atataacaaa gagttcc                                                   77

<210> SEQ ID NO 74
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggggaccact ttgtacaaga aagctgggtt tagtcggccg ccggggagga tttcttcttc    60
tcgc                                                                 64

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
caaaactatg tagagggttt tg                                             22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tcaaaactat gtgaatagtt ttga                                           24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcaaaaccct gtacagggtt ttga                                           24

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, t, g, unknown or other

<400> SEQUENCE: 78
```
caaaacnnnn nnnnnngttt tg                                            22

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcaaaacgtt gtacaacgtt ttga                                          24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tcaaaacgtt gtacagggtt ttga                                          24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tcaaaacgat gtaaatcgtt ttga                                          24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tcaaaacagt gtacgttgtt ttga                                          24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tcaaaacagc gtacattgtt ttga                                          24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcaaaacatg gtaccatgtt ttga                                          24

```
<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tcaaaacacg gtaccgtgtt ttga                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tcaaaactat gtaaatagtt ttga                                          24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tcaaaaccgt gtacgtggtt ttga                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tcaaaaccgc gtacatggtt ttga                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tcaaaacctg gtaccaggtt ttga                                          24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tcaaaacccg gtaccgggtt ttga                                          24
```

```
<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Ala Gly Leu Ile Asp Ala Asp Gly
1               5

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, t, g, unknown, other or not present
<220> FEATURE:
<221> NAME/KEY: modified_base
<222> LOCATION: (14)..(15)
<223> OTHER INFORMATION: 'ac' or 'ct'
<220> FEATURE:
<221> NAME/KEY: modified_base
<222> LOCATION: (16)..(18)
<223> OTHER INFORMATION: g, t, c or a
<220> FEATURE:
<221> NAME/KEY: modified_base
<222> LOCATION: (19)..(20)
<223> OTHER INFORMATION: 'gt' or 'tc'
<220> FEATURE:
<221> NAME/KEY: modified_base
<222> LOCATION: (21)..(22)
<223> OTHER INFORMATION: 'ga' or 'ac'
<220> FEATURE:
<221> NAME/KEY: modified_base
<222> LOCATION: (23)..(25)
<223> OTHER INFORMATION: g, t, c or a
<220> FEATURE:
<221> NAME/KEY: modified_base
<222> LOCATION: (26)..(27)
<223> OTHER INFORMATION: 'ag' or 'gt'
<220> FEATURE:
<221> NAME/KEY: modified_base
<222> LOCATION: (32)..(40)
<223> OTHER INFORMATION: a, c, t, g, unknown, other or not present
<220> FEATURE:
<223> OTHER INFORMATION: see specification as filed for detailed
      description of substitutions and preferred embodiments

<400> SEQUENCE: 92
nnnnnnnnnc aaannnnnnn nnnnnnnttt gnnnnnnnnn                              40
```

I-CREI MEGANUCLEASE VARIANTS WITH MODIFIED SPECIFICITY, METHOD OF PREPARATION AND USES THEREOF

Cross-Reference to Related Applications

The present application is a 35 U.S.C. §371 National Stage patent application of International patent application PCT/IB06/001203, filed on Mar. 15, 2006, which claims priority to International patent application PCT/IB05/003083, filed on Sep. 19, 2005, and International patent application PCT/IB05/000981, filed on Mar. 15, 2005.

The present invention relates to a method of preparing I-CreI meganuclease variants having a modified cleavage specificity. The invention relates also to the I-CreI meganuclease variants obtainable by said method and to their applications either for cleaving new DNA target or for genetic engineering and genome engineering fornon-therapeutic purposes.

The invention also relates to nucleic acids encoding said variants, to expression cassettes comprising said nucleic acids, to vectors comprising said expression cassettes, to cells or organisms, plants or animals except humans, transformed by said vectors.

Meganucleases are sequence specific endonucleases recognizing large (>12 bp; usually 14-40 bp) DNA cleavage sites (Thierry and Dujon, 1992). In the wild, meganucleases are essentially represented by homing endonucleases, generally encoded by mobile genetic elements such as inteins and class I introns (Belfort and Roberts, 1997; Chevalier and Stoddard, 2001). Homing refers to the mobilization of these elements, which relies on DNA double-strand break (DSB) repair, initiated by the endonuclease activity of the meganuclease. Early studies on the HO (Haber, 1998; Klar et al., 1984; Kostriken et al., 1983), I-SceI (Colleaux et al., 1988; Jacquier and Dujon, 1985; Perrin et al., 1993; Plessis et al., 1992) and I-TevI (Bell-Pedersen et al., 1990; Bell-Pedersen et al., 1989; Bell-Pedersen et al., 1991; Mueller et al., 1996) proteins have illustrated the biology of the homing process. On another hand, these studies have also provided a paradigm for the study of DSB repair in living cells.

General asymmetry of homing endonuclease target sequences contrasts with the characteristic dyad symmetry of most restriction enzyme recognition sites. Several homing endonucleases encoded by introns ORF or inteins have been shown to promote the homing of their respective genetic elements into allelic intronless or inteinless sites. By making a site-specific double-strand break in the intronless or inteinless alleles, these nucleases create recombinogenic ends, which engage in a gene conversion process that duplicates the coding sequence and leads to the insertion of an intron or an intervening sequence at the DNA level.

Homing endonucleases fall into 4 separated families on the basis of pretty well conserved amino acids motifs [for review, see Chevalier and Stoddard (Nucleic Acids Research, 2001, 29, 3757-3774)]. One of them is the dodecapeptide family (dodecamer, DOD, D1-D2, LAGLIDADG (SEQ ID NO: 91), P1-P2). This is the largest family of proteins clustered by their most general conserved sequence motif: one or two copies (vast majority) of a twelve-residue sequence: the dodecapeptide. Homing endonucleases with one dodecapetide (D) are around 20 kDa in molecular mass and act as homodimers. Those with two copies (DD) range from 25 kDa (230 amino acids) to 50 kDa (HO, 545 amino acids) with 70 to 150 residues between each motif and act as monomer. Cleavage is inside the recognition site, leaving 4 nt staggered cut with 3'OH overhangs. Enzymes that contain a single copy of the LAGLIDADG (SEQ ID NO: 91) motif, such as I-CeuI and I-CreI act as homodimers and recognize a nearly palindromic homing site.

The sequence and the structure of the homing endonuclease I-CreI (pdb accession code 1g9y) have been determined (Rochaix J D et al., NAR, 1985, 13, 975-984; Heath P J et al., Nat. Struct. Biol., 1997, 4, 468-476; Wang et al., NAR, 1997, 25, 3767-3776; Jurica et al. Mol. Cell, 1998, 2, 469-476) and structural models using X-ray crystallography have been generated (Heath et al., 1997).

I-CreI comprises 163 amino acids (pdb accession code 1g9y); said endonuclease cuts as a dimer. The LAGLIDADG (SEQ ID NO: 91) motif corresponds to residues 13 to 21; on either side of the LAGLIDADG (SEQ ID NO: 91) α-helices, a four β-sheet (positions 21-29; 37-48; 66-70 and 73-78) provides a DNA binding interface that drives the interaction of the protein with the half-site of the target DNA sequence. The dimerization interface involves the two LAGLIDADG (SEQ ID NO: 91) helix as well as other residues.

Figures 1, 8:
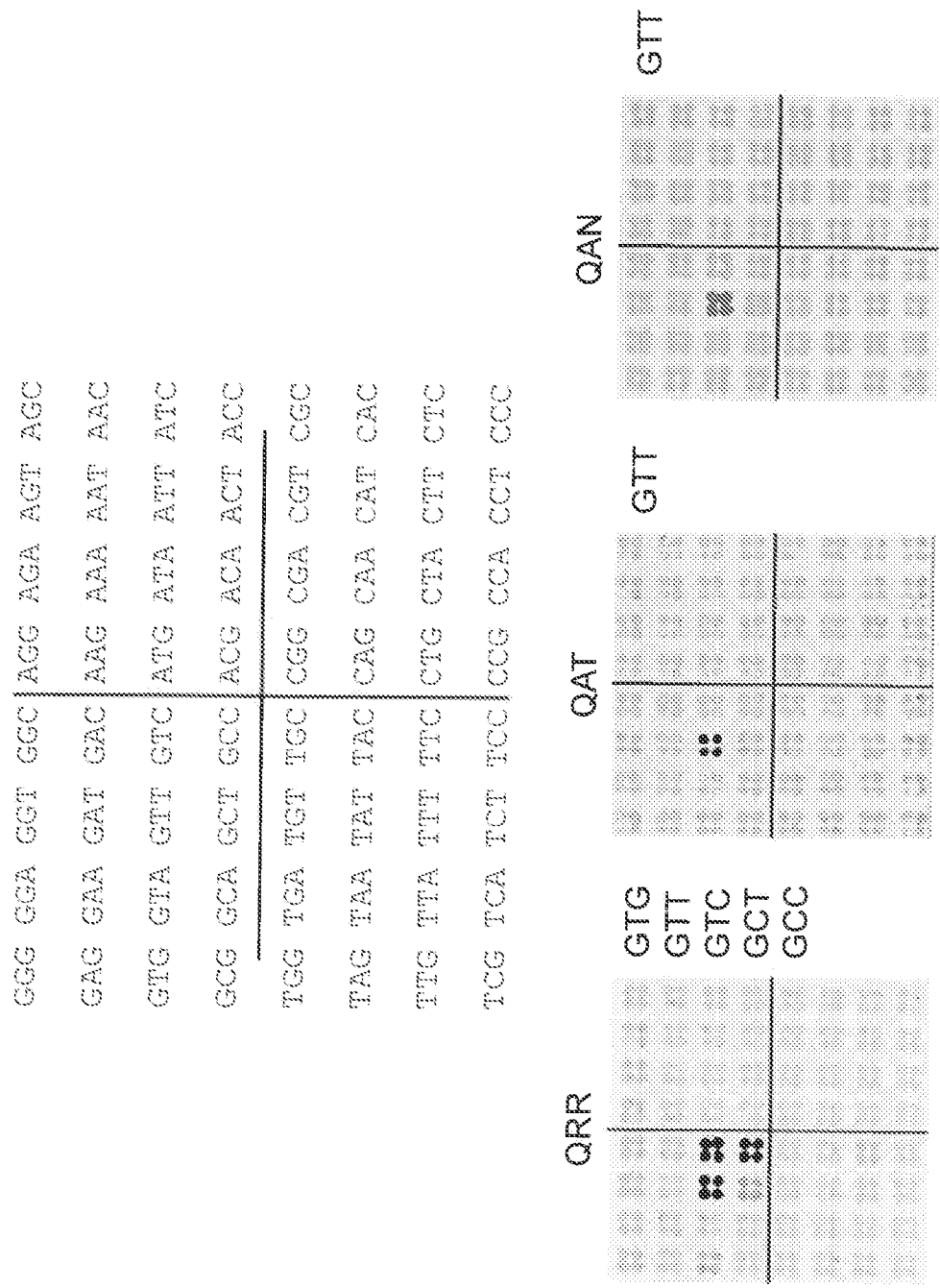
Figures 2, 8:
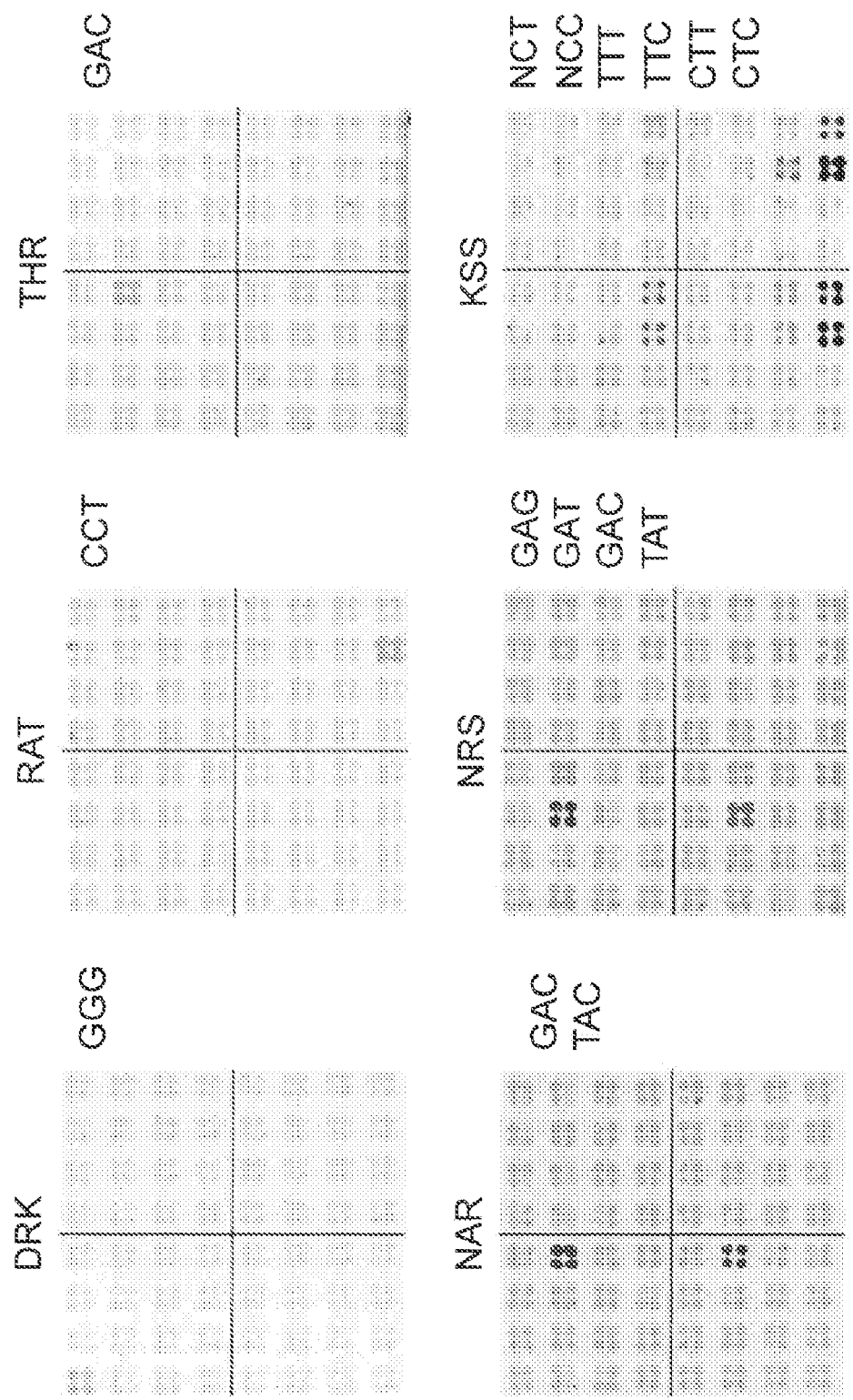

The homing site recognized and cleaved by I-CreI is 22-24 bp in length and is a degenerate palindrome (see FIG. 2 of Jurica M S et al, 1998 and SEQ ID NO:65). More precisely, said I-CreI homing site is a semi-palindromic 22 bp sequence, with 7 of 11 bp identical in each half-site (Seligman L M et al., NAR, 2002, 30, 3870-3879).

The endonuclease-DNA interface has also been described (see FIG. 4 of Jurica M S et al, 1998) and has led to a number of predictions about specific protein-DNA contacts (Seligman L M et al., Genetics, 1997, 147, 1653-1664; Jurica M S et al., 1998; Chevalier B. et al., Biochemistry, 2004, 43, 14015-14026).

It emerges from said documents that:

the residues G19, D20, Q47, R51, K98 and D137 are part of the endonucleolytic site of I-CreI;

homing site sequence must have at least 20 bp to achieve a maximal binding affinity of 0.2 nM;

sequence-specific contacts are distributed across the entire length of the homing site;

base-pair substitutions can be tolerated at many different homing site positions, without seriously disrupting homing site binding or cleavage;

R51 and K98 are located in the enzyme active site and are candidates to act as Lewis acid or to activate a proton donor in the cleavage reaction; mutations in each of these residues have been observed to sharply reduce I-CreI endonucleolytic activity (R51G, K98Q);

five additional residues, which when mutated abolish I-CreI endonuclease activity are located in or near the enzyme active site (R70A, L39R, L91/R, D75G, Q47H).

These studies have paved the way for a general use of meganuclease for genome engineering. Homologous gene targeting is the most precise way to stably modify a chromosomal locus in living cells, but its low efficiency remains a major drawback. Since meganuclease-induced DSB stimulates homologous recombination up to 10 000-fold, meganucleases are today the best way to improve the efficiency of gene targeting in mammalian cells (Choulika et al., 1995; Cohen-Tannoudji et al., 1998; Donoho et al., 1998; Elliott et al., 1998; Rouet et al., 1994), and to bring it to workable efficiencies in organisms such as plants (Puchta et al., 1993; Puchta et al., 1996) and insects (Rong and Golic, 2000; Rong and Golic, 2001; Rong et al., 2002).

Meganucleases have been used to induce various kinds of homologous recombination events, such as direct repeat recombination in mammalian cells (Liang et al., 1998), plants (Siebert and Puchta, 2002), insects (Rong et al., 2002), and bacteria (Posfai et al., 1999), or interchromosomal recombination (Moynahan and Jasin, 1997; Puchta, 1999; Richardson et al., 1998).

However, this technology is still limited by the low number of potential natural target sites for meganucleases: although several hundreds of natural homing endonucleases have been identified (Belfort and Roberts, 1997; Chevalier and Stoddard, 2001), the probability to have a natural meganuclease cleaving a gene of interest is extremely low. The making of artificial meganucleases with dedicated specificities would bypass this limitation.

Artificial endonucleases with novel specificity have been made, based on the fusion of endonucleases domains to zinc-finger DNA binding domains (Bibikova et al., 2003; Bibikova et al., 2001; Bibikova et al., 2002; Porteus and Baltimore, 2003).

Homing endonucleases have also been used as scaffolds to make novel endonucleases, either by fusion of different protein domains (Chevalier et al., 2002; Epinat et al., 2003), or by mutation of single specific amino acid residues (Seligman et al., 1997, 2002; Sussman et al., 2004; International PCT Application WO 2004/067736).

The International PCT Application WO 2004/067736 describes a general method for producing a custom-made meganuclease derived from an initial meganuclease, said meganuclease variant being able to cleave a DNA target sequence which is different from the recognition and cleavage site of the initial meganuclease. This general method comprises the steps of preparing a library of meganuclease variants having mutations at positions contacting the DNA target sequence or interacting directly or indirectly with said DNA target, and selecting the variants able to cleave the DNA target sequence. When the initial meganuclease is the I-CreI N75 protein a library, wherein residues 44, 68 and 70 have been mutated was built and screened against a series of six targets close to the I-CreI natural target site; the screened mutants have altered binding profiles compared to the I-CreI N75 scaffold protein; however, they cleave the I-CreI natural target site.

Seligman et al., 2002, describe mutations altering the cleavage specificity of I-CreI. More specifically, they have studied the role of the nine amino acids of I-CreI predicted to directly contact the DNA target (Q26, K28, N30, S32, Y33, Q38, Q44, R68 and R70). Among these nine amino acids, seven are thought to interact with nucleotides at symmetrical positions (S32, Y33, N30, Q38, R68, Q44 and R70). Mutants having each of said nine amino acids and a tenth (T140) predicted to participate in a water-mediated interaction, converted to alanine, were constructed and tested in a E. coli based assay.

The resulting I-CreI mutants fell into four distinct phenotypic classes in relation to the wild-type homing site:
S32A and T140A contacts appear least important for homing site recognition,
N30A, Q38A and Q44A displayed intermediate levels of activity in each assay,
Q26A, R68A and Y33A are inactive,
K28A and R70A are inactive and non-toxic.

It emerges from the results that I-CreI mutants at positions 30, 38, 44, 26, 68, 33, 28 and 70 have a modified behaviour in relation to the wild -type I-CreI homing site.

As regards the mutations altering the seven symmetrical positions in the I-CreI homing site, it emerges from the obtained results that five of the seven symmetrical positions in each half-site appear to be essential for efficient site recognition in vivo by wild-type I-CreI: 2/21, 3/20, 7/16, 8/15 and 9/14 (corresponding to positions −10/+10, −9/+9, −5/+5, −4/+4 and −3/+3 in SEQ ID NO:65). All mutants altered at these positions were resistant to cleavage by wild-type I-CreI in vivo; however, in vitro assay using E. coli appears to be more sensitive than the in vivo test and allows the detection of homing sites of wild-type I-CreI more effectively than the in vivo test; thus in vitro test shows that the DNA target of wild-type I-CreI may be the followings: gtc (recognized homing site in all the cited documents), gcc or gtt triplet at the positions −5 to −3, in reference to SEQ ID NO:65.

Seligman et al. have also studied the interaction between I-CreI position 33 and homing site bases 2 and 21 (±10) or between I-CreI position 32 and homing site bases 1 and 22 (±11); Y33C, Y33H, Y33R, Y33L, Y33S and Y33T mutants were found to cleave a homing site modified in positions ±10 that is not cleaved by I-CreI (Table 3). On the other hand, S32K and S32R were found to cleave a homing site modified in positions ±11 that is cleaved by I-CreI (Table 3).

Sussman et al., 2004, report studies in which the homodimeric LAGLIDADG (SEQ ID NO: 91) homing endonuclease I-CreI is altered at positions 26, and eventually 66, or at position 33, contacting the homing site bases in positions ±6 and ±10, respectively. The resulting enzymes constructs (Q26A, Q26C, Y66R, Q26C/Y66R, Y33C, Y33H) drive specific elimination of selected DNA targets in vivo and display shifted specificities of DNA binding and cleavage in vitro.

The overall result of the selection and characterization of enzyme point mutants against individual target site variants is both a shift and a broadening in binding specificity and in kinetics of substrate cleavage.

Each mutant displays a higher dissociation constant (lower affinity) against the original wild-type target site than does the wild-type enzyme, and each mutant displays a lower dissociation constant (higher affinity) against its novel target than does the wild-type enzyme.

The enzyme mutants display similar kinetics of substrate cleavage, with shifts and broadening in substrate preferences similar to those described for binding affinities.

To reach a larger number of DNA target sequences, it would be extremely valuable to generate new I-CreI variants with novel specificity, ie able to cleave DNA targets which are not cleaved by I-CreI or the few variants which have been isolated so far.

Such variants would be of a particular interest for genetic and genome engineering.

Here the inventors have found mutations in positions 44, 68 and 70 of I-CreI which result in variants able to cleave at least one homing site modified in positions ±3 to 5.

Therefore, the subject-matter of the present invention is a method of preparing a I-CreI meganuclease variant having a modified cleavage specificity, said method comprising:

(a) replacing amino acids Q44, R68 and/or R70, in reference with I -CreI pdb accession code 1g9y, with an amino acid selected in the group consisting of A, D, E, G, H, K, N, P, Q, R, S, T and Y;

(b) selecting the I-CreI meganuclease variants obtained in step (a) having at least one of the following $R_3$ triplet cleaving profile in reference to positions −5 to −3 in a double-strand DNA target, said positions −5 to −3 corresponding to $R_3$ of the following formula I:

(SEQ ID NO: 92)
5'-$R_1$CAAA$R_2R_3R_4$R'$_4$R'$_3$R'$_2$TTTGR'$_1$-3', wherein:

$R_1$ is absent or present; and when present represents a nucleic acid fragment comprising 1 to 9 nucleotides corresponding either to a random nucleic acid sequence or to a fragment of a I-CreI meganuclease homing site situated from position −20 to −12 (from 5' to 3'), $R_1$ corresponding at least to position −12 of said homing site, $R_2$ represents the nucleic acid doublet ac or ct and corresponds to positions −7 to −6 of said homing site, $R_3$ represents a nucleic acid triplet corresponding to said positions −5 to −3, selected among g, t, c and a, except the following triplets: gtc, gcc, gtg, gtt and gct; therefore said nucleic acid triplet is preferably selected among the following triplets: ggg, gga, ggt, ggc, gag, gaa, gat, gac, gta, gcg, gca, tgg, tga, tgt, tgc, tag, taa, tat, tac, ttg, tta, ttt, ttc, tcg, tca, tct, tcc, agg, aga, agt, agc, aag, aaa, aat, aac, atg, ata, att, atc, acg, aca, act, acc, cgg, cga, cgt, cgc, cag, caa, cat, cac, ctg, cta, ctt, ctc, ccg, cca, cct and ccc and more preferably among the following triplets: ggg, ggt, ggc, gag, gat, gac, gta, gcg, gca, tag, taa, tat, tac, ttg, ttt, ttc, tcg, tct, tcc, agg, aag, aat, aac, att, atc, act, acc, cag, cat, cac, ctt, ctc, ccg, cct and ccc, $R_4$ represents the nucleic acid doublet gt or tc and corresponds to positions −2 to −1 of said homing site, $R'_1$ is absent or present; and when present represents a nucleic acid fragment comprising 1 to 9 nucleotides corresponding either to a random nucleic acid sequence or to a fragment of a I-CreI meganuclease homing site situated from position +12 to +20 (from 5' to 3'), $R'_1$ corresponding at least to position +12 of said homing site, $R'_2$ represents the nucleic acid doublet ag or gt, and corresponds to positions +6 to +7 of said homing site, $R'_3$ represents a nucleic acid triplet corresponding to said positions +3 to +5, selected among g, t, c, and a; $R'_3$ being different from gac, ggc, cac, aac, and agc, when $R_3$ and $R'_3$ are non-palindromic, $R'_4$ represents the nucleic acid doublet ga or ac and corresponds to positions +1 to +2 of said homing site.

DEFINITIONS

Amino acid residues in a polypeptide sequence are designated herein according to the one-letter code, in which, for example, Q means Gln or Glutamine residue, R means Arg or Arginine residue and D means Asp or Aspartic acid residue.

In the present invention, unless otherwise mentioned, the residue numbers refer to the amino acid numbering of the I-CreI sequence SWISSPROT P05725 or the pdb accession code 1g9y. According to this definition, a variant named "ADR" is I-CreI meganuclease in which amino acid residues Q44 and R68 have been replaced by alanine and aspartic acid, respectively, while R70 has not been replaced. Other mutations that do not alter the cleavage activity of the variant are not indicated and the nomenclature adopted here does not limit the mutations to the only three positions 44, 68 and 70.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

In the present application, when a sequence is given for illustrating a recognition or homing site, it is to be understood that it represents, from 5' to 3', only one strand of the double-stranded polynucleotide.

The term "partially palindromic sequence", "partially symmetrical sequence", "degenerate palindrome", "pseudopalindromic sequence" are indiscriminately used for designating a palindromic sequence having a broken symmetry. For example the 22 bp sequence: $c_{-11}a_{-10}a_{-9}a_{-8}a_{-7}c_{-6}g_{-5}t_{-4}c_{-3}g_{-2}t_{-1}g_{+1}a_{+2}g_{+3}a_{+4}c_{+5}$ $a_{+6}$ $g_{+7}t_{+8}t_{+9}t_{+10}g_{+11}$ (SEQ ID NO: 71) is a partially palindromic sequence in which symmetry is broken at base-pairs +/−1, 2, 6 and 7. According to another formulation, nucleotide sequences of positions +/−8 to 11 and +/−3 to 5 are palindromic sequences. Symmetry axe is situated between the base-pairs in positions −1 and +1. Using another numbering, from the 5' extremity to the 3' extremity, palindromic sequences are in positions 1 to 4 and 19 to 22, and 7 to 9 and 14 to 16, symmetry is broken at base-pairs 5, 6, 10, 11, 12, 13, 17 and 18, and the symmetry axe is situated between the base-pairs in positions 11 and 12.

As used herein, the term "wild-type I-CreI" designates a I-CreI meganuclease having the sequence SWISSPROT P05725 or pdb accession code 1g9y.

The terms "recognition site", "recognition sequence", "target", "target sequence", "DNA target", "homing recognition site", "homing site", "cleavage site" are indiscriminately used for designating a 14 to 40 bp double-stranded, palindromic, non-palindromic or partially palindromic polynucleotide sequence that is recognized and cleaved by a meganuclease. These terms refer to a distinct DNA location, preferably a chromosomal location, at which a double stranded break (cleavage) is to be induced by the meganuclease.

For example, the known homing recognition site of wild-type I-CreI is represented by the 22 bp sequence 5'-caaaacgtcgtgagacagtttg-3' (SEQ ID NO: 71) or the 24 bp sequence 5'-tcaaaacgtcgtgagacagtttgg-3' presented in FIG. 2A (here named C1234, SEQ ID NO: 65; gtc in positions −5 to −3 and gac in positions +3 to +5). This particular site is hereafter also named "I-CreI natural target site". From the natural target can be derived two palindromic sequences by mutation of the nucleotides in positions +1, +2, +6, and +7 or −1, −2, −6 and −7: C1221 (SEQ ID NO: 12) and C4334 (SEQ ID NO:66), presented in FIG. 2A. Both have gtc in positions −5 to −3 and gac in positions +3 to +5, and are cut by I-CreI, in vitro and in yeast.

The term "modified specificity" relates to a meganuclease variant able to cleave a homing site that is not cleaved, in the same conditions by the initial meganuclease (scaffold protein) it is derived from; said initial or scaffold protein may be the wild-type meganuclease or a mutant thereof.

Figure 9A-1:
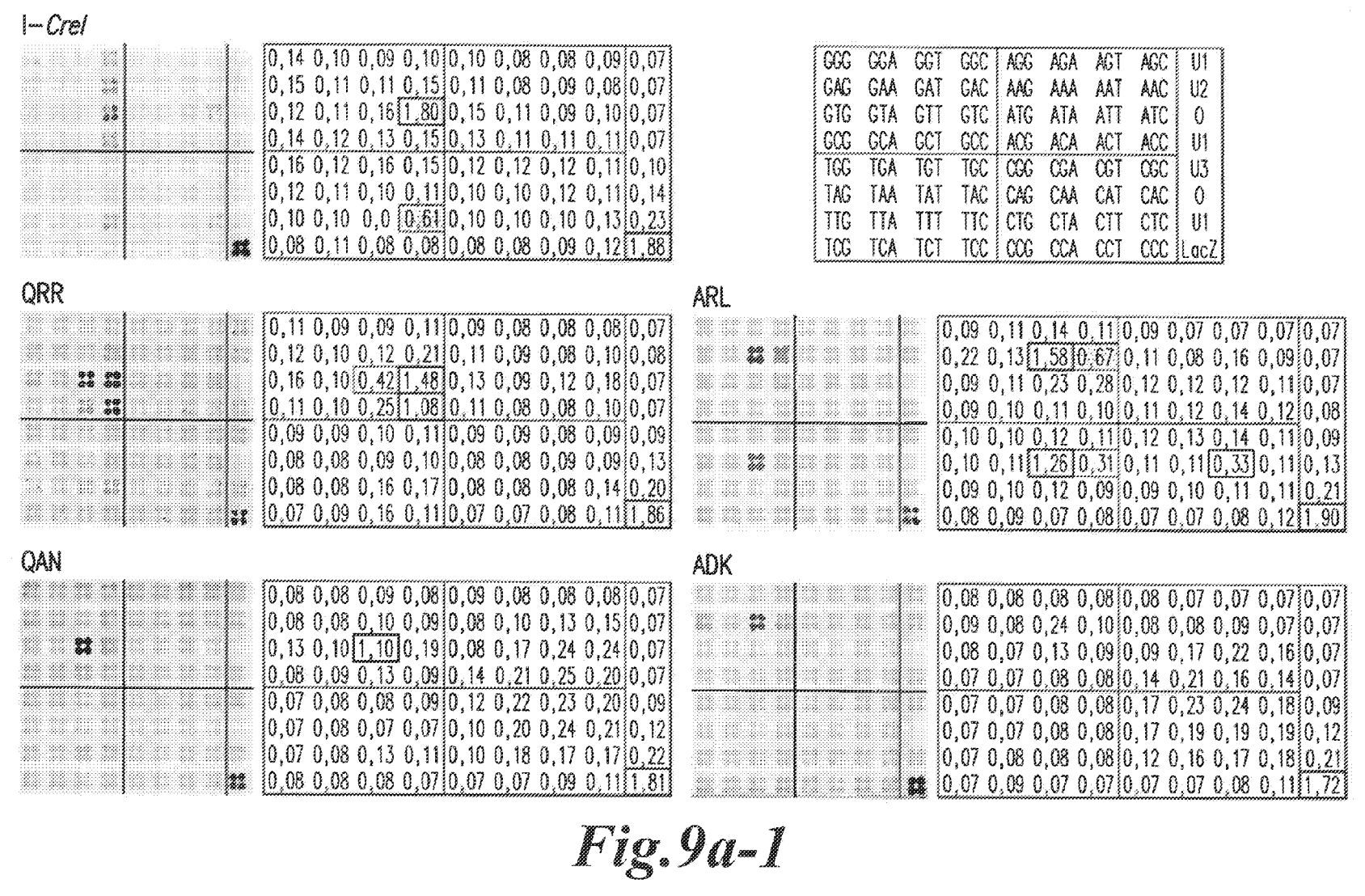

Indeed, when using an in vivo assay in a yeast strain, the Inventors found that wild-type I-CreI cleaves not only homing sites wherein the palindromic sequence in positions −5 to −3 is gtc (as in C1234, C1221 or C4334), but also gcc, gac, ggc, atc, ctc and ttc (FIG. 9a).

The I-CreI D75N mutant (I-CreI N75) which may also be used as scaffold protein for making variants with novel specificity, cleaves not only homing sites wherein the palindromic sequence in positions −5 to −3 is gtc, but also gcc, gtt, gtg, or gct (FIGS. 8 and 9a).

Heterodimeric form may be obtained for example by proceeding to the fusion of the two monomers. Resulting heterodimeric meganuclease is able to cleave at least one target site that is not cleaved by the homodimeric form. Therefore a meganuclease variant is still part of the invention when used in a heteromeric form. The other monomer chosen for the formation of the heterodimeric meganuclease may be another variant monomer, but it may also be a wild-type monomer, for example a I-CreI monomer or a I-DmoI monomer.

Thus, the inventors constructed a I-CreI variants library from a I-CreI scaffold protein (I-CreI D75N), each of them presenting at least one mutation in the amino acid residues in positions 44, 68 and/or 70 (pdb code 1g9y), and each of them being able to cleave at least one target site not cleaved by the I-CreI scaffold protein.

In this particular approach, the mutation consists of the replacement of at least one amino acid residue in position 44, 68, and/or 70 by another residue selected in the group comprising A, D, E, G, H, K, N, P, Q, R, S, T and Y. Each mutated amino acid residue is changed independently from the other residues, and the selected amino acid residues may be the same or may be different from the other amino acid residues in position 44, 68 and/or 70. In this approach, the homing site, cleaved by the I-CreI meganuclease variant according to the invention but not cleaved by the I-CreI scaffold protein, is the same as described above and illustrated in FIG. 2, except that the triplet sequence in positions −5 to −3 (corresponding to $R_3$ in formula I) and/or triplet sequence in positions +3 to +5 (corresponding to $R_3'$ in formula I) differ from the triplet sequence in the same positions in the homing sites cleaved by the I-CreI scaffold protein.

Unexpectedly, the I-CreI meganuclease variants, obtainable by the method described above, i.e. with a "modified specificity" are able to cleave at least one target that differs from the I-CreI scaffold protein target in positions −5 to −3 and/or in positions +3 to +5. It must be noted that said DNA target is not necessarily palindromic in positions +/−3 to 5. I-CreI is active in homodimeric form, but may be active in a heterodimeric form. Therefore I-CreI variants according to the instant invention could be active not only in a homodimeric form, but also in a heterodimeric form, and in both cases, they could recognize a target with either palindromic or non palindromic sequence in position +/−3 to 5, provided that when the I-CreI N75 protein is used as scaffold, the triplet in position −5 to −3 and/or +3 to +5 differs from gtc, gcc, gtg, gtt and gct, and from gac, ggc, cac, aac, and agc, respectively. Since each monomer of I-CreI variant binds a half of the homing site, a variant able to cleave a plurality of targets could also cleave a target which sequence in position +/−3 to 5 is not palindromic. Further, a variant could act both in a homodimeric form and in a heterodimeric form. I-CreI variant could form a heterodimeric meganuclease, in which the other variant could be a wild-type I-CreI monomer, another wild-type meganuclease monomer, such as I-DmoI, another I-CreI variant monomer, or a monomer of a variant from another meganuclease than I-CreI.

According to an advantageous embodiment of said method, the I-CreI meganuclease variant obtained in step (b) is selected from the group consisting of: A44/A68/A70, A44/A68/G70, A44/A68/H70, A44/A68/K70, A44/A68/N70, A44/A68/Q70, A44/A68/R70, A44/A68/S70, A44/A68/T70, A44/D68/H70, A44/D68/K70, A44/D68/R70, A44/G68/H70, A44/G68/K70, A44/G68/N70, A44/G68/P70, A44/G68/R70, A44/H68/A70, A44/H68/G70, A44/H68/H70, A44/H68/K70, A44/H68/N70, A44/H68/Q70, A44/H68/R70, A44/H68/S70, A44/H68/T70, A44/K68/A70, A44/K68/G70, A44/K68/H70, A44/K68/K70, A44/K68/N70, A44/K68/Q70, A44/K68/R70, A44/K68/S70, A44/K68/T70, A44/N68/A70, A44/N68/E70, A44/N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/H70, A44/Q68/N70, A44/Q68/R70, A44/Q68/S70, A44/R68/A70, A44/R68/D70, A44/R68/E70, A44/R68/G70, A44/R68/H70, A44/R68/K70, A44/R68/L70, A44/R68/N70, A44/R68/R70, A44/R68/S70, A44/R68/T70, A44/S68/A70, A44/S68/G70, A44/S68/K70, A44/S68/N70, A44/S68/Q70, A44/S68/R70, A44/S68/S70, A44/S68/T70, A44/T68/A70, A44/T68/G70, A44/T68/H70, A44/T68/K70, A44/T68/N70, A44/T68/Q70, A44/T68/R70, A44/T68/S70, A44/T68/T70, D44/D68/H70, D44/N68/S70, D44/R68/A70, D44/R68/K70, D44/R68/N70, D44/R68/Q70, D44/R68/R70, D44/R68/S70, D44/R68/T70, E44/H68/H70, E44/R68/A70, E44/R68/H70, E44/R68/N70, E44/R68/S70, E44/R68/T70, E44/S68/T70, G44/H68/K70, G44/Q68/H70, G44/R68/Q70, G44/R68/R70, G44/T68/D70, G44/T68/P70, G44/T68/R70, H44/A68/S70, H44/A68/T70, H44/R68/A70, H44/R68/D70, H44/R68/E70, H44/R68/G70, H44/R68/N70, H44/R68/R70, H44/R68/S70, H44/R68/T70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/N70, K44/A68/Q70, K44/A68/S70, K44/A68/T70, K44/D68/A70, K44/D68/T70, K44/E68/G70, K44/E68/N70, K44/E68/S70, K44/G68/A70, K44/G68/G70, K44/G68/N70, K44/G68/S70, K44/G68/T70, K44/H68/D70, K44/H68/E70, K44/H68/G70, K44/H68/N70, K44/H68/S70, K44/H68/T70, K44/K68/A70, K44/K68/D70, K44/K68/H70, K44/K68/T70, K44/N68/A70, K44/N68/D70, K44/N68/E70, K44/N68/G70, K44/N68/H70, K44/N68/N70, K44/N68/Q70, K44/N68/S70, K44/N68/T70, K44/P68/H70, K44/Q68/A70, K44/Q68/D70, K44/Q68/E70, K44/Q68/S70, K44/Q68/T70, K44/R68/A70, K44/R68/D70, K44/R68/E70, K44/R68/G70, K44/R68/H70, K44/R68/N70, K44/R68/Q70, K44/R68/S70, K44/R68/T70, K44/S68/A70, K44/S68/D70, K44/S68/H70, K44/S68/N70, K44/S68/S70, K44/S68/T70, K44/T68/A70, K44/T68/D70, K44/T68/E70, K44/T68/G70, K44/T68/H70, K44/T68/N70, K44/T68/Q70, K44/T68/S70, K44/T68/T70, N44/A68/H70, N44/A68/R70, N44/H68/N70, N44/H68/R70, N44/K68/G70, N44/K68/H70, N44/K68/R70, N44/K68/S70, N44/N68/R70, N44/P68/D70, N44/Q68/H70, N44/Q68/R70, N44/R68/A70, N44/R68/D70, N44/R68/E70, N44/R68/G70, N44/R68/H70, N44/R68/K70, N44/R68/N70, N44/R68/R70, N44/R68/S70, N44/R68/T70, N44/S68/G70, N44/S68/H70, N44/S68/K70, N44/S68/R70, N44/T68/H70, N44/T68/K70, N44/T68/Q70, N44/T68/R70, N44/T68/S70, P44/N68/D70, P44/T68/T70, Q44/A68/A70, Q44/A68/H70, Q44/A68/R70, Q44/G68/K70, Q44/G68/R70, Q44/K68/G70, Q44/N68/A70, Q44/N68/H70, Q44/N68/S70, Q44/P68/P70, Q44/Q68/G70, Q44/R68/A70, Q44/R68/D70, Q44/R68/E70, Q44/R68/G70, Q44/R68/H70, Q44/R68/N70, Q44/R68/Q70, Q44/R68/S70, Q44/S68/H70, Q44/S68/R70, Q44/S68/S70, Q44/T68/A70, Q44/T68/G70, Q44/T68/H70, Q44/T68/R70, R44/A68/G70, R44/A68/T70, R44/G68/T70, R44/H68/D70, R44/H68/T70, R44/N68/T70, R44/R68/A70, R44/R68/D70, R44/R68/E70, R44/R68/G70, R44/R68/N70, R44/R68/Q70, R44/R68/S70, R44/R68/T70, R44/S68/G70, R44/S68/N70, R44/S68/S70, R44/S68/T70, S44/D68/K70, S44/H68/R70, S44/R68/G70, S44/R68/N70, S44/R68/R70, S44/R68/S70, T44/A68/K70, T44/A68/R70, T44/H68/R70, T44/K68/R70, T44/N68/P70, T44/N68/R70, T44/Q68/K70, T44/Q68/R70, T44/R68/A70, T44/R68/D70, T44/R68/E70, T44/R68/G70, T44/R68/H70, T44/R68/K70, T44/R68/N70, T44/R68/Q70, T44/R68/R70, T44/R68/S70, T44/R68/T70, T44/S68/K70, T44/S68/R70, T44/T68/K70, and T44/T68/R70.

According to another advantageous embodiment of said method, the step (b) of selecting said I-CreI meganuclease variant is performed in vivo in yeast cells.

The subject-matter of the present invention is also the use of a I-CreI meganuclease variant as defined here above, i.e.

obtainable by the method as described above, in vitro or in vivo for non-therapeutic purposes, for cleaving a double-strand nucleic acid target comprising at least a 20-24 bp partially palindromic sequence, wherein at least the sequence in positions +/−8 to 11 is palindromic, and the nucleotide triplet in positions −5 to −3 and/or the nucleotide triplet in positions +3 to +5 differs from gtc, gcc, gtg, gtt, and gct, and from gac, ggc, cac, aac and agc, respectively. Formula I describes such a DNA target.

According to an advantageous embodiment of said use, said I-CreI meganuclease variant is selected from the group consisting of: A44/A68/A70, A44/A68/G70, A44/A68/H70, A44/A68/K70, A44/A68/N70, A44/A68/Q70, A44/A68/R70, A44/A68/S70, A44/A68/T70, A44/D68/H70, A44/D68/K70, A44/D68/R70, A44/G68/H70, A44/G68/K70, A44/G68/N70, A44/G68/P70, A44/G68/R70, A44/H68/A70, A44/H68/G70, A44/H68/H70, A44/H68/K70, A44/H68/N70, A44/H68/Q70, A44/H68/R70, A44/H68/S70, A44/H68/T70, A44/K68/A70, A44/K68/G70, A44/K68/H70, A44/K68/K70, A44/K68/N70, A44/K68/Q70, A44/K68/R70, A44/K68/S70, A44/K68/T70, A44/N68/A70, A44/N68/E70, A44/N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/H70, A44/Q68/N70, A44/Q68/R70, A44/Q68/S70, A44/R68/A70, A44/R68/D70, A44/R68/E70, A44/R68/G70, A44/R68/H70, A44/R68/K70, A44/R68/L70, A44/R68/N70, A44/R68/R70, A44/R68/S70, A44/R68/T70, A44/S68/A70, A44/S68/G70, A44/S68/K70, A44/S68/N70, A44/S68/Q70, A44/S68/R70, A44/S68/S70, A44/S68/T70, A44/T68/A70, A44/T68/G70, A44/T68/H70, A44/T68/K70, A44/T68/N70, A44/T68/Q70, A44/T68/R70, A44/T68/S70, A44/T68/T70, D44/D68/H70, D44/N68/S70, D44/R68/A70, D44/R68/K70, D44/R68/N70, D44/R68/Q70, D44/R68/R70, D44/R68/S70, D44/R68/T70, E44/H68/H70, E44/R68/A70, E44/R68/H70, E44/R68/N70, E44/R68/S70, E44/R68/T70, E44/S68/T70, G44/H68/K70, G44/Q68/H70, G44/R68/Q70, G44/R68/R70, G44/T68/D70, G44/T68/P70, G44/T68/R70, H44/A68/S70, H44/A68/T70, H44/R68/A70, H44/R68/D70, H44/R68/E70, H44/R68/G70, H44/R68/N70, H44/R68/R70, H44/R68/S70, H44/R68/T70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/N70, K44/A68/Q70, K44/A68/S70, K44/A68/T70, K44/D68/A70, K44/D68/T70, K44/E68/G70, K44/E68/N70, K44/E68/S70, K44/G68/A70, K44/G68/G70, K44/G68/N70, K44/G68/S70, K44/G68/T70, K44/H68/D70, K44/H68/E70, K44/H68/G70, K44/H68/N70, K44/H68/S70, K44/H68/T70, K44/K68/A70, K44/K68/D70, K44/K68/H70, K44/K68/T70, K44/N68/A70, K44/N68/D70, K44/N68/E70, K44/N68/G70, K44/N68/H70, K44/N68/N70, K44/N68/Q70, K44/N68/S70, K44/N68/T70, K44/P68/H70, K44/Q68/A70, K44/Q68/D70, K44/Q68/E70, K44/Q68/S70, K44/Q68/T70, K44/R68/A70, K44/R68/D70, K44/R68/E70, K44/R68/G70, K44/R68/H70, K44/R68/N70, K44/R68/Q70, K44/R68/S70, K44/R68/T70, K44/S68/A70, K44/S68/D70, K44/S68/H70, K44/S68/N70, K44/S68/S70, K44/S68/T70, K44/T68/A70, K44/T68/D70, K44/T68/E70, K44/T68/G70, K44/T68/H70, K44/T68/N70, K44/T68/Q70, K44/T68/S70, K44/T68/T70, N44/A68/H70, N44/A68/R70, N44/H68/N70, N44/H68/R70, N44/K68/G70, N44/K68/H70, N44/K68/R70, N44/K68/S70, N44/N68/R70, N44/P68/D70, N44/Q68/H70, N44/Q68/R70, N44/R68/A70, N44/R68/D70, N44/R68/E70, N44/R68/G70, N44/R68/H70, N44/R68/K70, N44/R68/N70, N44/R68/R70, N44/R68/S70, N44/R68/T70, N44/S68/G70, N44/S68/H70, N44/S68/K70, N44/S68/R70, N44/T68/H70, N44/T68/K70, N44/T68/Q70, N44/T68/R70, N44/T68/S70, P44/N68/D70, P44/T68/T70, Q44/A68/A70, Q44/A68/H70, Q44/A68/R70, Q44/G68/K70, Q44/G68/R70, Q44/K68/G70, Q44/N68/A70, Q44/N68/G70, Q44/N68/H70, Q44/N68/S70, Q44/P68/P70, Q44/Q68/G70, Q44/R68/A70, Q44/R68/D70, Q44/R68/E70, Q44/R68/G70, Q44/R68/H70, Q44/R68/N70, Q44/R68/Q70, Q44/R68/S70, Q44/S68/H70, Q44/S68/R70, Q44/S68/S70, Q44/T68/A70, Q44/T68/G70, Q44/T68/H70, Q44/T68/R70, R44/A68/G70, R44/A68/T70, R44/G68/T70, R44/H68/D70, R44/H68/T70, R44/N68/T70, R44/R68/A70, R44/R68/D70, R44/R68/E70, R44/R68/G70, R44/R68/N70, R44/R68/Q70, R44/R68/S70, R44/R68/T70, R44/S68/G70, R44/S68/N70, R44/S68/S70, R44/S68/T70, S44/D68/K70, S44/H68/R70, S44/R68/G70, S44/R68/N70, S44/R68/R70, S44/R68/S70, T44/A68/K70, T44/A68/R70, T44/H68/R70, T44/K68/R70, T44/N68/P70, T44/N68/R70, T44/Q68/K70, T44/Q68/R70, T44/R68/A70, T44/R68/D70, T44/R68/E70, T44/R68/G70, T44/R68/H70, T44/R68/K70, T44/R68/N70, T44/R68/Q70, T44/R68/R70, T44/R68/S70, T44/R68/T70, T44/S68/K70, T44/S68/R70, T44/T68/K70, and T44/T68/R70.

According to another advantageous embodiment of said use, the I-CreI meganuclease variant is a homodimer.

According to another advantageous embodiment of said use, said I-CreI meganuclease variant is a heterodimer.

Said heterodimer may be either a single-chain chimeric molecule consisting of the fusion of two different I-CreI variants as defined in the present invention or of I-CreI scaffold protein with a I-CreI variant as defined in the present invention. Alternatively, said heterodimer may consist of two separate monomers chosen from two different I-CreI variants as defined in the present invention or I-CreI scaffold protein and a I-CreI variant as defined in the present invention.

According to said use:
either the I-CreI meganuclease variant is able to cleave a DNA target in which sequence in positions +/−3 to 5 is palindromic,
or, said I-CreI meganuclease variant is able to cleave a DNA target in which sequence in positions +/−3 to 5 is non-palindromic.

According to another advantageous embodiment of said use the cleaved nucleic acid target is a DNA target in which palindromic sequences in positions −11 to −8 and +8 to +11 are caaa and tttg, respectively.

According to another advantageous embodiment of said use, said I-CreI meganuclease variant further comprises a mutation in position 75, preferably a mutation in an uncharged amino acid, more preferably an asparagine or a valine (D75N or D75V).

According to yet another advantageous embodiment of said use, said I-CreI meganuclease variant has an alanine (A) or an asparagine (N) in position 44, for cleaving a DNA target comprising nucleotide a in position −4, and/or t in position +4.

According to yet another advantageous embodiment of said use, said I-CreI meganuclease variant has a glutamine (Q) in position 44, for cleaving a DNA target comprising nucleotide t in position −4 or a in position +4.

According to yet another advantageous embodiment of said use, said I-CreI meganuclease variant has a lysine (K) in position 44, for cleaving a target comprising nucleotide c in position −4, and/or g in position +4.

The subject-matter of the present invention is also I-CreI meganuclease variants:
Obtainable by the method of preparation as defined above;
Having one mutation of at least one of the amino acid residues in positions 44, 68 and 70 of I-CreI; said mutations may be the only ones within the amino acids contacting directly the DNA target; and Having a modified cleavage specificity in positions ±3 to 5.

Such novel I-CreI meganucleases may be used either as very specific endonucleases in in vitro digestion, for restriction or mapping use, either in vivo or ex vivo as tools for genome engineering. In addition, each one can be used as a new scaffold for a second round of mutagenesis and selection/screening, for the purpose of making novel, second generation homing endonucleases.

The I-CreI meganuclease variants according to the invention are mutated only at positions 44, 68 and/or 70 of the DNA binding domain. However, the instant invention also includes different proteins able to form heterodimers: heterodimerization of two different proteins from the above list result also in cleavage of non palindromic sequences, made of two halves from the sites cleaved by the parental proteins alone. This can be obtained in vitro by adding the two different I-CreI variants in the reaction buffer, and in vivo or ex vivo by coexpression. Another possibility is to build a single-chain molecule, as described by Epinat et al. (Epinat et al., 2003). This single chain molecule would be the fusion of two different I-CreI variants, and should also result in the cleavage of chimeric, non-palindromic sequences.

According to an advantageous embodiment of said I-CreI meganuclease variant, the amino acid residue chosen for the replacement of the amino acid in positions 44, 68 and/or 70 is selected in the group comprising A, D, E, G, H, K, N, P, Q, R, S, T and Y.

According to another advantageous embodiment, said I-CreI meganuclease variant is selected in the group consisting of: A44/A68/A70, A44/A68/G70, A44/A68/H70, A44/A68/K70, A44/A68/N70, A44/A68/Q70, A44/A68/S70, A44/A68/T70, A44/D68/H70, A44/D68/K70, A44/D68/R70, A44/G68/H70, A44/G68/K70, A44/G68/N70, A44/G68/P70, A44/H68/A70, A44/H68/G70, A44/H68/H70, A44/H68/K70, A44/H68/N70, A44/H68/Q70, A44/H68/S70, A44/H68/T70, A44/K68/A70, A44/K68/G70, A44/K68/H70, A44/K68/N70, A44/K68/Q70, A44/K68/R70, A44/K68/S70, A44/K68/T70, A44/N68/A70, A44/N68/E70, A44/N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/H70, A44/Q68/N70, A44/Q68/S70, A44/R68/E70, A44/R68/K70, A44/R68/L70, A44/S68/A70, A44/S68/G70, A44/S68/N70, A44/S68/Q70, A44/S68/R70, A44/S68/S70, A44/S68/T70, A44/T68/A70, A44/T68/G70, A44/T68/H70, A44/T68/N70, A44/T68/Q70, A44/T68/S70, A44/T68/T70, D44/D68/H70, D44/N68/S70, D44/R68/A70, D44/R68/N70, D44/R68/Q70, D44/R68/R70, D44/R68/S70, D44/R68/T70, E44/H68/H70, E44/R68/A70, E44/R68/H70, E44/R68/N70, E44/R68/S70, E44/R68/T70, E44/S68/T70, G44/H68/K70, G44/Q68/H70, G44/R68/Q70, G44/T68/D70, G44/T68/P70, G44/T68/R70, H44/A68/S70, H44/A68/T70, H44/R68/D70, H44/R68/E70, H44/R68/G70, H44/R68/N70, H44/R68/R70, H44/R68/S70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/N70, K44/A68/Q70, K44/D68/A70, K44/D68/T70, K44/E68/G70, K44/E68/S70, K44/G68/A70, K44/G68/G70, K44/G68/N70, K44/G68/S70, K44/G68/T70, K44/H68/D70, K44/H68/E70, K44/H68/G70, K44/H68/N70, K44/H68/S70, K44/H68/T70, K44/K68/A70, K44/K68/D70, K44/K68/H70, K44/K68/T70, K44/N68/A70, K44/N68/D70, K44/N68/E70, K44/N68/G70, K44/N68/H70, K44/N68/N70, K44/N68/Q70, K44/N68/S70, K44/N68/T70, K44/P68/H70, K44/Q68/A70, K44/Q68/D70, K44/Q68/E70, K44/Q68/S70, K44/Q68/T70, K44/R68/A70, K44/R68/D70, K44/R68/E70, K44/R68/G70, K44/R68/H70, K44/R68/N70, K44/R68/S70, K44/S68/A70, K44/S68/D70, K44/S68/H70, K44/S68/N70, K44/S68/S70, K44/S68/T70, K44/T68/A70, K44/T68/D70, K44/T68/E70, K44/T68/G70, K44/T68/H70, K44/T68/N70, K44/T68/Q70, K44/T68/S70, K44/T68/T70, N44/A68/H70, N44/H68/N70, N44/H68/R70, N44/K68/G70, N44/K68/H70, N44/K68/R70, N44/K68/S70, N44/P68/D70, N44/Q68/H70, N44/R68/A70, N44/R68/D70, N44/R68/E70, N44/R68/K70, N44/S68/G70, N44/S68/H70, N44/S68/K70, N44/S68/R70, N44/T68/H70, N44/T68/K70, N44/T68/Q70, N44/T68/S70, P44/N68/D70, P44/T68/T70, Q44/G68/K70, Q44/G68/R70, Q44/K68/G70, Q44/N68/A70, Q44/N68/H70, Q44/N68/S70, Q44/P68/P70, Q44/Q68/G70, Q44/R68/D70, Q44/R68/E70, Q44/R68/G70, Q44/R68/Q70, Q44/S68/S70, Q44/T68/A70, Q44/T68/G70, Q44/T68/H70, R44/A68/G70, R44/A68/T70, R44/G68/T70, R44/H68/D70, R44/H68/T70, R44/N68/T70, R44/R68/A70, R44/R68/D70, R44/R68/E70, R44/R68/G70, R44/R68/Q70, R44/R68/S70, R44/R68/T70, R44/S68/G70, R44/S68/N70, R44/S68/S70, R44/S68/T70, S44/D68/K70, S44/R68/R70, S44/R68/S70, T44/A68/K70, T44/N68/P70, T44/N68/R70, T44/R68/E70, T44/R68/Q70, and T44/S68/K70; said I-CreI meganuclease variant is able to cleave at least one target, as defined above, that is not cleaved by the I-CreI N75 scaffold protein.

According to yet another advantageous embodiment, the I-CreI meganuclease variant has an alanine (A) or an asparagine (N), in position 44, and cleaves a target comprising the nucleotide a in position −4, and/or t in position +4, with the exclusion of the variants presented in Table 4 and Table 5 of the International PCT Application WO 2004/067736, preferably said variant has an alanine or an asparagine.

According to yet another advantageous embodiment, the I-CreI meganuclease variant has a glutamine (Q) and cleaves a target comprising the nucleotide t in position −4, and/or a in position +4 in position 44, with the exclusion of the variants presented in Table 3, Table 4 and Table 5 of the International PCT Application WO 2004/067736.

According to yet another advantageous embodiment, the I-CreI meganuclease variant of the invention has a lysine (K) in position 44, and cleaves a target comprising c in position −4, and/or g in position +4, with the exclusion of the variant presented Table 5 of the International PCT Application WO 2004/067736.

As specified hereabove, in the frame of the definition of the I-CreI meganuclease variant in the use application, said I-CreI meganuclease variant may be a homodimer or a heterodimer. It may be able to cleave a palindromic or a non -palindromic DNA target. It may further comprise a mutation in position 75, as specified hereabove.

The subject-matter of the present invention is also a polynucleotide, characterized in that it encodes a I-CreI meganuclease variant according to the invention.

Further, the subject-matter of the present invention is an expression cassette comprising said polynucleotide and regulation sequences such as a promoter, and an expression vector comprising said expression cassette. When said variant is an heterodimer consisting of two different monomers, each monomer may be expressed from a single vector (dual expression vector) or from two different vectors.

The subject-matter of the present invention is also an expression vector, as described above, further comprising a targeting DNA construct.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art and commercially available, such as the following bacterial vectors: pQE70, pQE6O, pQE-9 (Qiagen), pbs, pDIO, phagescript, psiX174. pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXTI, pSG (Stratagene); pSVK3, pBPV, pMSG, pSVL (Pharmacia); pQE-30 (QIAexpress), pET (Novagen).

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for S. cerevisiae; tetracycline, rifampicin or ampicillin resistance in E. coli.

Preferably said vectors are expression vectors, wherein the sequences encoding the polypeptides of the invention are placed under control of appropriate transcriptional and translational control elements to permit production or synthesis of said polypeptides. Therefore, said polynucleotides are comprised in expression cassette(s). More particularly, the vector comprises a replication origin, a promoter operatively linked to said encoding polynucleotide, a ribosome binding site, an RNA -splicing site (when genomic DNA is used), a polyadenylation site and a transcription termination site. It also can comprise an enhancer. Selection of the promoter will depend upon the cell in which the polypeptide is expressed.

According to an advantageous embodiment of said expression vector, said targeting DNA construct comprises a sequence sharing homologies with the region surrounding the cleavage site of the I-CreI meganuclease variant of the invention.

According to another advantageous embodiment of said expression vector, said targeting DNA construct comprises:

a) sequences sharing homologies with the region surrounding the cleavage site of the I-CreI meganuclease variant according to claim, and b) sequences to be introduced flanked by sequence as in a).

The subject-matter of the present invention is also a cell, characterized in that it is modified by a polynucleotide as defined above or by a vector as defined above.

The subject-matter of the present invention is also a transgenic plant, characterized in that it comprises a polynucleotide as defined above, or a vector as defined above.

The subject-matter of the present invention is also a non-human transgenic mammal, characterized in that it comprises a polynucleotide as defined above or a vector as defined above.

The polynucleotide sequences encoding the polypeptides as defined in the present invention may be prepared by any method known by the man skilled in the art. For example, they are amplified from a cDNA template, by polymerase chain reaction with specific primers. Preferably the codons of said cDNA are chosen to favour the expression of said protein in the desired expression system.

The recombinant vector comprising said polynucleotides may be obtained and introduced in a host cell by the well-known recombinant DNA and genetic engineering techniques.

The heterodimeric meganuclease of the invention is produced by expressing the two polypeptides as defined above; preferably said polypeptides are co -expressed in a host cell modified by two expression vectors, each comprising a polynucleotide fragment encoding a different polypeptide as defined above or by a dual expression vector comprising both polynucleotide fragments as defined above, under conditions suitable for the co-expression of the polypeptides, and the heterodimeric meganuclease is recovered from the host cell culture.

The subject-matter of the present invention is further the use of a I-CreI meganuclease variant, one or two polynucleotide(s), preferably both included in one expression vector (dual expression vector) or each included in a different expression vector, a cell, a transgenic plant, a non-human transgenic mammal, as defined above, for molecular biology, for in vivo or in vitro genetic engineering, and for in vivo or in vitro genome engineering, for non-therapeutic purposes.

Non therapeutic purposes include for example (i) gene targeting of specific loci in cell packaging lines for protein production, (ii) gene targeting of specific loci in crop plants, for strain improvements and metabolic engineering, (iii) targeted recombination for the removal of markers in genetically modified crop plants, (iv) targeted recombination for the removal of markers in genetically modified microorganism strains (for antibiotic production for example).

According to an advantageous embodiment of said use, it is for inducing a double-strand break in a site of interest comprising a DNA target sequence, thereby inducing a DNA recombination event, a DNA loss or cell death.

According to the invention, said double-strand break is for: repairing a specific sequence, modifying a specific sequence, restoring a functional gene in place of a mutated one, attenuating or activating an endogenous gene of interest, introducing a mutation into a site of interest, introducing an exogenous gene or a part thereof, inactivating or deleting an endogenous gene or a part thereof, translocating a chromosomal arm, or leaving the DNA unrepaired and degraded.

According to another advantageous embodiment of said use, said I-CreI meganuclease variant, polynucleotide, vector, cell, transgenic plant or non-human transgenic mammal are associated with a targeting DNA construct as defined above.

The subject-matter of the present invention is also a method of genetic engineering, characterized in that it comprises a step of double-strand nucleic acid breaking in a site of interest located on a vector, comprising a DNA target of a I-CreI meganuclease variant as defined hereabove, by contacting said vector with a I-CreI meganuclease variant as defined above, thereby inducing a homologous recombination with another vector presenting homology with the sequence surrounding the cleavage site of said I-CreI meganuclease variant.

The subject-matter of the present invention is also a method of genome engineering, characterized in that it comprises the following steps: 1) double-strand breaking a genomic locus comprising at least one recognition and cleavage site of a I-CreI meganuclease variant as defined above, by contacting said cleavage site with said I-CreI meganuclease variant; 2) maintaining said broken genomic locus under conditions appropriate for homologous recombination with a targeting DNA construct comprising the sequence to be introduced in said locus, flanked by sequences sharing homologies with the target locus.

The subject-matter of the present invention is also a method of genome engineering, characterized in that it comprises the following steps: 1) double-strand breaking a genomic locus comprising at least one recognition and cleavage site of a I-CreI meganuclease variant as defined above, by contacting said cleavage site with said I-CreI meganuclease variant; 2) maintaining said broken genomic locus under conditions appropriate for homologous recombination with chromosomal DNA sharing homologies to regions surrounding the cleavage site.

The subject-matter of the present invention is also a composition characterized in that it comprises at least one I-CreI meganuclease variant, a polynucleotide or a vector as defined above.

In a preferred embodiment of said composition, it comprises a targeting DNA construct comprising the sequence which repairs the site of interest flanked by sequences sharing homologies with the targeted locus.

The subject-matter of the present invention is also the use of at least one I-CreI meganuclease variant, a polynucleotide or a vector, as defined above for the preparation of a medicament for preventing, improving or curing a genetic disease in an individual in need thereof, said medicament being administrated by any means to said individual.

The subject-matter of the present invention is also the use of at least one I-CreI meganuclease variant, a polynucleotide or a vector as defined above for the preparation of a medicament for preventing, improving or curing a disease caused by an infectious agent that presents a DNA intermediate, in an individual in need thereof, said medicament being administrated by any means to said individual.

The subject-matter of the present invention is also the use of at least one I-CreI meganuclease variant, a polynucleotide or a vector, as defined above, in vitro, for inhibiting the propagation, inactivating or deleting an infectious agent that presents a DNA intermediate, in biological derived products or products intended for biological uses or for disinfecting an object.

In a particular embodiment, said infectious agent is a virus.

In addition to the preceding features, the invention further comprises other features which will emerge from the description which follows, which refers to examples illustrating the I-CreI meganuclease variants and their uses according to the invention, as well as to the appended drawings in which:

FIG. 1 illustrates the rationale of the experiments. (a) Structure of I-CreI bound to its DNA target. (b) Zoom of the structure showing residues 44, 68, 70 chosen for randomization, D75 and interacting base pairs. (c) Design of the library and targets. The interactions of I-CreI residues Q44, R68 an R70 with DNA targets are indicated (top). Other amino acid residues interacting directly or indirectly with the DNA target are not shown. Arginine (R) residue in position 44 of a I-CreI monomer directly interacts with guanine in position −5 of the target sequence, while glutamine (Q) residue of position 44 and Arginine (R) residue of position 70 directly interact with adenine in position +4 and guanine in position +3 of the complementary strand, respectively. The target described here (C1221, SEQ ID NO: 12) is a palindrome derived from the I-CreI natural target (C1234, SEQ ID NO:65), and cleaved by I-CreI (Chevalier et al., 2003, precited). Cleavage positions are indicated by arrowheads. In the library, residues 44, 68 and 70 are replaced with ADEGHKNPQRST. Since I-CreI is an homodimer, the library was screened with palindromic targets. Sixty four palindromic targets resulting from substitutions in positions ±3, ±4 and ±5 were generated. A few examples of such targets are shown (bottom; SEQ ID NO: 1 to 7).

FIG. 2 illustrates the target used in the study. A. Two palindromic targets derived from the natural I-CreI target (here named C1234, SEQ ID NO: 65). The I-CreI natural target contains two palindromes, boxed in grey: the −8 to −12 and +8 to +12 nucleotides on one hand, and the −5 to −3 and +3 to +5 nucleotide on another hand. Vertical dotted line, from which are numbered the nucleotide bases, represents the symmetry axe for the palindromic sequences. From the natural target can be derived two palindromic sequences, C1221 (SEQ ID NO: 12) and C4334 (SEQ ID NO:66). Both are cut by I-CreI, in vitro and in yeast. Only one strand of each target site is shown. B. The 64 targets. The 64 targets (SEQ ID NOS: 1-6, 81, 8-18, 82-83, 21-27, 84, 29-31, 85, 33-38, 86, 40-50, 87-88, 53-59 89, 61-63 and 90, respectively, in order of appearance) are derived from C1221 (SEQ ID NO: 12) a palindrome derived from the I-CreI natural target (C1234, SEQ ID NO:65), and cleaved by I-CreI (Chevalier et al., 2003, precited). They correspond to all the 24 by palindromes resulting from substitutions at positions −5, −4, −3, +3, +4 and +5.

FIG. 3 illustrates the screening of the variants. (a) Yeast are transformed with the meganuclease expressing vector, marked with the LEU2 gene, and individually mated with yeast transformed with the reporter plasmid, marked by the TRP1 gene. In the reporter plasmid, a LacZ reporter gene is interrupted with an insert containing the site of interest, flanked by two direct repeats. In diploids (LEU2 TRP1), cleavage of the target site by the meganuclease (white oval) induces homologous recombination between the two lacZ repeats, resulting in a functional beta-galactosidase gene (grey oval), which can be monitored by X-Gal staining. (b) Scheme of the experiment. A library of I-CreI variants is built using PCR, cloned into a replicative yeast expression vector and transformed in S. cerevisiae strain FYC2-6A (MATα, trp1Δ63, leu2Δ1, his3Δ200). The 64 palindromic targets are cloned in the LacZ-based yeast reporter vector, and the resulting clones transformed into strain FYBL2-7B (MATa, ura3Δ851, trp1Δ63, leu2Δ1, lys2Δ202). Robot-assisted gridding on filter membrane is used to perform mating between individual clones expressing meganuclease variants and individual clones harboring a reporter plasmid. After primary high throughput screening, the ORF of positive clones are amplified by PCR and sequenced. 410 different variants were identified among the 2100 positives, and tested at low density, to establish complete patterns, and 350 clones were validated. Also, 294 mutants were recloned in yeast vectors, and tested in a secondary screen, and results confirmed those obtained without recloning. Chosen clones are then assayed for cleavage activity in a similar CHO-based assay and eventually in vitro.

FIG. 4 represents the cDNA sequence encoding the I-CreI N75 scaffold protein and degenerated primers used for the Ulib2 library construction. A. The coding sequence (CDS) of the scaffold protein (SEQ ID NO: 69) is from base -pair 1 to base-pair 501 and the "STOP" codon TGA (not shown) follows the base-pair 501. In addition to the D75N mutation, the protein further contains mutations that do not alter its activity; in the protein sequence (SEQ ID NO:70), the two first N-terminal residues are methionine and alanine (MA), and the three C-terminal residues alanine, alanine and aspartic acid (AAD).B. Degenerated primers (SEQ ID NO: 67, 68).

Figure 5:
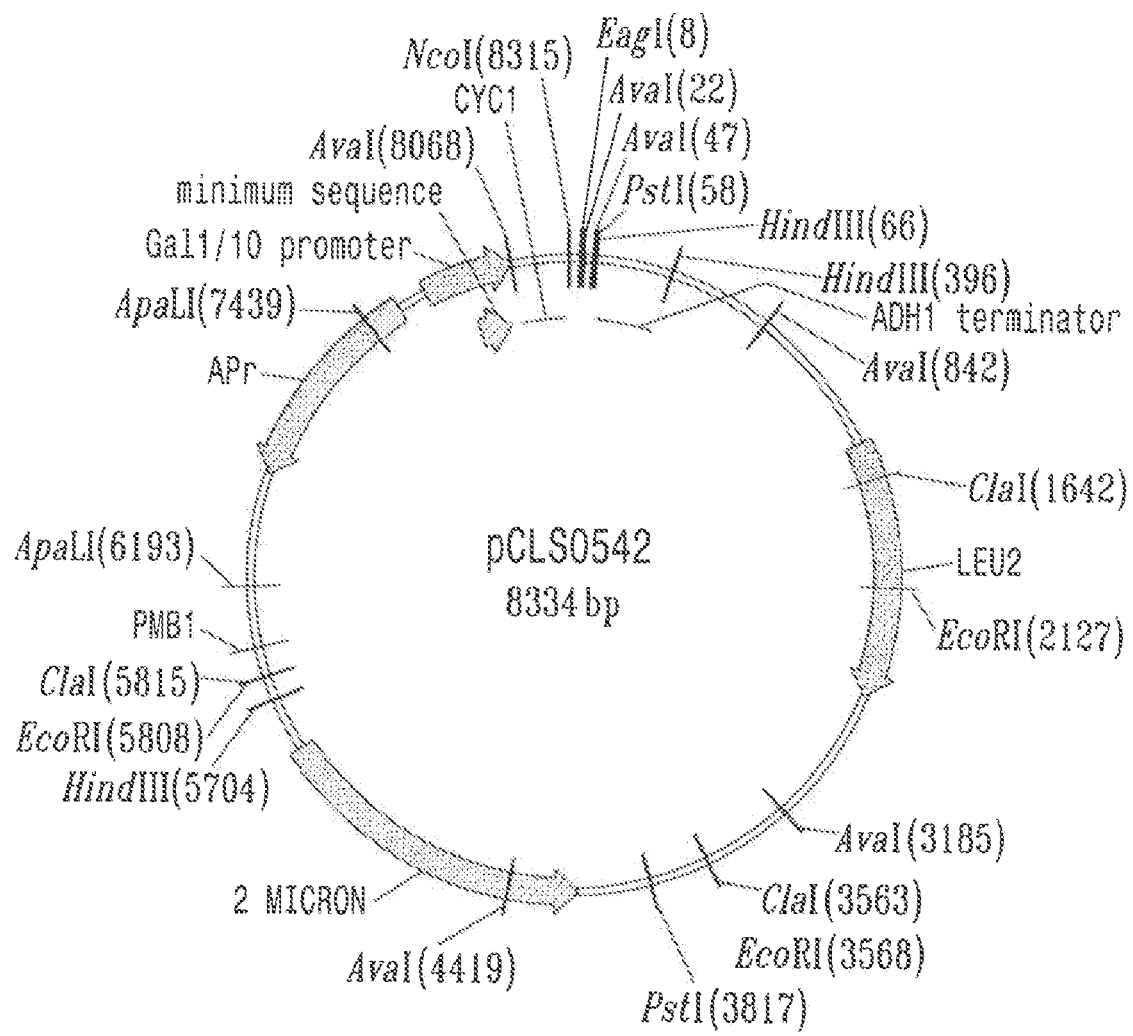

FIG. 5 represents the pCLS0542 meganuclease expression vector map. The meganuclease expression vector is marked with LEU2. cDNAs encoding I-CreI meganuclease variants are cloned into this vector digested with NcoI and EagI, in order to have the variant expression driven by the inducible Gal 10 promoter.

Figure 6:
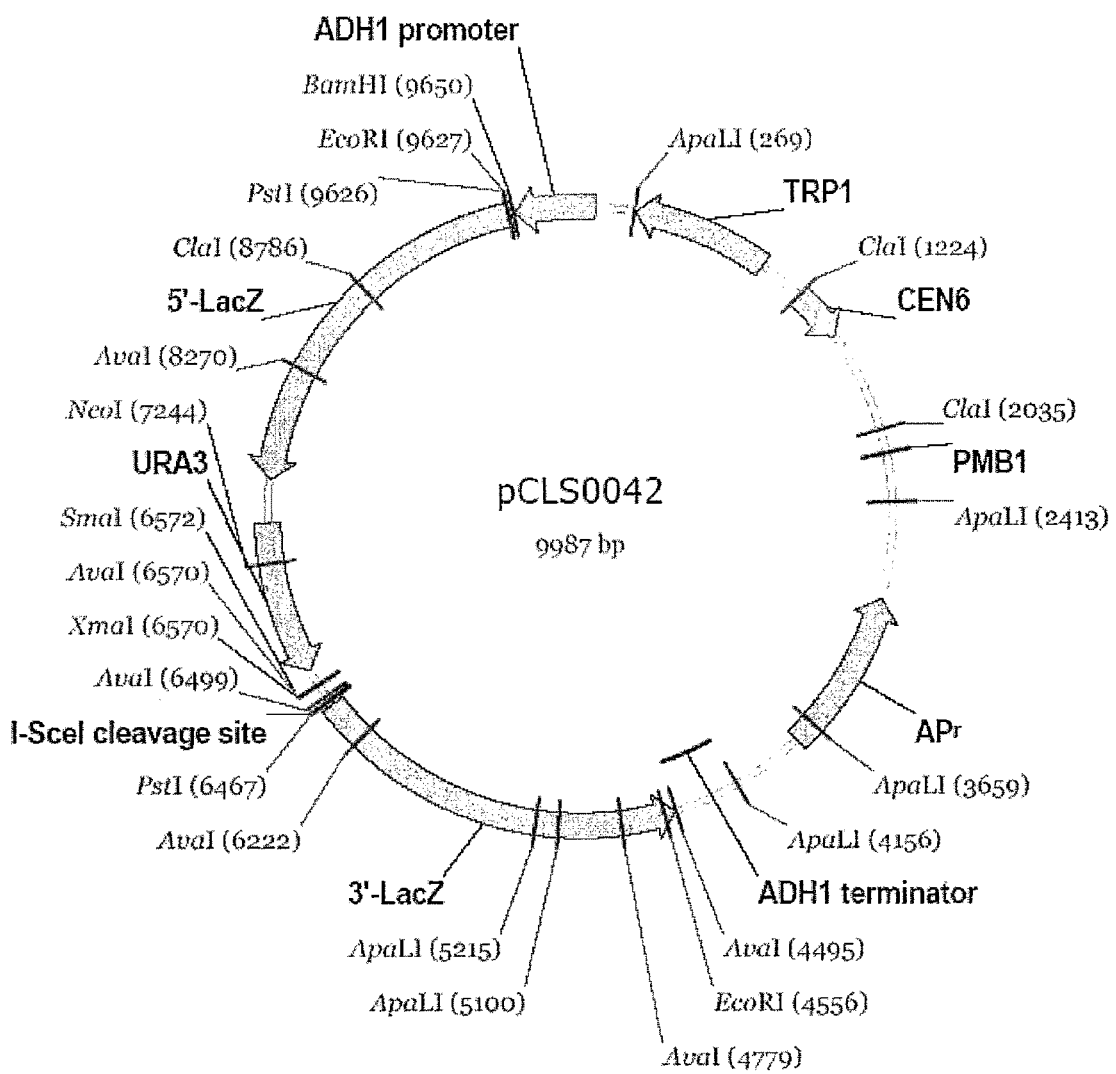

FIG. 6 represents the pCLS0042 reporter vector map. The reporter vector is marked with TRP1 and URA3. The LacZ tandem repeats share 800 bp of homology, and are separated by 1.3 kb of DNA. They are surrounded by ADH promoter and terminator sequences. Target sites are cloned into the SmaI site.

FIG. 7 illustrates the cleavage profile of 292 I-CreI meganuclease variants with a modified specificity. The variants derive from the I-CreI N75 scaffold protein. Proteins are defined by the amino acid present in positions 44, 68 and 70 (three first columns). Numeration of the amino acids is according to pdb accession code 1g9y. Targets are defined by nucleotides at positions –5 to –3. For each protein, observed cleavage (1) or non observed cleavage (0) is shown for each one of the 64 targets.

FIG. 8 illustrates eight examples I-CreI variants cleavage pattern. The meganucleases are tested 4 times against the 64 targets described in FIG. 2B. The position of the different targets is indicated on the top, left panel. The variants which derive from the I-CreI N75 scaffold protein, are identified by the amino acids in positions 44, 68 and 70 (ex: KSS is K44, S68, S70 and N75, or K44/S68/S70). Numeration of the amino acids is according to pdb code 1g9y. QRR corresponds to I-CreI N75. The cleaved targets are indicated besides the panels.

Figure 9A-2:
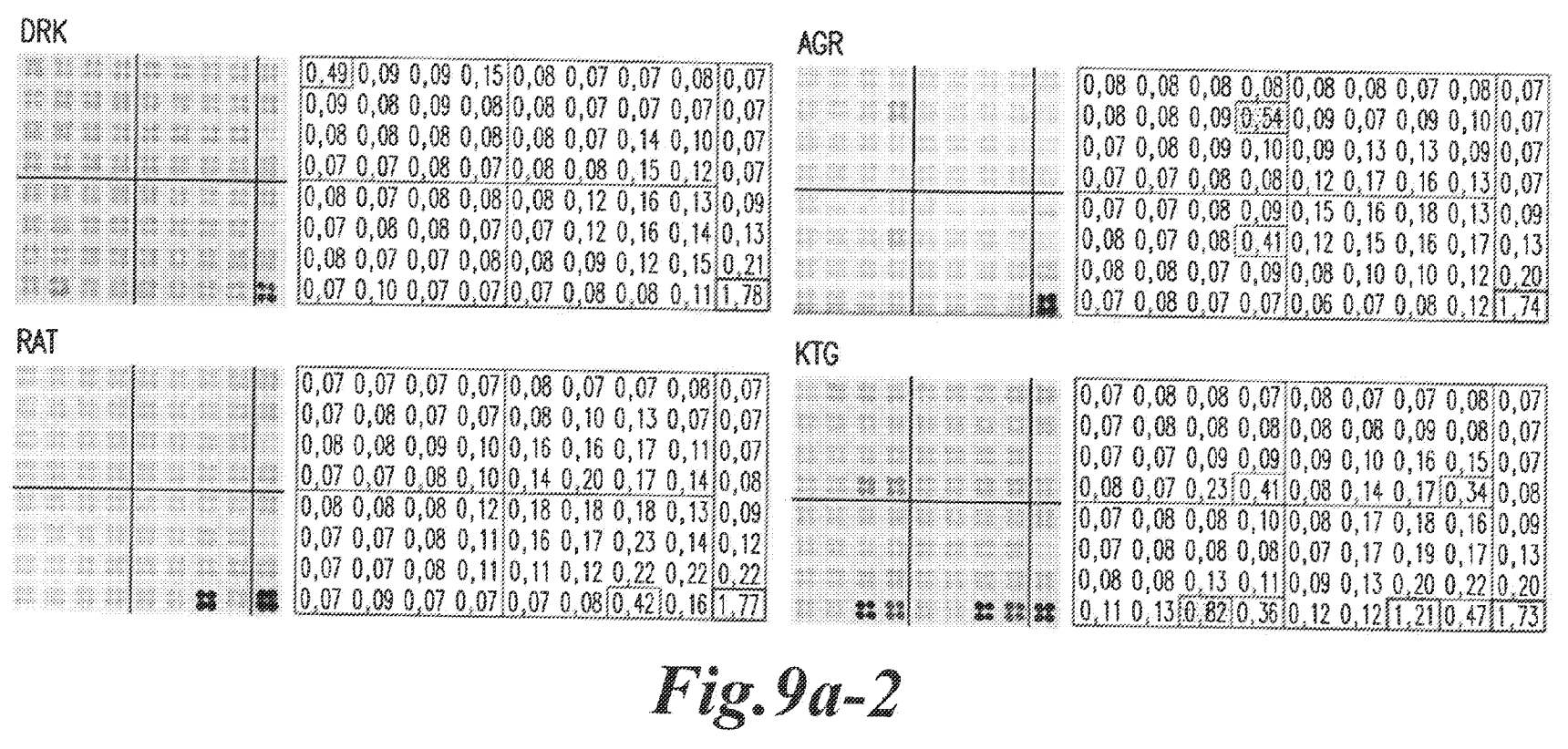

FIG. 9 illustrates the cleavage patterns of the variants. Mutants are identified by three letters, corresponding to the residues in positions 44, 68 and 70. Each mutant is tested versus the 64 targets derived from the I-CreI natural targets, and a series of control targets. Target map is indicated in the top right panel. (a) Cleavage patterns in yeast (left) and mammalian cells (right) for the wild-type I-CreI (I-CreI) and I-CreI N75 (QRR) proteins, and 7 derivatives of the I-CreI N75 protein. For yeast, the initial raw data (filter) is shown. For CHO cells, quantitative raw data (ONPG measurement) are shown, values superior to 0.25 are boxed, values superior to 0.5 are highlighted in medium grey, values superior to 1 in dark grey. LacZ: positive control. 0: no target. U1, U2 and U3: three different uncleaved controls. (b) Cleavage in vitro. I-CreI and four mutants are tested against a set of 2 or 4 targets, including the target resulting in the strongest signal in yeast and CHO. Digests are performed at 37° C. for 1 hour, with 2 nM linearized substrate, as described in Methods. Raw data are shown for I-CreI with two different targets. With both ggg and cct, cleavage is not detected with I-CreI.

Figure 10B:
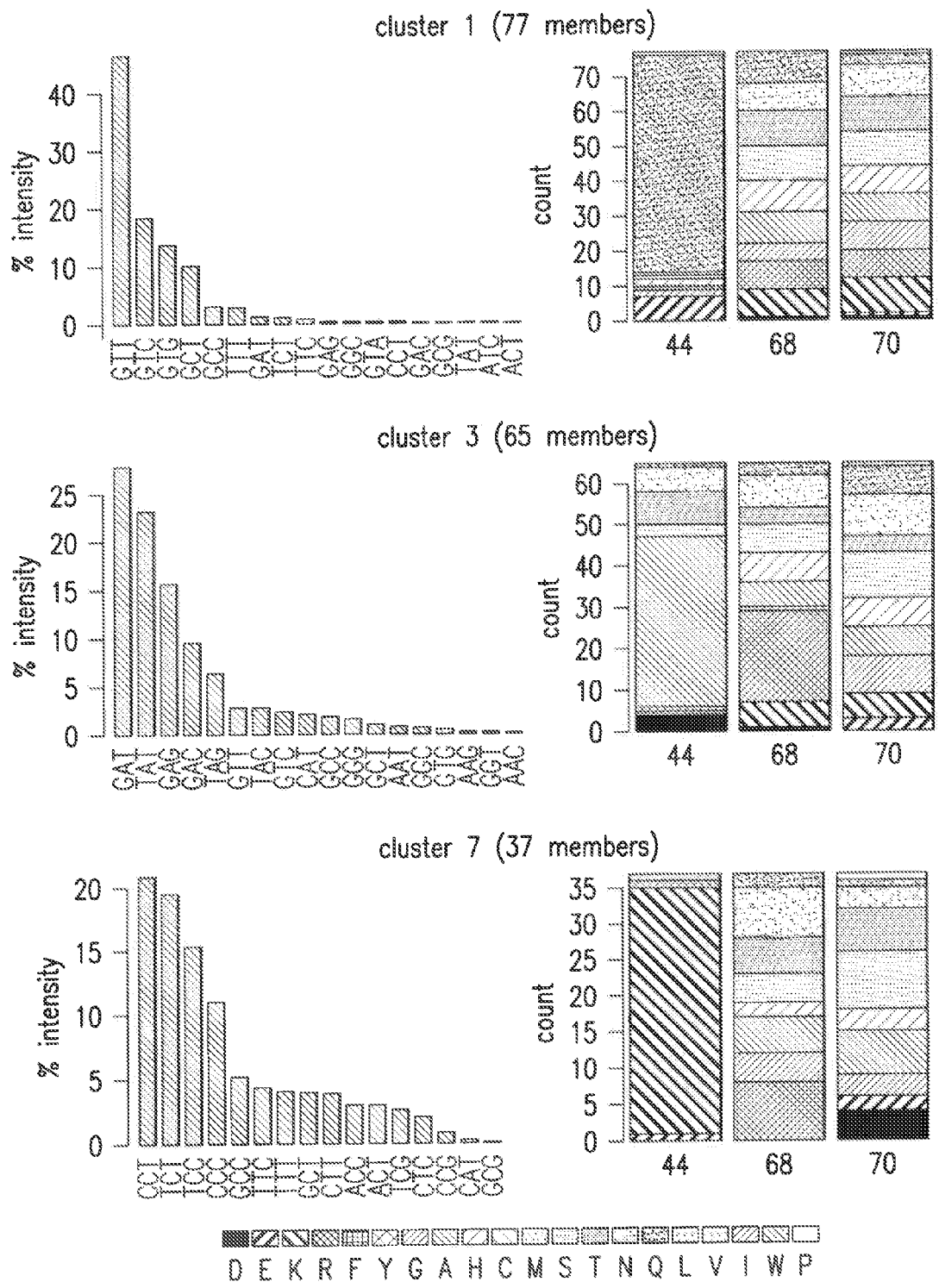
Figures 1, 10C:
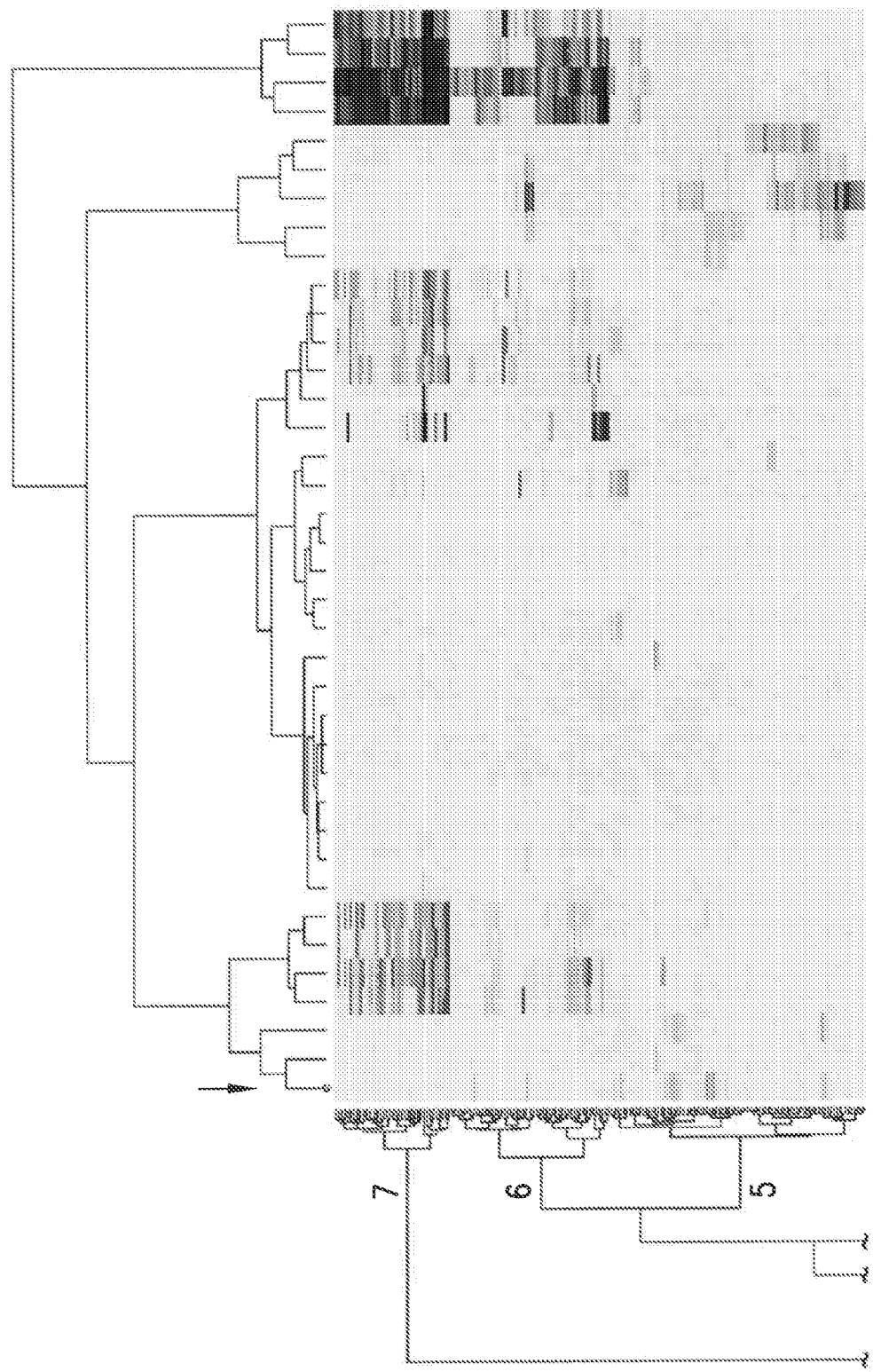
Figures 2, 10C:
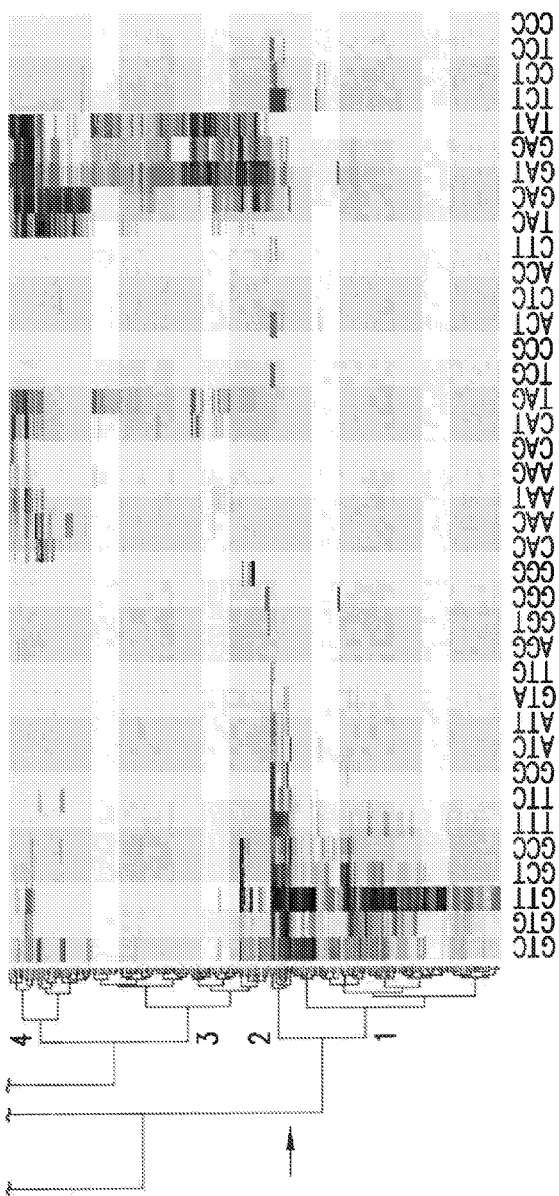

FIG. 10 represents the statistical analysis. (a) Cleaved targets: targets cleaved by I-CreI variants are colored in grey. The number of proteins cleaving each target is shown below, and the level of grey coloration is proportional to the average signal intensity obtained with these cutters in yeast. (b) Analysis of 3 out of the 7 clusters. For each mutant cluster (clusters 1, 3 and 7), the cumulated intensities for each target was computed and a bar plot (left column) shows in decreasing order the normalized intensities. For each cluster, the number of amino acid of each type at each position (44, 68 and 70) is shown as a coded histogram in the right column. The legend of amino-acid color code is at the bottom of the figure. (b) Hierarchical clustering of mutant and target data in yeast. Both mutants and targets were clustered using hierarchical clustering with Euclidean distance and Ward's method (Ward, J. H., American statist. Assoc., 1963, 58, 236-244). Clustering was done with hclust from the R package. Mutants and targets dendrograms were reordered to optimize positions of the clusters and the mutant dendrogram was cut at the height of 8 with deduced clusters. QRR mutant and GTC target are indicated by an arrow. Gray levels reflects the intensity of the signal.

FIG. 11 illustrates an example of hybrid or chimeric site: gtt (SEQ ID NO: 79) and cct (SEQ ID NO: 77) are two palindromic sites derived from the I-CreI site. The gtt/cct hybrid site (SEQ ID NO: 80) displays the gtt sequence on the top strand in –5, –4, –3 and the cct sequence on the bottom strand in 5, 4, 3.

Figure 12:
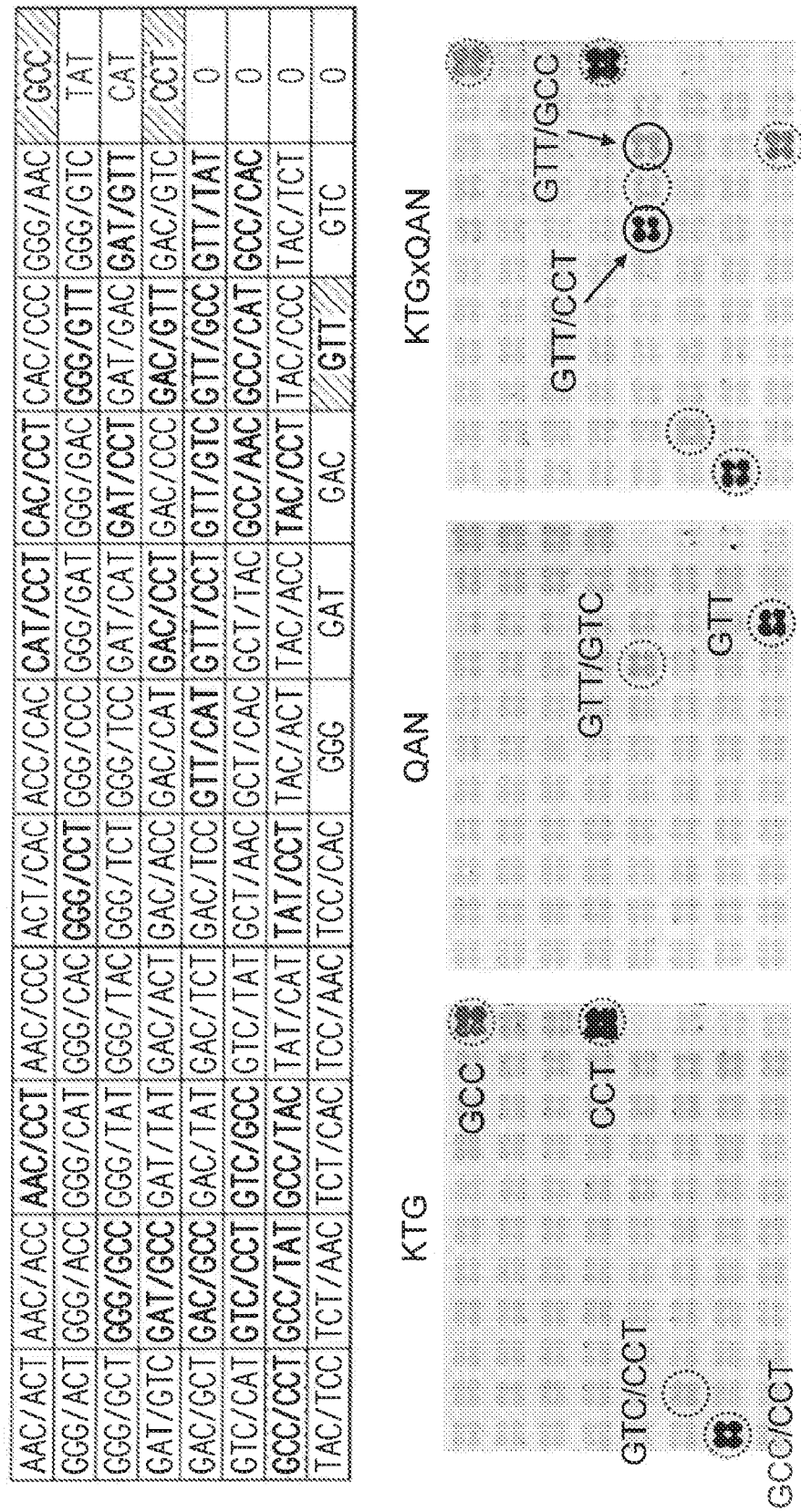

FIG. 12 illustrates the cleavage activity of the heterodimeric variants. Yeast were co-transformed with the KTG and QAN variants. Target organization is shown on the top panel: target with a single gtt, cct or gcc half site are in bold; targets with two such half sites, which are expected to be cleaved by homo- and/or heterodimers, are in bold and highlighted in grey; 0: no target. Results are shown on the three panels below. Unexpected faint signals are observed only for gtc/cct and gtt/gtc, cleaved by KTG and QAN, respectively.

Figure 13A:
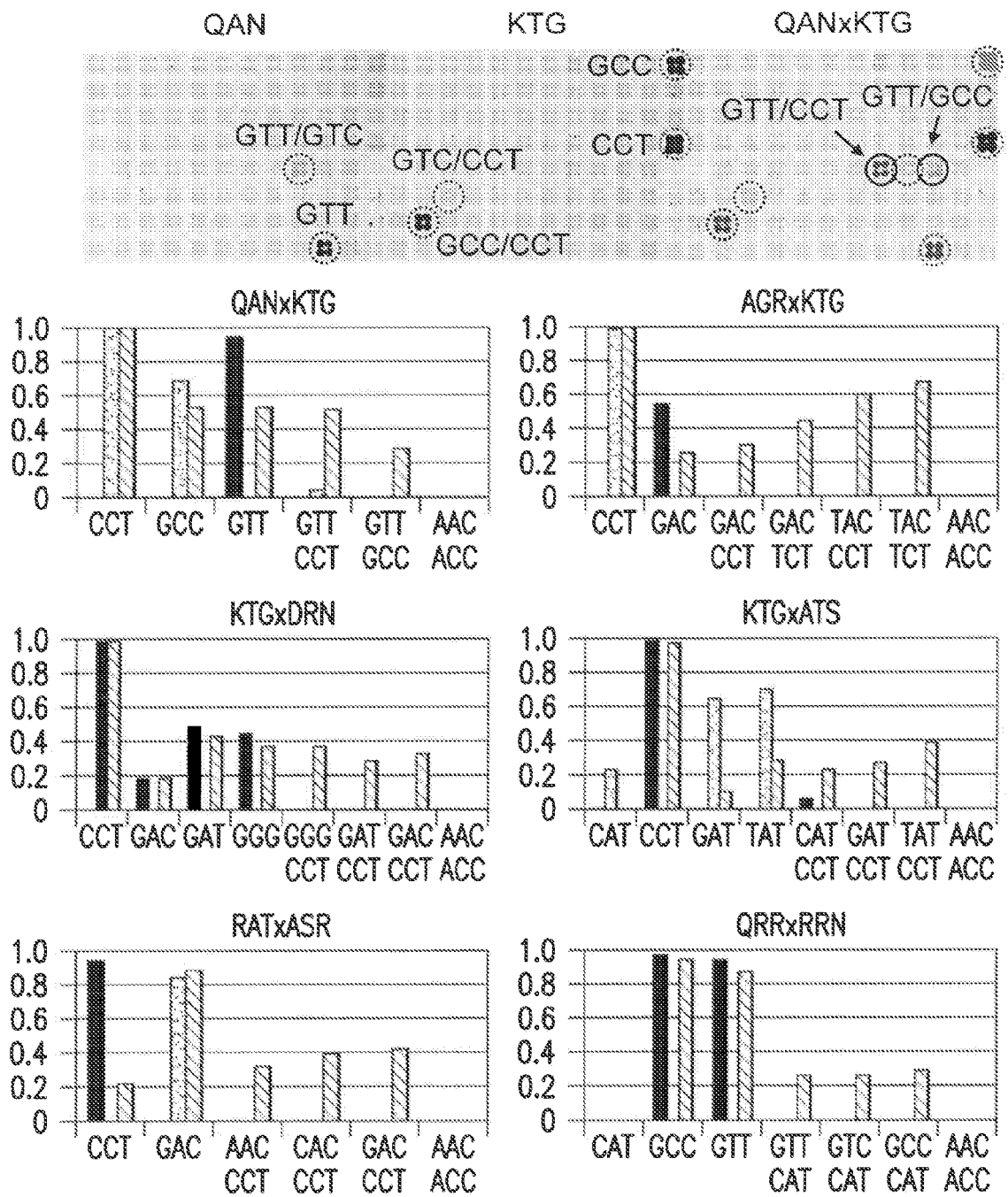

FIG. 13 represents the quantitative analysis of the cleavage activity of the heterodimeric variants. (a) Co-transformation of selected mutants in yeast. For clarity, only results on relevant hybrid targets are shown. The aac/acc target is always shown as an example of unrelated target. For the KTG×AGR couple, the palindromic tac and tct targets, although not shown, are cleaved by AGR and KTG, respectively. Cleavage of the cat target by the RRN mutant is very low, and could not be quantified in yeast. (b) Transient co-transfection in CHO cells. For (a) and (b), Black bars: signal for the first mutant alone; grey bars: signal for the second mutant alone; striped bars: signal obtained by co-expression or cotransfection.

Figure 14:
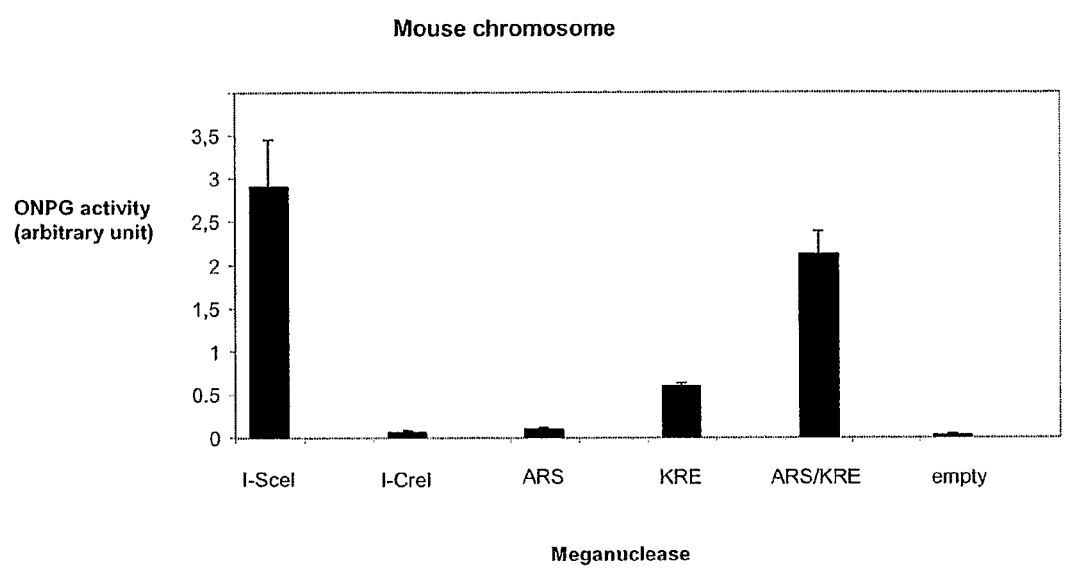

FIG. 14 illustrates the activity of the assembled heterodimer ARS-KRE on the selected mouse chromosome 17 DNA target. CHO-K1 cell line were co -transfected with equimolar of target LagoZ plasmid, ARS and KRE expression plasmids, and the beta galactosidase activity was measured. Cells co-transfected with the LagoZ plasmid and the I-SceI, I-CreI, ARS or KRE recombinant plasmid or an empty plasmid were used as control.

The following examples are presented here only for illustrating the invention and not for limiting the scope thereof. Other variants, obtained from a cDNA, which sequence differs from SEQ ID NO: 69, and using appropriate primers, are still part of the invention.

EXAMPLE 1

Screening for New Functional Endonucleases

Figure 3A:
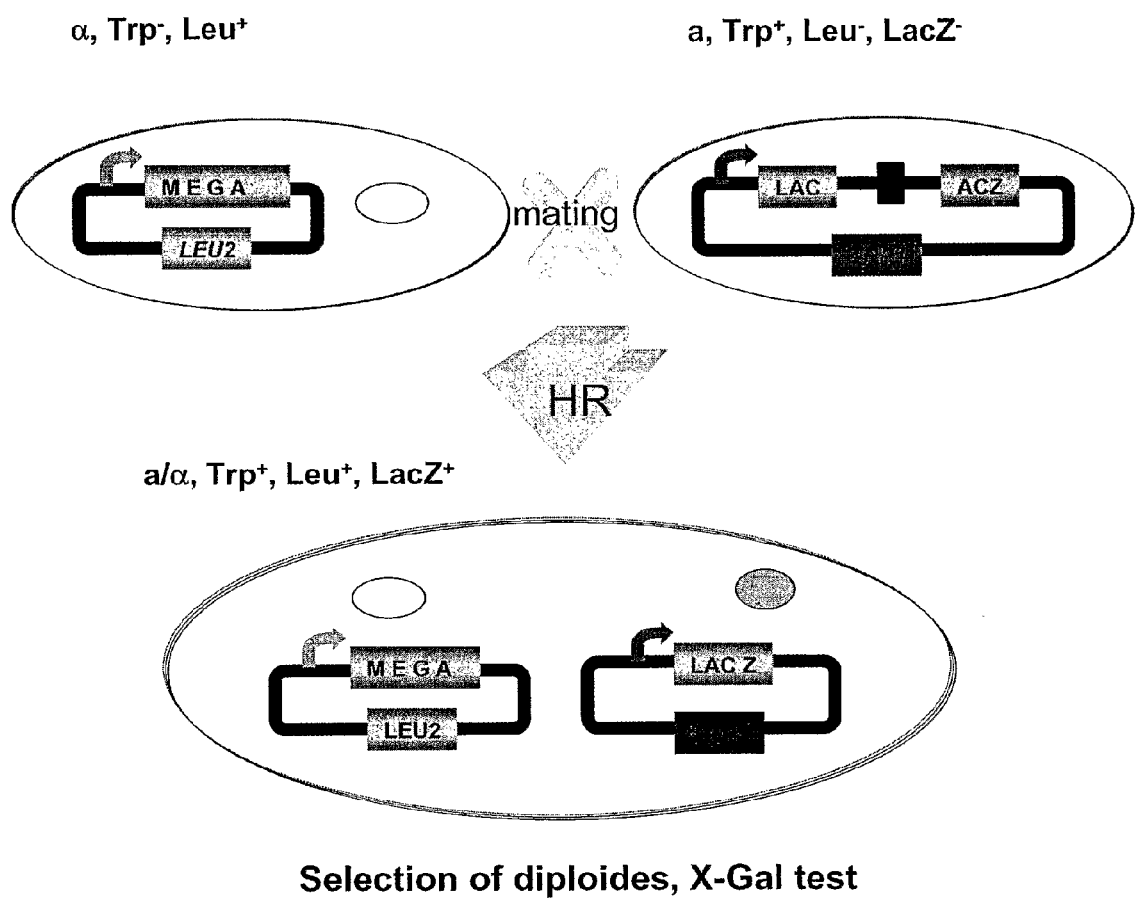
Figure 3B:
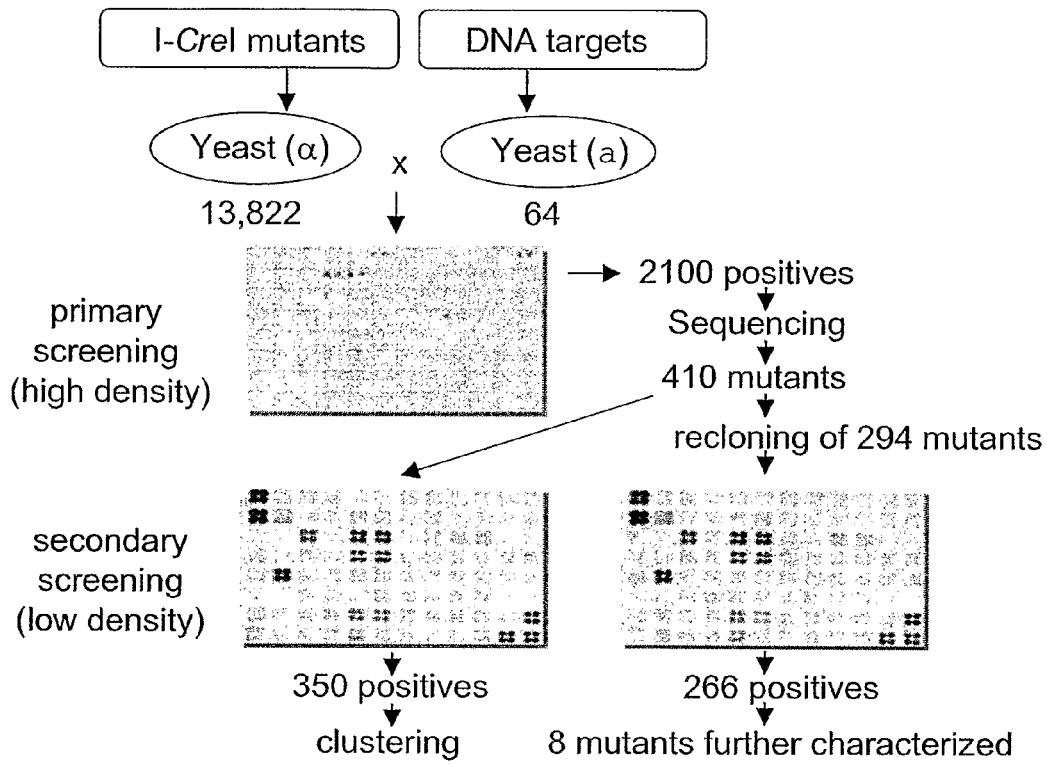

The method for producing meganuclease variants and the assays based on cleavage-induced recombination in mammal or yeast cells, which are used for screening variants with altered specificity, are described in the International PCT Application WO 2004/067736. These assays result in a functional LacZ reporter gene which can be monitored by standard methods (FIG. 3a).

A) Material and Methods a) Construction of Mutant Libraries

I-CreI wt and I-CreI D75N (or I-CreI N75) open reading frames (SEQ ID NO:69, FIG. 4A) were synthesized, as described previously (Epinat et al., N.A.R., 2003, 31, 2952-2962). Mutation D75N was introduced by replacing codon 75 with aac. The diversity of the meganuclease library was generated by PCR using degenerate primers from Sigma harboring codon VVK (18 codons, amino acids ADEGHKNPQRST) at position 44, 68 and 70 which interact directly with the bases at positions 3 to 5, and as DNA template, the I-CreI D75N gene. Such primers allow mutation of residues 44, 68 and 70 with a theoretical diversity of 12. Briefly, forward primer (5'-gtttaaacatcagctaagcttgacctttvvkgtgacttcaaaagacccag-3', SEQ ID NO: 67) and reverse primer (5'-gatgtagttggaaacggatccmbbatcmbbtacgtaaccaacgcc-3', SEQ ID NO: 68) were used to amplify a PCR fragment in 50 µl PCR reactions: PCR products were pooled, EtOH precipitated and resuspended in 50 µl 10 mM Tris. PCR products were cloned into a pET expression vector containing the I-CreI D75N gene, digested with appropriate restriction enzymes. Digestion of vector and insert DNA were conducted in two steps (single enzyme digestion) between which the DNA sample was extracted (using classic phenol:chloroform:isoamylalcohol-based methods) and EtOH-precipitated. 10 µg of digested vector DNA were used for ligation, with a 5:1 excess of insert DNA. E coli TG1 cells were transformed with the resulting vector by electroporation. To produce a number of cell clones above the theoretical diversity of the library, $6 \times 10^4$ clones were produced. Bacterial clones were scraped from plates and the corresponding plasmid vectors were extracted and purified.

The library was recloned in the yeast pCLS0542 vector (FIG. 5), by sub-cloning a NcoI-EagI DNA fragment containing the entire I-CreI D75N ORF. In this 2 micron-based replicative vector marked with the LEU2 gene, I-CreI variants are under the control of a galactose inducible promoter (Epinat et al., precited). After electroporation in E. coli, $7 \times 10^4$ clones were obtained $7 \times 10^4$ clones, representing 12 times the theoretical diversity at the DNA level (1 g3=5832). DNA was extracted and transformed into S. cerevisiae strain FYC2-6A (MATα, trp1Δ63, leu2Δ1, his3Δ200). 13824 colonies were picked using a colony picker (QpixII, GENETIX), and grown in 144 microtiter plates.

b) Construction of Target Clones

The C1221 twenty-four by palindrome (tcaaaacgtcgtacgacgttttga, SEQ ID NO: 12) is a repeat of the half-site of the nearly palindromic natural I-CreI target (tcaaaacgtcgtgagacagtttgg, SEQ ID NO: 65). C 1221 is cleaved as efficiently as the I-CreI natural target in vitro and ex vivo in both yeast and mammalian cells. The 64 palindromic targets were derived as follows: 64 pair of oligonucleotides (ggcatacaagtttcaaaacnnngtacnnngttttgacaatcgtctgtca (SEQ ID NO: 72) and reverse complementary sequences) corresponding to the two strands of the 64 DNA targets, with 12 pb of non palindromic extra sequence on each side, were ordered form Sigma, annealed and cloned into pGEM-T Easy (PROMEGA). Next, a 400 by PvuII fragment was excised from each one of the 64 pGEM-T-derived vector and cloned into the yeast vector pFL39-ADH-LACURAZ, described previously (Epinat et al., precited), also called pCLS0042 (FIG. 6), resulting in 64 yeast reporter vectors. Steps of excision, digestion and ligation are performed using typical methods known by those skilled in the art. Insertion of the target sequence is made at the SmaI site of pCLS0042. The 64 palindromic targets are described in FIG. 2B (positions −5 to −3 and +3 to +5, SEQ ID NOS: 1-6, 81, 8-18, 82-83, 21-27, 84, 29-31, 85, 33-38, 86, 40-50, 87-88, 53-59, 89, 61-63 and 90, respectively, in order of appearance).

c) Yeast Strains and Transformation

The library of meganuclease expression variants and the A44/R68/L70 variant, were transformed into strain FYC2-6A (MATα, trp1Δ63, leu2Δ1, his3Δ200).

The target plasmids were transformed into yeast strain FYBL2-7B: (MATa, ura3Δ851, trp1Δ63, leu2Δ1, lys2Δ202).

For transformation, a classical chemical/heat choc protocol can be used, and routinely gives $10^6$ independent transformants per µg of DNA; transformants were selected on leucine drop-out synthetic medium (Gietz and Woods, 2002).

d) Mating of Meganuclease Expressing Clones and Screening in Yeast

I-CreI variant clones as well as yeast reporter strains were stocked in glycerol (20%) stock and replicated in novel microplates. Mutants were gridded on nylon filters covering YPD plates, using a high gridding density (about 20 spots/cm$^2$). A second gridding process was performed on the same filters to spot a second layer consisting of 64 or 75 different reporter-harboring yeast strains for each variant. Briefly, each reporter strain was spotted 13 824 times on a nylon membrane, and on each one of this spot was spotted one out of the 13 824 yeast clones expressing a variant meganuclease. Membranes were placed on solid agar YPD rich medium, and incubated at 30° C. for one night, to allow mating. Next, filters were transferred to synthetic medium, lacking leucine and tryptophan, with galactose (1%) as a carbon source (and with G418 for coexpression experiments), and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Positive clones were identified after two days of incubation, according to staining. Results were analyzed by scanning and quantification was performed using a proprietary software. For secondary screening, the same procedure was followed with the 292 selected positives, except that each mutant was tested 4 times on the same membrane (see FIGS. 8 and 9a).

d) Sequence and Re-Cloning of Primary Hits

The open reading frame (ORF) of positive clones identified during the primary screening in yeast was amplified by PCR and sequenced. Then, ORFs were recloned using the Gateway protocol (Invitrogen). ORFs were amplified by PCR on yeast colonies (Akada et al., Biotechniques, 28, 668-670, 672-674), using primers:

```
                                      (SEQ ID NO: 73)
ggggacaagtttgtacaaaaaagcaggcttcgaaggagatagaaccatgg ccaataccaaatataacaaagagttcc
and
                                      (SEQ ID NO: 74)
ggggaccactttgtacaagaaagctgggtttagtcggccgccggggagga tttcttcttctcgc
``` from PROLIGO. PCR products were cloned in: (i) yeast gateway expression vector harboring a galactose inducible promoter, LEU2 or KanR as selectable marker and a 2 micron origin of replication, and (ii) a pET 24d(+) vector from NOVAGEN. Resulting clones were verified by sequencing (MILLEGEN).

B) Results

I-CreI is a dimeric homing endonuclease that cleaves a 22 bp pseudo-palindromic target. Analysis of I-CreI structure bound to its natural target has shown that in each monomer, eight residues establish direct interactions with seven bases (Jurica et al., 1998, precited). Residues Q44, R68, R70 contact three consecutive base pairs at position 3 to 5 (and −3 to −5, FIG. 1). An exhaustive protein library vs. target library approach was undertaken to engineer locally this part of the DNA binding interface. First, the I-CreI scaffold was mutated from D75 to N to decrease likely energetic strains caused by the replacement of the basic residues R68 and R70 in the library that satisfy the hydrogen-acceptor potential of the buried D75 in the I-CreI structure. Homodimers of mutant D75N (purified from *E. coli* cells wherein it was over-expressed using a pET expression vector) were shown to cleave the I-CreI homing site. The D75N mutation did not affect the protein structure, but decreased the toxicity of I-CreI in over-expression experiments. Next, positions 44, 68 and 70 were randomized and 64 palindromic targets resulting from substitutions in positions ±3, ±4 and ±5 of a palindromic target cleaved by I-CreI (Chevalier et al., 2003, precited) were generated, as described in FIGS. 1 and 2B. Eventually, mutants in the protein library corresponded to independent combinations of any of the 12 amino acids encoded by the vvk codon at three residue positions. In consequence, the maximal (theoretical) diversity of the protein library was $12^3$ or 1728. However, in terms of nucleic acids, the diversity is $18^3$ or 5832.

The resulting library was cloned in a yeast replicative expression vector carrying a LEU2 auxotrophic marker gene and transformed into a leu2 mutant haploid yeast strain (FYC2-6A). The 64 targets were cloned in the appropriate yeast reporter vector and transformed into an haploid strain (FYBL2-7B), resulting in 64 tester strains.

A robot-assisted mating protocol was used to screen a large number of meganucleases from our library. The general screening strategy is described in FIG. 3b. 13,8247 meganuclease expressing clones (about 2.3-fold the theoretical diversity) were spotted at high density (20 spots/cm$^2$) on nylon filters and individually tested against each one of the 64 target strains (884,608 spots). 2100 clones showing an activity against at least one target were isolated (FIG. 3b) and the ORF encoding the meganuclease was amplified by PCR and sequenced. 410 different sequences were identified and a similar number of corresponding clones were chosen for further analysis. The spotting density was reduced to 4 spots/cm$^2$ and each clone was tested against the 64 reporter strains in quadruplicate, thereby creating complete profiles (as in FIGS. 8 and 9a). 350 positives could be confirmed. Next, to avoid the possibility of strains containing more than one clone, mutant ORFs were amplified by PCR, and recloned in the yeast vector. The resulting plasmids were individually transformed back into yeast. 294 such clones were obtained and tested at low density (4 spots/cm$^2$). Differences with primary screening were observed mostly for weak signals, with 28 weak cleavers appearing now as negatives. Only one positive clone displayed a pattern different from what was observed in the primary profiling.

EXAMPLE 2

I-CreI Meganuclease Variants with Different Cleavage Profiles

The validated clones from example 1 showed very diverse patterns. Some of these new profiles shared some similarity with the initial scaffold whereas many others were totally different. Various examples of profiles, including wild-type I-CreI and I-CreI N75, are shown in FIGS. 8 and 9a. The overall results (only for the 292 variants with modified specificity) are summarized in FIG. 7.

Homing endonucleases can usually accommodate some degeneracy in their target sequences, and one of our first findings was that the original I-CreI protein itself cleaves seven different targets in yeast. Many of our mutants followed this rule as well, with the number of cleaved sequences ranging from 1 to 21 with an average of 5.0 sequences cleaved (standard deviation=3.6). Interestingly, in 50 mutants (14%), specificity was altered so that they cleaved exactly one target. 37 (11%) cleaved 2 targets, 61 (17%) cleaved 3 targets and 58 (17%) cleaved 4 targets. For 5 targets and above, percentages were lower than 10%. Altogether, 38 targets were cleaved by the mutants (FIG. 10a). It is noteworthy that cleavage was barely observed on targets with an A in position ±3, and never with targets with tgn and cgn at position ±5, ±4, ±3.

These results do not limit the scope of the invention, since FIG. 7 only shows results obtained with 292 variants (291 out of the 1728 (or $12^3$) I-CreI meganuclease variants obtainable in a complete library).

EXAMPLE 3

Novel Meganucleases can Cleave Novel Targets while Keeping High Activity and Narrow Specificity A) Material and Methods a) Construction of Target Clones The 64 palindromic targets were cloned into pGEM-T Easy (PROMEGA), as described in example 1. Next, a 400 bp PvuII fragment was excised and cloned into the mammalian vector pcDNA3.1-LACURAZ-AURA, described previously (Epinat et al., precited). The 75 hybrid targets sequences were cloned as follows: oligonucleotides were designed that contained two different half sites of each mutant palindrome (PROLIGO).

b) Re-Cloning of Primary Hits

The open reading frame (ORF) of positive clones identified during the primary screening in yeast was recloned in: (i) a CHO gateway expression vector pcDNA6.2, following the instructions of the supplier (INVITROGEN), and ii) a pET 24d(+) vector from NOVAGEN Resulting clones were verified by sequencing (MILLEGEN).

c) Mammalian Cells Assay

CHO-K1 cell line from the American Type Culture Collection (ATCC) was cultured in Ham's F12K medium supplemented with 10% Fetal Bovine Serum. For transient Single Strand Annealing (SSA) assays, cells were seeded in 12 well-plates at $13.10^3$ cells per well one day prior transfection. Cotransfection was carried out the following day with 400 ng of DNA using the EFFECTENE transfection kit (QIAGEN).

Equimolar amounts of target LagoZ plasmid and expression plasmid were used. The next day, medium was replaced and cells were incubated for another 72 hours. CHO-K1 cell monolayers were washed once with PBS. The cells were then lysed with 150 µl of lysis/revelation buffer added for β-galactosidase liquid assay (100 ml of lysis buffer (Tris-HCl 10 mM pH7.5, NaCl 150 mM, Triton X100 0.1%, BSA 0.1 mg/ml, protease inhibitors) and 900 ml of revelation buffer (10 ml of Mg 100× buffer (MgCl$_2$ 100 mM, β-mercaptoethanol 35%), 110 ml ONPG (8 mg/ml) and 780 ml of sodium phosphate 0.1 M pH7.5), 30 minutes on ice. Beta-galactosidase activity was assayed by measuring optical density at 415 nm. The entire process was performed on an automated Velocity11 BioCel platform. The beta-galactosidase activity is calculated as relative units normalized for protein concentration, incubation time and transfection efficiency.

d) Protein Expression and Purification

His-tagged proteins were over-expressed in *E. coli* BL21 (DE3)pLysS cells using pET-24d (+) vectors (NOVAGEN). Induction with IPTG (0.3 mM), was performed at 25° C. Cells were sonicated in a solution of 50 mM Sodium Phosphate (pH 8), 300 mM sodium chloride containing protease inhibitors (Complete EDTA-free tablets, Roche) and 5% (v/v) glycerol. Cell lysates were centrifuged at 100000 g for 60 min. His-tagged proteins were then affinity-purified, using 5 ml Hi-Trap chelating HP columns (Amersham Biosciences) loaded with cobalt. Several fractions were collected during elution with a linear gradient of imidazole (up to 0.25M imidazole, followed by plateau at 0.5 M imidazole, 0.3 M NaCl and 50 mM Sodium Phosphate pH 8). Protein-rich fractions (determined by SDS-PAGE) were applied to the second column. The crude purified samples were taken to pH 6 and applied to a 5 ml HiTrap Heparin HP column (Amersham Biosciences) equilibrated with 20 mM Sodium Phosphate pH 6.0. Bound proteins are eluted with a sodium chloride continuous gradient with 20 mM sodium phosphate and 1M sodium chloride. The purified fractions were submitted to SDS-PAGE and concentrated (10 kDa cut-off centriprep Amicon Ultra system), frozen in liquid nitrogen and stored at −80° C. Purified proteins were desalted using PD10 columns (Sephadex G-25M, Amersham Biosciences) in PBS or 10 mM Tris-HCl (pH 8) buffer.

e) In Vitro Cleavage Assays pGEM plasmids with single meganuclease DNA target cut sites were first linearized with XmnI. Cleavage assays were performed at 37° C. in 10 mM Tris-HCl (pH 8), 50 mM NaCl, 10 mM MgCl$_2$, 1 mM DTT and 50 µg/ml BSA. 2 nM was used as target substrate concentration. A dilution range between 0 and 85 mM was used for each protein, in 25 µl final volume reaction. Reactions were stopped after 1 hour by addition of 5 µl of 45% glycerol, 95 mM EDTA (pH 8), 1.5% (w/v) SDS, 1.5 mg/ml proteinase K and 0.048% (w/v) bromophenol blue (6× Buffer Stop) and incubated at 37° C. for 30 minutes. Digests were run on agarosse electrophoresis gel, and fragment quantified after ethidium bromide staining, to calculate the percentage of cleavage.

B) Results

Eight representative mutants (belonging to 6 different clusters, see below) were chosen for further characterization (FIG. 9). First, data in yeast were confirmed in mammalian cells, by using an assay based on the transient cotransfection of a meganuclease expressing vector and a target vector, as described in a previous report. The 8 mutant ORFs and the 64 targets were cloned into appropriate vectors, and a robot-assisted microtiter-based protocol was used to co-transfect in CHO cells each selected variant with each one the 64 different reporter plasmids. Meganuclease-induced recombination was measured by a standard, quantitative ONPG assay that monitors the restoration of a functional β-galactosidase gene. Profiles were found to be qualitatively and quantitatively reproducible in five independent experiments. As shown on FIG. 9a, strong and medium signals were nearly always observed with both yeast and CHO cells (with the exception of ADK), thereby validating the relevance of the yeast HTS process. However, weak signals observed in yeast were often not detected in CHO cells, likely due to a difference in the detection level (see QRR and targets gtg, get, and ttc). Four mutants were also produced in *E. coli* and purified by metal affinity chromatography. Their relative in vitro cleavage efficiencies against the wild-type site and their cognate sites was determined. The extent of cleavage under standardized conditions was assessed across a broad range of concentrations for the mutants (FIG. 9b). Similarly, the activity of I-CreI wt on these targets, was analysed. In many case, 100% cleavage of the substrate could not be achieved, likely reflecting the fact that these proteins may have little or no turnover (Perrin et al., EMBO J., 1993, 12, 2939-2947; Wang et al., Nucleic Acids Res., 1997, 25, 3767-3776). In general, in vitro assay confirmed the data obtained in yeast and CHO cells, but surprisingly, the gtt target was efficiently cleaved by I-CreI Specificity shifts were obvious from the profiles obtained in yeast and CHO: the I-CreI favorite gtc target was not cleaved or barely cleaved, while signals were observed with new targets. This switch of specificity was confirmed for QAN, DRK, RAT and KTG by in vitro analysis, as shown on FIG. 9b. In addition, these four mutants, which display various levels of activity in yeast and CHO (FIG. 9a) were shown to cleave 17-60% of their favorite target in vitro (FIG. 9b), with similar kinetics to I-CreI (half of maximal cleavage by 13-25 nM). Thus, activity was largely preserved by engineering. Third, the number of cleaved targets varied among the mutants: strong cleavers such as QRR, QAN, ARL and KTG have a spectrum of cleavage in the range of what is observed with I-CreI (5-8 detectable signals in yeast, 3-6 in CHO). Specificity is more difficult to compare with mutants that cleave weakly. For example, a single weak signal is observed with DRK but might represent the only detectable signal resulting from the attenuation of a more complex pattern. Nevertheless, the behavior of variants that cleave strongly shows that engineering preserves a very narrow specificity.

EXAMPLE 4

Hierarchical Clustering Defines Seven I-CreI Variant Families

A) Material and Methods

Clustering was done using hclust from the R package. We used quantitative data from the primary, low density screening. Both variants and targets were clustered using standard hierarchical clustering with Euclidean distance and Ward's method (Ward, J. H., American Stat. Assoc., 1963, 58, 236-244). Mutants and targets dendrograms were reordered to optimize positions of the clusters and the mutant dendrogram was cut at the height of 8 to define the cluster.

B) Results

Next, hierarchical clustering was used to determine whether families could be identified among the numerous and diverse cleavage patterns of the variants. Since primary and secondary screening gave congruent results, quantitative data from the first round of yeast low density screening was used for analysis, to permit a larger sample size. Both variants and targets were clustered using standard hierarchical clustering with Euclidean distance and Ward's method (Ward, J. H., precited) and seven clusters were defined (FIG. 10b). Detailed analysis is shown for 3 of them (FIG. 10c) and the results are summarized in Table I.

−4 (and the top strand of position +4, see FIG. 1b and 1c). These results suggests that this interaction is largely conserved in our mutants, and reveals a "code", wherein Q44 would establish contact with adenine, A44 (or less frequently N44) with thymine, and K44 with guanine. Such correlation was not observed for positions 68 and 70.

TABLE I

Cluster Analysis

| cluster | examples (FIG. 3a) | Three preferred targets [1] sequence | % cleavage | Nucleotide in position 4 (%) [1] | | preferred amino acid [2] 44 | 68 | 70 |
|---|---|---|---|---|---|---|---|---|
| 1 | QAN | gtt | 46.2 | g | 0.5 | Q | | |
| | | gtc | 18.3 | a | 2.0 | 80.5% | | |
| 77 proteins | | gtg | 13.6 | t | 82.4 | (62/77) | | |
| | | Σ = 78.1 | | c | 15.1 | | | |
| 2 | QRR | gtt | 13.4 | g | 0 | Q | R | |
| | | gtc | 11.8 | a | 4.9 | 100.0% | 100.0% | |
| 8 proteins | | tct | 11.4 | t | 56.9 | (8/8) | (8/8) | |
| | | Σ = 36.6 | | c | 38.2 | | | |
| 3 | ARL | gat | 27.9 | g | 2.4 | A | R | |
| | | tat | 23.2 | a | 88.9 | 63.0% | 33.8% | |
| 65 proteins | | gag | 15.7 | t | 5.7 | (41/65) | (22/65) | |
| | | Σ = 66.8 | | c | 3.0 | | | |
| 4 | AGR | gac | 22.7 | g | 0.3 | A&N | R | R |
| | | tac | 14.5 | a | 91.9 | 51.6% & 35.4% | 48.4% | 67.7% |
| 31 proteins | | gat | 13.4 | t | 6.6 | (16&11/31) | 15/31 | 21/31 |
| | | Σ = 50.6 | | c | 1.2 | | | |
| 5 | ADK | gat | 29.21 | g | 1.6 | | | |
| | DRK | tat | 15.4 | a | 73.8 | | | |
| 81 proteins | | gac | 11.4 | t | 13.4 | | | |
| | | Σ = 56.05.9 | | c | 11.2 | | | |
| 6 | KTG | cct | 30.1 | g | 0 | K | | |
| | RAT | tct | 19.6 | a | 4.0 | 62.7% | | |
| 51 proteins | | tcc | 13.9 | t | 6.3 | (32/51) | | |
| | | Σ = 63.6 | | c | 89.7 | | | |
| 7 | | cct | 20.8 | g | 0 | K | | |
| | | tct | 19.6 | a | 0.2 | 91.9% | | |
| 37 proteins | | tcc | 15.3 | t | 14.4 | (34/37) | | |
| | | Σ = 55.7 | | c | 85.4 | | | |

[1] frequencies according to the cleavage index, as described in FIG. 10c in each position, residues present in more than 1/3 of the cluster are indicated For each cluster, a set of preferred targets could be identified on the basis of the frequency and intensity of the signal (FIG. 10c). The three preferred targets for each cluster are indicated in Table 1, with their cleavage frequencies. The sum of these frequencies is a measurement of the specificity of the cluster. For example, in cluster 1, the three preferred targets (gtt/c/g), account for 78.1% of the observed cleavage, with 46.2% for gtt alone, revealing a very narrow specificity. Actually, this cluster includes several proteins which, as QAN, which cleaves mostly gtt (FIG. 9a). In contrast, the three preferred targets in cluster 2 represent only 36.6% of all observed signals. In accordance with the relatively broad and diverse patterns observed in this cluster, QRR cleaves 5 targets (FIG. 9a), while other cluster members' activity are not restricted to these 5 targets.

Analysis of the residues found in each cluster showed strong biases for position 44: Q is overwhelmingly represented in clusters 1 and 2, whereas A and N are more frequent in clusters 3 and 4, and K in clusters 6 and 7. Meanwhile, these biases were correlated with strong base preferences for DNA positions +4, with a large majority of t:a base pairs in cluster 1 and 2, a:t in clusters 3, 4 and 5, and c:g in clusters 6 and 7 (see Table I). The structure of I-CreI bound to its target shows that residue Q44 interacts with the bottom strand in position

EXAMPLE 5

Variants can be Assembled in Functional Heterodimers to Cleave New DNA Target Sequences A) Materials and Methods The 75 hybrid targets sequences were cloned as follows: oligonucleotides were designed that contained two different half sites of each mutant palindrome (PROLIGO). Double-stranded target DNA, generated by PCR amplification of the single stranded oligonucleotides, was cloned using the Gateway protocol (INVITROGEN) into yeast and mammalian reporter vectors. Yeast reporter vectors were transformed into S. cerevisiae strain FYBL2-7B (MATα, ura3Δ851, trp1Δ63, leu2Δ1, lys2Δ202).

B) Results

Variants are homodimers capable of cleaving palindromic sites. To test whether the list of cleavable targets could be extended by creating heterodimers that would cleave hybrid cleavage sites (as described in FIG. 11), a subset of I-CreI variants with distinct profiles was chosen and cloned in two different yeast vectors marked by LEU2 or KAN genes. Combinations of mutants having mutations at positions 44, 68 and/or 70 and N at position 75, were then co-expressed in yeast with a set of palindromic and non palindromic chimeric DNA targets. An example is shown on FIG. 12: co-expression of the K44, T68, G70, N75 (KTG) and Q44, A68, N70, N75 (QAN) mutants resulted in the cleavage of two chimeric targets, gtt/gcc and gtt/cct, that were not cleaved by either mutant alone. The palindromic gtt, cct and gcc targets (and other targets of KTG and QAN) were also cleaved, likely resulting from homodimeric species formation, but unrelated targets were not. In addition, a gtt, cct or gcc half-site was not sufficient to allow cleavage, since such targets were fully resistant (see ggg/gcc, gat/gcc, gcc/tac, and many others, on FIG. 12). Unexpected cleavage was observed only with gtc/cct and gtt/gtc, with KTG and QAN homodimers, respectively, but signal remained very weak. Thus, efficient cleavage requires the cooperative binding of two mutant monomers. These results demonstrate a good level of specificity for heterodimeric species.

Figure 13B:
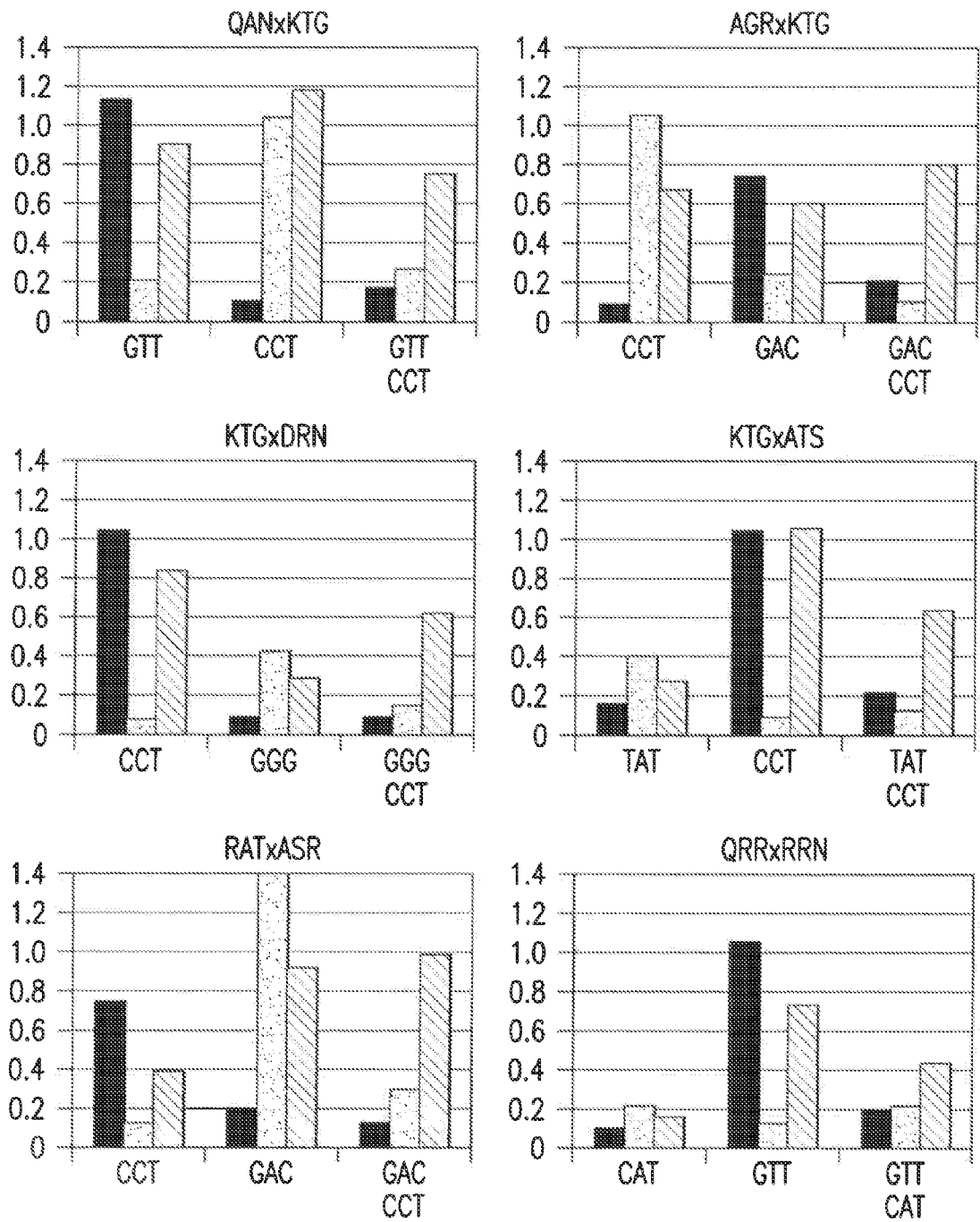

Altogether, a total of 112 combinations of 14 different proteins were tested in yeast, and 37.5% of the combinations (42/112) revealed a positive signal on their predicted chimeric target. Quantitative data are shown for six examples on FIG. 13*a*, and for the same six combinations, results were confirmed in CHO cells in transient co-transfection experiments, with a subset of relevant targets (FIG. 13*b*). As a general rule, functional heterodimers were always obtained when one of the two expressed proteins gave a strong signal as homodimer. For example, DRN and RRN, two low activity mutants, give functional heterodimers with strong cutters such as KTG or QRR (FIGS. 13*a* and 13*b*) whereas no cleavage of chimeric targets could be detected by co-expression of the same weak mutants

EXAMPLE 6

Cleavage of a Natural DNA Target by Assembled Heterodimer

A) Materials and Methods a) Genome Survey

A natural target potentially cleaved by a I-CreI variant, was identified by scanning the public databases, for genomic sequences matching the pattern caaaacnnnnnnnnnngttttg, wherein n is a, t, c, or g (SEQ ID NO: 78). The natural target DNA sequence caaaac<u>tatgtagagg</u>gttttg (SEQ ID NO: 75) was identified in mouse chromosome 17.

This DNA sequence is potentially cleaved by a combination of two I-CreI variants cleaving the sequences tcaaaac<u>tatgtaa</u>tagttttga (SEQ ID NO: 76) and tcaaaac<u>cct</u>gtga<u>aggg</u>ttttga (SEQ ID NO: 77), respectively.

b) Isolation of Meganuclease Variants

Variants were selected by the cleavage-induced recombination assay in yeast, as described in example 1, using the sequence tcaaaac<u>tatgtaatag</u>ttttga (SEQ ID NO: 76) or the sequence tcaaaac<u>cct</u>gtga<u>aggg</u>ttttga (SEQ ID NO: 77) as targets.

c) Construction of the Target Plasmid

Oligonucleotides were designed that contained two different half sites of each mutant palindrome (PROLIGO). Double-stranded target DNA, generated by PCR amplification of the single stranded oligonucleotides, was cloned using the Gateway protocol (INVITROGEN) into the mammalian reporter vector pcDNA3.1-LACURAZ-AURA, described previously (Epinat et al., precited), to generate the target LagoZ plasmid.

d) Construction of Meganuclease Expression Vector

The open reading frames (ORFs) of the clones identified during the screening in yeast were amplified by PCR on yeast colony and cloned individually in the CHO expression vector pcDNA6.2 (INVITROGEN), as described in example 1. I-CreI variants were expressed under the control of the CMV promoter.

e) Mammalian Cells Assay

CHO-K1 cell line were transiently co-transfected with equimolar amounts of target LagoZ plasmid and expression plasmids, and the beta galactosidase activity was measured as described in examples 3 and 5.

B) Results

A natural DNA target, potentially cleaved by I-CreI variants was identified by performing a genome survey of sequences matching the pattern caaaacnnnnnnnnngttttg (SEQ ID NO: 78). A randomly chosen DNA sequence (SEQ ID NO: 78) identified in chromosome 17 of the mouse was cloned into a reporter plasmid. This DNA target was potentially cleaved by a combination of the I-CreI variants A44, R68, S70, N75 (ARS) and K44, R68, E70, N75 (KRE).

The co-expression of these two variants in CHO cell leads to the formation of functional heterodimer protein as shown in FIG. 14. Indeed when the I-CreI variants were expressed individually, virtually no cleavage activity could be detected on the mouse DNA target although the KRE protein showed a residual activity. In contrast, when these two variants were co-expressed together with the plasmid carrying the potential target, a strong beta-galactosidase activity could be measured. All together these data revealed that heterodimerization occurred in the CHO cells and that heterodimers were functional.

These data demonstrate that heterodimers proteins created by assembling homodimeric variants, extend the list of natural occurring DNA target sequences to all the potential hybrid cleavable targets resulting from all possible combination of the variants.

Moreover, these data demonstrated that it is possible to predict the DNA sequences that can be cleaved by a combination of variant knowing their individual DNA target of homodimer. Furthermore, the nucleotides at positions 1 et 2 (and −1 and −2) of the target can be different from gtac, indicating that they play little role in DNA/protein interaction.

REFERENCES

Belfort, M. and Roberts, R. J. (1997) Homing endonucleases: keeping the house in order. Nucleic Acids Res, 25, 3379-3388.

Bell-Pedersen, D., Quirk, S., Clyman, J. and Belfort, M. (1990) Intron mobility in phage T4 is dependent upon a distinctive class of endonucleases and independent of DNA sequences encoding the intron core: mechanistic and evolutionary implications. Nucleic Acids Res, 18, 3763-3770.

Bell-Pedersen, D., Quirk, S. M., Aubrey, M. and Belfort, M. (1989) A site-specific endonuclease and co-conversion of flanking exons associated with the mobile td intron of phage T4. Gene, 82, 119-126.

Bell-Pedersen, D., Quirk, S. M., Bryk, M. and Belfort, M. (1991) I-TevI, the endonuclease encoded by the mobile td intron, recognizes binding and cleavage domains on its DNA target. Proc Natl Acad Sci USA, 88, 7719-7723.

Bibikova, M., Beumer, K., Trautman, J. K. and Carroll, D. (2003) Enhancing gene targeting with designed zinc finger nucleases. Science, 300, 764.

Bibikova, M., Carroll, D., Segal, D. J., Trautman, J. K., Smith, J., Kim, Y. G. and Chandrasegaran, S. (2001) Stimulation of homologous recombination through targeted cleavage by chimeric nucleases. Mol Cell Biol, 21, 289-297.

Bibikova, M., Golic, M., Golic, K. G. and Carroll, D. (2002) Targeted chromosomal cleavage and mutagenesis in Drosophila using zinc-finger nucleases. Genetics, 161, 1169-1175.

Chevalier, B., Sussman, D., Otis, C., Noël A.J., Turmel, M., Lemieux, C., Stephens, K., Monnat, R.Jr., Stoddard, B.L., (2004) Metal-Dependant DNA cleavage mechanism of the I-CreI LAGLIDADG (SEQ ID NO: 91) homing endonuclease. Biochemistry, 43, 14015-14026.

Chevalier, B. S., Kortemme, T., Chadsey, M. S., Baker, D., Monnat, R. J. and Stoddard, B. L. (2002) Design, activity, and structure of a highly specific artificial endonuclease. Mol Cell, 10, 895-905.

Chevalier, B. S. and Stoddard, B. L. (2001) Homing endonucleases: structural and functional insight into the catalysts of intron/intein mobility. Nucleic Acids Res, 29, 3757-3774.

Choulika, A., Perrin, A., Dujon, B. and Nicolas, J. F. (1995) Induction of homologous recombination in mammalian chromosomes by using the I-SceI system of Saccharomyces cerevisiae. Mol Cell Biol, 15, 1968-1973.

Cohen-Tannoudji, M., Robine, S., Choulika, A., Pinto, D., El Marjou, F., Babinet, C., Louvard, D. and Jaisser, F. (1998) I-SceI-induced gene replacement at a natural locus in embryonic stem cells. Mol Cell Biol, 18, 1444-1448.

Colleaux, L., D'Auriol, L., Galibert, F. and Dujon, B. (1988) Recognition and cleavage site of the intron-encoded omega transposase. Proc Natl Acad Sci USA, 85, 6022-6026.

Donoho, G., Jasin, M. and Berg, P. (1998) Analysis of gene targeting and intrachromosomal homologous recombination stimulated by genomic double-strand breaks in mouse embryonic stem cells. Mol Cell Biol, 18, 4070-4078.

Elliott, B., Richardson, C., Winderbaum, J., Nickoloff, J. A. and Jasin, M. (1998) Gene conversion tracts from double-strand break repair in mammalian cells. Mol Cell Biol, 18, 93-101.

Epinat, J. C., Arnould, S., Chames, P., Rochaix, P., Desfontaines, D., Puzin, C., Patin, A., Zanghellini, A., Paques, F. and Lacroix, E. (2003) A novel engineered meganuclease induces homologous recombination in yeast and mammalian cells. Nucleic Acids Res, 31, 2952-2962.

Gietz, R. D. and Woods, R. A. (2002) Transformation of yeast by lithium acetate/single-stranded carrier DNA/polyethylene glycol method. Methods Enzymol, 350, 87-96.

Haber, J. E. (1998) Mating-type gene switching in Saccharomyces cerevisiae. Annu Rev Genet, 32, 561-599.

Jacquier, A. and Dujon, B. (1985) An intron-encoded protein is active in a gene conversion process that spreads an intron into a mitochondrial gene. Cell, 41, 383-394.

Jurica, M.S., Monnat, R.J., Jr. and Stoddard, B.L. (1998) DNA recognition and cleavage by the LAGLIDADG (SEQ ID NO: 91) homing endonuclease I-CreI. Mol Cell, 2, 469-476.

Klar, A. J., Strathern, J. N. and Abraham, J. A. (1984) Involvement of double-strand chromosomal breaks for mating-type switching in Saccharomyces cerevisiae. Cold Spring Harb Symp Quant Biol, 49, 77-88.

Kostriken, R., Strathern, J. N., Klar, A. J., Hicks, J. B. and Heffron, F. (1983) A site-specific endonuclease essential for mating-type switching in Saccharomyces cerevisiae. Cell, 35, 167-174.

Liang, F., Han, M., Romanienko, P. J. and Jasin, M. (1998) Homology-directed repair is a major double-strand break repair pathway in mammalian cells. Proc Natl Acad Sci USA, 95, 5172-5177.

Moynahan, M. E. and Jasin, M. (1997) Loss of heterozygosity induced by a chromosomal double-strand break. Proc Natl Acad Sci USA, 94, 8988-8993.

Mueller, J. E., Smith, D. and Belfort, M. (1996) Exon coconversion biases accompanying intron homing: battle of the nucleases. Genes Dev, 10, 2158-2166.

Perrin, A., Buckle, M. and Dujon, B. (1993) Asymmetrical recognition and activity of the I-SceI endonuclease on its site and on intron-exon junctions. Embo J, 12, 2939-2947.

Plessis, A., Perrin, A., Haber, J. E. and Dujon, B. (1992) Site-specific recombination determined by I-SceI, a mitochondrial group I intron-encoded endonuclease expressed in the yeast nucleus. Genetics, 130, 451-460.

Porteus, M. H. and Baltimore, D. (2003) Chimeric nucleases stimulate gene targeting in human cells. Science, 300, 763.

Posfai, G., Kolisnychenko, V., Bereczki, Z. and Blattner, F. R. (1999) Markerless gene replacement in Escherichia coli stimulated by a double-strand break in the chromosome. Nucleic Acids Res, 27, 4409-4415.

Puchta, H. (1999) Double-strand break-induced recombination between ectopic homologous sequences in somatic plant cells. Genetics, 152, 1173-1181.

Puchta, H., Dujon, B. and Hohn, B. (1993) Homologous recombination in plant cells is enhanced by in vivo induction of double strand breaks into DNA by a site-specific endonuclease. Nucleic Acids Res, 21, 5034-5040.

Puchta, H., Dujon, B. and Hohn, B. (1996) Two different but related mechanisms are used in plants for the repair of genomic double-strand breaks by homologous recombination. Proc Natl Acad Sci USA, 93, 5055-5060.

Richardson, C., Moynahan, M. E. and Jasin, M. (1998) Double-strand break repair by interchromosomal recombination: suppression of chromosomal translocations. Genes Dev, 12, 3831-3842.

Rong, Y. S. and Golic, K. G. (2000) Gene targeting by homologous recombination in Drosophila. Science, 288, 2013-2018.

Rong, Y. S. and Golic, K. G. (2001) A targeted gene knockout in Drosophila. Genetics, 157, 1307-1312.

Rong, Y. S., Titen, S. W., Xie, H. B., Golic, M. M., Bastiani, M., Bandyopadhyay, P., Olivera, B. M., Brodsky, M., Rubin, G. M. and Golic, K. G. (2002) Targeted mutagenesis by homologous recombination in D. melanogaster. Genes Dev, 16, 1568-1581.

Rouet, P., Smih, F. and Jasin, M. (1994) Introduction of double-strand breaks into the genome of mouse cells by expression of a rare-cutting endonuclease. Mol Cell Biol, 14, 8096-8106.

Seligman et al., 1997, Genetics, 1997, 147, 1653-1664

Seligman, L. M., Chisholm, K. M., Chevalier, B. S., Chadsey, M. S., Edwards, S. T., Savage, J. H. and Veillet, A. L. (2002) Mutations altering the cleavage specificity of a homing endonuclease. Nucleic Acids Res, 30, 3870-3879.

Siebert, R. and Puchta, H. (2002) Efficient repair of genomic double-strand breaks by homologous recombination between directly repeated sequences in the plant genome. Plant Cell, 14, 1121-1131.

Sussman, D., Chadsey, M., Fauce, S., Engel, A., Bruett, A., Monnat, R., Jr., Stoddard, B. L. and Seligman, L. M. (2004) Isolation and characterization of new homing endonuclease specificities at individual target site positions. J Mol Biol, 342, 31-41.

Thierry, A. and Dujon, B. (1992) Nested chromosomal fragmentation in yeast using the meganuclease I-Sce I: a new method for physical mapping of eukaryotic genomes. Nucleic Acids Res, 20, 5625-5631.

The invention claimed is:

1. An isolated monomer of an I-CreI meganuclease variant comprising at least one mutation in the amino acid sequence of SEQ ID NO: 70, wherein said at least one mutation comprises a substitution at one or more of the amino acids residues at positions 44, 68 and 70 and said monomer further comprises at least one additional mutation of an amino acid residue directly contacting a DNA target sequence wherein said amino acid residue directly contacting a DNA target sequence is selected from the group consisting of positions 26, 28, 30, 32, 33 and 38,
    wherein said monomer when in a dimeric form is able to cleave DNA.

2. The monomer of an I-CreI meganuclease variant of claim 1 wherein said monomer comprises at least two mutations in positions 44, 68 and 70.

3. The monomer of an I-CreI meganuclease variant of claim 1 wherein said monomer comprises mutations in positions 44, 68 and 70.

4. The monomer of an I-CreI meganuclease variant of claim 1, wherein said monomer when in a dimeric form has a modified DNA cleavage specificity relative to the I-CreI meganuclease of SEQ ID NO: 70 in at least one nucleotide in the ±3 to 5 triplets.

5. The monomer of an I-CreI meganuclease variant of claim 1 having at least the mutations selected in the group consisting of: A44/A68/A70, A44/A68/G70, A44/A68/H70, A44/A68/K70, A44/A68/N70, A44/A68/Q70, A44/A68/ S70, A44/A68/T70, A44/D68/H70, A44/D68/K70, A44/D68/ R70, A44/G68/H70, A44/G68/K70, A44/G68/N70, A44/ G68/P70, A44/H68/A70, A44/H68/G70, A44/H68/H70, A44/H68/K70, A44/H68/N70, A44/H68/Q70, A44/H68/ S70, A44/H68/T70, A44/K68/A70, A44/K68/G70, A44/K68/ H70, A44/K68/N70, A44/K68/Q70, A44/K68/R70, A44/ K68/S70, A44/K68/T70, A44/N68/A70, A44/N68/E70, A44/ N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/ H70, A44/Q68/N70, A44/Q68/S70, A44/R68/E70, A44/R68/ K70, A44/R68/L70, A44/S68/A70, A44/S68/G70, A44/S68/ N70, A44/S68/Q70, A44/S68/R70, A44/S68/S70, A44/S68/ T70, A44/T68/A70, A44/T68/G70, A44/T68/H70, A44/T68/ N70, A44/T68/Q70, A44/T68/S70, A44/T68/T70, D44/D68/ H70, D44/N68/S70, D44/R68/A70, D44/R68/N70, D44/ R68/Q70, D44/R68/R70, D44/R68/S70, D44/R68/T70, E44/ H68/H70, E44/R68/A70, E44/R68/H70, E44/R68/N70, E44/ R68/S70, E44/R68/T70, E44/S68/T70, G44/H68/K70, G44/ Q68/H70, G44/R68/Q70, G44/T68/D70, G44/T68/P70, G44/T68/R70, H44/A68/S70, H44/A68/T70, H44/R68/D70, H44/R68/E70, H44/R68/G70, H44/R68/N70, H44/R68/R70, H44/R68/S70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/ N70, K44/A68/Q70, K44/D68/A70, K44/D68/T70, K44/ E68/G70, K44/E68/S70, K44/G68/A70, K44/G68/G70, K44/G68/N70, K44/G68/S70, K44/G68/T70, K44/H68/ D70, K44/H68/E70, K44/H68/G70, K44/H68/N70, K44/ H68/S70, K44/H68/T70, K44/K68/A70, K44/K68/D70, K44/K68/H70, K44/K68/T70, K44/N68/A70, K44/N68/ D70, K44/N68/E70, K44/N68/G70, K44/N68/H70, K44/ N68/N70, K44/N68/Q70, K44/N68/S70, K44/N68/T70, K44/P68/H70, K44/Q68/A70, K44/Q68/D70, K44/Q68/ E70, K44/Q68/S70, K44/Q68/T70, K44/R68/A70, K44/R68/ D70, K44/R68/E70, K44/R68/G70, K44/R68/H70, K44/ R68/N70, K44/R68/S70, K44/S68/A70, K44/S68/D70, K44/ S68/H70, K44/S68/N70, K44/S68/S70, K44/S68/T70, K44/ T68/A70, K44/T68/D70, K44/T68/E70, K44/T68/G70, K44/ T68/H70, K44/T68/N70, K44/T68/Q70, K44/T68/S70, K44/ T68/T70, N44/A68/H70, N44/H68/N70, N44/H68/R70, N44/K68/G70, N44/K68/H70, N44/K68/R70, N44/K68/ S70, N44/P68/D70, N44/Q68/H70, N44/R68/A70, N44/ R68/D70, N44/R68/E70, N44/R68/K70, N44/S68/G70, N44/S68/H70, N44/S68/K70, N44/S68/R70, N44/T68/H70, N44/T68/K70, N44/T68/Q70, N44/T68/S70, P44/N68/D70, P44/T68/T70, Q44/G68/K70, Q44/G68/R70, Q44/K68/G70, Q44/N68/A70, Q44/N68/H70, Q44/N68/S70, Q44/P68/P70, Q44/Q68/G70, Q44/R68/D70, Q44/R68/E70, Q44/R68/ G70, Q44/R68/Q70, Q44/S68/S70, Q44/T68/A70, Q44/T68/ G70, Q44/T68/H70, R44/A68/G70, R44/A68/T70, R44/ G68/T70, R44/H68/D70, R44/H68/T70, R44/N68/T70, R44/ R68/A70, R44/R68/D70, R44/R68/E70, R44/R68/G70, R44/ R68/Q70, R44/R68/S70, R44/R68/T70, R44/S68/G70, R44/ S68/N70, R44/S68/S70, R44/S68/T70, S44/D68/K70, S44/ R68/R70, S44/R68/S70, T44/A68/K70, T44/N68/P70, T44/ N68/R70, T44/R68/E70, T44/R68/Q70, and T44/S68/K70.

6. An I-CreI meganuclease variant homodimer, wherein said homodimer comprises two identical monomers according to claim 1.

7. An I-CreI meganuclease variant heterodimer, wherein said heterodimer comprises at least one monomer according to claim 1 and a second monomer selected from the group consisting of a different monomer according to claim 1, a wild -type monomer from I-CreI, a variant of the wild-type monomer from I-CreI, a wild-type monomer from I-DmoI, and a variant of the wild-type monomer from I-DmoI.

8. An I-CreI meganuclease variant heterodimer, wherein said heterodimer comprises two different monomers according to claim 1.

9. An I-CreI meganuclease variant heterodimer, wherein said heterodimer comprises one monomer according to claim 1 and a wild-type monomer from I -CreI.

10. An I-CreI meganuclease variant heterodimer, wherein said heterodimer comprises one monomer according to claim 1 and a variant of the wild-type monomer from I-CreI.

11. An I-CreI meganuclease variant heterodimer, wherein said heterodimer comprises one monomer according to claim 1 and a wild-type monomer from I -DmoI.

12. An I-CreI meganuclease variant heterodimer, wherein said heterodimer comprises one monomer according to claim 1 and a variant of the wild-type monomer from I-DmoI.

13. A single-chain chimeric meganuclease comprising the fusion of at least one monomer according to claim 1 and a second monomer selected from the group consisting of a different monomer according to claim 1, a wild-type monomer from I-CreI, a variant of the wild-type monomer from I-CreI, a wild-type monomer from I -DmoI, and a variant of the wild-type monomer from I-DmoI.

14. A single-chain chimeric meganuclease comprising the fusion of two different monomers according to claim 1.

15. A single-chain chimeric meganuclease comprising the fusion of one monomer according to claim 1 and a wild-type monomer from I-CreI.

16. A single-chain chimeric meganuclease comprising the fusion of one monomer according to claim 1 and a variant of the wild-type monomer from I-CreI.

17. A single-chain chimeric meganuclease comprising the fusion of one monomer according to claim 1 and a wild-type monomer from I-DmoI.

18. A single-chain chimeric meganuclease comprising the fusion of one monomer according to claim 1 and a variant of the wild-type monomer from I-DmoI.

19. A purified monomer of an I-CreI meganuclease variant comprising at least one mutation in the amino acid sequence of SEQ ID NO: 70, wherein said at least one mutation comprises a substitution at one or more of the amino acids residues at positions 44, 68 and 70 and said monomer further comprises at least one additional mutation of an amino acid residue directly contacting a DNA target sequence wherein said amino acid residue directly contacting a DNA target sequence is selected from the group consisting of positions 26, 28, 30, 32, 33 and 38,
  wherein said monomer when in a dimeric form is able to cleave DNA.

20. The monomer of an I-CreI meganuclease variant of claim 19 wherein said monomer comprises at least two mutations in positions 44, 68 and 70.

21. The monomer of an I-CreI meganuclease variant of claim 19 wherein said monomer comprises mutations in positions 44, 68 and 70.

22. The monomer of an I-CreI meganuclease variant of claim 19, wherein said monomer when in a dimeric form has a modified DNA cleavage specificity relative to the I-CreI meganuclease of SEQ ID NO: 70 in at least one nucleotide in the ±3 to 5 triplets.

23. The monomer of an I-CreI meganuclease variant of claim 19 having at least the mutations selected in the group consisting of: A44/A68/A70, A44/A68/G70, A44/A68/H70, A44/A68/K70, A44/A68/N70, A44/A68/Q70, A44/A68/ S70, A44/A68/T70, A44/D68/H70, A44/D68/K70, A44/D68/ R70, A44/G68/H70, A44/G68/K70, A44/G68/N70, A44/

G68/P70, A44/H68/A70, A44/H68/G70, A44/H68/H70, A44/H68/K70, A44/H68/N70, A44/H68/Q70, A44/H68/S70, A44/H68/T70, A44/K68/A70, A44/K68/G70, A44/K68/H70, A44/K68/N70, A44/K68/Q70, A44/K68/R70, A44/K68/S70, A44/K68/T70, A44/N68/A70, A44/N68/E70, A44/N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/H70, A44/Q68/N70, A44/Q68/S70, A44/R68/E70, A44/R68/K70, A44/R68/L70, A44/S68/A70, A44/S68/G70, A44/S68/N70, A44/S68/Q70, A44/S68/R70, A44/S68/S70, A44/S68/T70, A44/T68/A70, A44/T68/G70, A44/T68/H70, A44/T68/N70, A44/T68/Q70, A44/T68/S70, A44/T68/T70, D44/D68/H70, D44/N68/S70, D44/R68/A70, D44/R68/N70, D44/R68/Q70, D44/R68/R70, D44/R68/S70, D44/R68/T70, E44/H68/H70, E44/R68/A70, E44/R68/H70, E44/R68/N70, E44/R68/S70, E44/R68/T70, E44/S68/T70, G44/H68/K70, G44/Q68/H70, G44/R68/Q70, G44/T68/D70, G44/T68/P70, G44/T68/R70, H44/A68/S70, H44/A68/T70, H44/R68/D70, H44/R68/E70, H44/R68/G70, H44/R68/N70, H44/R68/R70, H44/R68/S70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/N70, K44/A68/Q70, K44/D68/A70, K44/D68/T70, K44/E68/G70, K44/E68/S70, K44/G68/A70, K44/G68/G70, K44/G68/N70, K44/G68/S70, K44/G68/T70, K44/H68/D70, K44/H68/E70, K44/H68/G70, K44/H68/N70, K44/H68/S70, K44/H68/T70, K44/K68/A70, K44/K68/D70, K44/K68/H70, K44/K68/T70, K44/N68/A70, K44/N68/D70, K44/N68/E70, K44/N68/G70, K44/N68/H70, K44/N68/N70, K44/N68/Q70, K44/N68/S70, K44/N68/T70, K44/P68/H70, K44/Q68/A70, K44/Q68/D70, K44/Q68/E70, K44/Q68/S70, K44/Q68/T70, K44/R68/A70, K44/R68/D70, K44/R68/E70, K44/R68/G70, K44/R68/H70, K44/R68/N70, K44/R68/S70, K44/S68/A70, K44/S68/D70, K44/S68/H70, K44/S68/N70, K44/S68/S70, K44/S68/T70, K44/T68/A70, K44/T68/D70, K44/T68/E70, K44/T68/G70, K44/T68/H70, K44/T68/N70, K44/T68/Q70, K44/T68/S70, K44/T68/T70, N44/A68/H70, N44/H68/N70, N44/H68/R70, N44/K68/G70, N44/K68/H70, N44/K68/R70, N44/K68/S70, N44/P68/D70, N44/Q68/H70, N44/R68/A70, N44/R68/D70, N44/R68/E70, N44/R68/K70, N44/S68/G70, N44/S68/H70, N44/S68/K70, N44/S68/R70, N44/T68/H70, N44/T68/K70, N44/T68/Q70, N44/T68/S70, P44/N68/D70, P44/T68/T70, Q44/G68/K70, Q44/G68/R70, Q44/K68/G70, Q44/N68/A70, Q44/N68/H70, Q44/N68/S70, Q44/P68/P70, Q44/Q68/G70, Q44/R68/D70, Q44/R68/E70, Q44/R68/G70, Q44/R68/Q70, Q44/S68/S70, Q44/T68/A70, Q44/T68/G70, Q44/T68/H70, R44/A68/G70, R44/A68/T70, R44/G68/T70, R44/H68/D70, R44/H68/T70, R44/N68/T70, R44/R68/A70, R44/R68/D70, R44/R68/E70, R44/R68/G70, R44/R68/Q70, R44/R68/S70, R44/R68/T70, R44/S68/G70, R44/S68/N70, R44/S68/S70, R44/S68/T70, S44/D68/K70, S44/R68/R70, S44/R68/S70, S44/R68/S70, T44/A68/K70, T44/N68/P70, T44/N68/R70, T44/R68/E70, T44/R68/Q70, and T44/S68/K70.

24. An I-CreI meganuclease variant homodimer, wherein said homodimer comprises two identical monomers according to claim 19.

25. An I-CreI meganuclease variant heterodimer, wherein said heterodimer comprises at least one monomer according to claim 19 and a second monomer selected from the group consisting of a different monomer according to claim 19, a wild-type monomer from I-CreI, a variant of the wild-type monomer from I-CreI, a wild-type monomer from I-DmoI, and a variant of the wild-type monomer from I-DmoI.

26. An I-CreI meganuclease variant heterodimer, wherein said heterodimer comprises two different monomers according to claim 19.

27. An I-CreI meganuclease variant heterodimer, wherein said heterodimer comprises one monomer according to claim 19 and a wild-type monomer from I-CreI.

28. An I-CreI meganuclease variant heterodimer, wherein said heterodimer comprises one monomer according to claim 19 and a variant of the wild-type monomer from I-CreI.

29. An I-CreI meganuclease variant heterodimer, wherein said heterodimer comprises one monomer according to claim 19 and a wild-type monomer from I-DmoI.

30. An I-CreI meganuclease variant heterodimer, wherein said heterodimer comprises one monomer according to claim 19 and a variant of the wild-type monomer from I-DmoI.

31. A single-chain chimeric meganuclease comprising the fusion of at least one monomer according to claim 19 and a second monomer selected from the group consisting of a different monomer according to claim 19, a wild-type monomer from I-CreI, a variant of the wild-type monomer from I-CreI, a wild-type monomer from I-DmoI, and a variant of the wild-type monomer from I-DmoI.

32. A single-chain chimeric meganuclease comprising the fusion of two different monomers according to claim 19.

33. A single-chain chimeric meganuclease comprising the fusion of one monomer according to claim 19 and a wild-type monomer from I-CreI.

34. A single-chain chimeric meganuclease comprising the fusion of one monomer according to claim 19 and a variant of the wild-type monomer from I-CreI.

35. A single-chain chimeric meganuclease comprising the fusion of one monomer according to claim 19 and a wild-type monomer from I-DmoI.

36. A single-chain chimeric meganuclease comprising the fusion of one monomer according to claim 19 and a variant of the wild-type monomer from I-DmoI.

37. A recombinant monomer of an I-CreI meganuclease variant comprising at least one mutation in the amino acid sequence of SEQ ID NO: 70, wherein said at least one mutation comprises a substitution at one or more of the amino acids residues at positions 44, 68 and 70 and said monomer further comprises at least one additional mutation of an amino acid residue directly contacting a DNA target sequence wherein said amino acid residue directly contacting a DNA target sequence is selected from the group consisting of positions 26, 28, 30, 32, 33 and 38,
wherein said monomer when in a dimeric form is able to cleave DNA.

38. The monomer of an I-CreI meganuclease variant of claim 37 wherein said monomer comprises at least two mutations in positions 44, 68 and 70.

39. The monomer of an I-CreI meganuclease variant of claim 37 wherein said monomer comprises mutations in positions 44, 68 and 70.

40. The monomer of an I-CreI meganuclease variant of claim 37, wherein said monomer when in a dimeric form has a modified DNA cleavage specificity relative to the I-CreI meganuclease of SEQ ID NO: 70 in at least one nucleotide in the ±3 to 5 triplets.

41. The monomer of an I-CreI meganuclease variant of claim 37 having at least the mutations selected in the group consisting of: A44/A68/A70, A44/A68/G70, A44/A68/H70, A44/A68/K70, A44/A68/N70, A44/A68/Q70, A44/A68/S70, A44/A68/T70, A44/D68/H70, A44/D68/K70, A44/D68/R70, A44/G68/H70, A44/G68/K70, A44/G68/N70, A44/G68/P70, A44/H68/A70, A44/H68/G70, A44/H68/H70, A44/H68/K70, A44/H68/N70, A44/H68/Q70, A44/H68/

S70, A44/H68/T70, A44/K68/A70, A44/K68/G70, A44/K68/H70, A44/K68/N70, A44/K68/Q70, A44/K68/R70, A44/K68/S70, A44/K68/T70, A44/N68/A70, A44/N68/E70, A44/N68/G70, A44/N68/H70, A44/N68/K70, A44/N68/N70, A44/N68/Q70, A44/N68/R70, A44/N68/S70, A44/N68/T70, A44/Q68/A70, A44/Q68/D70, A44/Q68/G70, A44/Q68/H70, A44/Q68/N70, A44/Q68/S70, A44/R68/E70, A44/R68/K70, A44/R68/L70, A44/S68/A70, A44/S68/G70, A44/S68/N70, A44/S68/Q70, A44/S68/R70, A44/S68/S70, A44/S68/T70, A44/T68/A70, A44/T68/G70, A44/T68/H70, A44/T68/N70, A44/T68/Q70, A44/T68/S70, A44/T68/T70, D44/D68/H70, D44/N68/S70, D44/R68/A70, D44/R68/N70, D44/R68/Q70, D44/R68/R70, D44/R68/S70, D44/R68/T70, E44/H68/H70, E44/R68/A70, E44/R68/H70, E44/R68/N70, E44/R68/S70, E44/R68/T70, E44/S68/T70, G44/H68/K70, G44/Q68/H70, G44/R68/Q70, G44/T68/D70, G44/T68/P70, G44/T68/R70, H44/A68/S70, H44/A68/T70, H44/R68/D70, H44/R68/E70, H44/R68/G70, H44/R68/N70, H44/R68/R70, H44/R68/S70, H44/S68/G70, H44/S68/S70, H44/S68/T70, H44/T68/S70, H44/T68/T70, K44/A68/A70, K44/A68/D70, K44/A68/E70, K44/A68/G70, K44/A68/H70, K44/A68/N70, K44/A68/Q70, K44/D68/A70, K44/D68/T70, K44/E68/G70, K44/E68/S70, K44/G68/A70, K44/G68/G70, K44/G68/N70, K44/G68/S70, K44/G68/T70, K44/H68/D70, K44/H68/E70, K44/H68/G70, K44/H68/N70, K44/H68/S70, K44/H68/T70, K44/K68/A70, K44/K68/D70, K44/K68/H70, K44/K68/T70, K44/N68/A70, K44/N68/D70, K44/N68/E70, K44/N68/G70, K44/N68/H70, K44/N68/N70, K44/N68/Q70, K44/N68/S70, K44/N68/T70, K44/P68/H70, K44/Q68/A70, K44/Q68/D70, K44/Q68/E70, K44/Q68/S70, K44/Q68/T70, K44/R68/A70, K44/R68/D70, K44/R68/E70, K44/R68/G70, K44/R68/H70, K44/R68/N70, K44/R68/S70, K44/S68/A70, K44/S68/D70, K44/S68/H70, K44/S68/N70, K44/S68/S70, K44/S68/T70, K44/T68/A70, K44/T68/D70, K44/T68/E70, K44/T68/G70, K44/T68/H70, K44/T68/N70, K44/T68/Q70, K44/T68/S70, K44/T68/T70, N44/A68/H70, N44/H68/N70, N44/H68/R70, N44/K68/G70, N44/K68/H70, N44/K68/R70, N44/K68/S70, N44/P68/D70, N44/Q68/H70, N44/R68/A70, N44/R68/D70, N44/R68/E70, N44/R68/K70, N44/S68/G70, N44/S68/H70, N44/S68/K70, N44/S68/R70, N44/T68/H70, N44/T68/K70, N44/T68/Q70, N44/T68/S70, P44/N68/D70, P44/T68/T70, Q44/G68/K70, Q44/G68/R70, Q44/K68/G70, Q44/N68/A70, Q44/N68/H70, Q44/N68/S70, Q44/P68/P70, Q44/Q68/G70, Q44/R68/D70, Q44/R68/E70, Q44/R68/G70, Q44/R68/Q70, Q44/S68/S70, Q44/T68/A70, Q44/T68/G70, Q44/T68/H70, R44/A68/G70, R44/A68/T70, R44/G68/T70, R44/H68/D70, R44/H68/T70, R44/N68/T70, R44/R68/A70, R44/R68/D70, R44/R68/E70, R44/R68/G70, R44/R68/Q70, R44/R68/S70, R44/R68/T70, R44/S68/G70, R44/S68/N70, R44/S68/S70, R44/S68/T70, S44/D68/K70, S44/R68/R70, S44/R68/S70, T44/A68/K70, T44/N68/P70, T44/N68/R70, T44/R68/E70, T44/R68/Q70, and T44/S68/K70.

42. An I-CreI meganuclease variant homodimer, wherein said homodimer comprises two identical monomers according to claim 37.

43. An I-CreI meganuclease variant heterodimer, wherein said heterodimer comprises at least one monomer according to claim 37 and a second monomer selected from the group consisting of a different monomer according to claim 37, a wild-type monomer from I-CreI, a variant of the wild-type monomer from I-CreI, a wild-type monomer from I-DmoI, and a variant of the wild-type monomer from I-DmoI.

44. An I-CreI meganuclease variant heterodimer, wherein said heterodimer comprises two different monomers according to claim 37.

45. An I-CreI meganuclease variant heterodimer, wherein said heterodimer comprises one monomer according to claim 37 and a wild-type monomer from I-CreI.

46. An I-CreI meganuclease variant heterodimer, wherein said heterodimer comprises one monomer according to claim 37 and a variant of the wild-type monomer from I-CreI.

47. An I-CreI meganuclease variant heterodimer, wherein said heterodimer comprises one monomer according to claim 37 and a wild-type monomer from I-DmoI.

48. An 1-CreI meganuclease variant heterodimer, wherein said heterodimer comprises one monomer according to claim 37 and a variant of the wild-type monomer from I-DmoI.

49. A single-chain chimeric meganuclease comprising the fusion of at least one monomer according to claim 37 and a second monomer selected from the group consisting of a different monomer according to claim 37, a wild-type monomer from I-CreI, a variant of the wild-type monomer from I-CreI, a wild-type monomer from I-DmoI, and a variant of the wild-type monomer from I-DmoI.

50. A single-chain chimeric meganuclease comprising the fusion of two different monomers according to claim 37.

51. A single-chain chimeric meganuclease comprising the fusion of one monomer according to claim 37 and a wild-type monomer from I-CreI.

52. A single-chain chimeric meganuclease comprising the fusion of one monomer according to claim 37 and a variant of the wild-type monomer from I-CreI.

53. A single-chain chimeric meganuclease comprising the fusion of one monomer according to claim 37 and a wild-type monomer from I-DmoI.

54. A single-chain chimeric meganuclease comprising the fusion of one monomer according to claim 37 and a variant of the wild-type monomer from I-DmoI.

* * * * *

UNITED STATES PATENT AND TRADEMARK OFFICE
CERTIFICATE OF CORRECTION

| | | |
|---|---|---|
| PATENT NO. | : 7,897,372 B2 | Page 1 of 1 |
| APPLICATION NO. | : 11/908798 | |
| DATED | : March 1, 2011 | |
| INVENTOR(S) | : Philippe Duchateau et al. | |

It is certified that error appears in the above-identified patent and that said Letters Patent is hereby corrected as shown below:

Title Page

Delete:

"(30) Foreign Application Priority Data

Mar. 15, 2005 (WO)................PCT/IB2005/000981
    Sep. 19, 2005 (WO)................PCT/IB2005/003083"

Title Page

After "(65) Prior Publication Data
US 2010/0021448 A1    Jan. 28, 2010" insert:

--(60) Related U.S. Application Data

The present application is a 35 U.S.C. §371 National Stage patent application of International patent application PCT/IB2006/001203, filed on Mar. 15, 2006, which claims priority under 35 U.S.C. §120 and 35 U.S.C. §365(c) to International patent application PCT/IB2005/003083, filed on Sep. 19, 2005, and also claims priority under 35 U.S.C. §120 and §365(c) to International patent application PCT/IB2005/000981, filed on Mar. 15, 2005.--

Signed and Sealed this
Tenth Day of January, 2012

David J. Kappos
*Director of the United States Patent and Trademark Office*

(12) INTER PARTES REEXAMINATION CERTIFICATE (991st)
United States Patent
Duchateau et al.

(10) Number: US 7,897,372 C1
(45) Certificate Issued: Nov. 5, 2014

(54) I-CREI MEGANUCLEASE VARIANTS WITH MODIFIED SPECIFICITY, METHOD OF PREPARATION AND USES THEREOF

(75) Inventors: Philippe Duchateau, Gandelu (FR); Frederic Paques, Bourg-la-Reine (FR)

(73) Assignee: Cellectis SA, Paris (FR)

Reexamination Request:
No. 95/002,160, Sep. 7, 2012

No. 90/011,665, May 10, 2011

Reexamination Certificate for:
Patent No.: 7,897,372
Issued: Mar. 1, 2011
Appl. No.: 11/908,798
Filed: Sep. 17, 2007

Certificate of Correction issued Jan. 10, 2012

(21) Appl. No.: 95/002,160
(22) PCT Filed: Mar. 15, 2006
(86) PCT No.: PCT/IB2006/001203
§ 371 (c)(1), (2), (4) Date: Sep. 17, 2007
(87) PCT Pub. No.: WO2006/097853
PCT Pub. Date: Sep. 21, 2006

(51) Int. Cl.
C12N 9/00 (2006.01)
C12N 15/00 (2006.01)
C12N 9/22 (2006.01)
C12N 1/12 (2006.01)
C07H 21/04 (2006.01)

(52) U.S. Cl.
USPC .............. 435/199; 435/320.1; 435/252.3; 435/183; 536/23.2

(58) Field of Classification Search
None
See application file for complete search history.

(56) References Cited

To view the complete listing of prior art documents cited during the proceedings for Reexamination Control Numbers 95/002,160 and 90/011,665, please refer to the USPTO's public Patent Application Information Retrieval (PAIR) system under the Display References tab.

*Primary Examiner* — Bruce Campell

(57) ABSTRACT

Method of preparing I-CreI meganuclease variants having a modified cleavage specificity, variants obtainable by said method and their applications either for cleaving new DNA target or for genetic engineering and genome engineering for non-therapeutic purposes. Nucleic acids encoding said variants, expression cassettes comprising said nucleic acids, vectors comprising said expression cassettes, cells or organisms, plants or animals except humans, transformed by said vectors.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-54 are cancelled.

\* \* \* \* \*